(12) United States Patent
Gharat et al.

(10) Patent No.: US 8,519,149 B2
(45) Date of Patent: Aug. 27, 2013

(54) TRICYCLIC COMPOUNDS AS MPGES-1 INHIBITORS

(75) Inventors: Laxmikant A. Gharat, Thane (IN); Nagarajan Muthukaman, Erode (IN); Lakshminarayana Narayana, Navi Mumbai (IN); Neelima Khairatkar-Joshi, Thane (IN); Vidya G. Kattige, Thane (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 5 days.

(21) Appl. No.: 13/283,786

(22) Filed: Oct. 28, 2011

(65) Prior Publication Data
US 2012/0108583 A1 May 3, 2012

Related U.S. Application Data

(60) Provisional application No. 61/416,400, filed on Nov. 23, 2010, provisional application No. 61/436,674, filed on Jan. 27, 2011, provisional application No. 61/479,463, filed on Apr. 27, 2011, provisional application No. 61/498,758, filed on Jun. 20, 2011, provisional application No. 61/523,970, filed on Aug. 16, 2011.

(30) Foreign Application Priority Data

| Oct. 29, 2010 | (IN) | 3009/MUM/2010 |
|---|---|---|
| Jan. 3, 2011 | (IN) | 9/MUM/2011 |
| Apr. 1, 2011 | (IN) | 1121/MUM/2011 |
| Jun. 2, 2011 | (IN) | 1632/MUM/2011 |
| Jul. 25, 2011 | (IN) | 2099/MUM/2011 |

(51) Int. Cl.
| A61K 31/424 | (2006.01) |
| A61K 31/429 | (2006.01) |
| A61K 31/4188 | (2006.01) |
| C07D 491/048 | (2006.01) |

(52) U.S. Cl.
USPC ........ 548/302.1; 548/218; 548/159; 549/470; 544/124; 544/139; 546/273.1; 514/231.2; 514/338; 514/367; 514/375; 514/393

(58) Field of Classification Search
USPC .............................. 548/302.1, 218; 549/470
See application file for complete search history.

(56) References Cited

U.S. PATENT DOCUMENTS
2005/0124638 A1  6/2005  Swayze et al.

FOREIGN PATENT DOCUMENTS
| WO | WO-2006063466 A1 | 6/2006 |
| WO | WO-2007059610 A1 | 5/2007 |
| WO | WO-2010034796 A1 | 4/2010 |
| WO | WO-2010100249 A1 | 9/2010 |

OTHER PUBLICATIONS

Golub et al., Science, vol. 286, Oct. 15, 1999, pp. 531-537.*
Punit P. Seth et al: "SAR by MS: Discovery of a New Class of RNA-Binding Small Molecules for the Hepat it is C Virus: Internal Ribosome Entry Site IIA Subdomain", Journal of Medicinal Chemistry, vol. 48, No. 23, Nov. 1, 2005, pp. 7099-7102.
International Search Report Issued in connection with PCT/EP2011/068967 dated Jan. 9, 2012.

* cited by examiner

*Primary Examiner* — Laura L. Stockton
(74) *Attorney, Agent, or Firm* — Blank Rome LLP

(57) ABSTRACT

The present invention relates to tricyclic compounds of formula (I) or pharmaceutically acceptable salt thereof as mPGES-1 inhibitors. These compounds are inhibitors of the microsomal prostaglandin E synthase-1 (mPGES-1) enzyme and are therefore useful in the treatment of pain and/or inflammation from a variety of diseases or conditions, such as asthma, osteoarthritis, rheumatoid arthritis, acute or chronic pain and neurodegenerative diseases.

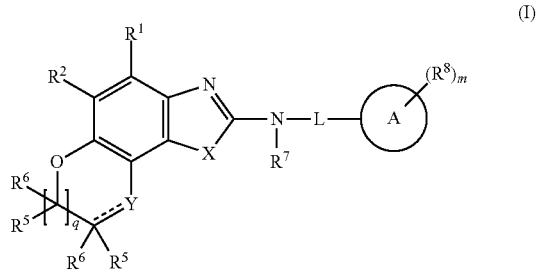

(I)

33 Claims, No Drawings

US 8,519,149 B2

TRICYCLIC COMPOUNDS AS MPGES-1 INHIBITORS

RELATED APPLICATIONS

This application claims benefit of Indian provisional application No(s). 3009/MUM/2010 filed on Oct. 29, 2010; 9/MUM/2011 filed on Jan. 3, 2011; 1121/MUM/2011 filed on Apr. 1, 2011; 1632/MUM/2011 filed on Jun. 2, 2011; and 2099/MUM/2011 filed on Jul. 25, 2011 and US provisional application No(s). 61/416,400 filed on Nov. 23, 2010; 61/436,674 filed on Jan. 27, 2011; 61/479,463 filed on Apr. 27, 2011; 61/498,758 filed on Jun. 20, 2011; and 61/523,970 filed on Aug. 16, 2011; all of which are hereby incorporated by reference in their entirety.

TECHNICAL FIELD

The present patent application relates to tricyclic compounds which may be useful as microsomal prostaglandin E synthase-1 (mPGES-1) inhibitors.

BACKGROUND

There are many diseases or disorders that are inflammatory in their nature. One of the major problems associated with existing treatments of inflammatory condition is inadequate efficacy and/or the prevalence of side effects. Inflammatory diseases that affect the population include asthma, inflammatory bowel disease, rheumatoid arthritis, osteoarthritis, rhinitis, conjunctivitis and dermatitis. Inflammation is also a common cause of pain.

The enzyme cyclooxygenase (COX) converts arachidonic acid to an unstable intermediate, prostaglandin $H_2$ ($PGH_2$) which is further converted to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. The COX enzyme exists in two forms, one that is constitutively expressed in many cells and tissues (COX-1), and other that in most cells and tissues are induced by pro-inflammatory stimuli, such as cytokines, during an inflammatory response (COX-2).

Among all prostaglandin metabolites, $PGE_2$ is particularly known to be a strong pro-inflammatory mediator, and is also known to induce fever and pain. Consequently, numerous drugs have been developed with a view to inhibiting the formation of $PGE_2$, including "NSAIDs" (non-steroidal anti-inflammatory drugs) and "coxibs" (selective COX-2 inhibitors). These drugs act predominantly by inhibition of COX-1 and/or COX-2, thereby reducing the formation of $PGE_2$. However, the inhibition of COXs has the disadvantage that it results in the reduction of the formation of all metabolites of $PGH_2$, thereby decreasing the beneficial properties of some of the metabolites. In view of this, drugs which act by inhibition of COXs are therefore known/suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

A combination of pharmacological, genetic and neutralizing antibody approaches demonstrates the importance of $PGE_2$ in inflammation. The conversion of $PGH_2$ to $PGE_2$ by prostaglandin E synthases (PGES) may therefore represent a pivotal step in the propagation of inflammatory stimuli.

Microsomal prostaglandin E synthase-1 (mPGES-1) is an inducible PGES after exposure to pro-inflammatory stimuli. mPGES-1 is induced in the periphery and CNS by inflammation and represents therefore a target for acute and chronic inflammatory disorders. $PGE_2$ is a major prostanoid, produced from arachidonic acid liberated by phospholipases (PLAs), which drives the inflammatory processes. Arachidonic acid is transformed by the action of prostaglandin H synthase (PGH synthase, cycloxygenase) into $PGH_2$ which is a substrate for mPGES-1, which is the terminal enzyme transforming $PGH_2$ to the pro-inflammatory $PGE_2$.

$PGH_2$ may be transformed to $PGE_2$ by prostaglandin E synthases (PGES). There are two microsomal prostaglandin E synthases (mPGES-1 and mPGES-2), and one cytosolic prostaglandin E synthase (cPGES). Thus, agents that are capable of inhibiting the action of mPGES-1, and thus reducing the formation of the specific arachidonic acid metabolite $PGE_2$, are likely to be of benefit in the treatment of inflammation. Further, agents that are capable of inhibiting the action of the proteins involved in the synthesis of the leukotrienes are also likely to be of benefit in the treatment of asthma and COPD.

Blocking the formation of $PGE_2$ in animal models of inflammatory pain results in reduced inflammation, pain and fever response (Kojima et. al, *The Journal of Immunology* 2008, 180, 8361-6; Xu et. al., *The Journal of Pharmacology and Experimental Therapeutics* 2008, 326, 754-63). In abdominal aortic aneurism, inflammation leads to connective tissue degradation and smooth muscle apoptosis ultimately leading to aortic dilation and rupture. In animals lacking mPGES-1 a slower disease progression and disease severity has been demonstrated (Wang et. al., *Circulation,* 2008, 117, 1302-1309).

Several lines of evidence indicate that $PGE_2$ is involved in malignant growth. $PGE_2$ facilitates tumor progression by stimulation of cellular proliferation and angiogenesis and by modulation of immunosupression. In support of a role for $PGE_2$ in cancers, genetic deletion of mPGES-1 in mice suppresses the intestinal tumourogenesis (Nakanishi et. al., *Cancer Research* 2008, 68(9), 3251-9). In human beings, mPGES-1 is also upregulated in cancers such as colorectal cancer (*Schroder Journal of Lipid Research* 2006, 47, 1071-80).

Myositis is chronic muscle disorder characterized by muscle weakness and fatigue. Proinflammatory cytokines and prostanoids have been implicated in the development of myositis. In skeletal muscle tissue from patients suffering from myositis an increase in cyclooxygenases and mPGES-1 has been demonstrated, implicating mPGES-1 as a target for treating this condition. (*Korotkova Annals of the Rheumatic Diseases* 2008, 67, 1596-1602).

In atherosclerosis inflammation of the vasculature leads to atheroma formation that eventually may progress into infarction. In patients with carotid atherosclerosis an increase in mPGES-1 in plaque regions have been reported (Gomez-Hernandez *Atherosclerosis* 2006, 187, 139-49). In an animal model of atherosclerosis, mice lacking the mPGES-1 receptor were found to show a retarded atherogenesis and a concomitant reduction in macrophage-derived foam cells together with an increase in vascular smooth muscle cells (Wang, *Proceedings of National Academy of Sciences* 2006, 103(39), 14507-12).

PCT publication numbers WO2006/063466, WO2007/059610, WO2010/034796, and WO2010/100249 disclose numerous heterocyclic compounds which are shown to be inhibitors of microsomal prostaglandin E synthase-1 (mPGES-1) enzyme.

The present invention is directed to novel compounds that are selective inhibitors of the mPGES-1 enzyme and would therefore be useful for the treatment of pain and inflammation in a variety of diseases or conditions.

SUMMARY

The present patent application relates to tricyclic compound of formula (I)

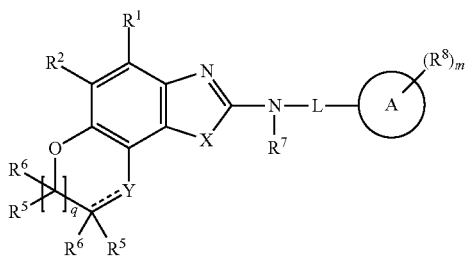

or a pharmaceutically acceptable salt thereof,
wherein,
A is aryl, heteroaryl or heterocyclyl;
X is selected from O, S and $NR^z$;
Y is selected from $—CR^3R^4—$, and $—NR^4—$;
L is a bond or is selected from $—(CR^xR^y)_n—$ and $—C(O)—$;
$R^1$ is selected from hydrogen, halogen, nitro, cyano, hydroxyl, substituted or unsubstituted alkyl, substituted or unsubstituted alkenyl, substituted or unsubstituted alkynyl, substituted or unsubstituted alkoxy, substituted or unsubstituted alkoxyalkyl, substituted or unsubstituted haloalkyl, substituted or unsubstituted haloalkoxy, substituted or unsubstituted hydroxyalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted aryloxy, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, $—C(O)R^a$, $—C(O)NR^aR^b$, $—C(O)OR^a$, $—NR^aR^b$, $—NR^aC(O)R^b$, $—NR^aC(O)NR^bR^c$, $—NR^aC(O)OR^b$, $—N(R^a)SO_2R^b$, $—OC(O)R^a$, $—OC(O)OR^a$, $—OC(O)NR^aR^b$, $—S(O)R^a$, $—SO_2R^a$, $—S(O)NR^aR^b$, $—SO_2NR^aR^b$ and $—SR^a$;
$R^2$ is selected from hydrogen, halogen, nitro, cyano, hydroxyl, substituted or unsubstituted alkyl, substituted or unsubstituted alkenyl, substituted or unsubstituted alkynyl, substituted or unsubstituted alkoxy, substituted or unsubstituted alkoxyalkyl, substituted or unsubstituted haloalkyl, substituted or unsubstituted haloalkoxy, substituted or unsubstituted hydroxyalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted aryloxy, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, $—C(O)R^a$, $—C(O)NR^aR^b$, $—C(O)OR^a$, $—NR^aR^b$, $—NR^aC(O)R^b$, $—NR^aC(O)NR^bR^c$, $—NR^aC(O)OR^b$, $—N(R^a)SO_2R^b$, $—OC(O)R^a$, $—OC(O)OR^a$ and $—OC(O)NR^aR^b$;

$R^3$ and $R^4$, which may be same or different, are independently selected from hydrogen, halogen, cyano, hydroxyl, $—NR^aR^b$, substituted or unsubstituted alkyl, substituted or unsubstituted alkoxy, substituted or unsubstituted cycloalkyl, substituted or unsubstituted aryl, substituted or unsubstituted heteroaryl and substituted or unsubstituted heterocyclyl;
$R^5$ and $R^6$, which may be same or different, are independently selected from hydrogen, substituted or unsubstituted alkyl, substituted or unsubstituted cycloalkyl, substituted or unsubstituted aryl, substituted or unsubstituted heteroaryl and substituted or unsubstituted heterocyclyl;
or $R^3$ and $R^4$ or $R^5$ and $R^6$ are taken together with the carbon atom to which they are attached to form a carbonyl ($—C=O$) or 3 to 7 membered cyclic ring;
$R^7$ is selected from hydrogen, substituted or unsubstituted alkyl, substituted or unsubstituted cycloalkyl, substituted or unsubstituted aryl, substituted or unsubstituted heteroaryl, substituted or unsubstituted heterocyclyl, $—C(O)R^a$, $—C(O)NR^aR^b$ and $—C(O)OR^a$;
at each occurrence $R^8$, which may be same or different, is independently selected from halogen, nitro, cyano, hydroxyl, substituted or unsubstituted alkyl, substituted or unsubstituted alkenyl, substituted or unsubstituted alkynyl, substituted or unsubstituted alkoxy, substituted or unsubstituted alkoxyalkyl, substituted or unsubstituted haloalkyl, substituted or unsubstituted haloalkoxy, substituted or unsubstituted hydroxyalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted aryloxy, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, $—C(O)R^a$, $—C(O)NR^aR^b$, $—C(O)OR^a$, $—NR^aR^b$, $—NR^aC(O)R^b$, $—NR^aC(O)NR^bR^c$, $—NR^aC(O)OR^b$, $—N(R^a)SO_2R^b$, $—OC(O)R^a$, $—OC(O)OR^a$, $—OC(O)NR^aR^b$, $—S(O)R^a$, $—SO_2R^a$, $—SONR^aR^b$, $—SO_2NR^aR^b$ and $—SR^a$;
at each occurrence, $R^a$, $R^b$ and $R^c$, which may be the same or different, are independently selected from hydrogen, substituted or unsubstituted alkyl, substituted or unsubstituted haloalkyl, substituted or unsubstituted alkoxyalkyl, substituted or unsubstituted hydroxyalkyl, substituted or unsubstituted haloalkoxy, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted aryloxy, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, $—(CH_2)_pNR^xR^y$, and $—(CH_2)_pCHR^xR^y$; or $R^a$ and $R^b$ together with the atom to which they are attached, form a cyclic ring which is substituted or unsubstituted and wherein the cyclic ring optionally contains one or more hetero atoms selected from O, N or S;
at each occurrence, $R^x$ and $R^y$, which may be the same or different, are independently selected from hydrogen, substituted or unsubstituted alkyl, substituted or unsubstituted cycloalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl; or $R^x$ and $R^y$ together with the atom to which they are attached, form a cyclic ring which is substituted or unsubstituted and wherein the cyclic ring optionally contains one or more hetero atoms selected from O, N or S;

$R^z$ is selected from hydrogen, substituted or unsubstituted alkyl, substituted or unsubstituted alkoxy, substituted or unsubstituted alkoxyalkyl, substituted or unsubstituted haloalkyl, substituted or unsubstituted cycloalkyl, substituted or unsubstituted aryl, substituted or unsubstituted heteroaryl, substituted or unsubstituted heterocyclyl, —C(O)$R^a$, —C(O)N$R^a R^b$ and —C(O)O$R^a$;

dotted line [—] inside the ring represents an optional bond; with a proviso that when dotted line [—] inside the ring represents a bond, then both $R^4$ and $R^5$ are absent;

'm' is an integer ranging from 0 to 5, both inclusive;
'n' is an integer ranging from 1 to 2, both inclusive;
'p' is an integer ranging from 0 to 6, both inclusive and
'q' is an integer ranging from 0 to 3, both inclusive.

The compounds of formula (I) may involve one or more embodiments. Embodiments of formula (I) include compounds of formula (II), compounds of formula (III) and compounds of formula (IV) as described hereinafter. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (I) as defined above wherein $R^1$ is hydrogen (according to an embodiment defined below) and $R^7$ is hydrogen (according to another embodiment defined below).

According to one embodiment, specifically provided are compounds of formula (I), in which A is substituted or unsubstituted aryl (e.g. phenyl) or substituted or unsubstituted heteroaryl (e.g. pyridyl). Where A is substituted aryl or substituted heteroaryl, the substituents on A may be one or more substitutents independently selected from halogen, nitro, cyano, hydroxyl, substituted or unsubstituted alkyl and substituted or unsubstituted haloalkyl. In particular, A may be substituted with 1, 2 or 3 substitutents independently selected from halogen, nitro, cyano, hydroxyl, $C_{1-4}$alkyl and halo$C_{1-4}$alkyl.

According to one embodiment, specifically provided are compounds of formula (I), in which X is O.

According to one embodiment, specifically provided are compounds of formula (I), in which X is S.

According to one embodiment, specifically provided are compounds of formula (I), in which X is N$R^z$.

According to one embodiment, specifically provided are compounds of formula (I), in which Y is —C$R^3 R^4$—.

According to one embodiment, specifically provided are compounds of formula (I), in which Y is —N$R^4$—.

According to one embodiment, specifically provided are compounds of formula (I), in which $R^3$ is hydrogen.

According to one embodiment, specifically provided are compounds of formula (I), in which $R^4$ is hydrogen.

According to one embodiment, specifically provided are compounds of formula (I), in which L is a bond.

According to one embodiment, specifically provided are compounds of formula (I), in which L is —(C$R^x R^y$)$_n$—.

According to one embodiment, specifically provided are compounds of formula (I), in which L is —C(O)—.

According to one embodiment, specifically provided are compounds of formula (I), in which $R^1$ is hydrogen.

According to a further embodiment, specifically provided are compounds of formula (I) wherein $R^2$ is selected from —C(O)O$R^a$, —C(O)N$R^a R^b$ and substituted or unsubstituted heterocyclyl ring selected from morpholinyl, oxazolinyl, oxazolidinyl, oxadiazolyl, thiazolinyl and thiazolidinyl. Where $R^2$ is substituted heterocyclyl ring, the substituents of $R^2$ may be one or more substituents independently selected from halogen, nitro, cyano, hydroxyl, substituted or unsubstituted alkyl and substituted or unsubstituted haloalkyl. In particular, $R^2$ may be substituted with 1, 2 or 3 substitutents independently selected from halogen, nitro, cyano, hydroxyl, $C_{1-4}$alkyl and halo$C_{1-4}$alkyl.

According to yet another embodiment, $R^a$ and $R^b$ which may be the same or different, are independently selected from hydrogen, substituted or unsubstituted alkyl, substituted or unsubstituted haloalkyl, substituted or unsubstituted haloalkoxy, substituted or unsubstituted alkoxyalkyl, substituted or unsubstituted hydroxyalkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, —(CH$_2$)$_p$N$R^x R^y$, and —(CH$_2$)$_p$CH$R^x R^y$; or $R^a$ and $R^b$ together with the atom to which they are attached, may form cyclic ring which is substituted or unsubstituted, and wherein the cyclic ring optionally contains one or more hetero atoms selected from O, N or S; and wherein, at each occurrence, $R^x$ and $R^y$, which may be the same or different, are independently selected from hydrogen, $C_{1-4}$ alkyl, substituted or unsubstituted aryl and substituted or unsubstituted arylalkyl. Where $R^a$ and/or $R^b$ are substituted, such as where $R^a$ is substituted aryl, the substituents of $R^a$ and/or $R^b$ may be one or more substituents independently selected from halogen, nitro, cyano, hydroxyl, alkyl and haloalkyl. Where $R^x$ and/or $R^y$ are substituted, such as where $R^x$ is substituted aryl, the substituents of $R^x$ and/or $R^y$ may be one or more substituents independently selected from halogen, nitro, cyano, hydroxyl, alkyl and haloalkyl.

According to yet another embodiment, specifically provided are compounds of formula (I), in which $R^5$ is hydrogen, methyl or cyclopropyl.

According to yet another embodiment, specifically provided are compounds of formula (I), in which $R^6$ is hydrogen, methyl or cyclopropyl.

According to yet another embodiment, specifically provided are compounds of formula (I), in which $R^5$ and $R^6$ are both methyl.

According to yet another embodiment, specifically provided are compounds of formula (I), in which $R^7$ is hydrogen.

According to yet another embodiment, specifically provided are compounds of formula (I), in which q is 0.

According to one embodiment, specifically provided are compounds of formula (I) with an IC$_{50}$ value of less than 500 nM, preferably, less than 100 nM, more preferably, less than 50 nM with respect to mPGES-1 activity.

Further embodiments relating to groups A, L, X, Y, m, p, q, $R^1$, $R^2$, $R^3$, $R^4$, $R^5$, $R^6$, $R^7$ and $R^8$ (and groups defined therein) are described hereinafter in relation to the compounds of formula (II), (III) and (IV). It is to be understood that these embodiments are not limited to use in conjunction with formula (II), (III) or (IV) but apply independently and individually to the compounds of formula (I). For example, in an embodiment described hereinafter, the invention specifically provides compounds of formula (II) in which $R^2$ is —C(O)N$R^a R^b$, and consequently there is also provided a compound of formula (I) wherein $R^2$ is —C(O)N$R^a R^b$. In another embodiment described hereinafter, there are provided compounds of formula (III) in which one of $R^a$ and $R^b$ is hydrogen and the other is substituted or unsubstituted alkyl (e.g. n-pentyl, n-hexyl, 3,3-dimethyl-butan-2-yl, 2,4,4-trimethylpentan-2-yl, 2-methylbutan-2-yl or 3-methylbutyl), substituted or unsubstituted alkoxyalkyl (e.g. 3-methoxypropyl), substituted or unsubstituted haloalkyl (e.g. fluoroethyl, 2,2,2-trifluoroethyl, or 2,2,3,3,3-pentafluoropropyl), substituted or unsubstituted hydroxyalkyl (e.g. 2-hydroxypropyl or hydroxypropanyl), substituted or unsubstituted cycloalkyl (e.g. cyclohexyl, 3,3-dimethylcyclohexyl, 4,4-difluorocyclohexyl, 3,6,6-trimethylbicyclo[3.1.1]hept-2-yl or adamantyl) and substituted or unsubstituted cycloalkylalkyl (e.g. 1-cyclohexylethyl, cyclopropylmethyl, cyclopentylmethyl or cyclohexylmethyl), and consequently there is also provided a compound of formula (I) wherein one of $R^a$ and $R^b$ is hydrogen and the other is substituted or unsubstituted alkyl (e.g. n-pentyl, n-hexyl, 3,3-dimethyl-butan-2-yl, 2,4,4-trimethylpentan-2-yl, 2-methylbutan-2-yl or 3-methylbutyl), substituted or unsubstituted alkoxyalkyl (e.g. 3-methoxypropyl), substituted or unsubstituted haloalkyl (e.g. fluoroethyl, 2,2,2-trifluoroethyl, or 2,2,3,3,3-pentafluoropropyl), substituted or unsubstituted hydroxyalkyl (e.g. 2-hydroxypropyl or hydroxypropanyl), substituted or unsubstituted cycloalkyl (e.g. cyclohexyl, 3,3-dimethylcyclohexyl, 4,4-difluorocyclohexyl, 3,6,6-trimethylbicyclo[3.1.1]hept-2-yl or adamantyl) and substituted or unsubstituted cycloalkylalkyl (e.g. 1-cyclohexylethyl, cyclopropylmethyl, cyclopentylmethyl or cyclohexylmethyl).

The invention also provides a compound of formula (II), which is an embodiment of a compound of formula (I).

Accordingly the invention provides the compound of formula (II);

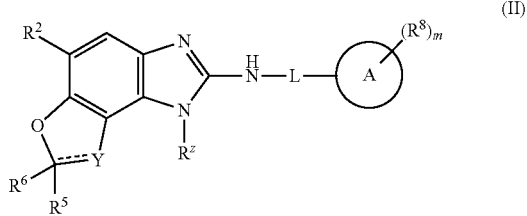

or a pharmaceutically acceptable salt thereof,
wherein,
A is phenyl or pyridinyl;
Y is selected from —$CR^3R^4$—, and —$NR^4$—;
L is a bond or is selected from —$CH_2$— and —$C(O)$—;
$R^2$ is selected from —$C(O)OR^a$, —$C(O)NR^aR^b$ and substituted or unsubstituted heterocyclyl ring selected from morpholinyl, oxazolinyl, oxazolidinyl, oxadiazolyl, thiazolinyl and thiazolidinyl;
$R^3$ and $R^4$, which may be same or different, are independently selected from hydrogen and $C_{1-4}$ alkyl;
$R^5$ and $R^6$, which may be same or different, are independently selected from hydrogen, $C_{1-4}$ alkyl and $C_{3-6}$ cycloalkyl;
at each occurrence $R^8$, which may be same or different, is independently selected from halogen, nitro, cyano, hydroxyl, substituted or unsubstituted alkyl and substituted or unsubstituted haloalkyl;
at each occurrence, $R^a$ and $R^b$ which may be the same or different, are independently selected from hydrogen, substituted or unsubstituted alkyl, substituted or unsubstituted haloalkyl, substituted or unsubstituted haloalkoxy, substituted or unsubstituted alkoxyalkyl, substituted or unsubstituted hydroxyalkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, —$(CH_2)_pNR^xR^y$, and —$(CH_2)_pCHR^xR^y$; or $R^a$ and $R^b$ together with the atom to which they are attached, may form cyclic ring which is substituted or unsubstituted, and wherein the cyclic ring optionally contains one or more hetero atoms selected from O, N or S;
at each occurrence, $R^x$ and $R^y$, which may be the same or different, are independently selected from hydrogen, $C_{1-4}$ alkyl, substituted or unsubstituted aryl and substituted or unsubstituted arylalkyl;
$R^z$ is selected from hydrogen, $C_{1-4}$ alkyl and substituted or unsubstituted alkoxyalkyl;
dotted line [—] inside the ring represents an optional bond;
with a proviso that when dotted line [—] inside the ring represents a bond then both $R^4$ and $R^5$ are absent;
'm' is an integer ranging from 0 to 5, both inclusive; and
'p' is an integer ranging from 0 to 6, both inclusive.

The compounds of formula (II) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (II) as defined above wherein Y is —$CR^3R^4$— (according to an embodiment defined below), $R^z$ is hydrogen (according to an embodiment defined below) and L is a bond (according to another embodiment defined below).

According to one embodiment, specifically provided are compounds of formula (II), in which Y is —$CR^3R^4$—.

According to another embodiment, specifically provided are compounds of formula (II), in which Y is —$NR^4$—.

According to yet another embodiment, specifically provided are compounds of formula (II), in which Y is —$CH_2$—.

According to yet another embodiment, specifically provided are compounds of formula (II), in which Y is —N— or —CH— and the line [—] inside the ring represents a bond.

According to yet another embodiment specifically provided are compounds of formula (II), in which $R^3$ or $R^4$ is hydrogen.

According to yet another embodiment specifically provided are compounds of formula (II), in which $R^5$ and $R^6$ both are methyl.

According to yet another embodiment, specifically provided are compounds of formula (II), in which $R^4$ and $R^5$ are absent and dotted line [—] inside the ring represents bond.

According to yet another embodiment, specifically provided are compounds of formula (II), in which $R^3$ is hydrogen or methyl.

According to yet another embodiment, specifically provided are compounds of formula (II), in which $R^6$ is hydrogen or methyl or cyclopropyl.

According to yet another embodiment, specifically provided are compounds of formula (II), in which $R^z$ is hydrogen.

According to yet another embodiment, specifically provided are compounds of formula (II), in which $R^z$ is methyl or methoxyethyl.

According to yet another embodiment, specifically provided are compounds of formula (II), in which L is a bond.

According to yet another embodiment, specifically provided are compounds of formula (II), in which L is $CH_2$ or CO.

According to yet another embodiment, specifically provided are compounds of formula (II), in which A is phenyl.

According to yet another embodiment, specifically provided are compounds of formula (II), in which A is pyridinyl, preferably pyridin-4-yl or pyridin-3-yl.

According to yet another embodiment, specifically provided are compounds of formula (II), in which $R^8$ is independently selected from halogen (e.g. F, Cl, Br or I), $C_{1-4}$alkyl (e.g methyl or tert-butyl) and unsubstituted haloalkyl (e.g. trifluoromethyl) and m is 1 or 2.

According to yet another embodiment, specifically provided are compounds of formula (II), in which $R^8$ is independently selected from Cl, F, methyl, tert-butyl and —$CF_3$.

According to yet another embodiment, specifically provided are compounds of formula (II), in which $R^2$ is substituted or unsubstituted oxadiazolyl, preferably substituted oxadiazolyl. In this embodiment, substituent(s) on oxadiazolyl is $C_{1-4}$ alkyl (e.g. isopropyl) or substituted or unsubstituted phenyl, more preferably substituted phenyl, wherein the substituent(s) on phenyl may be one or more and are independently selected from halogen (e.g. F, Cl), $C_{1-4}$ alkyl (e.g. methyl) and alkoxy (e.g. methoxy).

According to yet another embodiment, specifically provided are compounds of formula (II), in which $R^2$ is —C(O)$NR^aR^b$. In this embodiment, $R^a$ is $C_{1-6}$ alkyl (e.g. methyl or ethyl) or substituted or unsubstituted arylalkyl (e.g. benzyl).

According to yet another embodiment, specifically provided are compounds of formula (II), in which $R^2$ is —C(O)$NR^aR^b$. In this embodiment, one of the $R^a$ and $R^b$ is hydrogen and other is substituted or unsubstituted alkyl, substituted or unsubstituted alkoxyalkyl, substituted or unsubstituted haloalkyl, substituted or unsubstituted hydroxyalkyl, substituted or unsubstituted cycloalkyl, substituted or unsubstituted cycloalkylalkyl, substituted or unsubstituted heteroaryl, substituted or unsubstituted heterocyclyl, substituted or unsubstituted heterocyclylalkyl, substituted or unsubstituted aryl, substituted or unsubstituted arylalkyl or —$(CH_2)_pNR^xR^y$.

According to yet another embodiment, specifically provided are compounds of formula (II), in which $R^2$ is —C(O)$NR^aR^b$. In this embodiment, one of $R^a$ and $R^b$ is hydrogen and other is substituted or unsubstituted alkyl (e.g. n-pentyl, n-hexyl, 3,3-dimethyl-butan-2-yl, 2,4,4-trimethylpentan-2-yl, 2-methylbutan-2-yl or 3-methylbutyl), substituted or unsubstituted alkoxyalkyl (e.g. 3-methoxypropyl), substituted or unsubstituted haloalkyl (e.g. fluoroethyl, 2,2,2-trifluoroethyl or 2,2,3,3,3-pentafluoropropyl), substituted or unsubstituted hydroxyalkyl (e.g. 2-hydroxypropyl or hydroxypropanyl), substituted or unsubstituted cycloalkyl (e.g. cyclohexyl, 3,3-dimethylcyclohexyl, 4,4-difluorocyclohexyl, 3,6,6-trimethylbicyclo[3.1.1]hept-2-yl or adamantyl) and substituted or unsubstituted cycloalkylalkyl (e.g. 1-cyclohexylethyl, cyclopropylmethyl, cyclopentylmethyl or cyclohexylmethyl).

According to yet another embodiment, specifically provided are compounds of formula (II), in which $R^2$ is —C(O)$NR^aR^b$. In this embodiment, one of $R^a$ and $R^b$ is hydrogen and other is substituted cycloalkyl (e.g. cyclopropyl). In this embodiment, substituent(s) on cycloalkyl is substituted or unsubstituted aryl, preferably substituted aryl, more preferably substituted phenyl, wherein the substituent(s) on aryl or phenyl may be one or more and are independently selected from halogen (e.g. F), haloalkyl (e.g. trifluoromethyl) and alkyl (e.g. methyl).

According to yet another embodiment, specifically provided are compounds of formula (II), in which $R^2$ is —C(O)$NR^aR^b$. In this embodiment, one of $R^a$ and $R^b$ is hydrogen and other is —$(CH_2)_pNR^xR^y$, wherein both $R^x$ and $R^y$ are methyl and p is 2.

According to yet another embodiment, specifically provided are compounds of formula (II), in which $R^2$ is —C(O)$NR^aR^b$. In this embodiment, one of $R^a$ and $R^b$ is hydrogen and other is —$(CH_2)_pNR^xR^y$, wherein $R^x$ is hydrogen and $R^y$ is substituted or unsubstituted aryl (e.g. phenyl) and p is 0. In this embodiment, substituent(s) on aryl may be one or more and are independently selected from F, Cl, Br and I.

According to yet another embodiment, specifically provided are compounds of formula (II), in which $R^2$ is —C(O)$NR^aR^b$. In this embodiment, one of $R^a$ and $R^b$ is hydrogen and other is substituted or unsubstituted heteroaryl (e.g. thiadiazole, thiazole, pyridine or benzthiazole), substituted or unsubstituted heterocyclyl (e.g. pyrrolidine) or substituted or unsubstituted heterocyclylalkyl (e.g. morphonylethyl). In this embodiment, substituent(s) on heteroaryl or heterocyclic ring may be one or more and are independently selected from halogen (e.g. Cl, F, Br or I), alkyl (e.g. methyl, ethyl, or tert-butyl), alkoxy (e.g. methoxy or cyclopropylmethoxy), haloalkyl (e.g. trifluoromethyl), haloalkoxy (e.g. difluoromethoxy) and heterocyclyl (e.g. pyrrolidinyl).

According to yet another embodiment, specifically provided are compounds of formula (II), in which $R^2$ is —C(O)$NR^aR^b$. In this embodiment, one of $R^a$ and $R^b$ is hydrogen and other is substituted or unsubstituted aryl (e.g. phenyl) or substituted or unsubstituted arylalkyl (e.g. benzyl or phenylethyl). In this embodiment, substituent(s) on aryl or arylalkyl may be one or more and are independently selected from halogen (e.g. F, Cl, Br or I), cyano, alkyl (e.g. methyl, tert-butyl or 4-propan-2-yl), haloalkyl (e.g. trifluoromethyl or 1,1-difluoroethyl) and cycloalkyl (e.g. cyclopropyl).

According to yet another embodiment, specifically provided are compounds of formula (II), in which $R^2$ is —C(O)$NR^aR^b$. In this embodiment, one of $R^a$ and $R^b$ is hydrogen and other is substituted or unsubstituted aryl (e.g. phenyl). In this embodiment, substituent(s) on aryl is substituted alkyl (e.g. 2-cyanopropan-2-yl).

According to yet another embodiment, specifically provided are compounds of formula (II), in which $R^2$ is —C(O)$NR^aR^b$. In this embodiment, $R^a$ and $R^b$ together with the atom to which they are attached, form a cyclic ring, preferably heterocyclic ring (e.g. morpholinyl).

The invention also provides a compound of formula (III) which is an embodiment of a compound of formula (I).

Accordingly the invention provides the compound of formula (III):

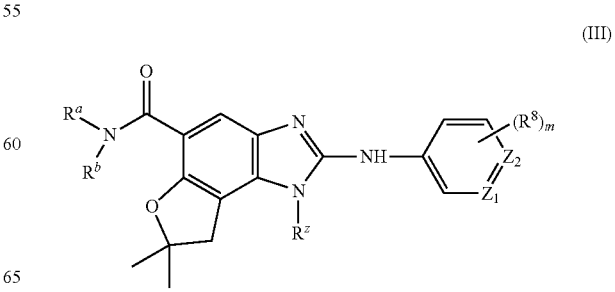

or a pharmaceutically acceptable salt thereof,
wherein, $Z_1$ and $Z_2$ are independently selected from —N— and —CH—; with the proviso that $Z_1$ and $Z_2$ simultaneously are not N;

at each occurrence $R^8$, which may be same or different, is independently selected from halogen, nitro, cyano, hydroxyl, substituted or unsubstituted alkyl and substituted or unsubstituted haloalkyl;

at each occurrence, $R^a$, and $R^b$ which may be the same or different, are independently selected from hydrogen, substituted or unsubstituted alkyl, substituted or unsubstituted haloalkyl, substituted or unsubstituted haloalkoxy, substituted or unsubstituted alkoxyalkyl, substituted or unsubstituted hydroxyalkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, —$(CH_2)_pNR^xR^y$, and —$(CH_2)_pCHR^xR^y$; or $R^a$ and $R^b$ together with the atom to which they are attached, may form cyclic ring; substituted or unsubstituted; the cyclic ring may optionally contain one or more hetero atoms selected from O, N or S;

at each occurrence, $R^x$ and $R^y$, which may be the same or different, are independently selected from hydrogen, $C_{1-4}$ alkyl, substituted or unsubstituted aryl and substituted or unsubstituted arylalkyl;

$R^z$ is selected from hydrogen, $C_{1-4}$ alkyl, and substituted or unsubstituted alkoxyalkyl;

'm' is an integer ranging from 0 to 5, both inclusive; and

'p' is an integer ranging from 0 to 6, both inclusive.

The compounds of formula (III) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (III) as defined above wherein both $Z_1$ and $Z_2$ are —CH— (according to an embodiment defined below) and $R^z$ is hydrogen (according to another embodiment defined below).

According to one embodiment, specifically provided are compounds of formula (III), in which both $Z_1$ and $Z_2$ are —CH—.

According to another embodiment, specifically provided are compounds of formula (III), in which $Z_1$ is —N— and $Z_2$ is —CH—.

According to yet another embodiment, specifically provided are compounds of formula (III), in which $Z_1$ is —CH— and $Z_2$ is —N—.

According to yet another embodiment, specifically provided are compounds of formula (III), in which $R^z$ is hydrogen.

According to yet another embodiment, specifically provided are compounds of formula (III), in which $R^z$ is methyl or methoxyethyl.

According to yet another embodiment, specifically provided are compounds of formula (III), in which $R^8$ is independently selected from halogen (e.g. F, Cl, Br or I), $C_{1-4}$ alkyl (e.g methyl or tert-butyl) and unsubstituted haloalkyl (e.g. trifluoromethyl) and m is 1 or 2.

According to yet another embodiment, specifically provided are compounds of formula (III), in which formula (III) has one $R^8$ substituent which is located at 2-position of the phenyl group.

According to yet another embodiment, specifically provided are compounds of formula (III), in which formula (III) has two $R^8$ substituents which are located at the 2- and 6-positions or 2- and 4-positions or 2- and 5-positions of the phenyl group.

According to yet another embodiment, specifically provided are compounds of formula (III), in which $R^8$ is independently selected from Cl, F, methyl, tert-butyl and —$CF_3$.

According to yet another embodiment, specifically provided are compounds of formula (III), in which one of $R^a$ and $R^b$ is hydrogen and other is substituted or unsubstituted alkyl (e.g. n-pentyl, n-hexyl, 3,3-dimethyl-butan-2-yl, 2,4,4-trimethylpentan-2-yl, 2-methylbutan-2-yl or 3-methylbutyl), substituted or unsubstituted alkoxyalkyl (e.g. 3-methoxypropyl), substituted or unsubstituted haloalkyl (e.g. fluoroethyl, 2,2,2-trifluoroethyl, or 2,2,3,3,3-pentafluoropropyl), substituted or unsubstituted hydroxyalkyl (e.g. 2-hydroxypropyl or hydroxypropanyl), substituted or unsubstituted cycloalkyl (e.g. cyclohexyl, 3,3-dimethylcyclohexyl, 4,4-difluorocyclohexyl, 3,6,6-trimethylbicyclo[3.1.1]hept-2-yl or adamantyl) and substituted or unsubstituted cycloalkylalkyl (e.g. 1-cyclohexylethyl, cyclopropylmethyl, cyclopentylmethyl or cyclohexylmethyl).

According to yet another embodiment, specifically provided are compounds of formula (III), in which one of $R^a$ and $R^b$ is hydrogen and other is substituted cycloalkyl (e.g. cyclopropyl). In this embodiment, substituent(s) on cycloalkyl is substituted or unsubstituted aryl, preferably substituted aryl, more preferably substituted phenyl, wherein the substituent(s) on aryl or phenyl may be one or more and are independently selected from halogen (e.g. F), haloalkyl (e.g. trifluoromethyl) and $C_{1-6}$ alkyl (e.g. methyl).

According to yet another embodiment, specifically provided are compounds of formula (III), in which one of $R^a$ and $R^b$ is hydrogen and other is —$(CH_2)_pNR^xR^y$, wherein $R^x$ and $R^y$ are methyl and p is 2.

According to yet another embodiment, specifically provided are compounds of formula (III), in which one of $R^a$ and $R^b$ is hydrogen and other is —$(CH_2)_pNR^xR^y$, wherein $R^x$ is hydrogen and $R^y$ substituted or unsubstituted aryl, preferably substituted or unsubstituted phenyl and p is 0. In this embodiment, substituent(s) on phenyl may be one or more are independently selected from F, Cl, Br and I.

According to yet another embodiment, specifically provided are compounds of formula (III), in which one of $R^a$ and $R^b$ is hydrogen and other is substituted or unsubstituted heteroaryl (e.g. thiadiazole, thiazole, pyridine or benzthiazole), substituted or unsubstituted heterocyclyl (e.g. pyrrolidine) or substituted or unsubstituted heterocyclylalkyl (e.g. morpholnylethyl). In this embodiment, substituent(s) on heteroaryl or heterocyclic ring may be one or more and are independently selected from halogen (e.g. Cl, F, Br or I), alkyl (e.g. methyl, ethyl, or tert-butyl), alkoxy (e.g. methoxy or cyclopropylmethoxy), haloalkyl (e.g. trifluoromethyl), haloalkoxy (e.g. difluoromethoxy) and heterocyclyl (e.g. pyrrolidinyl).

According to yet another embodiment, specifically provided are compounds of formula (III), in which one of $R^a$ and $R^b$ is hydrogen and other is substituted or unsubstituted aryl (e.g. phenyl) or substituted or unsubstituted arylalkyl (e.g. benzyl or phenylethyl). In this embodiment, substituent(s) on aryl or arylalkyl may be one or more and are independently selected from halogen (e.g. F, Cl, Br or I), cyano, alkyl (e.g.

methyl, tert-butyl or 4-propan-2-yl), haloalkyl (e.g. trifluoromethyl or 1,1-difluoroethyl) and cycloalkyl (e.g. cyclopropyl).

According to yet another embodiment, specifically provided are compounds of formula (III), in which one of $R^a$ and $R^b$ is hydrogen and other is substituted or unsubstituted phenyl or pyridine. In this embodiment, substituent(s) on phenyl or pyridine may be one or more and are independently selected from halogen (e.g. F, Cl, Br or I), cyano, alkyl (e.g. methyl, tert-butyl or 4-propan-2-yl), haloalkyl (e.g. trifluoromethyl or 1,1-difluoroethyl), haloalkoxy (e.g. difluoromethoxy), and cycloalkyl (e.g. cyclopropyl).

According to yet another embodiment, specifically provided are compounds of formula (III), in which $R^a$ and $R^b$ together with the atom to which they are attached, form a cyclic ring, preferably heterocyclic ring, more preferably morpholinyl ring.

The invention also provides a compound of formula (IV) which is an embodiment of a compound of formula (I).

Accordingly the invention provides the compound of formula (IV);

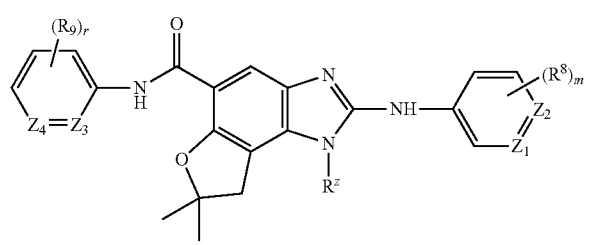

(IV)

or a pharmaceutically acceptable salt thereof,
wherein, $Z_1$ and $Z_2$ are independently selected from —N— or —CH—; with the proviso that $Z_1$ and $Z_2$ simultaneously are not N;

$Z_3$ and $Z_4$ are independently selected from —N— or —CH—; with the proviso that $Z_3$ and $Z_4$ simultaneously are not N;

at each occurrence $R^8$, which may be same or different, is independently selected from halogen, nitro, cyano, hydroxyl, substituted or unsubstituted alkyl and substituted or unsubstituted haloalkyl;

at each occurrence $R^9$, which may be same or different, is independently selected from halogen, nitro, cyano, hydroxyl, $C_{1-6}$ alkyl, $C_{3-6}$ cycloalkyl, substituted or unsubstituted alkoxy, substituted or unsubstituted alkoxyalkyl, substituted or unsubstituted haloalkyl, substituted or unsubstituted haloalkoxy, substituted or unsubstituted aryl, substituted or unsubstituted 5 to 7 membered heterocyclyl, substituted or unsubstituted 5 to 7 membered heterocyclylalkyl and substituted or unsubstituted heteroaryl;

$R^z$ is selected from hydrogen, $C_{1-4}$ alkyl and substituted or unsubstituted alkoxyalkyl;

'm' is an integer ranging from 0 to 5, both inclusive; and
'r' is an integer ranging from 0 to 5, both inclusive;

The compounds of formula (IV) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (IV) as defined above wherein $Z_1$, $Z_2$, $Z_3$ and $Z_4$ are —CH— (according to an embodiment defined below) and $R^z$ is hydrogen (according to an embodiment defined below).

According to one embodiment, specifically provided are compounds of formula (IV), in which $Z_1$, $Z_2$, $Z_3$ and $Z_4$ are —CH—.

According to another embodiment, specifically provided are compounds of formula (IV), in which $Z_1$ is —N— and $Z_2$ is —CH—.

According to yet another embodiment, specifically provided are compounds of formula (IV), in which $Z_1$ is —CH— and $Z_2$ is —N—.

According to another embodiment, specifically provided are compounds of formula (IV), in which $Z_3$ is —N— and $Z_4$ is —CH—.

According to yet another embodiment, specifically provided are compounds of formula (IV), in which $Z_3$ is —CH— and $Z_4$ is —N—.

According to yet another embodiment, specifically provided are compounds of formula (IV), in which $R^z$ is hydrogen.

According to yet another embodiment, specifically provided are compounds of formula (IV), in which $R^z$ is methyl or methoxyethyl.

According to yet another embodiment, specifically provided are compounds of formula (IV), in which $R^8$ is independently selected from halogen (e.g. F, Cl, Br or I), $C_{1-4}$ alkyl (e.g methyl or tert-butyl) and unsubstituted haloalkyl (e.g. trifluoromethyl) and m is 1 or 2.

According to yet another embodiment, specifically provided are compounds of formula (IV), in which formula (IV) has one $R^8$ substituents which is located at 2-position of the phenyl group.

According to yet another embodiment, specifically provided are compounds of formula (IV), in which formula (IV) has two $R^8$ substituents which are located at the 2- and 6-positions or 2- and 4-positions or 2- and 5-positions of the phenyl group.

According to yet another embodiment, specifically provided are compounds of formula (IV), in which $R^8$ is independently selected from Cl, F, methyl, tert-butyl and —$CF_3$.

According to yet another embodiment, specifically provided are compounds of formula (IV), in which $R^9$ is independently selected from halogen (e.g. F, Cl, Br or I), cyano, $C_{1-6}$ alkyl (e.g. methyl, ethyl, tert-butyl, 4-propan-2-yl), $C_{3-6}$ cycloalkyl (e.g. cyclopropyl), substituted or unsubstituted alkoxy (e.g. methoxy, cyclopropylmethoxy), substituted or unsubstituted haloalkyl (e.g. trifluoromethyl, 1,1-difluoroethyl), substituted or unsubstituted haloalkoxy (e.g. difluoromethoxy) and 5 membered heterocyclyl (e.g. pyrrolidinyl) and r is 1, 2 or 3.

According to yet another embodiment, specifically provided are compounds of formula (IV), in which $R^9$ is independently selected from F, Cl, Br, $CF_3$, $OCH_3$, CN, $CH_3$, $OCHF_2$, propan-2-yl, tert-butyl, pyrrolidinyl, 1,1-difluoroethyl, cyclopropyl, and cyclopropylmethoxy.

According to yet another embodiment, specifically provided are compounds of formula (IV), in which r is 1, 2 or 3.

It should be understood that the formulas (I), (II), (III) and (IV) structurally encompasses all geometrical isomers, stereoisomers, enantiomers and diastereomers, N-oxides, and pharmaceutically acceptable salts that may be contemplated from the chemical structure of the genera described herein.

The present invention also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present patent application may be associated with a pharmaceutically acceptable excipient (such as a carrier or a diluent) or be diluted by a carrier, or enclosed within a carrier which can be in the form of a capsule, sachet, paper or other container.

The compounds and pharmaceutical compositions of the present invention are useful for inhibiting the activity of mPGES-1, which is believed to be related to a variety of disease states.

The present patent application further provides a method of inhibiting mPGES-1 in a subject in need thereof by administering to the subject one or more compounds described herein in the amount effective to cause inhibition of such receptor.

DETAILED DESCRIPTION

Definitions

The invention is defined by the claims and not limited by the description provided herein below. The terms used in the appended claims are defined herein in this glossary section, with the proviso that the claim terms may be used in a different manner if so defined by express recitation.

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms. The term "$C_{1-4}$ alkyl" refers to an alkyl chain having 1 to 4 carbon atoms. Unless set forth or recited to the contrary, all alkyl groups described or claimed herein may be straight chain or branched, substituted or unsubstituted.

The term "alkenyl" refers to a hydrocarbon chain containing from 2 to 10 carbon atoms (i.e. $C_{2-10}$alkenyl) and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond, and having 2 to about 12 carbon atoms (with radicals having 2 to about 10 carbon atoms being preferred i.e. $C_{2-10}$alkynyl). Non-limiting examples of alkynyl groups include ethynyl, propynyl, and butynyl. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule (i.e. $C_{1-8}$ alkoxy). Representative examples of such groups are —OCH$_3$ and —OC$_2$H$_5$. Unless set forth or recited to the contrary, all alkoxy groups described or claimed herein may be straight chain or branched, substituted or unsubstituted.

The term "alkoxyalkyl" or "alkyloxyalkyl" refers to an alkoxy or alkyloxy group as defined above directly bonded to an alkyl group as defined above (i.e. $C_{1-8}$alkoxy$C_{1-8}$alkyl or $C_{1-8}$alkyloxy$C_{1-8}$alkyl). Example of such alkoxyalkyl moiety includes, but are not limited to, —CH$_2$OCH$_3$ and —CH$_2$OC$_2$H$_5$. Unless set forth or recited to the contrary, all alkoxyalkyl groups described herein may be straight chain or branched, substituted or unsubstituted.

The term "haloalkyl" refers to at least one halo group (selected from F, Cl, Br or I), linked to an alkyl group as defined above (i.e. halo$C_{1-8}$alkyl). Examples of such haloalkyl moiety include, but are not limited to, trifluoromethyl, difluoromethyl and fluoromethyl groups. Unless set forth or recited to the contrary, all haloalkyl groups described herein may be straight chain or branched, substituted or unsubstituted.

The term "haloalkoxy" refers to an alkoxy group substituted with one or more halogen atoms (i.e. halo$C_{1-8}$alkoxy). Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichloromethoxy, trichloromethoxy and 1-bromoethoxy. Unless set forth or recited to the contrary, all haloalkoxy groups described herein may be straight chain or branched, substituted or unsubstituted.

The term "hydroxyalkyl" refers to an alkyl group as defined above wherein one to three hydrogen atoms on different carbon atoms is/are replaced by hydroxyl groups (i.e. hydroxy$C_{1-8}$alkyl). Examples of hydroxyalkyl moiety include, but are not limited to —CH$_2$OH, —C$_2$H$_4$OH and —CH(OH)C$_2$H$_4$OH.

The term "cycloalkyl" denotes a non-aromatic mono or multicyclic ring system of 3 to about 12 carbon atoms, for example $C_{3-12}$cycloalkyl, such as cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or spirobicyclic groups, e.g., spiro(4,4)non-2-yl. The term "$C_{3-6}$ cycloalkyl" refers to the cyclic ring having 3 to 6 carbon atoms. Unless set forth or recited to the contrary, all cycloalkyl groups described or claimed herein may be substituted or unsubstituted.

The term "cycloalkylalkyl" refers to a cyclic ring-containing radical having 3 to about 8 carbon atoms directly attached to an alkyl group, for example $C_{3-8}$cycloalkyl$C_{1-8}$alkyl. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond, for example $C_{3-8}$ cycloalkenyl, such as cyclopropenyl, cyclobutenyl, and cyclopentenyl. Unless set forth or recited to the contrary, all cycloalkenyl groups described or claimed herein may be substituted or unsubstituted.

The term "cycloalkenylalkyl" refers to a cyclic ring-containing radical having 3 to about 8 carbon atoms with at least one carbon-carbon double bond, directly attached to an alkyl group, for example $C_{3-8}$cycloalkenyl$C_{1-8}$alkyl. The cycloalkenylalkyl group may be attached to the main structure at any carbon atom in the alkyl group that results in the creation of a stable structure. Unless set forth or recited to the contrary, all cycloalkenylalkyl groups described or claimed herein may be substituted or unsubstituted.

The term "aryl" refers to an aromatic radical having 6 to 14 carbon atoms (i.e. $C_{6-14}$aryl), including monocyclic, bicyclic and tricyclic aromatic systems, such as phenyl, naphthyl, tetrahydronapthyl, indanyl, and biphenyl. Unless set forth or recited to the contrary, all aryl groups described or claimed herein may be substituted or unsubstituted.

The term "aryloxy" refers to an aryl group as defined above attached via an oxygen linkage to the rest of the molecule (i.e. $C_{6-14}$aryloxy). Examples of aryloxy moiety include, but are not limited to phenoxy and naphthoxy. Unless set forth or recited to the contrary, all aryloxy groups described herein may be substituted or unsubstituted.

The term "arylalkyl" refers to an aryl group as defined above directly bonded to an alkyl group as defined above, i.e. $C_{6-14}$aryl$C_{1-8}$alkyl, such as —$CH_2C_6H_5$ and —$C_2H_4C_6H_5$. Unless set forth or recited to the contrary, all arylalkyl groups described or claimed herein may be substituted or unsubstituted.

The term "heterocyclic ring" or "heterocyclyl" unless otherwise specified refers to substituted or unsubstituted non-aromatic 3 to 15 membered ring radical which consists of carbon atoms and from one to five hetero atoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted.

The term "heterocyclylalkyl" refers to a heterocyclic ring radical directly bonded to an alkyl group (i.e. heterocyclyl$C_{1-8}$alkyl). The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroaryl" unless otherwise specified refers to substituted or unsubstituted 5 to 14 membered aromatic heterocyclic ring radical with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl. Unless set forth or recited to the contrary, all heteroaryl groups described or claimed herein may be substituted or unsubstituted.

The term "heteroarylalkyl" refers to a heteroaryl ring radical directly bonded to an alkyl group (i.e. heteroaryl$C_{1-8}$alkyl). The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted haloalkyl, substituted or unsubstituted hydroxyl alkyl, substituted or unsubstituted alkoxy, substituted or unsubstituted haloalkoxy, substituted or unsubstituted alkenyl, substituted or unsubstituted alkynyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted arylalkyl, substituted or unsubstituted heteroaryl, substituted or unsubstituted heteroarylalkyl, substituted or unsubstituted heterocyclylalkyl ring, substituted or unsubstituted heteroarylalkyl, substituted or unsubstituted heterocyclic ring, substituted or unsubstituted guanidine, —$COOR^{x'}$, —$C(O)R^{x'}$, —$C(S)R^{x'}$, —$C(O)NR^{x'}R^{y'}$, —$C(O)ONR^{x'}R^{y'}$, —$NR^{x'}CONR^{y'}R^{z'}$, —$N(R^{x'})SOR^{y'}$, —$N(R^{x'})SO_2R^{y'}$, —(=N—N($R^{x'}$)$R^{y'}$), —$NR^{x'}C(O)OR^{y'}$, —$NR^{x'}R^{y'}$, —$NR^{x'}C(O)R^{y'}$, —$NR^{x'}C(S)R^{y'}$, —$NR^{x'}C(S)NR^{y'}R^{z'}$, —$SONR^{x'}R^{y'}$, —$SO_2NR^{x'}R^{y'}$, —$OR^{y'}$, —$OC(O)NR^{y'}R^{z'}$, —$OC(O)OR^{y'}$, —$OC(O)R^{x'}$, —$OC(O)NR^{x'}R^{y'}$, —$SR^{x'}$, —$SOR^{x'}$, —$SO_2R^{x'}$, and —$ONO_2$, wherein $R^{x'}$, $R^{y'}$ and $R^{z'}$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, and substituted or unsubstituted heterocyclic ring. The substituents in the aforementioned "substituted" groups cannot be further substituted. For example, when the substituent on "substituted alkyl" is "substituted aryl", the substituent on "substituted aryl" can be unsubstituted alkenyl but cannot be "substituted alkenyl".

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The term "acute pain" is usually self-limiting. The sensation of pain can be triggered by any number of physical or chemical stimuli and the sensory neurons which mediate the response to this harmful stimulus are termed as "nociceptors". Nociceptors are primary sensory afferent (C and Aδ fibers) neurons that are activated by a wide variety of noxious stimuli including chemical, mechanical, thermal, and proton (pH<6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

The term "chronic pain" usually refers to pain which persists for 3 months or longer and can lead to significant changes in a patient's personality; lifestyle, functional ability and overall quality of life. Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant, and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

The compound described in the present patent application may form salts. Non-limiting examples of pharmaceutically acceptable salts forming part of this patent application include salts derived from inorganic bases salts of organic bases salts of chiral bases, salts of natural amino acids and salts of non-natural amino acids. Certain compounds of present patent application are capable of existing in stereoisomeric forms (e.g. diastereomers and enantiomers). With respect to the overall compounds described by the general formula (I) the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated. It is also to be understood that compounds of the invention may exist in solvated forms (such as hydrates) as well as unsolvated forms, and that the invention encompasses all such forms.

Pharmaceutical Compositions

The pharmaceutical composition of the present patent application includes at least one compound described herein and at least one pharmaceutically acceptable excipient (such as a pharmaceutically acceptable carrier or diluent). Preferably, the pharmaceutical composition comprises a therapeutically effective amount of at least one compound of the present invention. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavouring agents, colorants, or any combination of the foregoing. The pharmaceutical composition may be formulated so as to provide quick, sustained, or delayed release of the active ingredient after administration to the subject by employing procedures known in the art.

The pharmaceutical compositions may be prepared by techniques known in the art, e.g., as described in Remington: The Science and Practice of Pharmacy, $20^{th}$ Ed., 2003 (Lippincott Williams & Wilkins). For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application. The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Non-limiting examples of carriers for tablets, dragees, or capsules include lactose, cornstarch, and/or potato starch. A syrup or elixir can be used in cases where a sweetened vehicle can be employed. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

Compounds of the invention may also be combined with other therapeutic agents.

According to a further aspect of the invention, there is provided a combination product comprising: a compound of the invention, and another therapeutic agent, wherein each of components is formulated in admixture with a pharmaceutically-acceptable excipient.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Methods of Treatment

Compounds of the present invention are particularly useful because they may selectively inhibit the activity of prostaglandin E synthases {and particularly microsomal prostaglandin E synthase-1 (mPGES-1)}, i.e. they prevent the action of mPGES-1 or a complex of which the mPGES-1 enzyme forms a part, and/or may elicit mPGES-1 modulating effect. Compounds of the invention may thus be useful in the treatment of those conditions in which inhibition of a PGES, and particularly mPGES-1, is required.

Compounds of the invention are thus expected to be useful in the treatment of inflammation. The term "inflammation" will be understood by those skilled in the art to include any condition characterized by a localized or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white.

The term "inflammation" is also understood to include any inflammatory disease, disorder or condition per se, any condition that has an inflammatory component associated with it, and/or any condition characterized by inflammation as a symptom, including inter alia acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this invention, inflammatory pain, pain generally and/or fever.

The compounds of the present invention may also be useful in the treatment of asthma, chronic obstructive pulmonary disease, pulmonary fibrosis, inflammatory bowel disease, irritable bowel syndrome, inflammatory pain, chronic pain, acute pain, fever, migraine, headache, low back pain, fibromyalgia, myofascial disorders, viral infections (e.g. influenza, common cold, herpes zoster, hepatitis C and AIDS), bacterial infections, fungal infections, dysmenorrhea, burns, surgical or dental procedures, malignancies (e.g. breast cancer, colon cancer, and prostate cancer), hyperprostaglandin E syndrome, classic Bartter syndrome, atherosclerosis, gout, arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, neurodegenerative disorders such as Alzheimer's disease and multiple sclerosis, autoimmune diseases, allergic disorders, rhinitis, ulcers, mild to moderately active ulcerative colitis, familial adenomatous polyposis, coronary heart disease, sarcoidosis and any other disease with an inflammatory component.

Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases.

By virtue of the mPGES-1 inhibitory activity of compounds of the present invention, the compounds of Formula I are useful for the relief of pain, fever and inflammation of a variety of conditions including rheumatic fever, symptoms associated with influenza or other viral infections, common cold, low back and neck pain, dysmenorrhea, headache, migraine (acute and prophylactic treatment), toothache, sprains and strains, myositis, neuralgia, synovitis, arthritis, including rheumatoid arthritis, juvenile rheumatoid arthritis, degenerative joint diseases (osteoarthritis), acute gout and ankylosing spondylitis, acute, subacute and chronic musculoskeletal pain syndromes such as bursitis, burns, injuries, and pain following surgical and dental procedures as well as the preemptive treatment of surgical pain. In addition, such a compound may inhibit cellular neoplastic transformations and metastic tumor growth and hence can be used in the treatment of cancer. Compounds of Formula I may also be useful for the treatment or prevention of endometriosis, hemophilic arthropathy and Parkinson's disease.

Compounds of Formula I will also inhibit prostanoid-induced smooth muscle contraction by preventing the synthesis of contractile prostanoids and hence may be of use in the treatment of dysmenorrhea, premature labor and asthma.

In addition, the compound of the present invention may inhibit cellular neoplastic transformations and metastic tumor growth and hence can be used in the treatment of cancer.

Compounds of the invention are indicated both in the therapeutic and/or prophylactic treatment of the above-mentioned conditions. For the above-mentioned therapeutic uses the dosage administered will, of course, vary with the compound employed, the mode of administration, the treatment desired and the disorder indicated. The daily dosage of the compound of the invention may be in the range from 0.05 mg/kg to 100 mg/kg.

General Methods of Preparation

The compounds described herein, including compounds of general formula (I), (II), (III) and (IV) and specific examples are prepared using techniques known to one skilled in the art through the reaction sequences depicted in scheme 1-9 as well as by other methods. Furthermore, in the following schemes, where specific acids, bases, reagents, coupling agents, solvents, etc. are mentioned, it is understood that other suitable acids, bases, reagents, coupling agents etc. may be used and are included within the scope of the present invention. Modifications to reaction conditions, for example, temperature, duration of the reaction or combinations thereof, are envisioned as part of the present invention. The compounds obtained using the general reaction sequences may be of insufficient purity. These compounds can be purified using any of the methods for purification of organic compounds known to persons skilled in the art, for example, crystallization or silica gel or alumina column chromatography using different solvents in suitable ratios. All possible geometrical isomers and stereoisomers are envisioned within the scope of this invention.

The starting materials for the below reaction schemes are commercially available or can be prepared according to methods known to one skilled in the art or by methods disclosed herein. In general, intermediates and compounds of the present invention may be prepared through the reaction scheme as follows, wherein R' is either methyl or ethyl and all other symbols are as defined above.

A general approach for the preparation of compound of formula (Ia) is depicted in the scheme 1 (wherein $R^1$, $R^a$, $R^b$, $R^3$, $R^4$, $R^5$, $R^7$, $R^8$, $R^z$, L, A and m are as defined in compound of formula (I); R' is alkyl and $R^6$ is methyl).

Scheme 1:

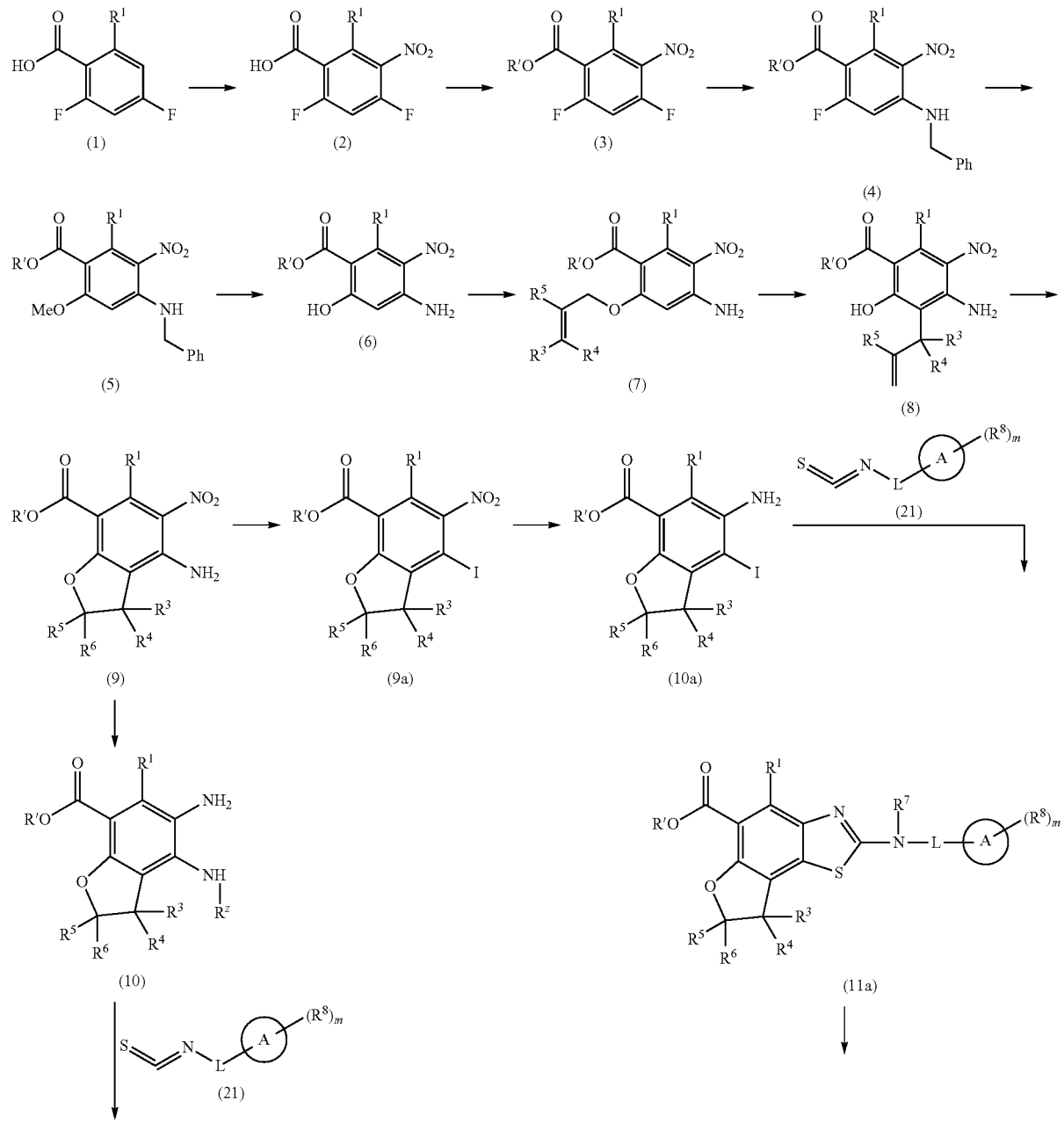

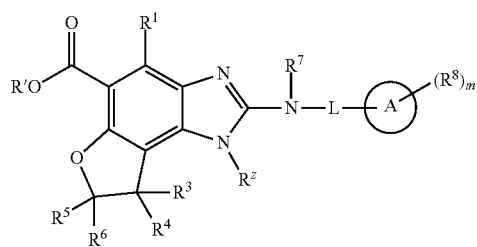

(11)

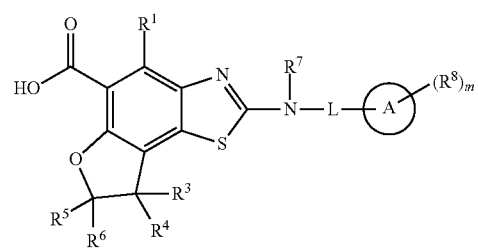

(12a)

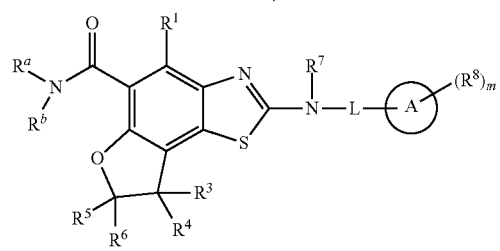

(IIa)

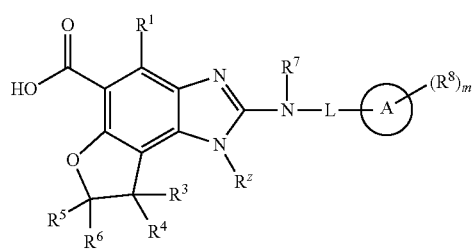

(12)

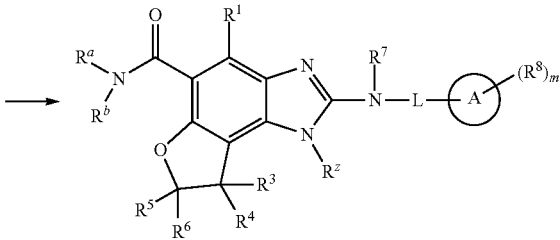

(Ia)

A compound of formula (1) may be converted to a compound of formula (2) by following nitration procedure known to those skilled in the art of organic synthesis, for example, using fuming nitric acid in the presence of an acid such as sulphuric acid. The compound of formula (2) can be converted to a compound of formula (3) under esterification condition using an acid catalyst such as sulphuric acid or hydrochloric acid or the like in a suitable solvent such as alcohol at suitable temperature, for example the temperature range may be of 60-100° C. The compound of formula (3) can be converted to a compound of formula (4) by reacting with an amine in the presence of a base such as triethylamine, diisopropylethylamine or the like in a suitable solvent such as THF, DMF or DMSO at a suitable temperature which may be in the range of 0-100° C. The compound of formula (4) can be converted to a compound of formula (5) by reacting with an alkoxide in an alcoholic solvent at a temperature range of 0-100° C. The compound of formula (5) can be converted to a compound of formula (6) by reacting with Lewis acid such as aluminium chloride or boron trifluoride or the like in a suitable solvent such as dichloromethane or dichloroethane or the like at a temperature range of 60-100° C. The compound of formula (6) can be converted to a compound of formula (7) by reacting with an appropriately substituted alkenyl halide in presence of a base such as potassium carbonate, triethylamine or the like in a suitable solvent such as DMF, dimethoxyethane, THF or dioxane at a temperature range of 60-100° C. The compound of formula (7) can be converted to a compound of formula (8) under Claisen rearrangement conditions in presence of a solvent such as N,N'-diethylaniline at a temperature range of 60-220° C. A compound of formula (8) can be converted to a compound of formula (9) under cyclization conditions in presence of a solvent such as formic acid at a temperature range of 60-100° C. The compound of formula (9) can be converted to a compound of formula (10) by optionally reacting with $R^z$—X' (wherein $R^z$ is not hydrogen and X' is a good leaving group such as Cl, Br or I under appropriate conditions), and/or by reduction under reductive conditions using a metal such as tin, iron or the like in presence of a catalyst such as hydrochloric acid in an alcoholic solvent at a temperature range of 20-100° C. Alternatively, the compound of formula (9) can also be converted to a compound of formula (10) by reacting with $R^z$—X' (wherein $R^z$ is not hydrogen and X' is good leaving group such as Cl, Br or I under appropriate conditions), followed by reduction under reductive conditions using hydrogen gas in a suitable solvent such as methanol, ethanol, ethyl acetate or the like at a temperature range of 20-100° C. The compound of formula (10) can be converted to a compound of formula (11) by first reacting with an isothiocyanate derivative of formula (21) under appropriate conditions followed by cyclization using a reagent such as diisopropylcarbodiimide, then optionally reacting with $R^7$—X' (wherein $R^7$ is not hydrogen and X' is good leaving group such as Cl, Br or I) under appropriate conditions. The compound of formula (11) can be converted to a compound of formula (12) under hydrolysis conditions in presence of a base such as sodium hydroxide, potassium carbonate, lithium hydroxide or the like in an alcoholic solvent in presence of water at a temperature range of 20-100° C. The compound of formula (12) can be converted to a compound of formula (Ia) under amidation conditions using an appropriate amine in presence of a coupling reagent such as TBTU, HATU, EDCI, BOP or the like in presence of a base such as triethylamine, diisopropylethylamine, N-methyl morpholine or the like in a suitable solvent such as DMF, THF or the like at an appropriate temperature range such as 20-100° C.

Compound of formula (9) can also be converted to a compound of formula (9a) under Sandmeyer Reaction conditions at a temperature range of 0-100° C. The compound of formula (9a) may be further converted to a compound of formula (IIa) via the intermediates (11a and 12a).

In another approach, the compound of formula (Ia) can be prepared following the synthetic steps depicted in scheme 2 (wherein $R^1$, $R^a$, $R^b$, $R^3$, $R^4$, $R^5$, $R^7$, $R^8$, $R^z$, L, A and m are as defined above in compound of formula (I); R' is alkyl and $R^6$ is methyl).

Scheme 2:

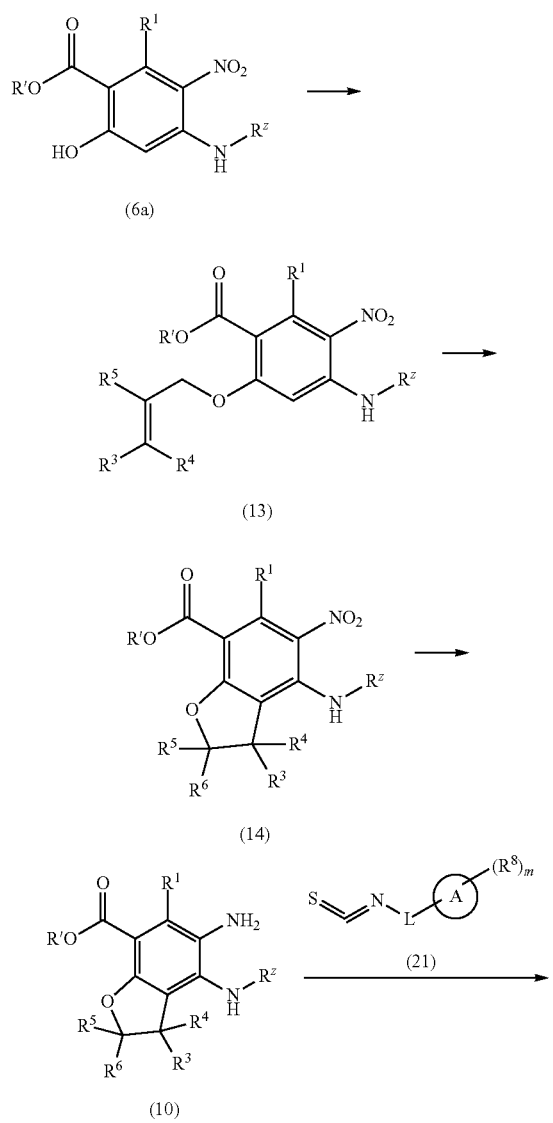

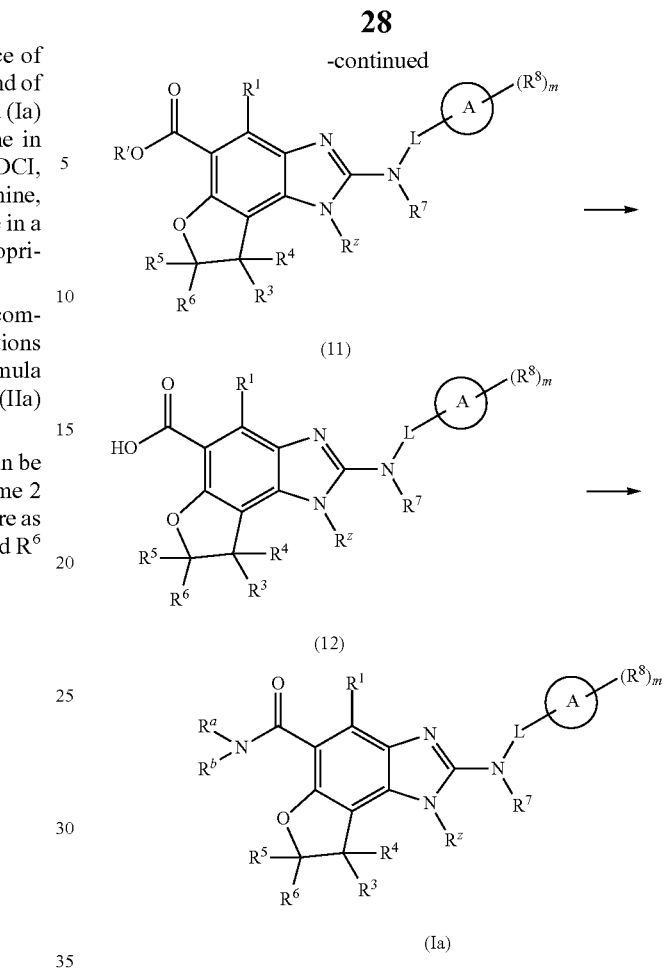

A compound of formula (6a) can be converted to a compound of formula (13) by reacting with an appropriately substituted alkenyl halide in the presence of a base such as potassium carbonate, triethylamine or the like in a suitable solvent such as DMF, dimethoxyethane, THF or dioxane at a temperature range of 60-100° C. The compound of formula (13) can be converted to a compound of formula (14) under Claisen rearrangement conditions in presence of a solvent such as N,N'-diethylaniline at a temperature range of 60-220° C. followed by cyclization in presence of a solvent such as formic acid at a temperature range of 60-100° C. The compound of formula (14) can be converted to a compound of formula (10) under reductive conditions using a metal such as tin, iron or the like in presence of a catalyst such as hydrochloric acid in an alcoholic solvent at a temperature range of 20-100° C. Alternatively, the compound of formula (14) can also be converted to a compound of formula (10) under hydrogenation conditions. The compound of formula (10) can be converted to a compound of formula (11) by reacting with an isothiocyanate derivative of formula (21) under appropriate conditions followed by cyclization using a reagent such as diisopropylcarbodiimide, then optionally reacting with $R^7$—X' (wherein $R^7$ is not hydrogen and X' is good leaving group such as Cl, Br or I) under appropriate conditions. The compound of formula (11) can be converted to a compound of formula (12) under hydrolysis conditions in presence of a base such as sodium hydroxide, potassium carbonate, lithium hydroxide or the like in a suitable solvent such as alcoholic solvent, optionally in the presence of water at a temperature range of 20-100° C. The compound of formula (12) can be converted to a compound of formula (Ia) under amidation conditions using an appropriate amine in presence of coupling reagent such as TBTU, HATU, EDCI, BOP or the like in presence of a base such as triethylamine, diisopropylethylamine, N-methyl morpholine or the like in a suitable solvent such as DMF, THF or the like at a temperature range of 20-100° C.

An approach for the preparation of compound of formula (Ib) is schematically represented in scheme 3 (wherein $R^1$, $R^a$, $R^b$, $R^3$, $R^6$, $R^7$, $R^8$, $R^z$, L, A and m are as defined above in compound of formula (I) and R' is alkyl).

Scheme 3:

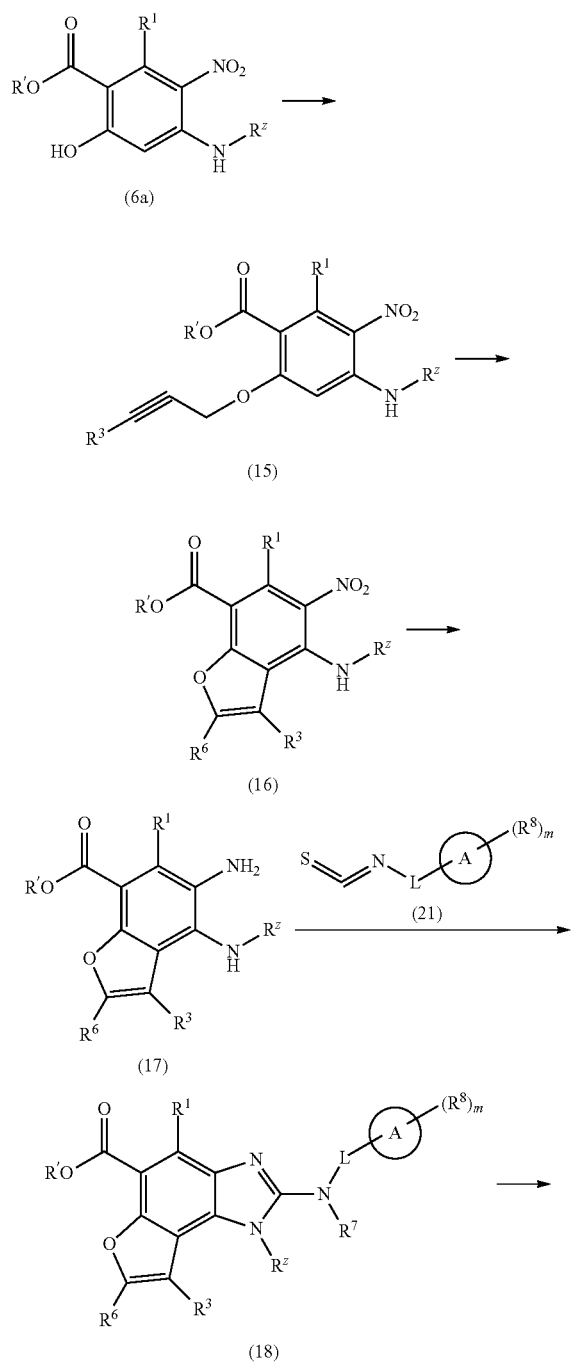

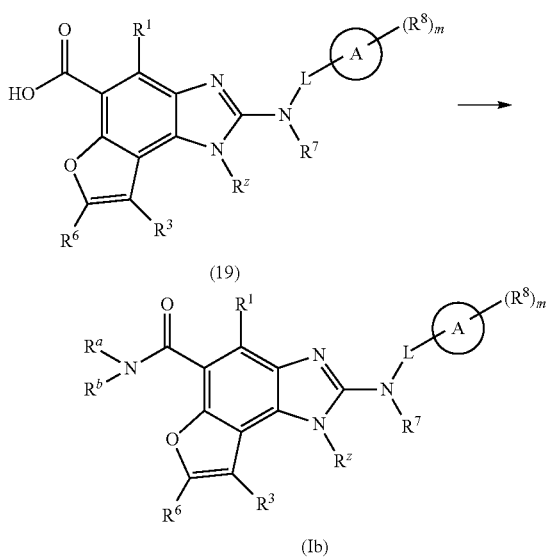

The compound of formula (6a) can be converted to a compound of formula (15) by reacting with an appropriately substituted alkynylhalide in presence of a base such as potassium carbonate, triethylamine or the like in a suitable solvent such as DMF, dimethoxyethane, THF or dioxane at a temperature range of 60-100° C. The compound of formula (15) can be converted to a compound of formula (16) under Claisen rearrangement conditions using a base such as cesiumfluoride or the like in presence of a solvent such as N,N'-diethylaniline at a temperature range of 60-220° C. The compound of formula (16) can be converted to a compound of formula (17) under reductive conditions using a metal such as tin, iron or the like in presence of a catalyst such as hydrochloric acid in an alcoholic solvent at a temperature range of 20-100° C. Alternatively the compound of formula (16) can also be converted to a compound of formula (17) under hydrogenation conditions. The compound of formula (17) can be converted to a compound of formula (18) by reacting with an isothiocyanate derivative of formula (21) under appropriate conditions followed by cyclization in presence of a reagent such as diisopropylcarbodiimide at a temperature range of 20-100° C., then optionally reacting with $R^7$—X' (wherein $R^7$ is not hydrogen and X' is good leaving group such as Cl, Br or I) under appropriate conditions. The compound of formula (18) can be converted to a compound of formula (19) under hydrolysis conditions in presence of a base such as sodium hydroxide, potassium carbonate, lithium hydroxide or the like in a suitable solvent such as alcoholic solvent, optionally in the presence of water at a temperature range of 20-100° C. The compound of formula (19) can be converted to a compound of formula (Ib) under amidation conditions using an appropriate amine in presence of coupling reagent such as TBTU, HATU, EDCI, BOP or the like in presence of a base such as triethylamine, diisopropylethylamine, N-methyl morpholine or the like in a suitable solvent such as DMF, THF or the like at a temperature range of 20-100° C.

An approach for the preparation of compound of formula (Ib') is schematically represented in scheme 4 (wherein $R^1$, $R^a$, $R^b$, $R^3$, $R^6$, $R^8$, A, L and m are as defined above in compound of formula (I) and R' is alkyl).

Scheme 4:

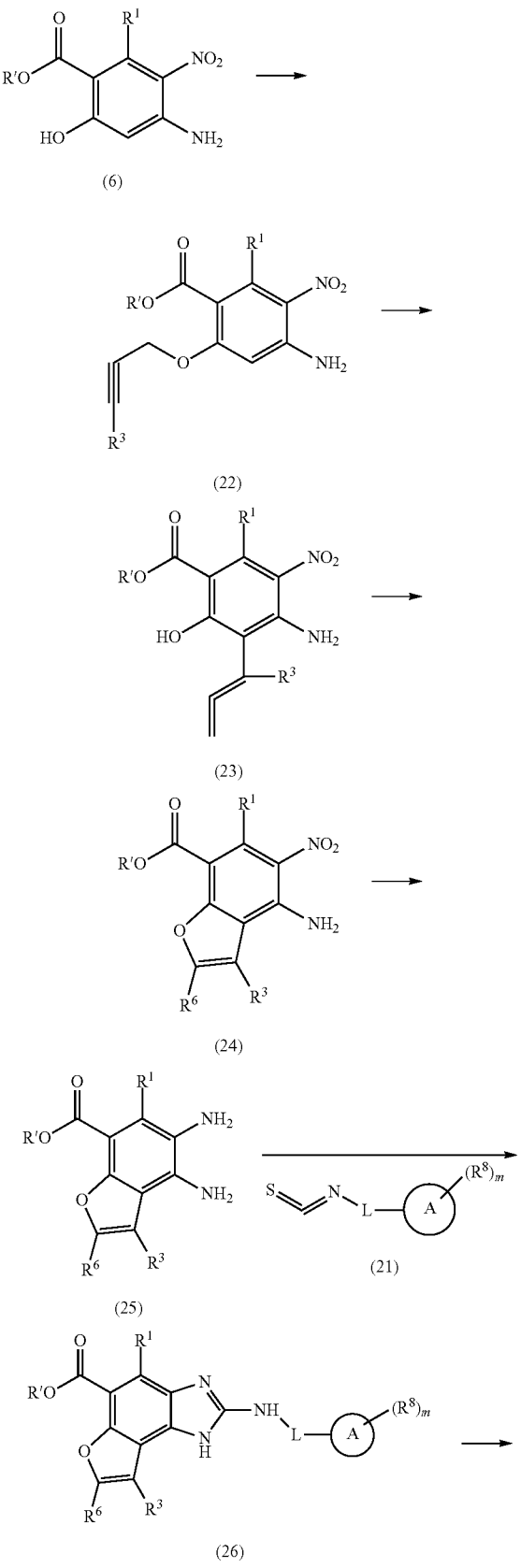

The compound of formula (6) may be prepared from compound of formula (1) following the process described in scheme 1. The compound of formula (6) can be converted to a compound of formula (22) by reacting with an appropriate alkynylhalide in presence of a base such as potassium carbonate, triethylamine or the like in a suitable solvent such as DMF, dimethoxyethane, THF or dioxane at a temperature range of 60-100° C. The compound of formula (22) can be converted to a compound of formula (24) through intermediate of formula (23) under Claisen rearrangement conditions using a base such as cesiumfluoride or the like in presence of a solvent such as N,N'-diethylaniline at a temperature range of 60-220° C. The compound of formula (24) can be converted to a compound of formula (25) under reductive conditions using a metal such as tin, iron or the like in presence of an appropriate catalyst such as hydrochloric acid in an alcoholic solvent at a temperature range of 20-100° C. Alternatively, the compound of formula (24) can also be converted to a compound of formula (25) under hydrogenation conditions. The compound of formula (25) can be converted to a compound of formula (26) by reacting with an isothiocyanate under appropriate conditions followed by cyclization in the presence of a reagent such as diisopropylcarbodiimide at a temperature range of 20-100° C. The compound of formula (26) can be converted to a compound of formula (27) under hydrolysis conditions in presence of a base such as sodium hydroxide, potassium carbonate, lithium hydroxide or the like in an alcoholic solvent in presence of water at a temperature range of 20-100° C. The compound of formula (27) can be converted to a compound of formula (Ib) under amidation conditions using an appropriate amine in presence of coupling reagent such as HOBT, TBTU, HATU, EDCI, BOP or the like in presence of a base such as triethylamine, diisopropylethylamine, N-methyl morpholine or the like in a suitable solvent such as DMF, THF or the like and at an appropriate temperature range such as 20-100° C.

The intermediate compound of formula (6a) may be prepared following the process as represented in scheme 5 (wherein $R^1$ and $R^z$ are as defined above in compound of formula (I) and R' is alkyl).

Scheme 5:

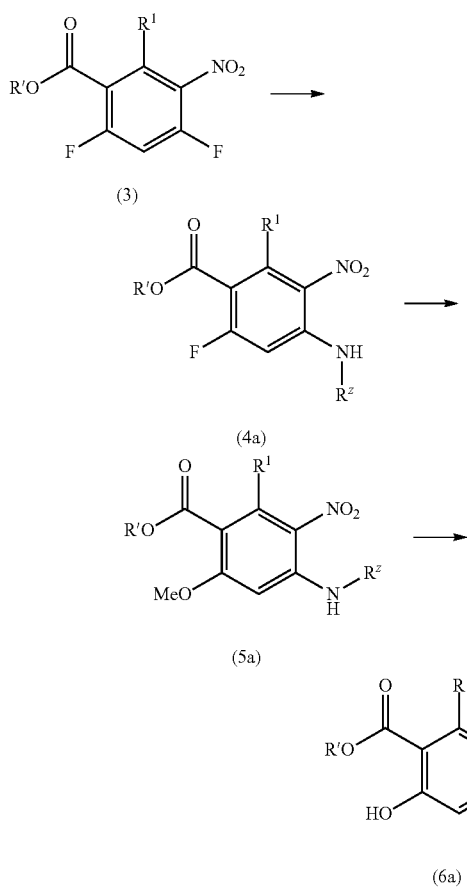

The compound of formula (3) can be converted to a compound of formula (4a) by reacting with an amine in presence of a base such as triethylamine, diisopropylethylamine or the like in a suitable solvent such as THF, DMF or DMSO at a temperature range of 0-100° C. The compound of formula (4a) can be converted to a compound of formula (5a) by reacting with an alkoxide in an alcoholic solvent at a temperature range of 0-100° C. The compound of formula (5a) can be converted to a compound of formula (6a) by reacting with a Lewis acid such as aluminium chloride or boron trifluoride or the like in a suitable solvent such as dichloromethane or dichloroethane or the like at a temperature range of 60-100° C.

Scheme-6:

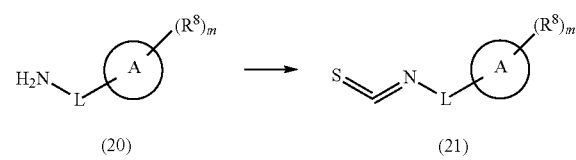

A compound of formula (20) [wherein L, R⁸ and m are as defined above in compound of formula (I)] can be converted to compound of formula (21) by reaction of amine of formula (20) with thiophosgene derivative in presence of bases such as N-ethyl di-isopropyl amine, TEA in solvent such as DCM, or ethyl acetate at a temperature range of 20-100° C. Also, corresponding N-substituted derivatives can be synthesized using N-substituted amines.

Scheme-7:

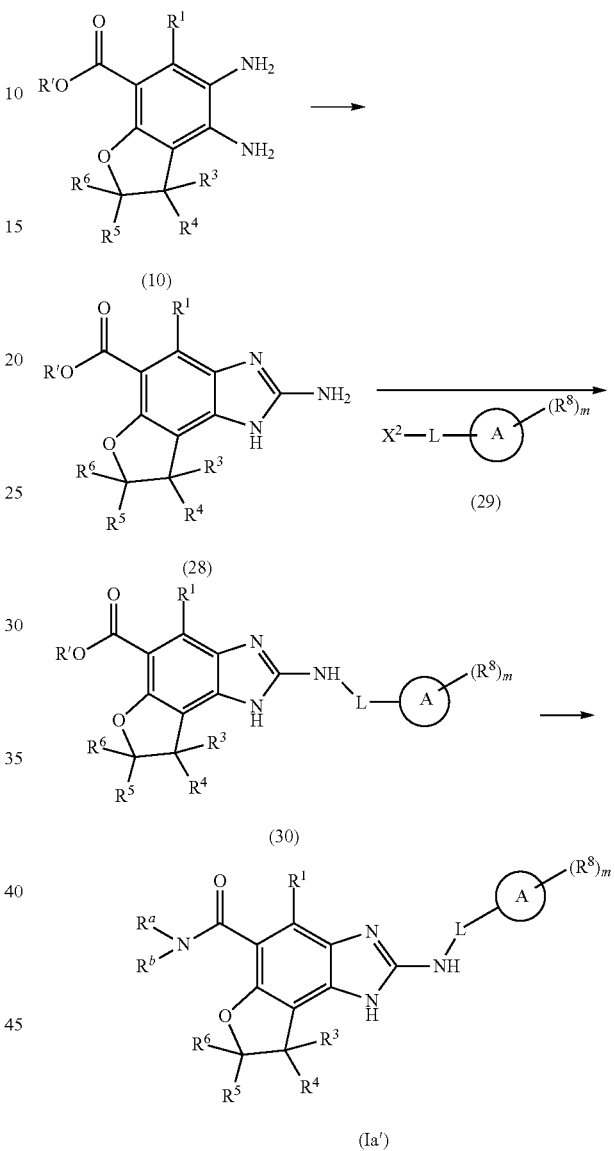

The compound of formula (10) can be converted to a compound of formula (28) by reacting with inorganic salts such as cyanogen bromide in the presence of protic solvent such as ethanol, methanol or the like at temperature range of 0-100° C. The compound of formula (28) can be converted to a compound of formula 30 using appropriate acids/halide of formula (29) (wherein, X² is OH or halogen) under amidation conditions (using an appropriate acids and a coupling reagent such as TBTU, HBTU, HATU, EDCI, HOBT, BOP) or by alkylation (using an appropriate halide in the presence of inorganic base such as sodium carbonate, potassium carbonate, sodium hydride) or the like in a organic base such as triethylamine, diisopropylethylamine, N-methyl morpholine or the like in a suitable solvent such as DMF, THF or the like at an appropriate temperature range such as 20-100° C.

Further, compound of formula 30 can be converted to a compound of formula (Ia′) using organometallic coupling reagents such as trimethyl aluminium or the like in presence of solvents such as toluene, acetonitrile at temperature range of 0-100° C.
The compound of formula (Ic) (wherein $R^1$, $R^6$, $R^7$, $R^8$, $R^b$, $R^z$, A, L and m are as defined for compound of formula (I)) is prepared according to the sequence depicted in Scheme 8.
Scheme-8:
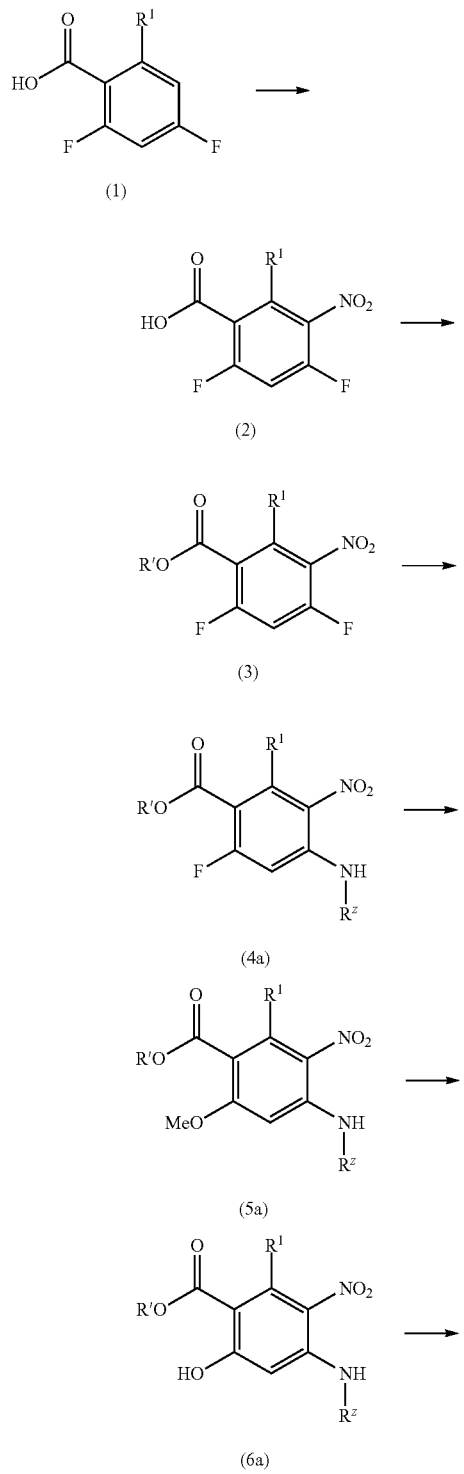
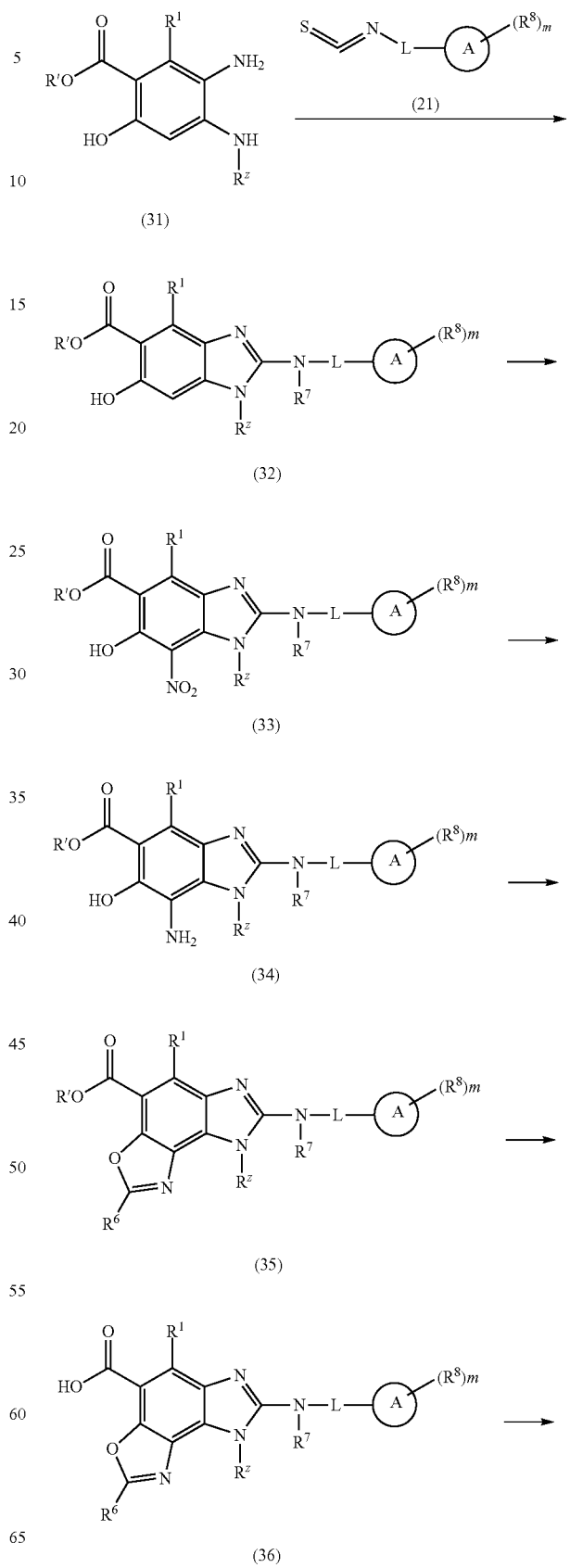

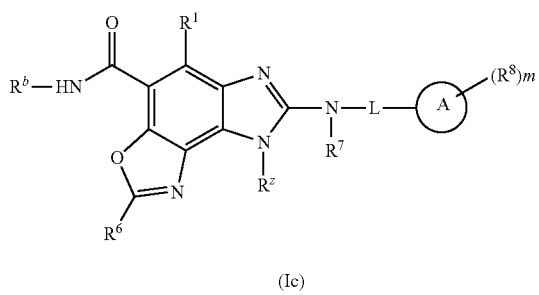

(Ic)

The compound of formula (1) is converted to the compound of formula (2) by following nitration procedure known to those skilled in the art of organic synthesis, for example, using fuming nitric acid in the presence of acid such as sulphuric acid. The compound of formula (2) can be reacted under the esterification condition with alcohol having formula R'—OH (wherein R' is alkyl such as methyl or ethyl) using an acid such as sulphuric acid or hydrochloric acid or the like at suitable temperature, for example the temperature range may be of 60-100° C., to obtain the compound of formula (3). The compound of formula (3) can be converted to the compound of formula (4a) by reacting with an substituted amine in the presence of a organic base such as triethylamine, diisopropylethylamine or the like in a suitable solvent such as THF, DMF or DMSO at a suitable temperature which may be in the range of 0-100° C. The compound of formula (4a) can be converted to the compound of formula (5a) by reacting with an alkoxide for e.g. sodium methoxide, sodium ethoxide or the like in an alcoholic solvent at a temperature range of 0-100° C. The compound of formula (5a) can be converted to the compound of formula (6a) by reacting with Lewis acid such as aluminium chloride or boron trifluoride or the like in a suitable solvent such as dichloromethane or dichloroethane or the like at a temperature range of 60-100° C. The compound of formula (6a) can be converted to a compound of formula (31) under reductive conditions using a metal such as Indium, tin, iron or the like in presence of an acid such as hydrochloric acid in an alcoholic solvent at a temperature range of 20-100° C. Alternatively, the compound of formula (6a) can also be converted to a compound of formula (31) under hydrogenation conditions. The compound of formula (31) can be converted to a compound of formula (32) by reacting with corresponding isothiocyanate of formula (21) under appropriate condition followed by cyclization in the presence of a reagent such as diisopropylcarbodiimide at a temperature range of 20-100° C., then optionally reacting with R$^7$—X' (wherein R$^7$ is not hydrogen and X' is good leaving group such as Cl, Br or I) under appropriate conditions. The compound of formula (32) is converted to a compound of formula (33) by following the procedure as described for the preparation of compound of formula 2. The compound of formula (33) can be converted to a compound of formula (34) by following the procedure as described for the preparation of compound of formula (31), which can be further cyclised by triethylortho formate or triethylortho acetate to give compound of formula (35). The compound of formula (35) can be converted to a compound of formula (36) under hydrolysis condition in the presence of an inorganic base such as sodium hydroxide, potassium carbonate, lithium hydroxide or the like in an alcoholic solvent in the presence of water at a temperature range of 20-100° C. The compound of formula (36) can be converted to a compound of formula (Ic) under amidation conditions using an appropriate amine in presence of coupling reagent such as TBTU, HOBT, DMAP, HATU, EDCI, BOP or the like in presence of a organic base such as triethylamine, diisopropylethylamine, N-methyl morpholine or the like in a suitable solvent such as DMF, THF, DMSO or the like at appropriate temperature range such as 20-100° C.

The compound of formula (Ic') and (Ic'') (wherein R$^1$, R$^4$, R$^5$, R$^6$, R$^7$, R$^8$, R$^b$, R$^z$, A and m are as defined for compound of formula (I)) is prepared according to the sequence depicted in Scheme 9.

Scheme 9

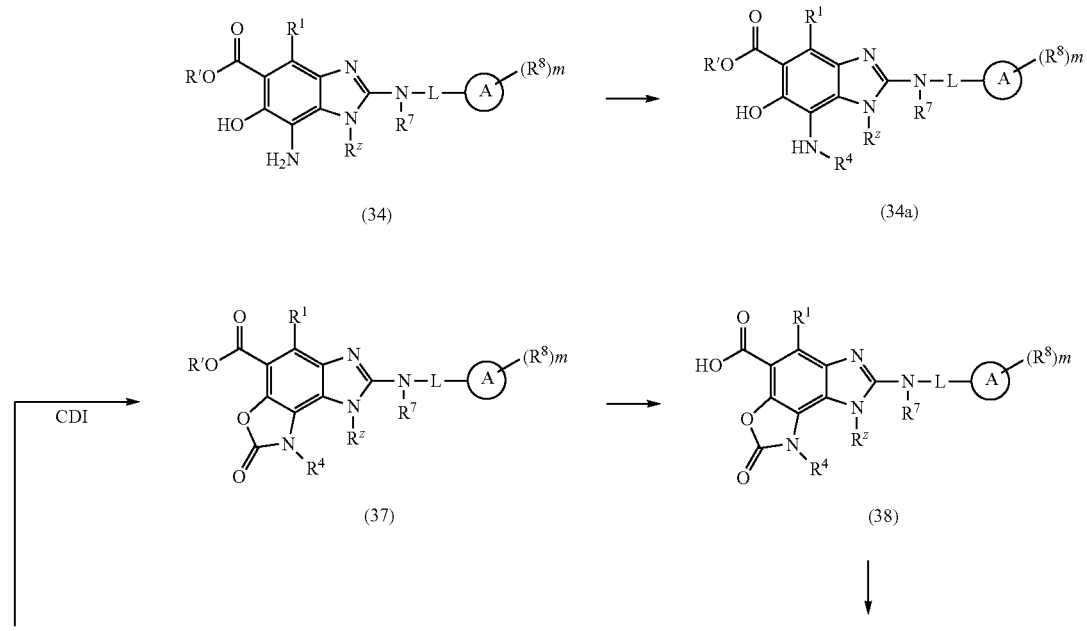

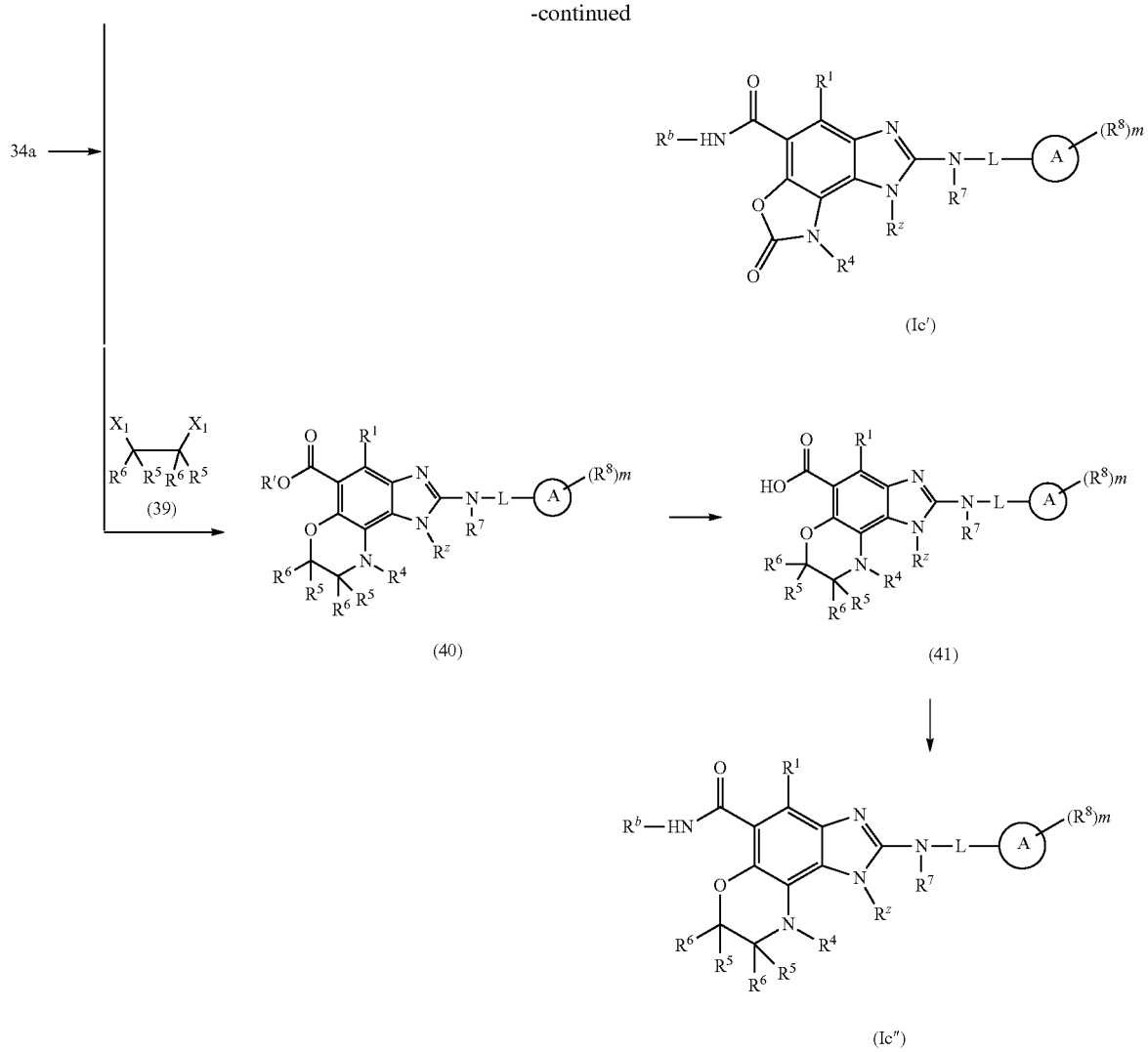

The compound of formula (34) is converted to a compound of formula (34a) following alkylation procedure known to those skilled in the art of organic synthesis for example, using an alkyl halide in presence of inorganic base such as sodium carbonate, potassium carbonate, sodium hydride or organic base such as triethyl amine, N,N-diethyl-isopropyl amine or the like in a solvent such as THF, DMF at temperature range of 0-100° C. Further, compound of formula (37) can be prepared by reacting compound of formula (34a) with CDI, Phosgene in presence of organic base such as triethyl amine, N,N-diethyl-isopropyl amine or the like in a solvent such as benzene, chloroform, dichloromethane at a temperature range of 0-100° C. The compound of formula (37) can be converted to compound of formula (38) and the successively to compound of formula (Ic') by following the procedure as described for preparation of compound of formula (36) and (Ic) respectively.

Alternatively, compound of formula (34a) can be converted to compound of formula (40) by coupling with substituted alkyl halide of compound of formula (39) (wherein $X_1$-halo, Tosyl or any good leaving group) in presence of inorganic base such as sodium carbonate, potassium carbonate or the like in suitable solvent such as DMF, acetone, DMSO or the like at temperature range of 0-100° C. The compound of formula (40) can be converted to compound of formula (41) and the further to compound of formula (Ic") by following the procedure as described for the preparation of compound of formula (36) and (Ic), respectively.

EXPERIMENTAL

Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase. The following abbreviations are used in the text: DMSO-$d_6$: hexadeuterodimethyl sulfoxide; DMF: N,N-dimethylformamide; THF: Tetrahydrofuran; HOBT: 1-Hydroxybenzotriazole; TBTU: O-(Benzotriazol-1-yl)-N,N,N',N'-tetramethyluronium tetrafluoroborate; HBTU: O-(Benzotriazol-1-yl)-N,N,N',N'-tetramethyluronium hexafluorophosphate; HATU: O-(7-Azabenzotriazol-1-yl)-N,N,N',N'-tetramethyluronium hexafluorophosphate: EDCI. HCl: N-(3-Dimethylaminopropyl)-N'-ethylcarbodiimide hydrochloride; BOP: (Benzotriazol-1-yloxy)tris(dimethylamino)phosphonium hexafluorophosphate; COMU: (1-Cyano-2-ethoxy-2-oxoethylidenaminooxy)dimethylamino-morpholino-carbenium hexafluorophosphate; CDI: 1,1'-Carbonyldiimidazole; TEA: Triethyl amine; DCM: Dihloromethane; DMAP: 4-Dimethylaminopyridine; EDC: Ethylene dichloride; J: coupling constant in units of Hz; RT: room temperature (22-26° C.); h: hour(s); aq.: aqueous; AcOEt: ethyl acetate; equiv.: equivalents.

Intermediates

Intermediate-1

Methyl 4,5-diamino-2,2-dimethyl-2,3-dihydro-1-benzofuran-7-carboxylate

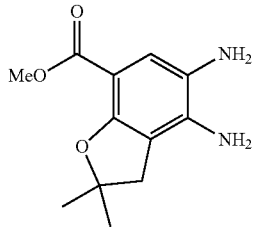 [SMILES: COC(=O)c1cc(N)c(N)c2c1OC(C)(C)C2]

Step 1:—Preparation of 2,4-difluoro-5-nitrobenzoic acid

To a cold mixture of 2,4-difluoro benzoic acid (3.0 g, 18.98 mmol) and conc. $H_2SO_4$ (10 mL), fuming $HNO_3$ (3 mL) was added at 0° C. The reaction mixture was stirred at 0-5° C. for 14 h and quenched in ice cold water and extracted with ethyl acetate. The organic layer was dried over anhydrous sodium sulphate and concentrated to afford 3.0 g of the desired product. $^1$HNMR (DMSO-$d_6$): δ 7.83-7.90 (m, 1H), 8.57-8.62 (m, 1H).

Step 2:—Preparation of ethyl 2,4-difluoro-5-nitrobenzoate

To a solution of step-1 intermediate (3.3 g, 16.25 mmol) in ethanol (20 mL), conc. $H_2SO_4$ (3 mL) was added. The reaction mixture was refluxed for 24 h. Excess of solvent was removed under vacuum and the reaction mixture was quenched in water and extracted with ethyl acetate. The organic layer was separated and dried over anhydrous sodium sulphate and concentrated to afford 3.5 g of the desired product. $^1$HNMR (CDCl$_3$): δ 1.42 (t, J=7.5 Hz, 3H), 4.44 (q, J=7.2 Hz, 2H), 7.10-7.16 (m, 1H), 8.76-8.81 (m, 1H).

Step 3:—Preparation of ethyl 4-(benzylamino)-2-fluoro-5-nitrobenzoate

To a solution of step-2 intermediate (3.5 g, 15.15 mmol) in THF, TEA (4.3 g, 43.06 mmol) was added. The reaction mixture was cooled at 0° C. The reaction mass was added benzyl amine (1.78 g, 16.63 mmol) and stirred at 0° C.-RT for 3-4 h. The reaction mixture was quenched in water and extracted with ethyl acetate. The organic layer was separated, dried over anhydrous sodium sulphate and concentrated to afford 3.0 g of the desired product. $^1$HNMR (DMSO-$d_6$): δ 1.27 (t, J=7.2 Hz, 3H), 4.26 (q, J=6.9 Hz, 2H), 4.68 (q, J=6.6 Hz, 2H), 6.68-6.75 (m, 1H), 7.22-7.44 (m, 5H), 8.65 (d, J=7.8 Hz, 1H), 9.15 (t, 1H).

Step 4:—Preparation of methyl 4-(benzylamino)-2-methoxy-5-nitrobenzoate

To a cold solution of step-3 intermediate (0.200 g, 0.628 mmol) in methanol (8.0 mL), sodium methoxide (0.135 g, 2.55 mmol) was added at 0-5° C. The reaction mixture was stirred at RT for 5-6 h. The reaction mixture was quenched in water and extracted with ethyl acetate. The organic layer was separated and dried over anhydrous sodium sulphate and concentrated to afford 0.150 g of the desired product. $^1$HNMR (DMSO-$d_6$): δ 3.73 (s, 6H), 4.70 (d, J=6.9 Hz, 2H), 6.29 (s, 1H), 7.12-7.42 (m, 4H), 7.64 (d, J=7.8 Hz, 1H), 8.57 (s, 1H), 9.12 (d, J=5.7 Hz, 1H); MS [M+H]$^+$: 317.35.

Step 5:—Preparation of methyl 4-amino-2-hydroxy-5-nitrobenzoate

To a solution of step-4 intermediate (0.050 g, 0.158 mmol) in EDC, anhydrous aluminum trichloride (0.042 g, 0.316 mmol) was added. The reaction mixture was refluxed for 2-4 h. The reaction mixture was quenched in water and extracted with ethyl acetate. The organic layer was separated, dried over anhydrous sodium sulphate and concentrated to afford 0.030 g of the desired product. $^1$HNMR (DMSO-$d_6$): δ 3.84 (s, 3H), 6.37 (s, 1H), 7.81 (s, 2H), 8.53 (s, 1H), 10.92 (s, 1H).

Step 6:—Preparation of methyl 4-amino-2-[(2-methylprop-2-en-1-yl)oxy]-5-nitrobenzoate To a solution of step-5 intermediate (0.015 g, 0.070 mmol) in DMF (2.0 mL), dry potassium carbonate (0.011 g, 0.079 mmol) was added. The reaction mixture was stirred at 80° C. for 30 minutes followed by addition of methallyl chloride (0.008 g, 0008 mmol). The reaction mixture was stirred at 80° C. for 8-9 h. The reaction mixture was filtered and the filtrate was concentrated under reduced pressure. The reaction mass was diluted with water and extracted with ethyl acetate. The organic layer was separated, dried over anhydrous sodium sulphate and concentrated and purified by column chromatography to afford 0.010 g of the desired product. $^1$HNMR (DMSO-$d_6$): δ 1.769 (s, 3H), 3.75 (s, 3H), 4.49 (s, 2H), 4.99 (s, 1H), 5.20 (s, 1H), 6.52 (s, 2H), 7.84 (s, 2H), 8.52 (s, 1H); MS [M–H]$^-$: 265.27.

Step 7:—Preparation of methyl 4-amino-2-hydroxy-3-(2-methylprop-2-en-1-yl)-5-nitrobenzoate The mixture of step-6 intermediate (0.300 g, 1.12 mmol) in N,N'-diethyl aniline (3.0 mL) was refluxed for 1.30 h. Excess of solvent was removed under vacuum and the reaction mixture was diluted with water and extracted with ethyl acetate. The organic layer was separated, dried over anhydrous sodium sulphate, concentrated and purified by column chromatography to afford 0.100 g of the desired product. $^1$HNMR (DMSO-$d_6$): δ 1.76 (s, 3H), 3.31 (s, 3H), 3.90 (s, 3H), 4.43 (s, 1H), 4.66 (s, 1H), 7.51 (s, 2H), 8.58 (s, 1H), 11.40 (s, 1H); MS [M–H]$^-$: 265.35.

Step 8:—Preparation of methyl 4-amino-2,2-dimethyl-5-nitro-2,3-dihydro-1-benzofuran-7-carboxylate The solution of step-7 intermediate (0.080 g, 0.300 mmol) in formic acid (3.0 mL) was stirred at 100° C. for 2-4 h. The reaction mixture was quenched in water and extracted with ethyl acetate. The organic layer was dried over anhydrous sodium sulphate and concentrated to afford 0.015 g of the desired product. $^1$HNMR (DMSO-$d_6$): δ 1.47 (s, 6H), 2.87 (s, 2H), 3.71 (s, 3H), 7.48 (s, 2H), 8.51 (s, 1H).

Step 9:—Preparation of methyl 4,5-diamino-2,2-dimethyl-2,3-dihydro-1-benzofuran-7-carboxylate To a solution of step-8 intermediate (0.050 g, 0.187 mmol) in methanol, iron powder (0.050 g, 0.892 mmol) was added. The reaction mixture was cooled at 0° C. followed by addition of conc. HCl (0.5 mL). The reaction mixture was stirred at RT for 1 h. The reaction mixture was quenched in water and basified with sodium bicarbonate and extracted with DCM. The organic layer was separated, dried over anhydrous sodium sulphate and concentrated to afford 0.020 g of the desired product. $^1$HNMR (DMSO-$d_6$): δ 1.37 (s, 6H), 2.70 (s, 2H), 3.63 (s, 3H), 4.30 (s, 2H), 5.23 (s, 2H), 6.84 (s, 1H); MS [M+H]$^+$: 237.20.

Intermediate-2

3,5-Dichloro-4-isothiocyanatopyridine

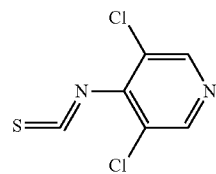 [SMILES: S=C=Nc1c(Cl)cncc1Cl]

To a solution of 3,5-dichloropyridin-4-amine (4.0 g, 24.53 mmol) in DCM (20 mL), was added N-ethyl di-isopropyl amine (6.3 g, 48.83 mmol). The reaction mixture was stirred at RT for 30 minutes. The reaction mixture was cooled at 0° C. and thiophosgene (2.76 g, 24.00 mmol) was added drop wise. The reaction mixture was stirred at 0° C. to RT for 3-4 h. The reaction mixture was diluted with DCM and the obtained crude was purified by column chromatography to afford 1.0 g of the desired product. $^1$HNMR (DMSO-$d_6$): δ 8.77 (s, 2H); MS [M+H]$^+$: 205.20.

Intermediate-3

2-[(3,5-Dichloropyridin-4-yl)amino]-7,7-dimethyl-7,8-dihydro-1H-furo[3,2-e]benzimidazole-5-carboxylic acid

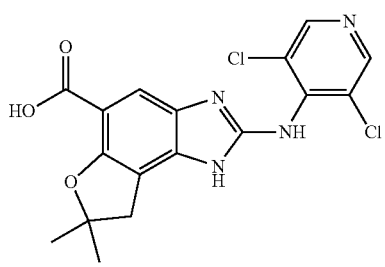 [SMILES: CC1(C)Cc2c(c(C(=O)O)cc3nc(Nc4c(Cl)cncc4Cl)[nH]c23)O1]

Step 1:—Preparation of methyl 2-[(3,5-dichloropyridin-4-yl)amino]-7,7-dimethyl-7,8-dihydro-1H-furo[3,2-e]benzimidazole-5-carboxylate To a solution of intermediate-1 (0.020 g, 0.084 mmol) in acetonitrile (3.0 mL), intermediate-2 (0.030 g, 0.146 mmol) was added. The reaction mixture was stirred at RT for 24 h. followed by addition of N,N-di-isopropyl carbodimide (0.5 mL). The reaction mixture stirred at RT for 4-6 h. The reaction mixture was cooled and filtered to afford 0.010 g of the desired product. $^1$HNMR (DMSO-$d_6$): δ 1.44 (s, 6H), 2.95 (s, 2H), 3.73 (s, 3H), 7.10 (s, 1H), 8.44 (s, 2H), 10.90 (s, 1H), 11.40 (s, 1H); MS [M+H]$^+$: 237.20.

Step 2:—Preparation of 2-[(3,5-dichloropyridin-4-yl)amino]-7,7-dimethyl-7,8-dihydro-1H-furo[3,2-e]benzimidazole-5-carboxylic acid To a solution of step-1 intermediate (0.015 g, 0.036 mmol) in methanol (2.0 mL), was added (50%) aqueous sodium hydroxide (0.011 g, 0.275 mmol). The reaction mixture was stirred at 60° C. for 8-10 h. The reaction mixture was quenched in water and acidified with dilute acetic acid and obtained solid was filtered to afford 0.010 g of the desired product. $^1$HNMR (DMSO-$d_6$): δ 1.41 (s, 3H), 1.76 (s, 3H), 2.90 (s, 2H), 7.14 (s, 1H), 8.38 (s, 2H), 11.50-12.00 (m, 3H); MS [M–H]$^-$: 391.25.

Intermediate-4

1-[2-(Trifluoromethyl)phenyl]methanamine

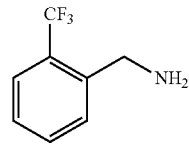

Step 1:—Preparation of 2-(trifluoromethyl)benzyl Azide

To a solution of 1-(bromomethyl)-2-(trifluoromethyl)benzene (0.250 g, 0.104 mmol) in DMSO (3.0 mL) was added sodium azide (0.101 g, 0.156 mmol). The reaction mixture was stirred at RT for 3-4 h. The reaction mixture was quenched in water and extracted with ethyl acetate. The organic layer was separated, dried over anhydrous sodium sulphate and concentrated to afford 0.200 g of the desired product. $^1$HNMR (DMSO-$d_6$): δ 4.63 (s, 2H), 7.60 (d, J=7.8 Hz, 1H), 7.70-7.80 (m, 3H).

Step 2:—Preparation of 1-[2-(trifluoromethyl)phenyl]methanamine

To a solution of step-1 intermediate (0.200 g, 0.993 mmol) in conc. HCl tin (II)chloride (0.673 g, 2.98 mmol) was added. The reaction mixture was stirred at 80° C. for 2 h. The reaction mixture quenched in water, neutralized with sodium bicarbonate and extracted with mixture of (1-1.5%) methanol:DCM. The organic layer was separated, dried over anhydrous sodium sulphate and concentrated to afford 0.150 g of the desired product. ¹HNMR (DMSO-d₆): δ 7.43 (d, J=7.2 Hz, 2H), 7.64-7.66 (m, 3H), 7.78 (m, 1H).

Intermediate-5

1,3-Dichloro-2-isothiocyanatobenzene

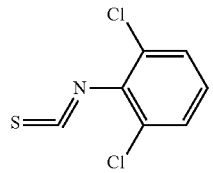 [SMILES: S=C=Nc1c(Cl)cccc1Cl]

The title compound was prepared following the procedure described for intermediate-2 using 2,6-dichloro aniline (2.0 g, 12.34 mmol), thiophosgene (1.41 g, 12.34 mmol) and N-ethyl di-isopropyl amine (7.42 g, 57.51 mmol) in DCM (20 mL) to afford 1.0 g of the desired product. ¹HNMR (DMSO-d₆): δ 7.62 (d, J=7.8 Hz, 2H), 7.39 (t, J=7.8 Hz, 1H).

Intermediate-6

2-[(2,6-Dichlorophenyl)amino]-7,7-dimethyl-7,8-dihydro-1H-furo[3,2-e]benzimidazole-5-carboxylic acid

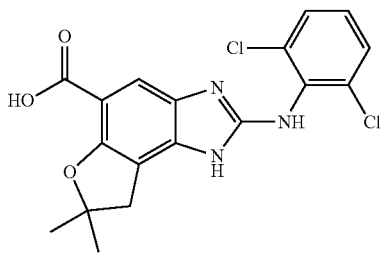 [SMILES: CC1(C)Cc2c(c(C(=O)O)cc3nc(Nc4c(Cl)cccc4Cl)[nH]c23)O1]

Step 1:—Preparation of methyl 2-[(2,6-dichlorophenyl)amino]-7,7-dimethyl-7,8-dihydro-1H-furo[3,2-e]benzimidazole-5-carboxylate The title compound was prepared following the procedure described for step-1 of intermediate-3 using intermediate-1 (0.800 g, 3.38 mmol), acetonitrile (5.0 mL), intermediate-5 (0.800 g, 3.92 mmol) and N,N-di-isopropyl carbodimide (1.0 mL) to afford 0.400 g of the desired product. ¹HNMR (DMSO-d₆): δ 1.42 (s, 6H), 2.96 (s, 2H), 3.72 (s, 3H), 7.21 (brs, 2H), 7.51 (d, J=7.8 Hz, 2H), 10.00-11.00 (s, 2H).

Step 2:—Preparation of 2-[(2,6-dichlorophenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.400 g, 0.987 mmol), methanol (2.0 mL) and (50%) aqueous solution of sodium hydroxide (1.2 g, 30.0 mmol) to afford 0.250 g of the desired product. ¹HNMR (DMSO-d₆): δ 1.43 (s, 6H), 2.99 (s, 2H), 7.29 (m, 2H), 7.55 (m, 2H), 11.50-12.50 (m, 3H); MS [M+H]⁺: 392.15.

Intermediate-7

Methyl 4,5-diamino-2-methyl-1-benzofuran-7-carboxylate

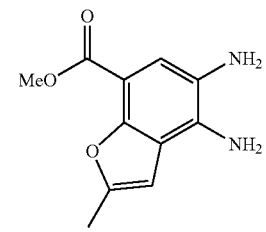 [SMILES: COC(=O)c1cc(N)c(N)c2cc(C)oc12]

Step 1:—Preparation of methyl 4-amino-5-nitro-2-(prop-2-yn-1-yloxy)benzoate

The title compound was prepared following the procedure described for step-6 of intermediate-1 using step-5 intermediate-1 (2.00 g, 9.43 mmol), potassium carbonate (1.95 g, 14.13 mmol), DMF (2.0 mL) and 3-bromoprop-1-yne (1.22 g, 10.33 mmol) to afford 1.3 g of the desired product. ¹HNMR (DMSO-d₆): δ 1.98 (s, 2H), 3.74 (s, 3H), 4.87 (s, 1H), 6.61 (s, 1H), 7.92 (s, 2H), 8.51 (s, 1H).

Step 2:—Preparation of methyl 4-amino-2-methyl-5-nitro-1-benzofuran-7-carboxylate The title compound was prepared following the procedure described for step-7 of intermediate-1 using step-1 intermediate (1.300 g, 5.2 mmol), cesium fluoride (1.1 g, 7.23 mmol) and N,N'-diethyl aniline (5.0 mL) to afford 0.300 g of the desired product. ¹HNMR (DMSO-d₆): δ 2.46 (s, 3H), 3.85 (s, 3H), 7.14 (s, 1H), 8.31 (s, 2H), 8.51 (s, 1H).

Step 3:—Preparation of methyl 4,5-diamino-2-methyl-1-benzofuran-7-carboxylate

The title compound was prepared following the procedure described for step-9 of intermediate-1 using step-2 intermediate (0.050 g, 0.187 mmol), iron powder (catalytic amount), methanol (4 mL) and HCl (1.0 mL) to afford 0.100 g of the desired product. ¹HNMR (DMSO-d₆): δ 2.37 (s, 3H), 3.76 (s, 3H), 4.46 (s, 2H), 5.67 (s, 2H), 7.61 (s, 1H), 7.11 (s, 1H).

Intermediate-8

2-[(3,5-Dichloropyridin-4-yl)amino]-7-methyl-1H-furo[3,2-e]benzimidazole-5-carboxylic acid

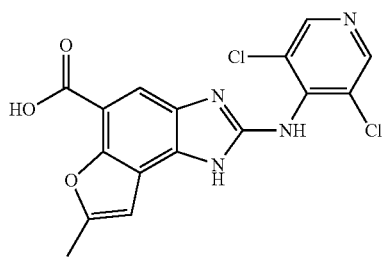 [SMILES: Cc1cc2c(o1)c(C(=O)O)cc1nc(Nc3c(Cl)cncc3Cl)[nH]c12]

Step 1:—Preparation of methyl 2-[(3,5-dichloropyridin-4-yl)amino]-7-methyl-1H-furo[3,2-e]benzimidazole-5-carboxylate The title compound was prepared following the procedure described for step-1 of intermediate-3 using intermediate-7 (0.150 g, 0.681 mmol), intermediate-2 (0.203 g, 0.738 mmol), acetonitrile (5.0 mL) and N,N-di-isopropyl carbodimide (1.0 mL) to afford 0.080 g of the desired product. ¹HNMR (DMSO-d₆): δ 2.48 (s, 3H), 3.85 (s, 3H), 6.60 (s, 1H), 7.37 (s, 1H), 8.45 (s, 2H), 11.25 (s, 1H), 11.88 (s, 1H); MS [M+H]⁺: 391.30.

Step 2:—Preparation of 2-[(3,5-dichloropyridin-4-yl)amino]-7-methyl-1H-furo[3,2-e]benzimidazole-5-carboxylic acid The title compound was prepared following the procedure described for step-2 of intermediate-3 using step-1 intermediate (0.080 g, 0.204 mmol), methanol (3.0 mL) and sodium hydroxide (0.024 g, 0.613 mmol) to afford 0.050 g of the desired product. ¹HNMR (DMSO-d₆): δ 2.50 (s, 3H), 6.56 (s, 1H), 7.36 (s, 1H), 8.43 (s, 2H), 11.00-12.00 (s, 3H); MS [M+H]⁺: 377.29.

Intermediate-9

2-[(2,6-Dichlorophenyl)amino]-7-methyl-1H-furo[3,2-e]benzimidazole-5-carboxylic acid

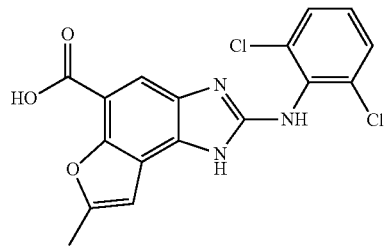 [SMILES: Cc1cc2c(o1)c(C(=O)O)cc1nc(Nc3c(Cl)cccc3Cl)[nH]c12]

Step 1:—Preparation of methyl 2-[(2,6-dichlorophenyl)amino]-7-methyl-1H-furo[3,2-e]benzimidazole-5-carboxylate The title compound was prepared following the procedure described for step-1 of intermediate-3 using intermediate-7 (0.110 g, 0.500 mmol), intermediate-5 (0.200 g, 0.730 mmol), acetonitrile (5.0 mL) and N,N-di-isopropyl carbodimide (1.0 mL) to afford 0.100 g of the desired product. ¹HNMR (DMSO-d₆): δ 2.50 (s, 3H), 3.86 (s, 3H), 6.68 (s, 1H), 7.39 (s, 1H), 7.60-7.65 (m, 2H), 9.40 (s, 1H), 11.40 (s, 2H); MS [M+H]⁺: 391.30.

Step 2:—Preparation of 2-[(2,6-dichlorophenyl)amino]-7-methyl-1H-furo[3,2-e]benzimidazole-5-carboxylic acid The title compound was prepared following the procedure described for step-2 of intermediate-3 using step-1 intermediate (0.100 g, 0.255 mmol), methanol (3.0 mL), and sodium hydroxide (0.024 g, 0.613 mmol) to afford 0.050 g of the desired product. ¹HNMR (DMSO-d₆): δ 2.44 (s, 3H), 6.58 (s, 1H), 7.25 (s, 2H), 7.50-7.55 (m, 2H); MS [M+H]⁺: 376.28.

Intermediate-10

1-Chloro-2-isothiocyanatobenzene

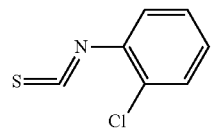

The title compound was prepared following the procedure described for intermediate-2 using 2-chloro aniline (2.0 g, 15.74 mmol), thiophosgene (1.81 g, 15.73 mmol), and N-ethyl di-isopropyl amine (4.0 g, 31.00 mmol) to afford 1.0 g of the desired product. ¹HNMR (DMSO-d₆): δ 7.62 (m, 3H), 7.39 (t, J=7.8 Hz, 1H).

Intermediate-11

2-[(2-Chlorophenyl)amino]-7-methyl-1H-furo[3,2-e]benzimidazole-5-carboxylic acid

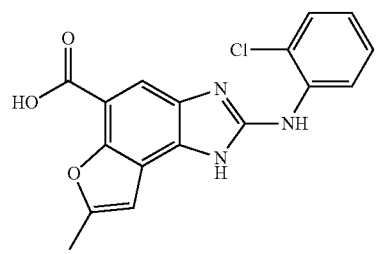 [SMILES: Cc1cc2c(o1)c(C(=O)O)cc1nc(Nc3ccccc3Cl)[nH]c12]

Step 1:—Preparation of methyl 2-[(2-chlorophenyl)amino]-7-methyl-1H-furo[3,2-e]benzimidazole-5-carboxylate The title compound was prepared following the procedure described for step-1 of intermediate-3 using intermediate-7 (0.100 g, 0.454 mmol), intermediate-10 (0.150 g, 0.887 mmol), acetonitrile (5.0 mL) and N,N-di-isopropyl carbodimide (1.0 mL) to afford 0.100 g of the desired product. ¹HNMR (DMSO-d₆): δ 2.26-2.50 (m, 3H), 3.33-3.86 (m, 3H), 6.84 (s, 1H), 7.06 (m, 2H), 7.24-7.60 (m, 3H), 10.82 (s, 1H), 11.42 (s, 1H); MS [M+H]⁺: 356.28.

Step 2:—Preparation of 2-[(2-chlorophenyl)amino]-7-methyl-1H-furo[3,2-e]benzimidazole-5-carboxylic acid The title compound was prepared following the procedure described for step-2 of intermediate-3 using step-1 intermediate (0.100 g, 0.281 mmol), methanol (3.0 mL) and sodium hydroxide (0.034 g, 0.850 mmol) to afford 0.050 g of the desired product. ¹HNMR (DMSO-d₆): δ 2.50 (s, 3H), 6.80 (s, 1H), 7.06 (s, 1H), 7.51 (s, 1H), 7.84 (s, 1H), 8.64 (s, 1H), 9.06 (s, 1H), 10.89 (s, 1H), 11.28 (s, 1H), 12.65 (s, 1H); MS [M+H]⁺: 342.26.

Intermediate-12

2-[(2-Chlorophenyl)amino]-7,7-dimethyl-7,8-dihydro-1H-furo[3,2-e]benzimidazole-5-carboxylic acid

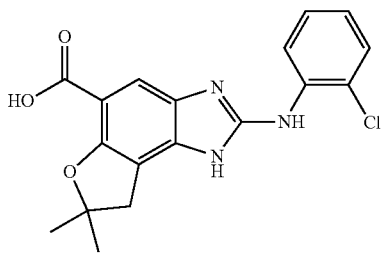 [SMILES: CC1(C)Cc2c(c(C(=O)O)cc3nc(Nc4ccccc4Cl)[nH]c23)O1]

Step 1:—Preparation of methyl 2-[(2-chlorophenyl)amino]-7,7-dimethyl-7,8-dihydro-1H-furo[3,2-e]benzimidazole-5-carboxylate The title compound was prepared following the procedure described for step-1 of intermediate-3 using intermediate-1 (0.800 g, 3.38 mmol), acetonitrile (5.0 mL), intermediate-10 (0.571 g, 3.37 mmol) and N,N-di-isopropyl carbodimide (1.0 mL) to afford 0.500 g of the desired product. $^1$HNMR (DMSO-d$_6$): δ 1.42 (s, 6H), 3.11 (s, 2H), 3.68-3.75 (s, 3H), 7.04 (m, 1H), 7.37 (t, J=8.1 Hz, 1H), 7.49 (d, J=7.8 Hz, 1H), 7.62 (s, 1H), 8.60 (s, 1H), 9.05 (s, 1H), 10.80 (s, 1H); MS [M+H]$^+$: 372.23.

Step 2:—Preparation of 2-[(2-chlorophenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.400 g, 1.07 mmol), methanol (2.0 mL) and (50%) aqueous solution of sodium hydroxide (1.2 g, 30.0 mmol) to afford 0.200 g of the desired product. $^1$HNMR (DMSO-d$_6$): δ 1.46 (s, 6H), 3.10 (s, 2H), 7.02 (t, J=7.2 Hz, 1H), 7.37 (t, J=7.8 Hz, 1H), 7.47 (d, J=7.8 Hz, 1H), 7.59 (s, 1H), 8.60 (d, J=8.1 Hz, 1H), 12.00 (s, 1H); MS [M+H]$^+$: 358.18.

Intermediate-13

2-[(3,5-Dichloropyridin-4-yl)amino]-7,7-dimethyl-7,8-dihydrofuro[2,3-g][1,3]benzothiazole-5-carboxylic acid

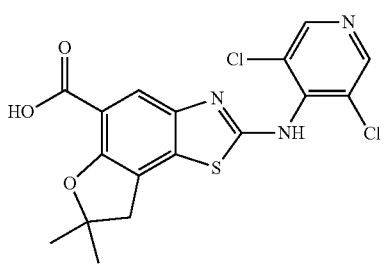 [SMILES: CC1(C)Cc2c(c(C(=O)O)cc3nc(Nc4c(Cl)cncc4Cl)sc23)O1]

Step 1:—Preparation of methyl 4-iodo-2,2-dimethyl-5-nitro-2,3-dihydro-1-benzofuran-7-carboxylate To a cold solution of step-8 of intermediate-1 (0.500 g, 1.879 mmol) in water: HCl (2 ml: 4 mL) sodium nitrite (0.337 g, 3744 mmol) was added. The reaction mixture was stirred at 0° C. for 30 minutes with addition of potassium iodide (0.622 g, 3.746 mmol). The reaction mixture was stirred at RT for 3-4 h. The reaction mixture was quenched in water and extracted with ethyl acetate. The organic layer was dried over anhydrous sodium sulphate and concentrated to afford 0.150 g of the desired product. $^1$HNMR (DMSO-d$_6$): δ 1.68 (s, 6H), 3.11 (s, 2H), 3.84 (s, 3H), 8.25 (s, 1H).

Step 2:—Preparation of methyl 5-amino-4-iodo-2,2-dimethyl-2,3-dihydro-1-benzofuran-7-carboxylate To a solution of step-1 intermediate (0.150 g, 0.397 mmol) in acetic acid (5 mL), iron powder (0.500 g, 8.92 mmol) was added. The reaction mixture was stirred at RT for 4-5 h. The reaction mixture was quenched in water and neutralized by sodium bicarbonate and extracted with ethyl acetate. The organic layer was separated, dried over anhydrous sodium sulphate and concentrated to afford 0.100 g of the desired product. $^1$HNMR (DMSO-d$_6$): δ 1.39 (s, 6H), 2.88 (s, 2H), 3.73 (s, 3H), 4.87 (s, 2H), 7.02 (s, 1H).

Step 3:—Preparation of Methyl 2-[(3,5-dichloropyridin-4-yl)amino]-7,7-dimethyl-7,8-dihydrofuro[2,3-g][1,3]benzothiazole-5-carboxylate To a solution of step-2 intermediate (0.100 g, 0.288 mmol) in DMSO potassium carbonate (0.040 g, 0.288 mmol), copper iodide (0.008 g, 0.04 mmol) and Intermediate-2 (0.118 g, 0.576 mmol) were added. The reaction mixture was stirred at RT for 14-16 h. The reaction mixture was quenched in water and extracted with ethyl acetate. The organic layer was separated, dried over anhydrous sodium sulphate and concentrated to afford 0.150 g of the desired product. $^1$HNMR (DMSO-d$_6$): δ 1.43 (s, 6H), 2.97 (s, 2H), 3.78 (s, 3H), 7.30 (s, 1H), 8.60 (m, 2H), 12.14 (s, 1H); MS [M+H]$^+$: 424.17.

Step 4:—Preparation of 2-[(3,5-dichloropyridin-4-yl)amino]-7,7-dimethyl-7,8-dihydrofuro[2,3-g][1,3]benzothiazole-5-carboxylic acid The title compound was prepared following the procedure described for step-2 of intermediate-3 using methyl 2-[(3,5-dichloropyridin-4-yl)amino]-7,7-dimethyl-7,8-dihydrofuro[2,3-g][1,3]benzothiazole-5-carboxylate (0.080 g, 0.188 mmol), methanol (2.0 mL) and (50%) aqueous solution of sodium hydroxide (0.200 g, 5.00 mmol) to afford 0.050 g of the desired product. $^1$HNMR (DMSO-d$_6$): δ 1.43 (s, 6H), 2.98 (s, 2H), 7.37 (s, 1H), 7.30 (s, 1H), 8.61 (m, 2H), 12-13 (s, 1H); MS [M+H]$^+$: 424.18.

Intermediate-14

1-Chloro-3-fluoro-2-isothiocyanatobenzene

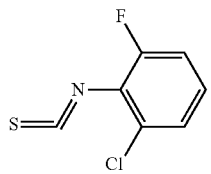 [SMILES: Fc1cccc(Cl)c1N=C=S]

The title compound was prepared following the procedure described for intermediate-2 using 2-chloro-6-fluoro aniline (3.0 g, 19.35 mmol), thiophosgene (5.01 g, 43.47 mmol) and N-ethyl di-isopropyl amine (8.0 g, 64.00 mmol) to afford 1.0 g of the desired product. $^1$HNMR (DMSO-d$_6$): δ 7.26 (m, 2H), 7.06 (t, J=9.6 Hz, 1H).

Intermediate-15

2-[(2-Chloro-6-fluorophenyl)amino]-7,7-dimethyl-7,8-dihydro-1H-furo[3,2-e]benzimidazole-5-carboxylic acid

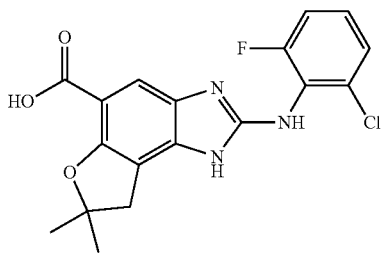 [SMILES: CC1(C)Cc2c(c(C(=O)O)cc3nc(Nc4c(F)cccc4Cl)[nH]c23)O1]

Step 1:—Preparation of methyl 2-[(2-chloro-6-fluorophenyl)amino]-7,7-dimethyl-7,8-dihydro-1H-furo[3,2-e]benzimidazole-5-carboxylate The title compound was prepared following the procedure described for step-1 of intermediate-3 using intermediate-1 (0.800 g, 3.38 mmol), acetonitrile (8.0 mL), intermediate-14 (1.0 g, 5.37 mmol) and N,N-di-isopropyl carbodimide (0.6 mL) to afford 0.600 g of the desired product. $^1$HNMR (DMSO-d$_6$): δ 1.42 (s, 6H), 2.97 (s, 2H), 3.72 (s, 3H), 7.30 (m, 3H), 7.83 (m, 1H), 10-11 (s, 2H); MS [M+H]$^+$: 390.18.

Step 2:—Preparation of 2-[(2-chloro-6-fluorophenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.650 g, 1.66 mmol), methanol (2.0 mL) and (50%) aqueous solution of sodium hydroxide (1.8 g, 45.0 mmol) to afford 0.450 g of the desired product. $^1$HNMR (DMSO-d$_6$): δ 1.42 (s, 6H), 2.96 (s, 2H), 7.29 (m, 3H), 7.37 (m, 1H), 11-12 (s, 3H); MS [M+H]$^+$: 376.19.

Intermediate-16

1-Cyclopentylmethanamine

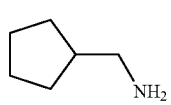

Step 1:—Preparation of 1-cyclopentyl-N-hydroxymethanimine

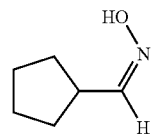

To a solution of cyclopentyl carboxyaldehyde (0.200 g, 2.04 mmol) in ethanol was added hydroxylamine hydrochloride (0.170 g, 2.46 mmol) and pyridine (1 mL). The reaction mixture was refluxed for 3-4 h. The reaction mixture was concentrated and the obtained solid was quenched in water and extracted with ethyl acetate. The organic layer was dried over anhydrous sodium sulphate and concentrated to get 0.200 g of the desired product. $^1$HNMR (DMSO-d$_6$): δ 1.29-1.31 (m, 4H), 1.72-1.76 (m, 4H), 2.54-2.62 (m, 1H), 7.24 (d, J=6.3 Hz, 1H), 10.23 (s, 1H).

Step 2:—Preparation of 1-cyclopentylmethanamine

A solution of step-1 intermediate (0.180 g) in ethanol (6 mL) and PdCl$_2$ (0.075 g) was stirred in Parr apparatus under pressure 60 psi for 4-5 h. The reaction mixture was filtered through celite and concentrated the filtrate to get 0.100 g of the desired product. $^1$HNMR (DMSO-d$_6$): δ 1.20 (m, 4H), 1.72 (m, 4H), 2.09 (s, 1H), 4.19 (s, 2H), 8.19 (s, 2H); MS [M+H]$^+$: 100.08.

Intermediate-17

2-[(2-Chloro-6-fluorophenyl)amino]-7-methyl-1H-furo[3,2-e]benzimidazole-5-carboxylic acid

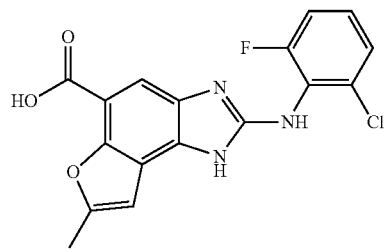 [SMILES: Cc1cc2c(o1)c(C(=O)O)cc1nc(Nc3c(F)cccc3Cl)[nH]c12]

Step 1:—Preparation of methyl 2-[(2-chloro-6-fluorophenyl)amino]-7-methyl-1H-furo[3,2-e]benzimidazole-5-carboxylate The title compound was prepared following the procedure described for step-1 of intermediate-3 using intermediate-7 (0.700 g, 3.18 mmol), acetonitrile (10.0 mL), intermediate-14 (0.800 g, 4.27 mmol) and N,N-di-isopropyl carbodimide (1.0 mL) to afford 0.500 g of the desired product.

Step 2:—Preparation of 2-[(2-chloro-6-fluorophenyl)amino]-7-methyl-1H-furo[3,2-e]benzimidazole-5-carboxylic acid The title compound was prepared following the procedure described for step-2 of intermediate-3 using step-1 intermediate (0.500 g, 1.34 mmol), methanol (2.0 mL) and (50%) aqueous solution of sodium hydroxide (1.5 g, 37.0 mmol) to afford 0.400 g of the desired product. ¹HNMR (DMSO-d₆): δ 3.66 (s, 3H), 6.66 (s, 1H), 7.33-7.42 (m, 4H), 7.59 (s, 1H), 11-12 (s, 2H); MS [M−H]⁻: 358.09.

Intermediate-18

2-Chloro-4-fluoro-1-isothiocyanatobenzene

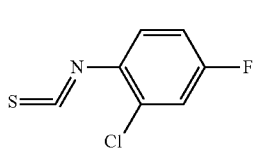 [SMILES: Fc1ccc(N=C=S)c(Cl)c1]

The title compound was prepared following the procedure described for intermediate-2 using 2-chloro-4-fluoro aniline (5.0 g, 34.48 mmol), thiophosgene (3.95 g, 34.34 mmol), N-ethyl di-isopropyl amine (8.80 g, 68.00 mmol) to afford 3.0 g of the desired product.

Intermediate-19

2-[(2-Chloro-4-fluorophenyl)amino]-7,7-dimethyl-7,8-dihydro-1H-furo[3,2-e]benzimidazole-5-carboxylic acid

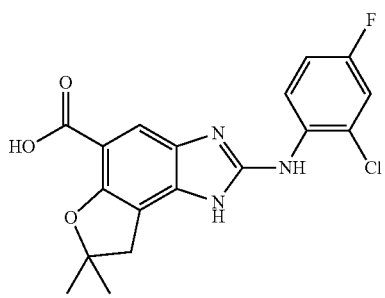

Step 1:—Preparation of methyl 2-[(2-chloro-4-fluorophenyl)amino]-7,7-dimethyl-7,8-dihydro-1H-furo[3,2-e]benzimidazole-5-carboxylate The title compound was prepared following the procedure described for step-1 of intermediate-3 using intermediate-1 (0.600 g, 2.54 mmol), acetonitrile (3.0 mL), intermediate-18 (0.600 g, 3.20 mmol) and N,N-di-isopropyl carbodimide (2.0 mL) to afford 0.450 g of the desired product. ¹HNMR (DMSO-d₆): δ 1.43 (s, 6H), 3.09 (s, 2H), 3.75 (s, 3H), 7.20-7.33 (m, 2H), 7.47-7.52 (m, 1H), 7.59 (s, 1H), 9.11 (s, 1H), 10.87 (s, 1H).

Step 2:—Preparation of 2-[(2-chloro-4-fluorophenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.450 g, 1.15 mmol), methanol (2.0 mL) and (50%) aqueous solution of sodium hydroxide (0.600 g, 15.0 mmol) to afford 0.350 g of the desired product. ¹HNMR (DMSO-d₆):
δ 1.44 (s, 6H), 3.07 (s, 2H), 7.23 (t, J=8.1 Hz, 1H), 7.46 (d, J=6.0 Hz, 1H), 7.55 (s, 1H), 8.57 (t, J=6.6 Hz, 1H), 9.72 (s, 1H), 11.85 (s, 2H); MS [M−H]⁻: 374.26.

Intermediate-20

2-Chloro-1-isothiocyanato-4-methylbenzene

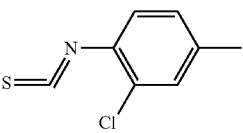

The title compound was prepared following the procedure described for intermediate-2 using 2-chloro-4-methyl aniline (2.0 g, 14.00 mmol), thiophosgene (1.62 g, 14.00 mmol) and N-ethyl di-isopropyl amine (3.63 g, 28.00 mmol) to afford 1.5 g of the desired product.

Intermediate-21

2-[(2-Chloro-4-methylphenyl)amino]-7,7-dimethyl-7,8-dihydro-1H-furo[3,2-e]benzimidazole-5-carboxylic acid

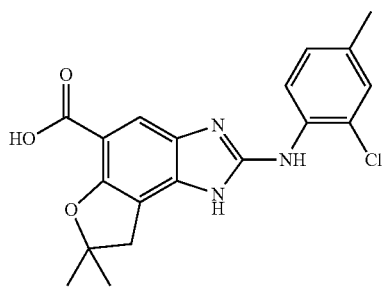 [SMILES: Cc1ccc(Nc2nc3cc(C(=O)O)c4c(c3[nH]2)CC(C)(C)O4)c(Cl)c1]

Step 1:—Preparation of methyl 2-[(2-chloro-4-methylphenyl)amino]-7,7-dimethyl-7,8-dihydro-1H-furo[3,2-e]benzimidazole-5-carboxylate The title compound was prepared following the procedure described for step-1 of intermediate-3 using intermediate-1 (1.000 g, 4.23 mmol), acetonitrile (5.0 mL), intermediate-20 (1.000 g, 5.42 mmol) and N,N-di-isopropyl carbodimide (1.0 mL) to afford 0.700 g of the desired product. ¹HNMR (DMSO-d₆): δ 1.45 (s, 6H), 2.28 (s, 3H), 3.09 (s, 2H), 3.75 (s, 3H), 7.18 (d, J=7.8 Hz, 1H), 7.31 (s, 1H), 7.58 (s, 1H), 8.36 (s, 1H), 8.96 (s, 1H), 10.87 (s, 1H); MS [M+H]⁺: 386.32.

Step 2:—Preparation of 2-[(2-chloro-4-methylphenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.700 g, 1.81 mmol), methanol (2.0 mL) and (50%) aqueous solution of sodium hydroxide (1.200 g, 30.0 mmol) to afford 0.500 g of the desired product. ¹HNMR (DMSO-d₆):
δ 1.44 (s, 6H), 2.26 (s, 3H), 3.04 (s, 2H), 7.14 (d, J=8.4 Hz, 1H), 7.25 (s, 1H), 7.53 (s, 1H), 8.45 (d, J=8.4 Hz, 1H), 9.58 (s, 1H), 12.13 (s, 2H); MS [M−H]⁻: 374.26.

Intermediate-22

2-(4-Aminophenyl)-2-methylpropanenitrile

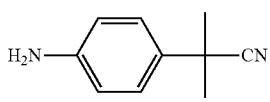

Step 1:—Preparation of 2-methyl-2-(4-nitrophenyl)propanenitrile

To a solution of 4-nitrophenyl acetonitrile (9.0 g, 55.5 mol) in DCM (75 mL) iodomethane (26.0 g, 183.0 mol) and sodium hydroxide (6.0 g, 150 mol) and tetrabutyl ammonium bromide (1.0 g, 3.1 mol) were added. The reaction mixture was stirred at RT for 16 h. The organic layer was separated and dried over anhydrous sodium sulphate and concentrated to afford 10.8 g of the desired compound.

Step 2:—Preparation of 2-(4-aminophenyl)-2-methylpropanenitrile

To a solution of step-1 intermediate (4.6 g, 24.21 mol) in ethyl acetate, tin (II) chloride (27.31 g, 121 mol) was added. The reaction mixture was refluxed for 3 h. The reaction mixture was quenched in water and basified with 50% sodium hydroxide. The reaction mixture was extracted with ethyl acetate and concentrated to afford 3.20 g of the desired product. ¹HNMR (CDCl₃): δ 1.67 (s, 6H), 3.48 (s, 2H), 6.68 (d, J=8.7 Hz, 2H), 7.24 (d, J=8.7 Hz, 2H).

Intermediate-23

2,4-Dichloro-1-isothiocyanatobenzene

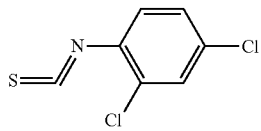

The title compound was prepared following the procedure described for intermediate-2 using 2,4-dichloro aniline (5.0 g, 30.86 mmol), thiophosgene (3.54 g, 30.86 mmol) and N-ethyl di-isopropyl amine (7.94 g, 61.55 mmol) to afford 4.0 g of the desired product. ¹HNMR (CDCl₃): δ 7.39 (s, 1H), 7.39-7.12 (m, 2H).

Intermediate-24

2-[(2,4-Dichlorophenyl)amino]-7,7-dimethyl-7,8-dihydro-1H-furo[3,2-e]benzimidazole-5-carboxylic acid

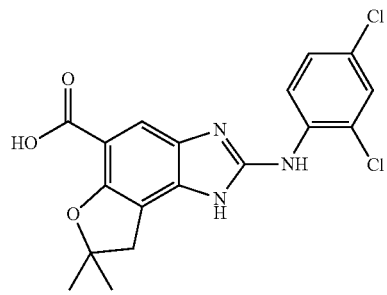

Step 1:—Preparation of methyl 2-[(2,4-dichlorophenyl)amino]-7,7-dimethyl-7,8-dihydro-1H-furo[3,2-e]benzimidazole-5-carboxylate The title compound was prepared following the procedure described for step-1 of intermediate-3 using intermediate-1 (1.0 g, 3.80 mmol), acetonitrile (5.0 mL), intermediate-23 (1.000 g, 4.90 mmol) and N,N-di-isopropyl carbodimide (2.0 mL) to afford 0.400 g of the desired product.

Step 2:—Preparation of 2-[(2,4-dichlorophenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.400 g, 1.01 mmol), methanol (1.0 mL) and (50%) aqueous solution of sodium hydroxide (0.600 g, 15.0 mmol) to afford 0.300 g of the desired product. ¹HNMR (DMSO-d₆): δ 1.45 (s, 6H), 3.09 (s, 2H), 7.46 (d, J=8.7 Hz, 1H), 7.61 (d, J=5.4 Hz, 2H), 8.66 (d, J=9.3 Hz, 1H), 9-10 (s, 1H), 11.0-12.0 (s, 2H); MS [M−H]⁻: 392.24.

Intermediate-25

6-(Pyrrolidin-1-yl)pyridin-3-amine

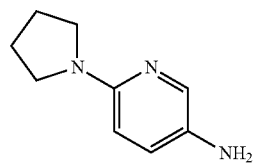

Step 1:—Preparation of 5-nitro-2-(pyrrolidin-1-yl)pyridine

To a solution of 2-chloro-5-nitropyridine (5.0 g, 0.0315 mol) in ethanol, pyrrolidine (5.5 g, 0.094 mol) was added. The reaction mixture was refluxed for 4-5 h. Ethanol was removed under vacuum and was diluted with water. The reaction mixture was extracted with ethyl acetate and concentrated to afford 5.0 g of the desired product. ¹HNMR (CDCl₃): δ 2.09 (s, 4H), 3.47-3.71 (m, 4H), 6.34 (d, J=6.3 Hz, 1H), 8.18 (dd, J=1.8 Hz, 1.8 Hz, 1H), 9.05 (s, 1H); MS [M+H]⁺: 194.30

Step 2:—Preparation of 6-(pyrrolidin-1-yl)pyridin-3-amine

To a solution of step-1 intermediate (3.0 g, 0.015 mol) in ethanol (10 mL) Pd/C (catalytic amount) was added. The reaction mixture was subjected for hydrogenation in Parr apparatus under 30 psi for 5-6 hours. The reaction mixture was filtered and concentrated the filtrate to afford 1.0 g of the desired product. $^1$HNMR (CDCl$_3$): δ 1.86-1.90 (m, 4H), 3.22 (m, 4H), 4.00-5.00 (s, 2H), 6.26 (d, J=8.7 Hz, 1H), 9.01 (dd, J=3.0 Hz, 1H), 7.53 (s, 1H); MS [M+H]$^+$: 164.38.

Intermediate-26

1-Chloro-2-isothiocyanato-4-methylbenzene

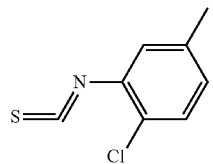

Step 1:—Preparation of 2-chloro-5-methylaniline

To a solution of 1-chloro-4-methyl-2-nitrobenzene (10.0 g, 0.058 mol) in methanol (50 mL), iron powder (3.0 g, 0.055 mol) and conc. HCl (10 mL) were added. The reaction mixture was stirred at RT for 2 h. The reaction mixture was diluted with water and basified with NaHCO$_3$ solution and extracted with DCM. The organic layer was separated and dried over anhydrous sodium sulphate and concentrated to afford 5.0 g of the desired compound. $^1$HNMR (CDCl$_3$): δ 2.23 (s, 3H), 3.94 (s, 2H), 6.50 (d, J=7.8 Hz, 1H), 6.57 (s, 1H), 7.10 (d, J=7.8 Hz, 1H); MS [M+H]$^+$: 142.25.

Step 2:—Preparation of 1-chloro-2-isothiocyanato-4-methylbenzene

The title compound was prepared following the procedure described for intermediate-2 using step-1 intermediate (5.0 g, 0.035 mol), thiophosgene (4.05 g, 0.035 mol) and N-ethyl di-isopropyl amine (9.1 g, 0.070 mol) to afford 3.0 g of the desired product. $^1$HNMR (CDCl$_3$): δ 2.30 (s, 3H), 6.98 (d, J=8.4 Hz, 1H), 7.05 (s, 1H), 7.28 (d, J=8.4 Hz, 1H); MS [M-H]$^-$: 182.27.

Intermediate-27

2-[(2-Chloro-5-methylphenyl)amino]-7,7-dimethyl-7,8-dihydro-1H-furo[3,2-e]benzimidazole-5-carboxylic acid

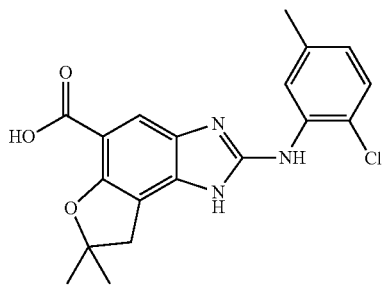 [SMILES: Cc1ccc(Cl)c(Nc2nc3cc(C(=O)O)c4c(c3[nH]2)CC(C)(C)O4)c1]

Step 1:—Preparation methyl 2-[(2-chloro-5-methylphenyl)amino]-7,7-dimethyl-7,8-dihydro-1H-furo[3,2-e]benzimidazole-5-carboxylate The title compound was prepared following the procedure described for step-1 of intermediate-3 using intermediate-1 (0.100 g, 0.450 mmol), acetonitrile (10.0 mL), 1-chloro-2-isothiocyanato-4-methylbenzene (intermediate-26) (1.000 g, 5.49 mmol) and N,N-di-isopropyl carbodimide (2.0 mL) to afford 0.600 g of the desired product. $^1$HNMR (DMSO-d$_6$): δ 1.44 (s, 6H), 2.03 (s, 3H), 3.14 (s, 2H), 3.73 (s, 3H), 6.84 (d, J=8.4 Hz, 1H), 7.32 (d, J=8.4 Hz, 1H), 7.59 (s, 1H), 8.26 (s, 1H), 8.81 (s, 1H), 11.0 (brs, 1H); MS [M+H]$^+$: 386.31.

Step 2:—Preparation of 2-[(2-chloro-5-methylphenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.600 g, 1.55 mmol), methanol (1.0 mL) and (50%) aqueous solution of sodium hydroxide (0.600 g, 15.0 mmol) to afford 0.400 g of the desired product. $^1$HNMR (DMSO-d$_6$): δ 1.43 (s, 6H), 2.29 (s, 3H), 3.03 (s, 2H), 6.75 (d, J=7.8 Hz, 1H), 7.25 (d, J=8.4 Hz, 1H), 7.51 (s, 1H), 8.44 (s, 1H), 9-10 (s, 1H), 11.0 (brs, 1H).

Intermediate-28

1-tert-Butyl-2-isothiocyanatobenzene

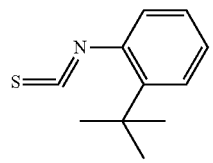

The title compound was prepared following the procedure described for intermediate-2 using 2-tert-butylaniline (5.0 g, 0.033 mol), thiophosgene (3.80 g, 0.033 mol) and N-ethyl di-isopropyl amine (8.5 g, 0.066 mol) to afford 3.0 g of the desired product.

Intermediate-29

2-[(2-tert-Butylphenyl)amino]-7,7-dimethyl-7,8-dihydro-1H-furo[3,2-e]benzimidazole-5-carboxylic acid

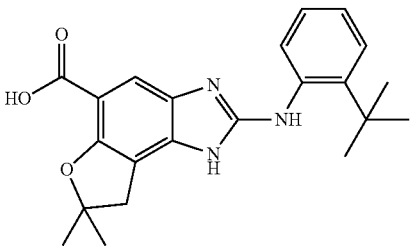 [SMILES: CC1(C)Cc2c(c(C(=O)O)cc3nc(Nc4ccccc4C(C)(C)C)[nH]c23)O1]

Step 1:—Preparation of methyl 2-[(2-tert-butylphenyl)amino]-7,7-dimethyl-7,8-dihydro-1H-furo[3,2-e]benzimidazole-5-carboxylate The title compound was prepared following the procedure described for step-1 of intermediate-3 using intermediate-1 (0.100 g, 0.450 mmol), acetonitrile (10.0 mL), intermediate-28 (1.000 g, 5.23 mmol) and N,N-di-isopropyl carbodimide (2.0 mL) to afford 0.700 g of the desired product. $^1$HNMR (DMSO-$d_6$): δ 1.25 (s, 9H), 1.36 (s, 6H), 3.00 (s, 2H), 3.71 (s, 3H), 7.27-7.46 (m, 5H), 8.67 (s, 1H), 10.62 (s, 1H); MS [M+H]$^+$: 394.51.

Step 2:—Preparation of 2-[(2-tert-butylphenyl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.700 g, 1.77 mmol), methanol (1.0 mL) and (50%) aqueous solution of sodium hydroxide (0.700 g, 17.50 mmol) to afford 0.400 g of the desired product. $^1$HNMR (DMSO-$d_6$): δ 1.37 (s, 9H), 1.42 (s, 6H), 2.98 (s, 2H), 7.21-7.45 (m, 5H), 9.00-10.00 (s, 1H), 11.0 (s, 1H); MS [M+H]$^+$: 380.31.

Intermediate-30

Methyl 5-amino-4-[(2-methoxyethyl)amino]-2,2-dimethyl-2,3-dihydro-1-benzofuran-7-carboxylate

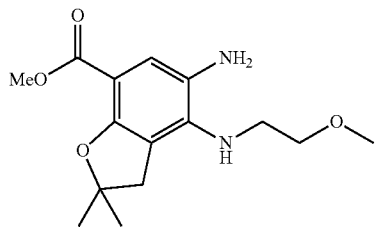

Step 1:—Preparation of methyl 2,4-difluoro-5-nitrobenzoate

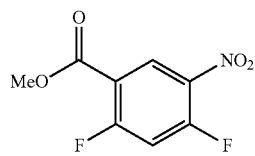 [SMILES: COC(=O)c1cc([N+](=O)[O-])c(F)cc1F]

The title compound was prepared following the procedure described for step-2 of intermediate-1 using 2,4-difluoro benzoic acid (13.0 g, 0.640 mol), methanol (300 mL) and conc. H$_2$SO$_4$ (130 mL) to afford 12.0 g of the desired product. $^1$HNMR (DMSO-$d_6$): 3.90 (s, 3H), 7.90 (t, J=10.1 Hz, 1H), δ 8.60 (t, J=7.8 Hz, 1H).

Step 2:—Preparation of methyl 2-fluoro-4-[(2-methoxyethyl)amino]-5-nitrobenzoate

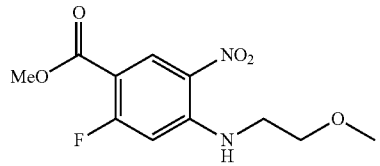 [SMILES: COCCNc1cc(F)c(C(=O)OC)cc1[N+](=O)[O-]]

The title compound was prepared following the procedure described for step-3 of intermediate-1 using step-1 intermediate (5.5 g, 0.025 mol), 2-methoxyethanamine (2.09 g, 0.027 mol), TEA (15 mL) and THF (30 mL) to afford 7.0 g of the desired product. $^1$HNMR (DMSO-$d_6$): δ 3.30 (s, 3H), 3.33 (d, J=8.4 Hz, 2H), 3.48-3.51 (m, 1H), 3.57 (s, 3H), 3.81 (s, 2H), 6.99 (d, J=14.4 Hz, 1H), 8.57-8.62 (s, 1H); MS [M−H]$^-$: 271.26.

Step 3:—Preparation of methyl 2-methoxy-4-([2-methoxyethyl)amino]-5-nitrobenzoate

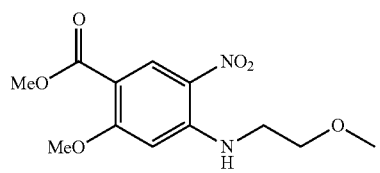 [SMILES: COCCNc1cc(OC)c(C(=O)OC)cc1[N+](=O)[O-]]

The title compound was prepared following the procedure described for step-4 of intermediate-1 using step-2 intermediate (7.0 g, 0.025 mol), sodium methoxide (11.1 g, 0.205 mol) and methanol (300 mL) to afford 4.5 g of the desired product. $^1$HNMR (DMSO-$d_6$): δ 3.34 (s, 4H), 3.62 (s, 3H), 3.75 (s, 3H), 3.92 (s, 3H), 6.43 (s, 1H), 8.56 (s, 2H); MS [M+H]$^+$: 285.23.

Step 4:—Preparation of methyl 2-hydroxy-4-([2-methoxyethyl)amino]-5-nitrobenzoate

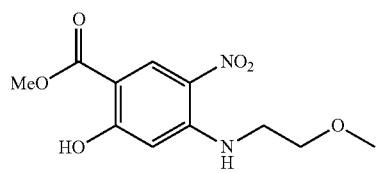

The title compound was prepared following the procedure described for step-5 of intermediate-1 using step-3 intermediate (3.0 g, 0.010 mol), anhydrous aluminum trichloride (6.320 g, 0.047 mol) and EDC (500 mL) to afford 2.4 g of the desired product.

Step 5:—Preparation of methyl 4-[(2-methoxyethyl) amino]-2-[(2-methylprop-2-en-1-yl)oxy]-5-nitrobenzoate

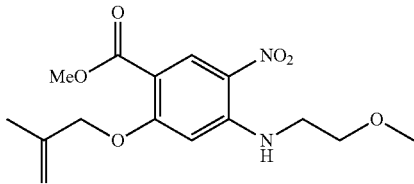 [SMILES: C=C(C)COc1cc(NCCOC)c([N+](=O)[O-])cc1C(=O)OC]

The title compound was prepared following the procedure described for step-6 of intermediate-1 using step-4 intermediate (2.40 g, 0.088 mol), DMF (15.0 mL), dry potassium carbonate (2.19 g, 0.015 mol) and methallyl chloride (1.43 g, 0.015 mol) to afford 2.2 g of the desired product.

Step 6:—Preparation of methyl 2-hydroxy-4-([2-methoxyethyl)amino]-3-(2-methylprop-2-en-1-yl)-5-nitrobenzoate

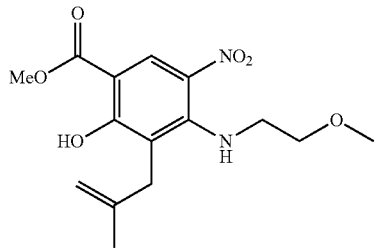 [SMILES: C=C(C)Cc1c(O)c(C(=O)OC)cc([N+](=O)[O-])c1NCCOC]

The title compound was prepared following the procedure described for step-7 of intermediate-1 using step-5 intermediate (2.200 g, 6.79 mmol) and N,N'-diethylaniline (50.0 mL) to afford 0.900 g of the desired product. $^1$HNMR (DMSO-d$_6$): δ 1.78 (s, 3H), 3.24 (s, 3H), 3.40-3.44 (m, 6H), 3.90 (s, 3H), 4.43 (s, 1H), 4.79 (s, 1H), 4.27 (s, 1H), 8.45 (s, 1H), 11.47 (s, 1H).

Step 7:—Preparation of methyl 4-[(2-methoxyethyl) amino]-2,2-dimethyl-5-nitro-2,3-dihydro-1-benzofuran-7-carboxylate

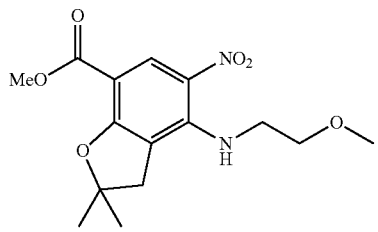 [SMILES: COCCNc1c([N+](=O)[O-])cc(C(=O)OC)c2c1CC(C)(C)O2]

The title compound was prepared following the procedure described for step-8 of intermediate-1 using step-6 intermediate (0.900 g, 2.77 mmol) and formic acid (20.0 mL) to afford 0.370 g of the desired product. $^1$HNMR (DMSO-d$_6$): δ 1.40 (s, 6H), 3.24 (s, 2H), 3.40 (s, 3H), 3.58 (t, J=4.8 Hz, 2H), 3.71 (t, J=4.8 Hz, 2H), 3.83 (s, 3H), 8.66 (s, 1H), 8.79 (s, 1H).

Step 8:—Preparation of methyl 5-amino-4-([2-methoxyethyl)amino]-2,2-dimethyl-2,3-dihydro-1-benzofuran-7-carboxylate The title compound was prepared following the procedure described for step-8 of intermediate-1 using step-7 intermediate (0.370 g, 1.14 mmol), methanol (10 mL), iron powder (catalytic amount) and conc. HCl (0.5 mL) to afford 0.300 g of the desired product. $^1$HNMR (DMSO-d$_6$): δ 1.35 (s, 6H), 3.02 (s, 2H), 3.24 (s, 3H), 3.40 (s, 4H), 3.63 (s, 3H), 4.35 (s, 2H), 4.88 (s, 1H), 6.94 (s, 1H).

Intermediate-31

2-[(2,6-Dichlorophenyl)amino]-1-(2-methoxyethyl)-7,7-dimethyl-7,8-dihydro-1H-furo[3,2-e]benzimidazole-5-carboxylic acid

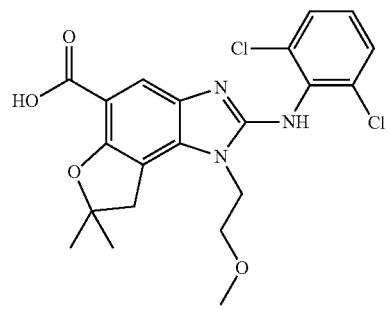 [SMILES: COCCn1c(Nc2c(Cl)cccc2Cl)nc2cc(C(=O)O)c3c(c21)CC(C)(C)O3]

Step 1:—Preparation of methyl 2-[(2,6-dichlorophenyl)amino]-1-(2-methoxyethyl)-7,7-dimethyl-7,8-dihydro-1H-furo[3,2-e]benzimidazole-5-carboxylate The title compound was prepared following the procedure described for step-1 of intermediate-3 using intermediate-30 (0.300 g, 1.02 mmol), acetonitrile (5.0 mL), intermediate-5 (0.300 g, 1.47 mmol) and N,N-di-isopropyl carbodimide (1.0 mL) to afford 0.370 g of the desired product. MS [M+H]$^+$: 464.37.

Step 2:—Preparation of 2-[(2,6-dichlorophenyl) amino]-1-(2-methoxyethyl)-7,7-dimethyl-7,8-dihydro-1H-furo[3,2-e]benzimidazole-5-carboxylic acid The title compound was prepared following the procedure described for step-2 of intermediate-3 using step-1 intermediate (0.370 g, 0.799 mmol), methanol (3.0 mL) and (50%) aqueous solution of sodium hydroxide (0.800 g, 20.0 mmol) to afford 0.200 g of the desired product. $^1$HNMR (DMSO-d$_6$): δ 1.43 (s, 6H), 3.20-3.33 (s, 5H), 3.84 (s, 2H), 4.09 (s, 2H), 6.98-7.02 (s, 2H), 7.34-7.43 (m, 1H), 7.54 (d, J=7.8 Hz, 1H), 10.31 (s, 1H), 12.03 (s, 1H); MS [M+H]$^+$: 450.41.

Intermediate-32

3-Isothiocyanato-2,6-dimethylpyridine

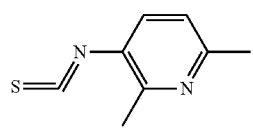

The title compound was prepared following the procedure described for intermediate-2 using 2,6-dimethylpyridin-3-amine (1.0 g, 8.26 mmol), thiophosgene (0.949 g, 8.25 mmol) and N-ethyl di-isopropyl amine (3.20 g, 24.80 mmol) in DCM (20 mL) to afford 0.900 g of the desired product. $^1$HNMR (DMSO-d$_6$): δ 2.44 (s, 6H), 7.18 (d, J=8.1 Hz, 1H), 7.70 (t, J=8.1 Hz, 1H); MS [M+H]$^+$: 165.28.

Intermediate-33

2-[(2,6-Dimethylpyridin-3-yl)amino]-7,7-dimethyl-7,8-dihydro-1H-furo[3,2-e]benzimidazole-5-carboxylic acid

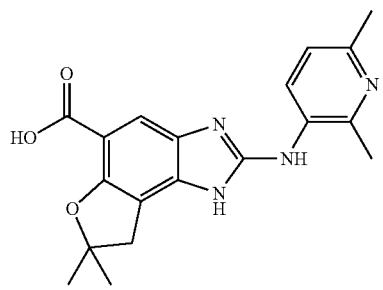 [SMILES: Cc1ccc(Nc2nc3cc(C(=O)O)c4c(c3[nH]2)CC(C)(C)O4)c(C)n1]

Step 1:—Preparation of methyl 2-[(2,6-dimethylpyridin-3-yl)amino]-7,7-dimethyl-7,8-dihydro-1H-furo[3,2-e]benzimidazole-5-carboxylate The title compound was prepared following the procedure described for step-1 of intermediate-3 using intermediate-1 (0.100 g, 0.450 mmol), acetonitrile (10.0 mL), intermediate-32 (0.850 g, 5.21 mmol) and N,N-di-isopropyl carbodimide (2.0 mL) to afford 0.500 g of the desired product. $^1$HNMR (DMSO-d$_6$): δ 1.44 (s, 6H), 2.40 (s, 3H), 2.49 (s, 3H), 3.05 (s, 2H), 3.74 (s, 3H), 7.11 (d, J=8.4 Hz, 1H), 7.51 (s, 1H), 8.19 (d, J=7.8 Hz, 1H), 8.90 (s, 1H), 10.76 (s, 1H); MS [M+H]$^+$: 367.60.

Step 2:—Preparation of 2-[(2,6-dimethylpyridin-3-yl)amino]-7,7-dimethyl-7,8-dihydro-1H-furo[3,2-e]benzimidazole-5-carboxylic acid The title compound was prepared following the procedure described for step-2 of intermediate-3 using step-1 intermediate (0.500 g, 1.36 mmol), methanol (1.0 mL) and (50%) aqueous solution of sodium hydroxide (0.500 g, 12.50 mmol) to afford 0.30 g of the desired product. $^1$HNMR (DMSO-d$_6$): δ 1.44 (s, 6H), 2.38 (s, 3H), 2.47 (s, 3H), 3.04 (s, 2H), 7.06 (d, J=7.8 Hz, 1H), 7.45 (s, 1H), 8.41 (s, 1H), 9.89 (s, 1H), 11.50 (s, 1H), 12-13.00 (s, 1H); MS [M+H]$^+$: 353.22.

Intermediate-34

1-Chloro-2-isothiocyanato-3-methylbenzene

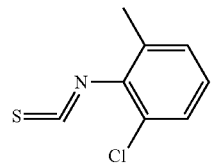

The title compound was prepared following the procedure described for Intermediate-2 using 2-chloro-6-methylaniline (1.0 g, 0.01 mol), thiophosgene (1.15 g, 0.01 mol) and N-ethyl di-isopropyl amine (2.58 g, 0.020 mol) to afford 0.500 g of the desired product. $^1$HNMR (CDCl$_3$): δ 2.39 (s, 3H), 7.10 (s, 2H), 7.21-7.25 (m, 1H); MS [M+H]$^+$: 183.32.

Intermediate-35

2-[(2-Chloro-6-methylphenyl)amino]-7,7-dimethyl-7,8-dihydro-1H-furo[3,2-e]benzimidazole-5-carboxylic acid

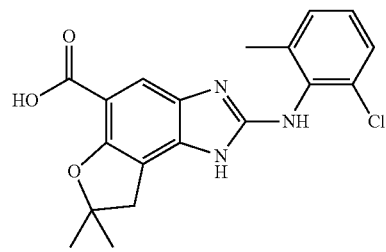 [SMILES: Cc1cccc(Cl)c1Nc1nc2cc(C(=O)O)c3c(c2[nH]1)CC(C)(C)O3]

Step 1:—Preparation methyl 2-[(2-chloro-6-methylphenyl)amino]-7,7-dimethyl-7,8-dihydro-1H-furo[3,2-e]benzimidazole-5-carboxylate

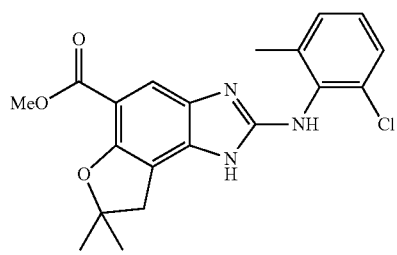 [SMILES: COC(=O)c1cc2nc(Nc3c(C)cccc3Cl)[nH]c2c2c1OC(C)(C)C2]

The title compound was prepared following the procedure described for Step-1 of Intermediate-3 using methyl 4,5-diamino-2,2-dimethyl-2,3-dihydro-1-benzofuran-7-carboxylate (Intermediate-1, 0.600 g, 2.54 mmol), acetonitrile (10.0 mL), 1-chloro-2-isothiocyanato-3-methylbenzene (Intermediate-34, 0.500 g, 2.73 mmol) and N,N-di-isopropyl carbodimide (0.300 g) to afford 0.500 g of the desired product. $^1$HNMR (DMSO-d$_6$): δ 1.42 (s, 6H), 2.23 (s, 3H), 2.98 (s, 2H), 3.71 (s, 3H), 7.02 (d, J=7.5 Hz, 1H), 7.23-7.41 (m, 3H), 9.00 (s, 1H), 10.82 (s, 1H); MS [M+H]$^+$: 386.32.

Step 2:—Preparation of 2-[(2-chloro-6-methylphenyl)amino]-7,7-dimethyl-7,8-dihydro-1H-furo[3,2-e]benzimidazole-5-carboxylic acid The title compound was prepared by following the procedure described for Step-2 of Intermediate-3 using methyl 2-[(2-chloro-6-methylphenyl)amino]-7,7-dimethyl-7,8-dihydro-1H-furo[3,2-e]benzimidazole-5-carboxylate (0.500 g, 1.29 mmol), methanol (1.0 mL) and (50%) aqueous solution of sodium hydroxide (0.500 g, 12.50 mmol) to afford 0.400 g of the desired product. $^1$HNMR (DMSO-$d_6$): δ 1.40 (s, 6H), 2.21 (s, 3H), 2.94 (s, 2H), 7.18-7.34 (m, 4H), 11.0-12.00 (s, 3H), 12-13.00 (s, 1H); MS [M+H]$^+$: 372.34.

Intermediate-36

6-(Difluoromethoxy)pyridin-3-amine

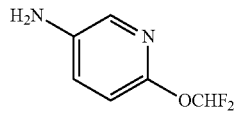 [SMILES: Nc1ccc(OC(F)F)nc1]

Step-1:—Preparation of 2-(difluoromethoxy)-5-nitropyridine

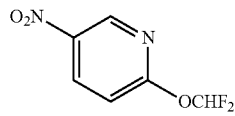

To a solution of 2-hydroxy-5-nitro pyridine (10 g, 0.071 mol) in acetonitrile (100 mL) was added sodium chlorodifluoroacetate (11.5 g, 0.075 mol). The reaction mass was refluxed for 72 h. The excess of solvent was removed under vacuum and the reaction mass was diluted with ethyl acetate and water. The organic layer was separated, dried over anhydrous sodium sulphate and concentrated. The obtained crude was purified by column chromatography on neutral alumina eluting with 10% EtOAc: Pet.ether to afford 0.900 g of the desired product. $^1$HNMR (DMSO-$d_6$): δ 7.05 (d, J=8.7 Hz, 1H), 7.53 (d, J=71.4 Hz, 1H), 8.54 (dd, J=8.1 Hz & 5.4 Hz, 1H), 7.91 (s, 1H); MS [M]$^-$: 190.83.

Step-2:—Preparation of 6-(difluoromethoxy)pyridin-3-amine

To a solution of 2-(difluoromethoxy)-5-nitropyridine (0.900 g, 2.35 mmol) in ethanol (5.0 mL), was added iron powder (0.400 g, 7.14 mmol) and conc. HCl (0.2 mL). The reaction mass was refluxed for ½ h. Ethanol was removed under vacuum. To the reaction mass, water was added, basified with NaHCO$_3$ and extracted with DCM. The organic layer was separated, dried over anhydrous sodium sulphate and concentrated to afford 0.400 g of the desired product. $^1$HNMR (DMSO-$d_6$): δ 7.65 (s, 1H), 7.52-7.03 (t, J=72.0 Hz, 1H), 7.27 (s, 1H), 6.73 (d, J=8.4 Hz, 1H); MS [M–H]$^-$: 159.14.

Intermediate-37

1-[4-(Trifluoromethyl)phenyl]cyclopropanamine

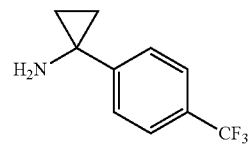

To a cold solution of 4-(trifluoromethyl)benzonitrile (1.03 g, 5.84 mmol) in ether (50 mL) was added titanium isopropoxide (1.50 mL, 5.83 mmol) and ethyl magnesium bromide (3.0M in ether) (1.55 g, 11.67 mmol) at –70° C. The reaction mass was stirred at RT for 1 h and boron trifluoride etherate (4.0 mL) was added. The reaction mass was stirred at RT for 1 h. The reaction mass was quenched in HCl:NaOH (30 mL). The reaction mass was extracted with ether and the organic layer was concentrated to afford 0.420 g of the desired product. $^1$HNMR (CDCl$_3$): δ 1.05 (s, 2H), 1.60 (s, 2H), 1.78 (s, 2H), 7.36 (d, J=7.8 Hz, 2H), 7.55 (d, J=8.1 Hz, 2H).

Intermediate-38

1-[2-(Trifluoromethyl)phenyl]cyclopropanamine

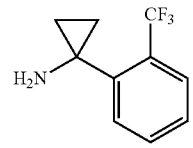

The title compound was prepared following the procedure described for Intermediate-37 using 2-(trifluoromethyl)benzonitrile (1.03 g, 5.84 mmol), ethyl magnesium bromide (3.0M in ether) (1.55 g, 11.67 mmol), boron trifluoride etherate (4.0 mL) and HCl:NaOH (30 mL) to afford 0.380 g of the desired product. $^1$H NMR (300 MHz, DMSO $d_6$): δ 0.82-0.84 (s, 2H), 0.91-0.93 (s, 2H), 2.24 (s, 2H), 7.41 (t, J=6.6 Hz, 1H), 7.58-7.67 (m, 3H).

Intermediate-39

3-(1,1-Difluoroethyl)aniline

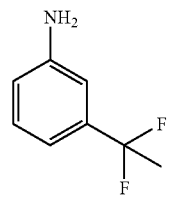

Step-1:—Preparation of 1-(1,1-difluoroethyl)-3-nitrobenzene

To a cold solution of 1-(3-nitrophenyl)ethanone (2.0 g, 0.012 mol) in DCM (20 mL) was added DAST (3.9 g, 0.024 mol) at −78° C. The reaction mass was stirred at RT for 24 h. The reaction mass was quenched in water, basified with NaHCO$_3$ and extracted with DCM. The organic layer was separated, dried over anhydrous sodium sulphate and concentrated. The obtained crude was purified by column chromatography on neutral alumina eluting with 3% EtOAc: Pet. ether to afford 1.0 g of the desired product. $^1$HNMR (DMSO-d$_6$): δ 2.04 (t, J=19.5 Hz, 3H), 7.81 (t, J=8.1 Hz, 1H), 8.04 (d, J=7.8 Hz, 1H), 8.33-8.38 (m, 2H).

Step-2:—Preparation of 3-(1,1-Difluoroethyl)aniline

To a solution of 1-(1,1-difluoroethyl)-3-nitrobenzene (1.00 g, 5.34 mmol) in methanol (5.0 mL) was added Pd/C (catalytic amount) and ethylene diamine (catalytic amount). The reaction mixture was subjected for hydrogenation in Parr apparatus under 30 psi for 5-6 h. The excess of solvent was removed under vacuum to afford 0.800 g of the desired product. $^1$HNMR (DMSO-d$_6$): δ 1.88 (d, J=18.0 Hz, 3H), 3.74 (s, 1H), 7.72 (t, J=8.4 Hz, 1H), 6.81 (s, 1H), 6.87 (d, J=7.8 Hz, 1H), 7.19 (t, J=7.8 Hz, 1H).

Intermediate-40

2-Amino-5-chloropyridine 1-oxide

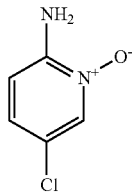

To a solution of 5-chloropyridin-2-amine (0.500 g, 3.90 mmol) in acetic acid (2.0 mL) was added 50% hydrogen peroxide (2.0 mL). The reaction mass was refluxed for 24 h. The excess of solvent was removed under vacuum to afford 0.450 g of the desired product. $^1$HNMR (DMSO-d$_6$): δ 6.79 (d, J=8.7 Hz, 1H), 6.93 (s, 2H), 7.21 (d, J=8.7 Hz, 1H), 8.25 (s, 1H); MS [M+H]$^+$: 145.23.

Intermediate-41

2-Amino-5-(trifluoromethyl)pyridine 1-oxide

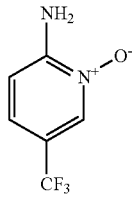

The title compound was prepared by following the procedure described for Intermediate-40 using 5-(trifluoromethyl)pyridin-2-amine (0.500 g, 3.08 mmol), acetic acid (5.0 mL) and 50% hydrogen peroxide (2.0 mL) to afford 0.475 g of the desired product. $^1$HNMR (DMSO-d$_6$): δ 6.88 (d, J=8.7 Hz, 1H), 7.40 (d, J=8.7 Hz, 1H), 7.49 (s, 2H), 8.49 (s, 1H).

Intermediate-42

6-(Cyclopropylmethoxy)pyridin-3-amine

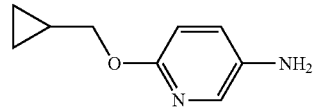

Step-1:—Preparation of 2-(cyclopropylmethoxy)-5-nitropyridine

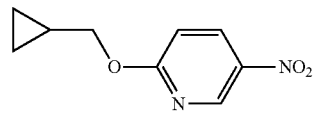

To a cold solution of 2-hydroxy-5-nitro pyridine (0.500 g, 3.57 mmol) in DMF (4.0 mL) was added cyclopropyl methyl bromide (0.481 g, 3.57 mmol) at 0° C. The reaction mass was stirred at RT for 5-6 h. The reaction mass was quenched in water and extracted with ethyl acetate. The organic layer was separated, dried over anhydrous sodium sulphate and concentrated. The obtained crude was purified by column chromatography on neutral alumina eluting with 10% EtOAc: Pet.ether to afford 0.200 g of the desired product. $^1$HNMR (DMSO-d$_6$): δ 0.45-0.48 (m, 2H), 0.70-0.75 (m, 2H), 1.10-1.28 (m, 1H), 3.87 (d, J=7.2 Hz, 2H), 6.57 (d, J=10.2 Hz, 1H), 8.10 (dd, J=3.0 Hz & 2.4 Hz, 1H), 8.77 (s, 1H).

Step-2:—Preparation of 6-(cyclopropylmethoxy)pyridin-3-amine

To a solution of 2-(cyclopropylmethoxy)-5-nitropyridine (2.0 g) in ethanol (10.0 mL) was added Pd/C (0.500 g) and ethylene diamine (5.0 mL). The reaction mixture was subjected for hydrogenation in Parr apparatus under 40 psi for 2-3 h. The reaction mass was quenched in water and extracted with DCM and concentrated the organic layer to afford 0.400 g of the desired product. $^1$HNMR (CDCl$_3$): δ 0.31-0.32 (m, 2H), 0.43-0.46 (m, 2H), 1.07-1.12 (m, 1H), 3.62 (d, J=6.6 Hz, 2H), 4.25 (s, 2H), 6.24 (d, J=6.6 Hz, 1H), 6.89 (s, 1H), 7.05 (dd, J=3.0 Hz & 2.4 Hz, 1H); MS [M+H]$^+$: 165.13.

Intermediate-43

2-Amino-5-chloro-3-fluoropyridine 1-oxide

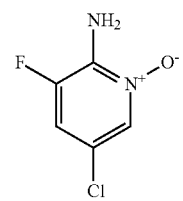

The title compound was prepared following the procedure described for Intermediate-40 using 5-chloro-3-fluoropyridin-2-amine (0.500 g, 3.42 mmol), acetic acid (5.0 mL) and 50% hydrogen peroxide (2.0 mL) to afford 0.450 g of the desired product. $^1$HNMR (DMSO-d$_6$): δ 7.14 (s, 2H), 7.55 (d, J=10.8 Hz, 1H), 8.25 (s, 1H).

Intermediate-44

1-[3-(Trifluoromethyl)phenyl]cyclopropanamine

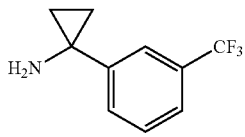 [SMILES: NC1(c2cccc(C(F)(F)F)c2)CC1]

The title compound was prepared following the procedure described for Intermediate-37 using 3-(trifluoromethyl)benzonitrile (1.03 g, 5.84 mmol), ethyl magnesium bromide (3.0M in ether) (1.55 g, 11.67 mmol), boron trifluoride etherate (4.0 mL) and HCl:NaOH (30 mL) to afford 0.300 g of the desired product. $^1$H NMR (300 MHz, DMSO d$_6$): δ 1.08 (t, J=6.0 Hz, 2H), 1.31 (t, J=6.3 Hz, 2H), 3.45-3.54 (s, 2H), 7.42-7.50 (m, 2H), 7.55 (t, J=7.2 Hz, 1H), 7.65 (s, 1H).

Intermediate-45

(4-Fluoro-2-(trifluoromethyl)phenyl)methanamine

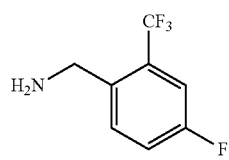 [SMILES: NCc1ccc(F)cc1C(F)(F)F]

To a solution of 4-fluoro-2-(trifluoromethyl)benzonitrile (2.0 g) in ethanol (10.0 mL) was added Raney Ni (catalytic amount). The reaction mixture was subjected for hydrogenation in Parr apparatus under 50 psi for 2-3 h. The reaction mass filtered through celite and concentrated the filtrate to afford 0.400 g of the desired product. $^1$HNMR (CDCl$_3$): δ 3.98 (s, 2H), 7.24 (t, J=9.0 Hz, 1H), 7.34 (d, J=8.7 Hz, 1H), 7.54 (t, J=7.8 Hz, 1H); MS [M+H]$^+$: 194.03.

Intermediate-46

5-(Difluoromethyl)-2-fluoroaniline

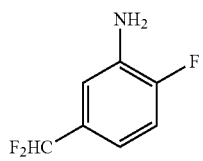

Step 1:—Preparation of 4-fluoro-3-nitrobenzaldehyde

To a cold solution of 4-fluorobenzaldehyde (1 g) in conc. H$_2$SO$_4$ was added conc. HNO$_3$ drop-wise at 0° C. The reaction mass was stirred at 0° C. for 1 h. The reaction mass was quenched in water and filtered to afford 1.2 g of the desired product. $^1$H NMR (300 MHz, DMSO d$_6$): δ 7.82 (t, J=9.3 Hz, 1H), 8.32 (m, 1H), 8.68 (d, J=7.2 Hz, 1H), 10.06 (s, 1H); MS [M+H]$^+$: 184.08.

Step 2:—Preparation of 4-(difluoromethyl)-1-fluoro-2-nitrobenzene

To a cold solution of 4-fluoro-3-nitrobenzaldehyde (0.300 g, 1.77 mmol) in DCM (5.0 mL) was added DAST (0.571 g, 3.54 mmol) at −78° C. The reaction mass was stirred at RT for 24 h. The reaction mass was quenched in water basified with NaHCO$_3$ and extracted with DCM. The organic layer was dried over anhydrous sodium sulphate and concentrated. The obtained crude was purified by column chromatography on neutral alumina eluting with 3% EtOAc: Pet. Ether to afford 0.200 g of the desired product. $^1$H NMR (300 MHz, DMSO d$_6$): δ 7.17 (t, J=54.9 Hz, 1H), 7.76 (t, J=10.5 Hz, 1H), 8.04 (m, 1H), 8.39 (d, J=6.6 Hz, 1H); MS [M+H]$^+$: 191.01.

Step-3:—Preparation of 5-(difluoromethyl)-2-fluoroaniline

To a solution of 4-(difluoromethyl)-1-fluoro-2-nitrobenzene (0.200 g, 1.04 mmol) in methanol (10 mL) was added iron powder (0.500 g, 8.92 mmol). The reaction mass was cooled at 0° C. followed by drop-wise addition of conc. HCl (3.0 mL). The reaction mass was stirred at RT for 1 h. The reaction mass was diluted with water and basified with sodium bicarbonate, extracted with DCM. The organic layer was separated, dried over anhydrous sodium sulphate and concentrated to afford 0.150 g of the desired product. $^1$H NMR (300 MHz, DMSO d$_6$): δ 5.44 (s, 2H), 6.67 (m, 1H), 6.86 (s, 1H), 6.93 (d, J=8.1 Hz, 1H), 7.05-7.12 (m, 1H); MS [M+H]$^+$: 160.13.

Intermediate-47

5-Cyclopropyl-2-fluoroaniline

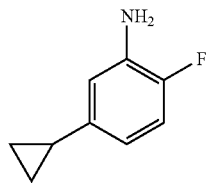 [SMILES: Nc1cc(C2CC2)ccc1F]

Step-1:—Preparation of 4-cyclopropyl-1-fluoro-2-nitrobenzene

Degas the solution of cyclopropyl boronic acid (0.585 g, 6.80 mmol) in dry toluene (6 mL) for 30 minutes. Then added tetrakis(triphenylphosphine) Palladium (0.090 g, 0.089 mmol) and 4-bromo-1-fluoro-2-nitrobenzene (1.0 g, 4.56 mmol) to the solution. The reaction mass was again degassed for 30 minutes and then added potassium carbonate (0.0628 g, 4.55 mmol). The reaction mass was refluxed for 48 h. The excess of solvent was removed under vacuum and the reaction mass was quenched in water and extracted with ethyl acetate. The organic layer was dried over anhydrous sodium sulphate and concentrated. The obtained crude was purified by column chromatography to afford 0.700 g of the desired product. $^1$H NMR (300 MHz, DMSO $d_6$): δ 0.74-0.76 (m, 2H), 1.00-1.02 (m, 2H), 2.08 (m, 1H), 7.45-7.48 (m, 2H), 7.83 (d, J=6.9 Hz, 1H); MS [M+H]$^+$: 164.13.

Step-2:—Preparation of 5-cyclopropyl-2-fluoroaniline

To a solution of 4-cyclopropyl-1-fluoro-2-nitrobenzene (0.700 g, 4.26 mmol) in acetic acid (6.0 mL) was added iron powder (1.0 g). The reaction mass was stirred at RT for 2 h. The reaction mass was quenched in water and basified with NaHCO$_3$, extracted with ethyl acetate. The organic layer was dried over anhydrous sodium sulphate and concentrated to afford 0.500 g of the desired product. $^1$H NMR (300 MHz, DMSO $d_6$): δ 0.50-0.52 (m, 2H), 0.83-0.85 (m, 2H), 1.71-1.74 (m, 1H), 4.97 (s, 2H), 6.21 (m, 1H), 6.44 (d, J=9.0 Hz, 1H), 6.77-6.84 (m, 1H).

Intermediate-48

Methyl 2-((2-chloro-4-methylpyridin-3-yl)amino)-7,7-dimethyl-7,8-dihydro-1H-benzofuro[4,5-d]imidazole-5-carboxylate

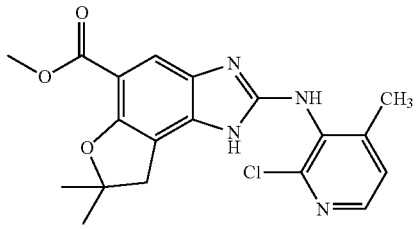

Step 1:—Preparation of 2-chloro-3-isothiocyanato-4-methylpyridine

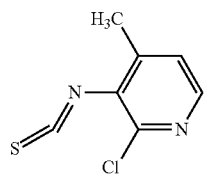

The title compound was prepared following the procedure described for Intermediate-2 using 2-chloro-4-methylpyridin-3-amine (4.0 g, 28 mmol), thiophosgene (3.2 g, 28 mmol), N-ethyl di-isopropyl amine (5 mL) in DCM (20 mL) to afford 0.900 g of the desired product.

Step 2:—Preparation of methyl 2-((2-chloro-4-methylpyridin-3-yl)amino)-7,7-dimethyl-7,8-dihydro-1H-benzofuro[4,5-d]imidazole-5-carboxylate The title compound was prepared following the procedure described for Step-1 of Intermediate-3 using methyl 4,5-diamino-2,2-dimethyl-2,3-dihydro-1-benzofuran-7-carboxylate (Intermediate-1, 1.00 g, 0.450 mmol), acetonitrile (10.0 mL), 2-chloro-3-isothiocyanato-4-methylpyridine (Step 1 product, 0.95 g, 0.521 mmol) and N,N-di-isopropyl carbodimide (2.0 mL) to afford 0.400 g of the desired product.

$^1$HNMR (DMSO-$d_6$): δ 1.42 (s, 6H), 2.24 (s, 3H), 2.98 (s, 2H), 3.72 (s, 3H), 7.31 (s, 1H), 7.37 (d, J=4.8 Hz, 1H), 8.15 (d, 1H), 10-11 (s, 2H); MS [M+H]$^+$: 387.24.

Intermediate-49

2-((2-Chloro-6-fluorophenyl)amino)-1,7,7-trimethyl-7,8-dihydro-1H-benzofuro[4,5-d]imidazole-5-carboxylic acid

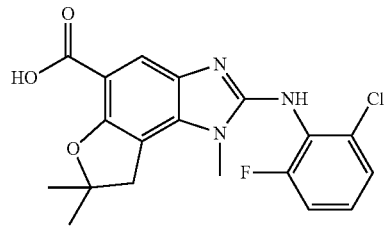 [SMILES: Cn1c(Nc2c(F)cccc2Cl)nc2cc(C(=O)O)c3c(c21)CC(C)(C)O3]

Step 1:—Preparation of methyl 2-fluoro-4-(methylamino)-5-nitrobenzoate

The title compound was prepared following the procedure described for Step-3 of Intermediate-1 using methyl 2,4-difluoro-5-nitrobenzoate (14.00 g, 0.0645 mmol), methyl amine.HCl (5.7 g, 0.083), TEA (6.0 mL) and THF (200.0 mL) to afford 12.00 g of the desired product. $^1$HNMR (DMSO-$d_6$): δ 2.96 (d, J=4.8 Hz, 3H), 3.81 (s. 3H), 6.82 (s, 1H), 6.86 (s, 1H), 8.57 (bs, 1H); [M+H]$^+$: 229.09.

Step 2:—Preparation of methyl 2-methoxy-4-(methylamino)-5-nitrobenzoate

The title compound was prepared following the procedure described for Step-4 of Intermediate-1 using methyl 2-fluoro-4-(methylamino)-5-nitrobenzoate (12.00 g, 0.0562 mmol) and sodium methoxide (22.73 g, 0.4210 mmol), methanol to afford 4.00 g of the desired product. $^1$HNMR (DMSO-$d_6$): δ 3.02 (d, J=4.5 Hz, 3H), 3.75 (s, 3H), 3.94 (s, 3H), 6.28 (s, 1H), 8.57 (s, 1H), 8.62 (bs, 1H).

Step 3:—Preparation of methyl 2-hydroxy-4-(methylamino)-5-nitrobenzoate

The title compound was prepared following the procedure described for Step-5 of Intermediate-1 using methyl 2-methoxy-4-(methylamino)-5-nitrobenzoate (4.00 g, 0.0166 mmol), anhydrous aluminium chloride (6.64 g, 0.0499 mmol) and EDC to afford 4.00 g of crude desired product. $^1$HNMR (DMSO-$d_6$): δ 2.93 (d, J=5.1 Hz, 3H), 3.86 (s, 3H), 6.28 (s, 1H), 8.48 (bs, 1H), 8.59 (s, 1H), 11.15 (s, 1H).

Step 4:—Preparation of methyl 2-((2-methylallyl)oxy)-4-(methylamino)-5-nitrobenzoate The title compound was prepared following the procedure described for Step-6 of Intermediate-1 using methyl 2-hydroxy-4-(methylamino)-5-nitrobenzoate (4.00 g, 0.0176 mmol), methallyl chloride (2.8 g, 0.0318 mmol), potassium carbonate (4.38 g, 0.037 mmol) and DMF (50.0 mL) to afford 3.500 g of desired product. $^1$HNMR (DMSO-$d_6$): δ 1.81 (s, 3H), 3.00 (d, J=4.8 Hz, 3H), 3.76 (s, 3H), 4.65 (s, 2H), 5.00 (s, 1H), 5.24 (s, 1H), 6.30 (s, 1H), 8.59 (s, 2H); [M+H]$^+$: 281.00.

Step 5:—Preparation of methyl 2,2-dimethyl-4-(methylamino)-5-nitro-2,3-dihydrobenzofuran-7-carboxylate

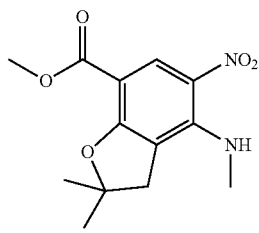 [SMILES: CNc1c([N+](=O)[O-])cc(C(=O)OC)c2c1CC(C)(C)O2]

To a solution of methyl 2-((2-methylallyl)oxy)-4-(methylamino)-5-nitrobenzoate (3.50 g, 0.0125 mmol) in DCM (50 mL), was added aluminium chloride (0.660 g, 0.0050 mmol) at −78° C. in lot wise manner. The reaction mass was stirred at RT for 18 h. The reaction mass was quenched in water and extracted with DCM. The organic layer was dried over anhydrous sodium sulphate and concentrated. The obtained crude was purified by column chromatography to afford 1.30 g of the desired product. $^1$HNMR (DMSO-$d_6$): δ 1.45 (s, 1H), 3.19 (d, J=5.4 Hz, 3H), 3.45 (s, 2H), 3.74 (s, 3H), 8.40 (bs, 1H), 8.53 (s, 1H); [M+H]$^+$: 281.11.

Step 6:—Preparation of methyl 5-amino-2,2-dimethyl-4-(methylamino)-2,3-dihydrobenzofuran-7-carboxylate

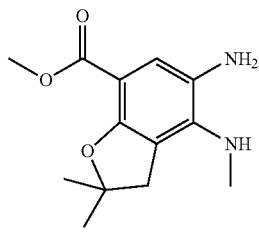

The title compound was prepared following the procedure described for Step-9 of Intermediate-1 using methyl 2,2-dimethyl-4-(methylamino)-5-nitro-2,3-dihydrobenzofuran-7-carboxylate (1.3 g), iron powder (cat. amt.), conc HCl (catalytic amount) and methanol (100.0 mL) to afford 1.1 g of desired product.

Step 7:—Preparation of methyl 2-((2-chloro-6-fluorophenyl)amino)-1,7,7-trimethyl-7,8-dihydro-1H-benzofuro[4,5-d]imidazole-5-carboxylate

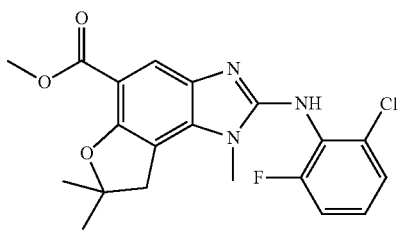 [SMILES: COC(=O)c1cc2nc(Nc3c(F)cccc3Cl)n(C)c2c2c1OC(C)(C)C2]

The title compound was prepared following the procedure described for Step-1 of Intermediate-3 using methyl 5-amino-2,2-dimethyl-4-(methylamino)-2,3-dihydrobenzofuran-7-carboxylate (1.10 g, 4.4 mmol), 1-chloro-3-fluoro-2-isothiocyanatobenzene (Intermediate-14, 1.0 g, 5.3 mmol), N,N-diisopropyl carbodiimide (0.5 mL) and acetonitrile (3.0 mL) to afford 1.0 g of the desired product. $^1$HNMR (DMSO-$d_6$): δ 1.46 (s, 6H), 3.34 (s, 2H), 3.53 (s, 3H), 3.72 (s, 3H), 7.00 (m, 1H), 7.06 (s, 1H), 7.17 (t, J=9.3 Hz, 1H), 7.28 (d, J=8.4 Hz, 1H), 10.39 (s, 1H).

Step 8:—Preparation of 2-((2-chloro-6-fluorophenyl)amino)-1,7,7-trimethyl-7,8-dihydro-1H-benzofuro[4,5-d]imidazole-5-carboxylic acid The title compound was prepared following the procedure described for Step-2 of Intermediate-3 using methyl 2-((2-chloro-6-fluorophenyl)amino)-1,7,7-trimethyl-7,8-dihydro-1H-benzofuro[4,5-d]imidazole-5-carboxylate (1.0 g, 2.47 mmol), Aq. NaOH (2.0 g, 50.0 mmol) and methanol (2.0 mL) to afford 0.9 g of desired product. $^1$HNMR (DMSO-$d_6$): δ 1.46 (s, 6H), 3.34 (s, 2H), 3.53 (s, 3H), 6.99 (m, 1H), 7.06 (s, 1H), 7.18 (m, 1H), 7.27 (m, 1H), 10.36 (bs, 1H), 12.08 (bs, 1H).

Intermediate-50

4-Cyclopropylaniline

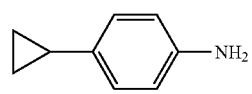

Step 1:—Preparation of 1-cyclopropyl-4-nitrobenzene

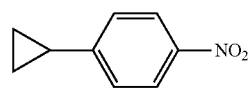 [SMILES: O=[N+]([O-])c1ccc(C2CC2)cc1]

To a solution of cyclopropyl boronic acid (0.637 g, 0.00742 mmol) in dry toluene, were added 4-bromo nitrobenzene (1.00 g, 0.00495 mmol) and tetrakis triphenylphosphine palladium (0.099 g, 0.0099 mol). Degassed the reaction mixture for 30 minutes then added potassium carbonate (1.36 g, 0.009 mmol). The reaction mass was refluxed for 48 h. The excess of solvent was removed under vacuum and the reaction mass was diluted with water and extracted with ethyl acetate. The organic layer was separated, dried over anhydrous sodium sulphate and concentrated. The obtained crude was purified by column chromatography on silica gel eluting with 4% DCM: MeOH to afford 0.750 g of the desired product. $^1$HNMR (DMSO-$d_6$): δ 0.82-0.84 (m, 2H), 1.09-1.13 (m, 2H), 2.01 (m, 1H), 7.32 (d, J=8.7 Hz, 2H), 8.09 (d, J=8.7 Hz, 2H).

Step 2:—Preparation of 4-cyclopropylaniline

The title compound was prepared following the procedure described for Step-9 of Intermediate-1 using 1-cyclopropyl-4-nitrobenzene (0.400 g, 0.407 mmol), methanol (10 mL), iron powder (catalytic amount) and conc. HCl (0.5 mL) to afford 0.300 g of the desired product. ¹HNMR (DMSO-d₆): δ 0.43-0.48 (m, 2H), 0.74-0.80 (m, 2H), 1.23-1.74 (m, 1H), 4.79 (s, 2H), 6.44 (d, J=8.1 Hz, 2H), 6.73 (d, J=8.1 Hz, 2H); [M+H]⁺: 134.20.

Intermediate-51

Methyl 2-(2-chloro-6-fluorobenzamido)-7,7-dimethyl-7,8-dihydro-1H-benzofuro[4,5-d]imidazole-5-carboxylate

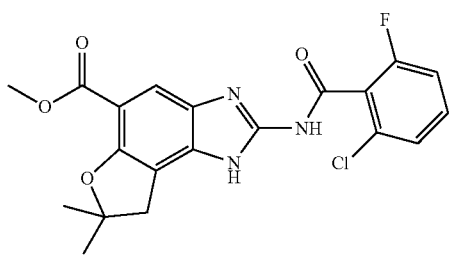 [SMILES: COC(=O)c1cc2nc(NC(=O)c3c(F)cccc3Cl)[nH]c2c2c1OC(C)(C)C2]

Step 1:—Preparation of methyl 2-amino-7,7-dimethyl-7,8-dihydro-1H-benzofuro[4,5-d]imidazole-5-carboxylate

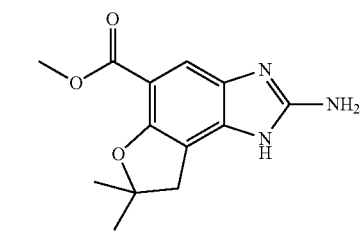 [SMILES: COC(=O)c1cc2nc(N)[nH]c2c2c1OC(C)(C)C2]

To a solution of methyl 4,5-diamino-2,2-dimethyl-2,3-dihydro-1-benzofuran-7-carboxylate (Intermediate-1, 2.00 g, 8.47 mmol) in ethanol:water (50:4 mL) was added cyanogen bromide (1.07 g, 10.16 mmol). The reaction mass was refluxed for 4-5 h. The reaction mass was quenched in water, neutralised with sodium bicarbonate and extracted with solution of (10%) DCM: methanol. The organic layer was dried over anhydrous sodium sulphate and concentrated to afford 1.0 g of the desired product. ¹HNMR (DMSO-d₆): δ 1.42 (s, 6H), 3.03 (s, 2H), 3.71 (s, 3H), 6.67 (bs, 2H), 7.33 (s, 1H), 10-11 (bs, 1H). MS [M+H]⁺: 237.03.

Step 2:—Preparation of methyl 2-(2-chloro-6-fluorobenzamido)-7,7-dimethyl-7,8-dihydro-1H-benzofuro[4,5-d]imidazole-5-carboxylate To a solution of methyl 2-amino-7,7-dimethyl-7,8-dihydro-1H-benzofuro[4,5-d]imidazole-5-carboxylate (1.00 g, 3.81 mmol) in THF (25 mL) was added EDCI.HCl (1.4 g, 7.62 mmol), HOBT (1.00 g, 7.62 mmol), 2-chloro-6-fluorobenzoic acid (1.32 g 7.62 mmol) and TEA (3 mL). The reaction mass was stirred for 18 h. The reaction mass was quenched in water extracted with 10% DCM: methanol. The organic layer was dried over anhydrous sodium sulphate and concentrated. The obtained crude was purified by column chromatography on basic alumina eluting with 0.7% DCM: MeOH to afford 0.700 g of the desired product. ¹HNMR (DMSO-d₆): δ 1.43 (s, 6H), 3.02 (s, 2H), 3.58 (s, 3H), 6.08 (bs, 1H), 7.59-7.69 (m, 2H), 7.83 (q, J=6.6 Hz, 1H), 8.14 (bs, 2H); MS [M+H]⁺: 418.05.

Intermediate-52

Methyl 2-((2-chlorobenzyl)amino)-7,7-dimethyl-7,8-dihydro-1H-benzofuro[4,5-d]imidazole-5-carboxylate

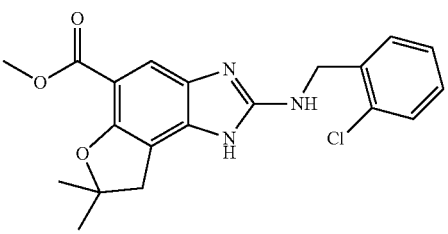 [SMILES: COC(=O)c1cc2nc(NCc3ccccc3Cl)[nH]c2c2c1OC(C)(C)C2]

Step 1:—Preparation of 1-chloro-2-(isothiocyanatomethyl)benzene

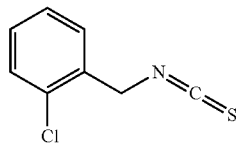 [SMILES: S=C=NCc1ccccc1Cl]

The title compound was prepared following the procedure described for Intermediate-2 using 2-chloro benzyl amine (5.0 g, 35 mmol), thiophosgene (4.38 g, 38.5 mmol) and N-ethyl di-isopropyl amine (13.5 g, 105 mmol) to afford 3.0 g of the desired product. ¹HNMR (DMSO-d₆): δ 5.00 (s, 2H), 7.41 (m, 2H), 7.54 (m, 2H).

Step 2:—Preparation of methyl 2-((2-chlorobenzyl)amino)-7,7-dimethyl-7,8-dihydro-1H-benzofuro[4,5-d]imidazole-5-carboxylate The title compound was prepared following the procedure described for Step-1 of Intermediate-3 using methyl 4,5-diamino-2,2-dimethyl-2,3-dihydro-1-benzofuran-7-carboxylate (Intermediate-1, 2.5 g, 10.59 mmol), 1-chloro-2-(isothiocyanatomethyl)benzene (2.5 g, 13.6 mmol), N,N-diisopropyl carbodimide (0.5 mL) and acetonitrile (10.0 mL) to afford 2.00 g of the desired product. ¹HNMR (DMSO-d₆): δ 1.41 (s, 6H), 3.00 (s, 2H), 3.71 (s, 3H), 4.60 (d, J=5.3 Hz, 2H), 7.30-7.45 (m, 5H), 7.55 (t, J=6.6 Hz), 10.80 (s, 1H); MS [M+H]⁺: 386.05.

Intermediate-53

3-Chloro-4-fluoro-N'-hydroxybenzimidamide

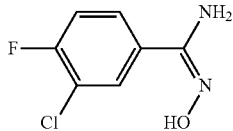

To a solution of 3-chloro-4-fluoro benzonitrile (1.0 g, 6.42 mmol) in ethanol (20 mL), was added hydroxylamine hydrochloride (0.665 g, 9.64 mmol), followed by addition of potassium carbonate (2.66 g, 19.28 mmol). The reaction mass was refluxed for 10-12 h. Excess of solvent was removed under vacuum and the reaction mass was diluted with water, acidified with dilute HCl and filtered to afford 0.400 g the desired product. $^1$HNMR (DMSO-$d_6$): δ 5.95 (s, 2H), 7.42 (t, J=8.7 Hz, 1H), 7.69 (m, 1H), 7.83 (dd, 1H), 9.80 (s, 1H); MS [M+H]$^+$: 189.12.

Intermediate-54

N'-Hydroxy-3,5-dimethoxybenzimidamide

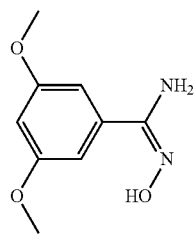

The title compound was prepared following the procedure described for of Intermediate-53 using of 3,5-dimethoxybenzonitrile (1.0 g, 6.12 mmol), ethanol (20 mL), hydroxylamine hydrochloride (0.634 g, 9.23 mmol) and potassium carbonate (2.53 g, 18.40 mmol) to afford 0.500 g of the desired product. $^1$HNMR (DMSO-$d_6$): δ 3.75 (s, 6H), 5.79 (s, 2H), 6.49 (s, 1H), 6.84 (s, 2H), 9.62 (s, 1H); MS [M+H]$^+$: 197.11.

Intermediate-55

7-[(2,6-Dichlorophenyl)amino]-2-methyl-8H-imidazo[4,5-e][1,3]benzoxazole-4-carboxylic acid

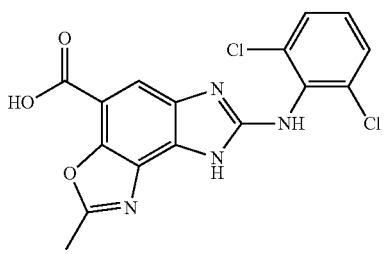 [SMILES: Cc1nc2c(o1)c(C(=O)O)cc1nc(Nc3c(Cl)cccc3Cl)[nH]c12]

Step-1:—Preparation of methyl 4,5-diamino-2-hydroxybenzoate

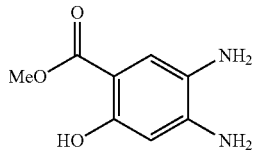 [SMILES: COC(=O)c1cc(N)c(N)cc1O]

To a solution of methyl 4-amino-2-hydroxy-5-nitrobenzoate (step 5 of intermediate-1) (0.500 g, 2.35 mmol) in methanol (15.0 mL), iron powder (0.646 g, 11.7 mmol) was added with conc. HCl (5 mL). The reaction mass was refluxed for 2 h. Methanol was removed under vacuum and then water was added. The reaction mass was basified with $Na_2CO_3$ and extracted with DCM. The organic layer was dried over anhydrous sodium sulphate and concentrated to afford 0.500 g of the desired product. $^1$HNMR (DMSO-$d_6$): δ 3.76 (s, 3H), 4.29 (s, 2H), 5.64 (s, 2H), 6.01 (s, 1H), 6.89 (s, 1H), 10.28 (s, 1H).

Step-2:—Preparation of methyl 2-[(2,6-dichlorophenyl)amino]-6-hydroxy-1H-benzimidazole-5-carboxylate

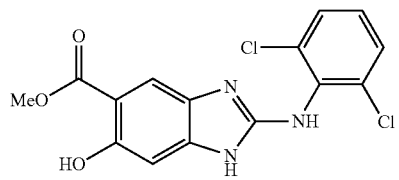 [SMILES: COC(=O)c1cc2nc(Nc3c(Cl)cccc3Cl)[nH]c2cc1O]

To a solution of methyl 4,5-diamino-2-hydroxybenzoate (0.500 g, 2.74 mmol) in acetonitrile (15.0 mL) was added 1,3-dichloro-2-isothiocyanatobenzene (Intermediate-5, 0.550 g, 2.72 mmol). The reaction mass was stirred at RT for 24 h and N,N-di-isopropyl carbodimide (1.0 mL) was added to it. The reaction mass stirred at RT for 4-6 h. The reaction mass was cooled and filtered to afford 0.500 g of the desired product. $^1$HNMR (DMSO-$d_6$): δ 3.86 (s, 3H), 6.56 (s, 1H), 7.22 (t, J=7.8 Hz, 1H), 7.38 (s, 1H), 7.52 (d, J=7.8 Hz, 2H), 10.49-10.64 (s, 3H); MS [M+H]$^+$: 352.08.

Step-3:—Preparation of methyl 2-[(2,6-dichlorophenyl)amino]-6-hydroxy-7-nitro-1H-benzimidazole-5-carboxylate

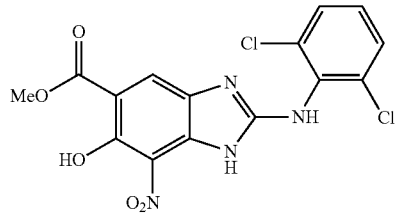 [SMILES: COC(=O)c1cc2nc(Nc3c(Cl)cccc3Cl)[nH]c2c([N+](=O)[O-])c1O]

To a mixture of methyl 2-[(2,6-dichlorophenyl)amino]-6-hydroxy-1H-benzimidazole-5-carboxylate (0.050 g, 0.142 mmol) and conc. $H_2SO_4$ (2.0 mL) was added $KNO_3$ (0.014 g, 0.142 mmol) at 10-15° C. The reaction mass was stirred for 30 minutes at the same temperature. The reaction mass was quenched in water and filtered off to afford 0.050 g of the desired product. $^1$HNMR (DMSO-$d_6$): δ 3.91 (s, 3H), 7.43 (t, J=8.1 Hz, 1H), 7.61-7.77 (m, 3H), 10.80 (s, 1H), 11-12.00 (s, 2H); MS [M+H]$^+$: 397.02.

Step-4:—Preparation of methyl 7-[(2,6-dichlorophenyl)amino]-2-methyl-8H-imidazo[4,5-e][1,3]benzoxazole-4-carboxylate

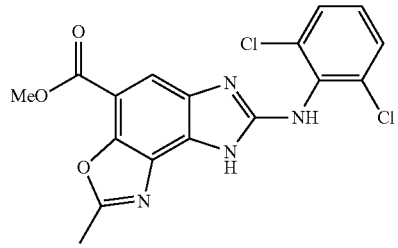 [SMILES: COC(=O)c1cc2nc(Nc3c(Cl)cccc3Cl)[nH]c2c2nc(C)oc12]

To a solution of methyl 2-[(2,6-dichlorophenyl)amino]-6-hydroxy-7-nitro-1H-benzimidazole-5-carboxylate (0.150 g, 0.370 mmol) in benzene (5 mL), indium (0.172 g, 1.51 mmol), acetic acid (0.468 g, 7.54 mmol) and trimethyl orthoacetate (0.480 g, 2.96 mmol) were added under $N_2$ atmosphere. The reaction mass was refluxed for 3-4 h. A mixture of MeOH:DCM (15%) was added to the reaction mixture. The reaction mass was filtered. The organic layer was concentrated. The obtained product was further purified by column chromatography on neutral alumina eluting with 1.5-2.0% MeOH: DCM to afford 0.075 g of the desired product. $^1$HNMR (DMSO-$d_6$): δ 2.63 (s, 3H), 3.88 (s, 3H), 7.40 (m, 1H), 7.61-7.69 (m, 3H), 9.56 (s, 1H), 11.56 (s, 1H); MS [M+H]$^+$: 391.33.

Step-5:—Preparation of 7-[(2,6-dichlorophenyl)amino]-2-methyl-8H-imidazo[4,5-e][1,3]benzoxazole-4-carboxylic acid To a solution of methyl 7-[(2,6-dichlorophenyl)amino]-2-methyl-8H-imidazo[4,5-e][1,3]benzoxazole-4-carboxylate (0.100 g, 0.256 mmol) in MeOH (15 mL), sodium hydroxide (0.052 g, 1.3 mmol) was added. The reaction mass was refluxed for 3 h. Methanol was removed under vacuum. Water was added and reaction mixture was acidified with dilute acetic acid. The reaction mixture was filtered and obtained solid was dried to afford 0.060 g of the desired product. $^1$HNMR (DMSO-$d_6$): δ 2.62 (s, 3H), 7.37 (m, 1H), 7.60 (d, J=7.8 Hz, 2H), 7.65 (s, 1H), 9.80 (s, 1H), 11.53 (s, 1H), 13.00 (s, 1H).

Intermediate-56

7-[(2-Chloro-6-fluorophenyl)amino]-2-methyl-8H-imidazo[4,5-e][1,3]benzoxazole-4-carboxylic acid

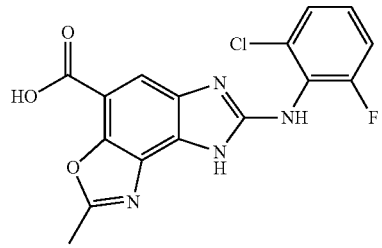 [SMILES: Cc1nc2c(o1)c(C(=O)O)cc1nc(Nc3c(F)cccc3Cl)[nH]c12]

Step-1:—Preparation of methyl 2-[(2-chloro-6-fluorophenyl)amino]-6-hydroxy-1H-benzimidazole-5-carboxylate

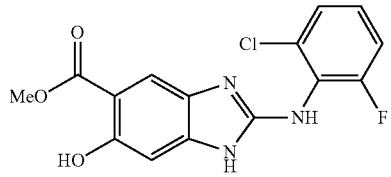 [SMILES: COC(=O)c1cc2nc(Nc3c(F)cccc3Cl)[nH]c2cc1O]

The title compound was prepared following the procedure described for step-2 of intermediate-55 using methyl 4,5-diamino-2-hydroxybenzoate (step-1 of Intermediate-55, 0.700 g, 3.840 mmol), acetonitrile (5.0 mL), 1-chloro-3-fluoro-2-isothiocyanatobenzene (Intermediate-14, 0.700 g, 3.760 mmol) and N,N-di-isopropyl carbodimide (1.0 mL) to afford 0.5 g of the desired product. $^1$HNMR (DMSO-$d_6$): δ 3.87 (s, 3H), 6.61 (s, 1H), 7.29-7.46 (m, 4H), 10.62 (s, 1H); MS [M+H]$^+$: 336.17.

Step-2:—Preparation of methyl 2-[(2-chloro-6-fluorophenyl)amino]-6-hydroxy-7-nitro-1H-benzimidazole-5-carboxylate

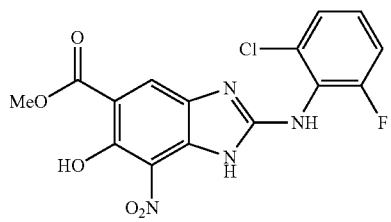 [SMILES: COC(=O)c1cc2nc(Nc3c(F)cccc3Cl)[nH]c2c([N+](=O)[O-])c1O]

The title compound was prepared following the procedure described for step-3 of intermediate-55 using methyl 2-[(2-chloro-6-fluorophenyl)amino]-6-hydroxy-1H-benzimidazole-5-carboxylate (0.380 g, 1.134 mmol), conc. $H_2SO_4$ (1.2 mL) and $KNO_3$ (0.109 g, 1.077 mmol) to afford 0.320 g of the desired product. $^1$HNMR (DMSO-$d_6$): δ 3.92 (s, 3H), 7.40-7.47 (m, 3H), 7.72 (s, 1H), 9.98 (m, 1H), 11.00-12.00 (s, 2H); MS [M+H]$^+$: 381.03.

Step-3:—Preparation of methyl 7-[(2-chloro-6-fluorophenyl)amino]-2-methyl-8H-imidazo[4,5-e][1,3]benzoxazole-4-carboxylate

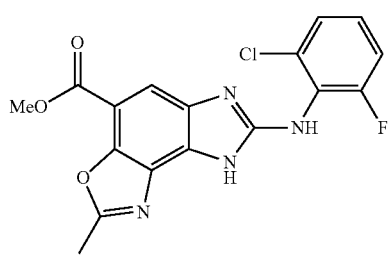 [SMILES: COC(=O)c1cc2nc(Nc3c(F)cccc3Cl)[nH]c2c2nc(C)oc12]

The title compound was prepared following the procedure described for step-4 of Intermediate-55 using methyl 2-[(2- chloro-6-fluorophenyl)amino]-6-hydroxy-7-nitro-1H-benzimidazole-5-carboxylate (0.320 g, 0.840 mmol), benzene (6 mL), indium (0.386 g, 3.363 mmol), acetic acid (0.505 g, 8.40 mmol) and trimethyl orthoacetate (0.812 g, 2.96 mmol) to afford 0.195 g of the desired product. $^1$HNMR (DMSO-$d_6$): δ 2.63 (s, 3H), 3.88 (s, 3H), 7.439-7.46 (m, 3H), 7.71 (s, 1H), 9.0-10.0 (s, 1H), 11.60 (s, 1H); MS [M+H]$^+$: 375.34.

Step-4:—Preparation of 7-[(2-chloro-6-fluorophenyl)amino]-2-methyl-8H-imidazo[4,5-e][1,3]benzoxazole-4-carboxylic acid The title compound was prepared following the procedure described for Step-5 of Intermediate-55 using methyl 7-[(2-chloro-6-fluorophenyl)amino]-2-methyl-8H-imidazo[4,5-e][1,3]benzoxazole-4-carboxylate (0.190 g, 0.508 mmol), MeOH (3.0 mL) and sodium hydroxide (0.101 g, 2.52 mmol) to afford 0.136 g of the desired product. $^1$HNMR (DMSO-$d_6$): δ 2.60 (s, 3H), 7.35 (s, 2H), 7.44 (s, 1H), 7.64 (s, 1H), 12.0-13.0 (s, 3H); MS [M+H]$^+$: 360.2.

Intermediate-57

HCl salt of ethyl cyclopropanecarboximidate

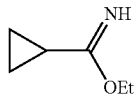

To a cold solution of cyclopropyl carbonitrile (1.00 g, 14.92 mmol) in DEE (5.0 mL) was added ethanol (0.823 g, 17.91 mmol) and HCl saturated DEE (diethyl ether) (10.0 mL) at 0-5° C. The reaction mass was stirred at 0-5° C. for 1 h. The reaction mass was cooled at 5-10° C. for 48 h and the desired product (1.2 g) precipitated out as solid. $^1$HNMR (DMSO-$d_6$): δ 1.24 (s, 4H), 1.42 (s, 3H), 2.42 (s, 1H), 4.59 (s, 2H), 11.14 (s, 1H), 12.22 (s, 1H).

Intermediate-58

2-Cyclopropyl-7-[(2,6-dichlorophenyl)amino]-8H-imidazo[4,5-e][1,3]benzoxazole-4-carboxylic acid

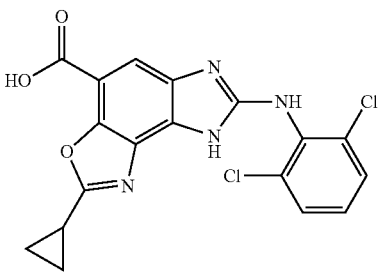 [SMILES: O=C(O)c1cc2nc(Nc3c(Cl)cccc3Cl)[nH]c2c2nc(C3CC3)oc12]

Step-1:—Preparation of methyl 7-amino-2-[(2,6-dichlorophenyl)amino]-6-hydroxy-1H-benzimidazole-5-carboxylate

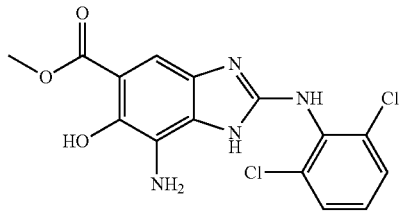 [SMILES: COC(=O)c1cc2nc(Nc3c(Cl)cccc3Cl)[nH]c2c(N)c1O]

To a solution of methyl 2-[(2,6-dichlorophenyl)amino]-6-hydroxy-7-nitro-1H-benzimidazole-5-carboxylate (Step-3 of Intermediate-55, 0.500 g) in benzene (2.0 mL) were added iron powder (0.500 g) and acetic acid (2.0 mL). The reaction mass was refluxed for 3 h. Decant the reaction mass removed the solvent under vacuum. The obtained solid mass was washed with water. The reaction mass was extracted with MeOH:DCM (5%). The organic layer was dried over anhydrous sodium sulphate and concentrated to afford 0.440 g of the desired product. $^1$HNMR (DMSO-$d_6$): δ 3.87 (s, 3H), 4.45 (s, 2H), 7.28-7.47 (m, 1H), 7.53-7.59 (m, 3H), 11.00 (s, 2H).

Step-2:—Preparation of methyl 2-cyclopropyl-7-[(2,6-dichlorophenyl)amino]-8H-imidazo[4,5-e][1,3]benzoxazole-4-carboxylate

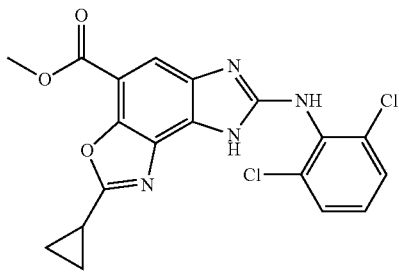 [SMILES: COC(=O)c1cc2nc(Nc3c(Cl)cccc3Cl)[nH]c2c2nc(C3CC3)oc12]

Under $N_2$ atmosphere to a cold solution of methyl 7-amino-2-[(2,6-dichlorophenyl)amino]-6-hydroxy-1H-benzimidazole-5-carboxylate (0.400 g, 1.05 mmol) in DCM (25 mL) was added HCl salt of ethyl cyclopropanecarboximidate (Intermediate-57, 0.234 g, 1.57 mmol) at 0° C. The reaction mass was stirred at 0-5° C. for 1 h and at RT for 24 h. The obtained crude was purified by column chromatography on neutral alumina eluting with 1.0-2.0% MeOH:DCM to afford 0.150 g of the desired product. (DMSO-$d_6$): δ 1.06-1.14 (m, 4H), 3.88 (s, 3H), 2.3 (m, 1H), 7.41 (s, 1H), 7.62 (d, J=7.8 Hz, 2H), 7.69 (s, 1H), 9.47 (s, 1H), 11.55 (s, 1H).

Step-3:—Preparation of 2-cyclopropyl-7-[(2,6-dichlorophenyl)amino]-8H-imidazo[4,5-e][1,3]benzoxazole-4-carboxylic acid The title compound was prepared following the procedure described for Step-5 of Intermediate-55 using methyl 2-cyclopropyl-7-[(2,6-dichlorophenyl)amino]-8H-imidazo[4,5-e][1,3]benzoxazole-4-carboxylate (0.100 g, 0.234 mmol), MeOH (3.0 mL) and sodium hydroxide (0.047 g, 1.17 mmol) to afford 0.075 g of the desired product. $^1$HNMR (DMSO-$d_6$):

δ 1.07 (s, 4H), 2.32 (s, 1H), 6.56 (m, 1H), 7.07 (m, 1H), 7.31 (s, 1H), 7.57 (s, 1H), 12.15 (s, 2H).

Intermediate-59

Methyl 7-((2-chloro-6-fluorophenyl)amino)-2-cyclopropyl-8H-imidazo[4',5':5,6]benzo[1,2-d]oxazole-4-carboxylate

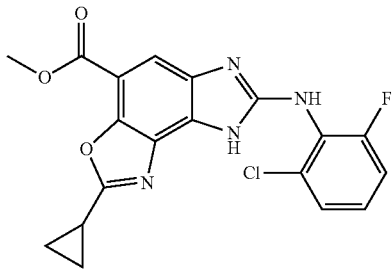 [SMILES: COC(=O)c1cc2nc(Nc3c(F)cccc3Cl)[nH]c2c2nc(C3CC3)oc12]

Step-1:—Preparation of methyl 7-amino-2-((2-chloro-6-fluorophenyl)amino)-6-hydroxy-1H-benzo[d]imidazole-5-carboxylate

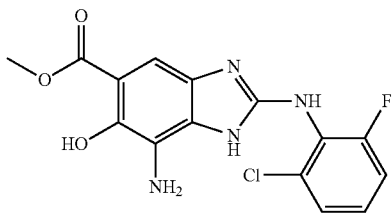 [SMILES: COC(=O)c1cc2nc(Nc3c(F)cccc3Cl)[nH]c2c(N)c1O]

To a solution of methyl 2-[(2-chloro-6-fluorophenyl)amino]-6-hydroxy-7-nitro-1H-benzimidazole-5-carboxylate (Step-2 of Intermediate-56, 0.500 g) in benzene (2.0 mL), were added iron powder (0.500 g) and acetic acid (4.0 mL). The reaction mass was refluxed for 3 h. Decant the reaction mass removed the solvent under vacuum. The obtained solid mass was washed with water. The reaction mass was extracted with MeOH:DCM (5%). The organic layer was dried over anhydrous sodium sulphate and concentrated to afford 0.440 g of the desired product.

Step-2:—Preparation of methyl 7-((2-chloro-6-fluorophenyl)amino)-2-cyclopropyl-8H-imidazo[4',5':5,6]benzo[1,2-d]oxazole-4-carboxylate Under N₂ atmosphere to a cold solution of methyl 7-amino-2-[(2-chloro-6-fluorophenyl)amino]-6-hydroxy-1H-benzimidazole-5-carboxylate (0.400 g, 1.05 mmol) in DCM (25 mL), was added HCl salt of ethyl cyclopropanecarboximidate (Intermediate-57, 0.234 g, 1.57 mmol) at 0° C. The reaction mass was stirred at 0-5° C. for 1 h and at RT for 24 h. The obtained crude was purified by column chromatography on neutral alumina eluting with 1.0-2.0% MeOH:DCM to afford 0.150 g of the desired product. (DMSO-d₆): δ 1.23 (m, 4H), 2.26 (m, 1H), 3.88 (s, 3H), 6.75 (s, 1H), 7.39 (m, 1H), 7.51 (m, 2H), 7.70 (s, 1H), 9.37 (s, 1H), 11.59 (s, 1H); MS [M+H]⁺: 401.21.

Intermediate-60

Methyl 2-((3,5-dichloropyridin-4-yl)amino)-1,7,7-trimethyl-7,8-dihydro-1H-benzofuro[4,5-d]imidazole-5-carboxylate

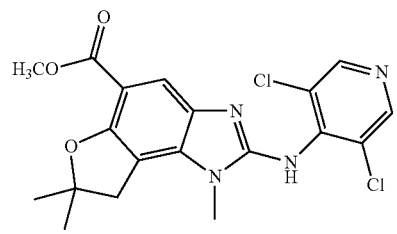 [SMILES: COC(=O)c1cc2nc(Nc3c(Cl)cncc3Cl)n(C)c2c2c1OC(C)(C)C2]

The title compound was prepared following the procedure described for step-1 of Intermediate-3 using methyl 5-amino-2,2-dimethyl-4-(methylamino)-2,3-dihydrobenzofuran-7-carboxylate (step-6 of Intermediate-49, 2.00 g, 8.0 mmol), 3,5-dichloro-4-isothiocyanatopyridine (Intermediate-2, 1.96 g, 9.6 mmol), N,N-di-isopropyl carbodimide (0.5 mL) and acetonitrile (10.0 mL) to afford 2.0 g of the desired product. ¹HNMR (DMSO-d₆): 1.47 (s, 6H), 3.49 (s, 2H), 3.56 (s, 3H), 3.73 (s, 3H), 7.10 (s, 1H), 8.46 (s, 2H), 10.79 (s, 1H).

Intermediate-61

2-((3,5-Dichloropyridin-4-yl)amino)-1,7,7-trimethyl-7,8-dihydro-1H-benzofuro[4,5-d]imidazole-5-carboxylic acid

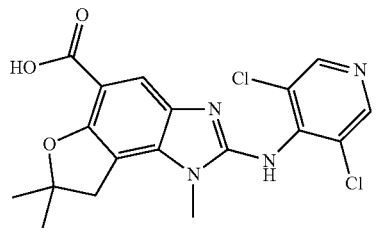 [SMILES: Cn1c(Nc2c(Cl)cncc2Cl)nc2cc(C(=O)O)c3c(c21)CC(C)(C)O3]

The title compound was prepared following the procedure described for step-2 of Intermediate-3 using methyl 2-((3,5-dichloropyridin-4-yl)amino)-1,7,7-trimethyl-7,8-dihydro-1H-benzofuro[4,5-d]imidazole-5-carboxylate (Intermediate-60, 2.00 g, 4.7 mmol), (50%) aqueous solution of sodium hydroxide (0.920 g, 23.0 mmol) methanol (2.0 mL) to afford 1.5 g of the desired product. ¹HNMR (DMSO-d₆): 1.46 (s, 6H), 3.37 (s, 2H), 3.56 (s, 3H), 7.10 (s, 1H), 8.45 (s, 2H), 10.77 (br s, 1H), 12.17 (br s, 1H).

EXAMPLES

Example-1

N-Cyclohexyl-2-[(3,5-dichloropyridin-4-yl)amino]-7,7-dimethyl-7,8-dihydro-1H-furo[3,2-e]benzimidazole-5-carboxamide

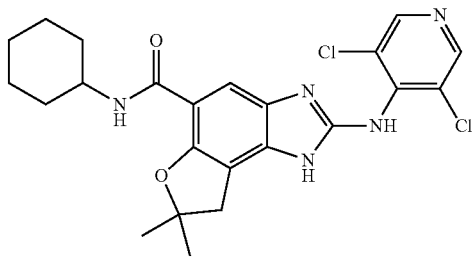 [SMILES: CC1(C)Cc2c(c(C(=O)NC3CCCCC3)cc3nc(Nc4c(Cl)cncc4Cl)[nH]c23)O1]

To a solution 2-[(3,5-dichloropyridin-4-yl)amino]-7,7-dimethyl-7,8-dihydro-1H-furo[3,2-e]benzimidazole-5-carboxylic acid (Intermediate-3, 0.050 g, 0.127 mmol) in mixture of DMF (0.5 mL) and THF (3.0 mL), were added O-(benzotriazol-1-yl)-N,N,N',N'-tetramethyluronium tetrafluoroborate (0.082 g, 0.255 mmol, TBTU), N-methyl morpholine (1.0 mL). The reaction mass was stirred at RT for 30 minutes. Then to the reaction mass added cyclohexyl amine (0.020 g, 0.202 mmol). The reaction mass was stirred at RT for 14-16 h. The reaction mass was quenched in water and extracted with ethyl acetate. The organic layer was washed with sodium bicarbonate and dilute HCl solution, and dried over anhydrous sodium sulphate and concentrated to afford 0.005 g of the desired product. $^1$HNMR (DMSO-$d_6$): δ 1.15-1.35 (m, 7H), 1.48 (s, 3H), 1.58 (m, 2H), 1.79 (m, 2H), 3.00-3.07 (m, 4H), 3.80 (m, 1H), 7.20 (s, 1H), 7.66 (d, J=7.5 Hz, 1H), 8.41 (s, 2H), 10.89 (s, 1H), 11.39 (s, 1H); MS [M−H]$^-$: 472.43.

Example-2

2-[(3,5-Dichloropyridin-4-yl)amino]-7,7-dimethyl-N-[2-(trifluoromethyl)benzyl]-7,8-dihydro-1H-furo[3,2-e]benzimidazole-5-carboxamide

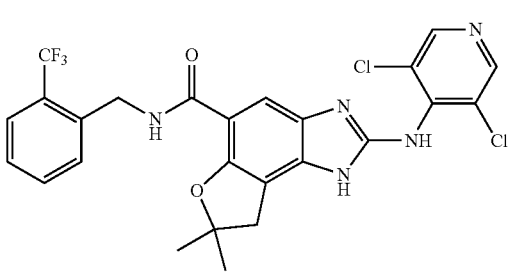 [SMILES: CC1(C)Cc2c(c(C(=O)NCc3ccccc3C(F)(F)F)cc3nc(Nc4c(Cl)cncc4Cl)[nH]c23)O1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.050 g, 0.127 mmol), O-(benzotriazol-1-yl)-N,N,N',N'-tetramethyluronium tetrafluoroborate (0.082 g, 0.255 mmol), N-methyl morpholine (0.5 mL), DMF (1.0 mL), THF (5.0 mL) and 1-[2-(trifluoromethyl)phenyl]methanamine (Intermediate-4, 0.027 g, 0.154 mmol) to afford 0.015 g of the desired product. $^1$HNMR (DMSO-$d_6$): δ 1.21 (s, 3H), 1.48 (s, 3H), 3.01 (s, 2H), 4.68 (m, 2H), 7.19 (s, 1H), 7.46-7.51 (m, 2H), 7.62 (d, J=7.8 Hz, 1H), 7.72 (d, J=7.8 Hz, 1H), 8.27 (m, 1H), 8.41 (s, 2H), 10.89 (s, 1H), 11.42 (s, 1H); MS [M+H]$^+$: 550.31.

Example-3

2-[(3,5-Dichloropyridin-4-yl)amino]-N-hexyl-7,7-dimethyl-7,8-dihydro-1H-furo[3,2-e]benzimidazole-5-carboxamide

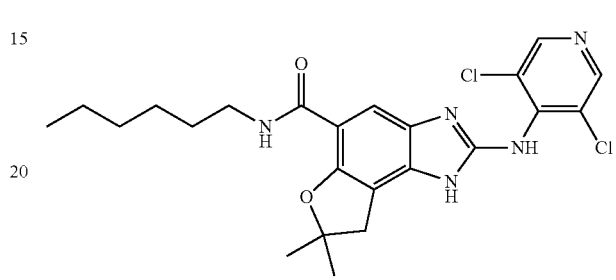

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.050 g, 0.127 mmol), O-(Benzotriazol-1-yl)-N,N,N',N'-tetramethyluronium tetrafluoroborate (0.082 g, 0.225 mmol), N-methyl morpholine (0.025 g, 0.247 mmol), DMF (0.5 mL), THF (3.0 mL) and n-hexyl amine (0.026 g, 0.257 mmol) to afford 0.010 g of the desired product. $^1$HNMR (DMSO-$d_6$): δ 0.86 (s, 3H), 1.23 (s, 3H), 1.28 (m, 8H), 1.49 (s, 3H), 3.01 (s, 2H), 7.32-7.33 (m, 2H), 7.21 (s, 1H), 7.69 (s, 1H), 8.43 (s, 2H), 10.91 (s, 1H), 11.39 (s, 1H); MS [M+H]$^+$: 476.33.

Example-4

2-[(3,5-Dichloropyridin-4-yl)amino]-7,7-dimethyl-N-pentyl-7,8-dihydro-1H-furo[3,2-e]benzimidazole-5-carboxamide

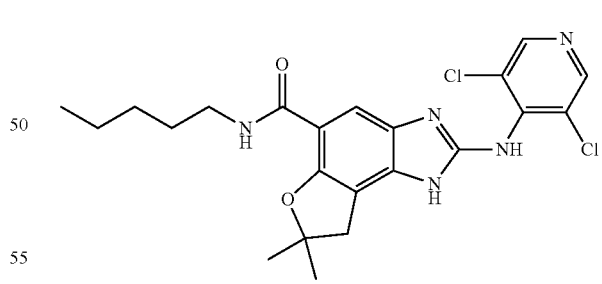

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.050 g, 0.127 mmol), O-(benzotriazol-1-yl)-N,N,N',N'-tetramethyluronium tetrafluoroborate (0.082 g, 0.225 mmol), N-methyl morpholine (0.5 mL), DMF (1.0 mL), THF (5.0 mL) and n-pentyl amine (0.022 g, 0.254 mmol) to afford 0.012 g of the desired product. $^1$HNMR (DMSO-$d_6$): δ 1.29 (t, J=6.3 Hz, 3H), 1.64 (s, 3H), 1.71 (s, 6H), 1.91 (s, 3H), 3.42 (s, 2H), 3.68-3.74 (m, 2H), 7.62 (s, 1H), 8.10 (m, 1H), 8.84 (s, 2H), 11.23 (s, 1H), 11.81 (s, 1H); MS [M+H]⁺: 462.43.

Example-5

N-(1-Cyclohexylethyl)-2-[(3,5-dichloropyridin-4-yl)amino]-7,7-dimethyl-7,8-dihydro-1H-furo[3,2-e]benzimidazole-5-carboxamide

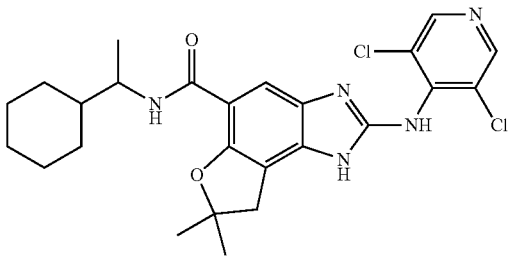 [SMILES: CC(NC(=O)c1cc2nc(Nc3c(Cl)cncc3Cl)[nH]c2c2c1OC(C)(C)C2)C1CCCCC1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.050 g, 0.127 mmol), O-(Benzotriazol-1-yl)-N,N,N',N'-tetramethyluronium tetrafluoroborate (0.081 g, 0.254 mmol), N-methyl morpholine (0.5 mL), DMF (1.0 mL), THF (5.0 mL) and R-(−)-1-cyclohexyl ethyl amine (0.032 g, 0.254 mmol) to afford 0.015 g of the desired product. ¹HNMR (DMSO-d₆): δ 1.09 (d, J=6.3 Hz, 3H), 1.14-1.23 (m, 4H), 1.40 (s, 3H), 1.48 (s, 3H), 1.52-1.63 (m, 7H), 2.72 (s, 2H), 3.84 (m, 1H), 7.21 (s, 1H), 7.62 (d, J=7.8 Hz, 1H), 8.40 (s, 2H), 11.00 (s, 2H); MS [M+H]⁺: 502.45.

Example-6

2-[(3,5-Dichloropyridin-4-yl)amino]-N—[R(−)3,3-dimethylbutan-2-yl)]-7,7-dimethyl-7,8-dihydro-1H-furo[3,2-e]benzimidazole-5-carboxamide

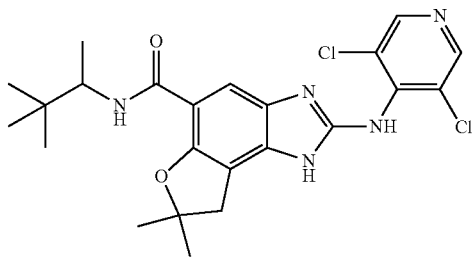 [SMILES: CC(NC(=O)c1cc2nc(Nc3c(Cl)cncc3Cl)[nH]c2c2c1OC(C)(C)C2)C(C)(C)C]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.050 g, 0.127 mmol), (benzotriazol-1-yl)-N,N,N',N'-tetramethyluronium tetrafluoroborate (0.081 g, 0.127 mmol), N-methyl morpholine (0.025 g, 0.247 mmol), DMF (0.5 mL), THF (3.0 mL) and R-(−)-3,3-dimethyl-2-butyl amine (0.026 g, 0.254 mmol) to afford 0.012 g of the desired product. ¹HNMR (DMSO-d₆): δ 0.90 (s, 9H), 1.05 (d, J=6.9 Hz, 3H), 1.47 (s, 3H), 1.52 (s, 3H), 3.03 (s, 2H), 3.80 (m, 1H), 7.22 (s, 1H), 7.68 (d, J=8.7 Hz, 1H), 8.43 (s, 2H), 10.91 (s, 1H), 11.47 (s, 1H); MS [M+H]⁺: 476.38.

Example-7

N-Cyclohexyl-2-[(2,6-dichlorophenyl)amino]-7,7-dimethyl-7,8-dihydro-1H-furo[3,2-e]benzimidazole-5-carboxamide

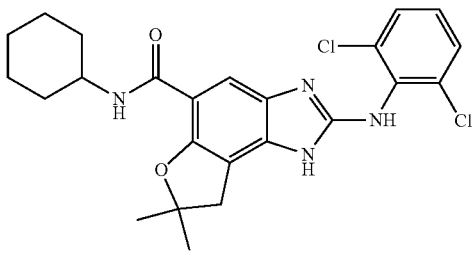 [SMILES: CC1(C)Cc2c(c(C(=O)NC3CCCCC3)cc3nc(Nc4c(Cl)cccc4Cl)[nH]c23)O1]

The title compound was prepared following the procedure as described for Example-1 using [(2,6-dichlorophenyl)amino]-7,7-dimethyl-7,8-dihydro-1H-furo[3,2-e]benzimidazole-5-carboxylic acid (Intermediate-6, 0.090 g, 0.229 mmol), O-(Benzotriazol-1-yl)-N,N,N',N'-tetramethyluronium tetrafluoroborate (0.147 g, 0.458 mmol), N-methyl morpholine (1.0 mL), DMF (1.0 mL), THF (5.0 mL), cyclohexyl amine (0.046 g, 0.458 mmol) to afford 0.040 g of the desired product. ¹HNMR (DMSO-d₆): δ 1.23-1.41 (m, 6H), 1.49 (s, 6H), 1.61 (m, 2H), 1.81 (m, 2H), 3.03 (s, 2H), 3.82 (s, 1H), 7.20 (s, 1H), 7.32 (s, 1H), 7.51 (d, J=7.5 Hz, 2H), 7.73 (d, J=7.5 Hz, 1H), 10.84 (s, 1H), 12.91 (s, 1H); MS [M+H]⁺: 473.35.

Example-8

N-(4-Bromophenyl)-2-[(3,5-dichloropyridin-4-yl)amino]-7,7-dimethyl-7,8-dihydro-1H-furo[3,2-e]benzimidazole-5-carboxamide

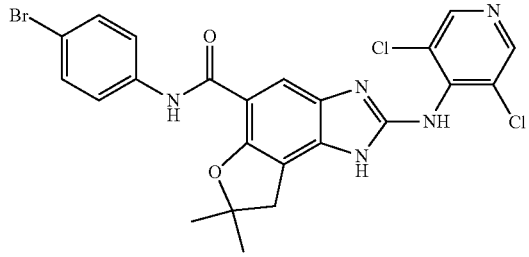 [SMILES: CC1(C)Cc2c(c(C(=O)Nc3ccc(Br)cc3)cc3nc(Nc4c(Cl)cncc4Cl)[nH]c23)O1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.070 g, 0.177 mmol), benzotriazole-1-yl-oxy-tris-(dimethylamino)-phosphonium hexafluorophosphate (0.157 g, 0.355 mmol), N-methyl morpholine (0.5 mL), DMF (1.0 mL), THF (5.0 mL) and 4-bromo aniline (0.092 g, 0.531 mmol) to afford 0.010 g of the desired product. ¹HNMR (DMSO-d₆): δ 1.23 (s, 3H), 1.57 (s, 3H), 3.06 (s, 2H), 7.24 (s, 1H), 7.52 (d, J=8.7 Hz, 2H), 7.68

(d, J=8.7 Hz, 2H), 8.44 (s, 2H), 9.72 (s, 1H), 10.98 (s, 1H), 11.52 (s, 1H); MS [M−H]⁻: 546.22.

Example-9

2-[(2,6-Dichlorophenyl)amino]-7,7-dimethyl-N-pentyl-7,8-dihydro-1H-furo[3,2-e]benzimidazole-5-carboxamide

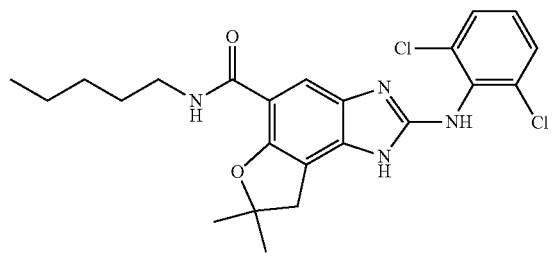 [SMILES: CCCCCNC(=O)c1cc2nc(Nc3c(Cl)cccc3Cl)[nH]c2c2c1OC(C)(C)C2]

The title compound was prepared following the procedure as described for Example-1 using 2-[(2,6-dichlorophenyl)amino]-7,7-dimethyl-7,8-dihydro-1H-furo[3,2-e]benzimidazole-5-carboxylic acid (Intermediate-6, 0.070 g, 0.178 mmol), O-(benzotriazol-1-yl)-N,N,N',N'-tetramethyluronium tetrafluoroborate (0.114 g, 0.306 mmol), N-methyl morpholine (1.0 mL), DMF (1.0 mL), THF (5.0 mL) and pentan-1-amine (0.031 g, 0.356 mmol) to afford 0.025 g of the desired product. ¹HNMR (DMSO-d₆): δ 0.880 (m, 3H), 1.23-1.33 (m, 8H), 1.49 (s, 6H), 3.03 (s, 2H), 7.19 (m, 1H), 7.32 (s, 1H), 7.50 (d, J=7.8 Hz, 2H), 7.71 (s, 1H), 10.50-11 (s, 2H); MS [M+H]⁺: 461.55.

Example-10

2-[(3,5-Dichloropyridin-4-yl)amino]-7,7-dimethyl-N-[4-(trifluoromethyl)phenyl]-7,8-dihydro-1H-furo[3,2-e]benzimidazole-5-carboxamide

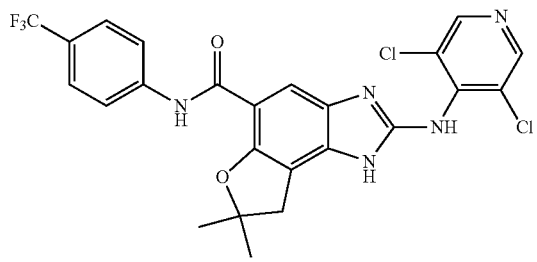 [SMILES: CC1(C)Cc2c(c(C(=O)Nc3ccc(C(F)(F)F)cc3)cc3nc(Nc4c(Cl)cncc4Cl)[nH]c23)O1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.100 g, 0.254 mmol), O-(benzotriazol-1-yl)-N,N,N',N'-tetramethyluronium tetrafluoroborate (0.163 g, 0.509 mmol), N-methyl morpholine (1.0 mL), DMF (1.5 mL), THF (7.0 mL) and 4-trifluoro methyl aniline (0.082 g, 0.509 mmol) to afford 0.020 g of the desired product. ¹HNMR (DMSO-d₆): δ 1.58 (s, 6H), 3.07 (s, 2H), 7.25 (s, 1H), 7.72 (d, J=8.1 Hz, 2H), 7.90

(d, J=8.4 Hz, 2H), 8.45 (s, 2H), 9.91 (s, 1H), 10.99 (s, 1H), 11.55 (s, 1H); MS [M+H]⁺: 536.22.

Example-11

N-(4-Bromophenyl)-2-[(2,6-dichlorophenyl)amino]-7,7-dimethyl-7,8-dihydro-1H-furo[3,2-e]benzimidazole-5-carboxamide

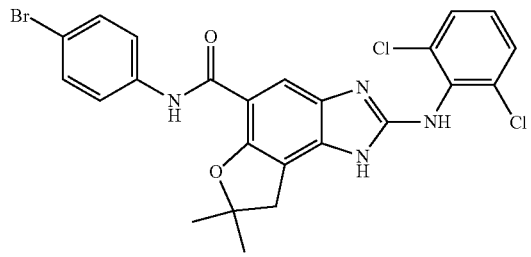 [SMILES: CC1(C)Cc2c(c(C(=O)Nc3ccc(Br)cc3)cc3nc(Nc4c(Cl)cccc4Cl)[nH]c23)O1]

The title compound was prepared following the procedure as described for Example-1 using 2-[(2,6-dichlorophenyl)amino]-7,7-dimethyl-7,8-dihydro-1H-furo[3,2-e]benzimidazole-5-carboxylic acid (Intermediate-6, 0.080 g, 0.204 mmol), O-(benzotriazol-1-yl)-N,N,N',N'-tetramethyluronium tetrafluoroborate (0.130 g, 0.400 mmol), TEA (1.5 mL), DMF (1.5 mL), THF (7.0 mL) and 4-bromo aniline (0.070 g, 0.400 mmol) to afford 0.015 g of the desired product. ¹HNMR (DMSO-d₆): δ 1.30-1.45 (m, 3H), 1.46-1.56 (m, 3H), 3.08 (s, 2H), 7.39 (m, 2H), 7.53 (d, J=8.7 Hz, 4H), 7.68 (d, J=8.7 Hz, 2H), 9.78 (s, 1H), 11.50-12.00 (s, 2H); MS [M+H]⁺: 547.16.

Example-12

N-Cyclohexyl-2-[(3,5-dichloropyridin-4-yl)amino]-7-methyl-1H-furo[3,2-e]benzimidazole-5-carboxamide

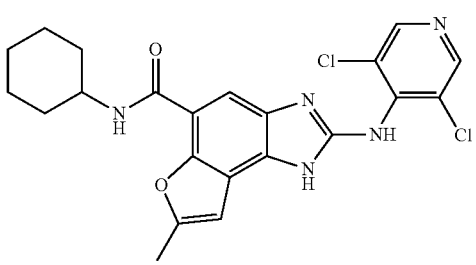 [SMILES: Cc1cc2c(o1)c(C(=O)NC1CCCCC1)cc1nc(Nc3c(Cl)cncc3Cl)[nH]c12]

The title compound was prepared following the procedure as described for Example-1 using 2-[(3,5-dichloropyridin-4-yl)amino]-7-methyl-1H-furo[3,2-e]benzimidazole-5-carboxylic acid (Intermediate-8, 0.050 g, 0.132 mmol), O-(benzotriazol-1-yl)-N,N,N',N'-tetramethyluronium tetrafluoroborate (0.085 g, 0.265 mmol), THF (5.0 mL), DMF (1.0 mL) and cyclohexyl amine (0.026 g, 0.265 mmol) to afford 0.020 g of the desired product. ¹HNMR (DMSO-d₆): δ 1.23 (s, 3H), 1.36 (t, J=9.6 Hz, 3H), 1.71 (m, 2H), 1.88 (m, 2H), 2.50 (s, 3H), 3.84 (m, 1H), 6.62 (s, 1H), 7.31 (m, 1H), 7.75 (d, J=7.8 Hz, 1H), 8.44 (s, 2H), 11.23 (s, 1H), 11.74 (s, 1H); MS [M+H]⁺: 458.38.

Example-13

N-Cyclohexyl-2-[(2,6-dichlorophenyl)amino]-7-methyl-1H-furo[3,2-e]benzimidazole-5-carboxamide

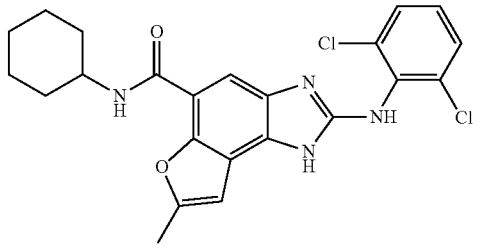 [SMILES: Cc1cc2c(o1)c(C(=O)NC1CCCCC1)cc1nc(Nc3c(Cl)cccc3Cl)[nH]c12]

The title compound was prepared following the procedure as described for Example-1 using 2-[(2,6-dichlorophenyl)amino]-7-methyl-1H-furo[3,2-e]benzimidazole-5-carboxylic acid (Intermediate-9, 0.050 g, 0.132 mmol), O-(benzotriazol-1-yl)-N,N,N',N'-tetramethyluronium tetrafluoroborate (0.085 g, 0.265 mmol), TEA (1 mL), THF (5.0 mL), DMF (1.0 mL) and cyclohexyl amine (0.026 g, 0.265 mmol) to afford 0.008 g of the desired product. ¹HNMR (DMSO-d₆): δ 1.23-1.30 (m, 2H), 1.31-1.36 (m, 4H), 1.89 (m, 4H), 3.85 (m, 1H), 4.19 (s, 3H), 6.74 (s, 1H), 7.41-7.94 (m, 4H), 9.07 (s, 1H), 11.00-12.00 (s, 2H).

Example-14

2-[(3,5-Dichloropyridin-4-yl)amino]-N-(3,3-dimethylcyclohexyl)-7,7-dimethyl-7,8-dihydro-1H-furo[3,2-e]benzimidazole-5-carboxamide

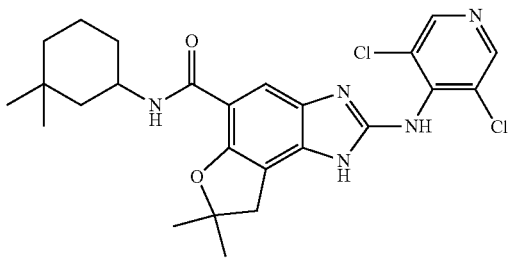 [SMILES: CC1(C)CCCC(NC(=O)c2cc3nc(Nc4c(Cl)cncc4Cl)[nH]c3c3c2OC(C)(C)C3)C1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.070 g, 0.178 mmol), O-(benzotriazol-1-yl)-N,N,N',N'-tetramethyluronium tetrafluoroborate (0.114 g, 0.355 mmol), TEA (1.0 mL), DMF (1.0 mL), THF (5.0 mL) and 3,3-dimethylcyclohexanamine (0.100 g, 0.787 mmol) to afford 0.010 g of the desired product. ¹HNMR (DMSO-d₆): δ 0.93 (s, 6H), 1.07-1.11 (m, 2H), 1.23-1.29 (m, 2H), 1.33 (s, 6H), 1.49-1.54 (m, 2H), 1.80 (s, 2H), 3.00 (s, 2H), 3.80 (m, 1H), 7.20 (s, 1H), 7.48 (d, J=8.4 Hz, 1H), 8.43 (s, 2H), 10.89 (s, 1H), 11.41 (s, 1H); MS [M+H]⁺: 502.31.

Example-15

N-(4-Chlorophenyl)-2-[(3,5-dichloropyridin-4-yl)amino]-7,7-dimethyl-7,8-dihydro-1H-furo[3,2-e]benzimidazole-5-carboxamide

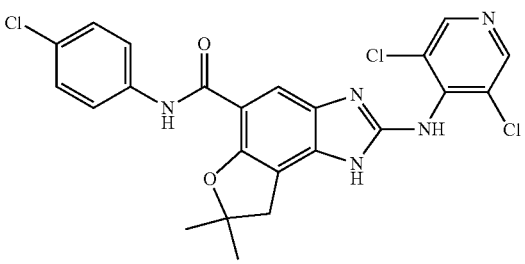 [SMILES: CC1(C)Cc2c(c(C(=O)Nc3ccc(Cl)cc3)cc3nc(Nc4c(Cl)cncc4Cl)[nH]c23)O1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.080 g, 0.203 mmol), O-(benzotriazol-1-yl)-N,N,N',N'-tetramethyluronium tetrafluoroborate (0.128 g, 0.400 mmol), TEA (1.0 mL), DMF (1.0 mL), THF (5.0 mL) and 4-chloro aniline (0.052 g, 0.400 mmol) to afford 0.010 g of the desired product. ¹HNMR (DMSO-d₆): δ 1.57 (s, 6H), 3.07 (s, 2H), 7.14 (s, 1H), 7.40 (d, J=9.0 Hz, 2H), 7.72 (d, J=12.3 Hz, 2H), 8.45 (s, 2H), 9.72 (s, 1H), 11.00 (s, 1H), 11.45 (s, 1H); MS [M−H]⁻: 500.25.

Example-16

2-[(2-Chlorophenyl)amino]-N-cyclohexyl-7-methyl-1H-furo[3,2-e]benzimidazole-5-carboxamide

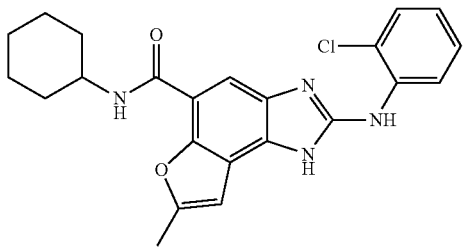 [SMILES: Cc1cc2c(o1)c(C(=O)NC1CCCCC1)cc1nc(Nc3ccccc3Cl)[nH]c12]

The title compound was prepared following the procedure as described for Example-1 using 2-[(2-chlorophenyl)amino]-7-methyl-1H-furo[3,2-e]benzimidazole-5-carboxylic acid (Intermediate-11, 0.050 g, 0.146 mmol), O-(benzotriazol-1-yl)-N,N,N',N'-tetramethyluronium tetrafluoroborate (0.094 g, 0.293 mmol), TEA (1.0 mL), DMF (1.0 mL), THF (5.0 mL) and cyclohexyl amine (0.029 g, 0293 mmol) to afford 0.016 g of the desired product. ¹HNMR (DMSO-d₆): δ 1.23-1.39 (m, 4H), 1.39-1.52 (m, 1H), 1.58 (m, 1H), 1.74 (m, 2H), 1.90 (m, 2H), 3.33 (m, 3H), 3.88 (m, 1H), 6.85 (s, 1H), 7.05 (m, 1H), 7.40 (t, J=7.2 Hz, 1H), 7.50 (d, J=7.8 Hz, 1H), 7.61-7.70 (m, 2H), 8.62 (s, 1H), 10.20 (s, 1H), 11.25 (s, 1H); MS [M+H]+: 423.41.

Example-17

2-[(3,5-Dichloropyridin-4-yl)amino]-7,7-dimethyl-N-(3,6,6-trimethylbicyclo[3.1.1]hept-2-yl)-7,8-dihydro-1H-furo[3,2-e]benzimidazole-5-carboxamide

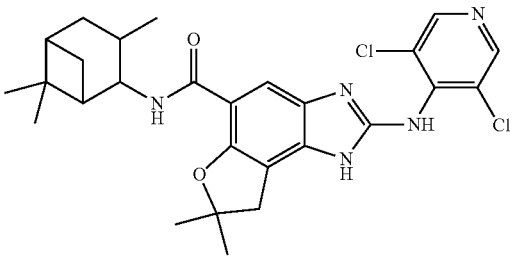 [SMILES: CC1CC2CC(C1NC(=O)c1cc3nc(Nc4c(Cl)cncc4Cl)[nH]c3c3c1OC(C)(C)C3)C2(C)C]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.050 g, 0.121 mmol), O-(benzotriazol-1-yl)-N,N,N',N'-tetramethyluronium tetrafluoroborate (0.081 g, 0.255 mmol), N-methyl morpholine (0.5 mL), DMF (1.0 mL), THF (5.0 mL) and 1R,2R,3R,5(−)-isopinocampheyl amine (0.039 g, 0.254 mmol) to afford 0.008 g of the desired product. $^1$HNMR (DMSO-d$_6$): δ 1.03 (s, 3H), 1.08 (d, J=6.9 Hz, 3H), 1.22 (s, 6H), 1.50 (s, 7H), 1.83-1.85 (m, 2H), 1.95 (m, 1H), 3.02 (s, 2H), 4.26 (m, 1H), 7.21 (s, 1H), 7.70 (d, J=8.4 Hz, 1H), 8.43 (s, 2H), 10.91 (brs, 1H), 11.42 (s, 1H); MS [M+H]+: 528.39.

Example-18

N-(4-Chlorophenyl)-2-[(2-chlorophenyl)amino]-7,7-dimethyl-7,8-dihydro-1H-furo[3,2-e]benzimidazole-5-carboxamide

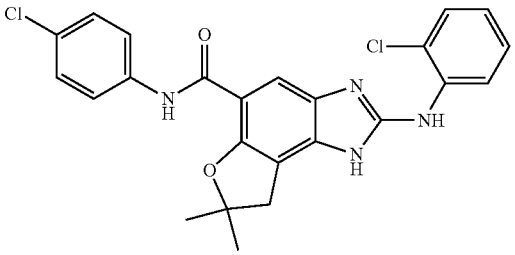 [SMILES: CC1(C)Cc2c(c(C(=O)Nc3ccc(Cl)cc3)cc3nc(Nc4ccccc4Cl)[nH]c23)O1]

The title compound was prepared following the procedure as described for Example-1 using 2-[(2-chlorophenyl)amino]-7,7-dimethyl-7,8-dihydro-1H-furo[3,2-e]benzimidazole-5-carboxylic acid (Intermediate-12, 0.050 g, 0.139 mmol), O-(benzotriazol-1-yl)-N,N,N',N'-tetramethyluronium tetrafluoroborate (0.089 g, 0.277 mmol), TEA (1.0 mL), DMF (1.0 mL), THF (5.0 mL) and 4-chloro aniline (0.035 g, 0275 mmol) to afford 0.015 g of the desired product. $^1$HNMR (DMSO-d$_6$): δ 1.60 (s, 6H), 3.17 (s, 2H), 7.05 (t, J=7.5 Hz, 1H), 7.36-7.43 (m, 2H), 7.49 (d, J=7.8 Hz, 2H), 7.75 (d, J=8.1 Hz, 2H), 8.58-8.60 (m, 1H), 9.07 (s, 1H), 9.87 (s, 1H), 11.02 (s, 1H), 11.36 (s, 1H); MS [M+H]+: 467.23.

Example-19

N-Adamantan-1-yl-2-[(3,5-dichloropyridin-4-yl)amino]-7,7-dimethyl-7,8-dihydro-1H-furo[3,2-e]benzimidazole-5-carboxamide

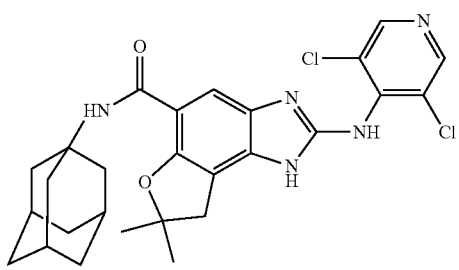 [SMILES: CC1(C)Cc2c(c(C(=O)NC34CC5CC(CC(C5)C3)C4)cc3nc(Nc4c(Cl)cncc4Cl)[nH]c23)O1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.080 g, 0.203 mmol), O-(benzotriazol-1-yl)-N,N,N',N'-tetramethyluronium tetrafluoroborate (0.130 g, 0.406 mmol), TEA (0.5 mL), DMF (1.0 mL), THF (5.0 mL) and adamantly amine (0.092 g, 0.609 mmol) to afford 0.015 g of the desired product. $^1$HNMR (DMSO-d$_6$): δ 1.49 (s, 6H), 1.66 (s, 6H), 2.01 (s, 9H), 3.01 (s, 2H), 7.19 (s, 1H), 7.51 (s, 1H), 8.42 (s, 2H), 10.87 (s, 1H), 11.39 (s, 1H); MS [M+H]+: 526.38.

Example-20

{2-[(3,5-Dichloropyridin-4-yl)amino]-7,7-dimethyl-7,8-dihydro-1H-furo[3,2-e]benzimidazol-5-yl}(morpholin-4-yl)methanone

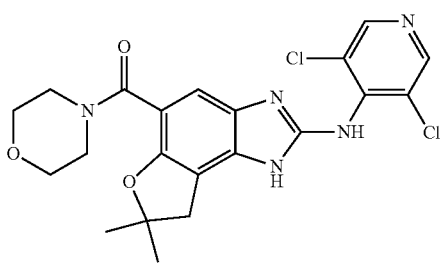 [SMILES: CC1(C)Cc2c(c(C(=O)N3CCOCC3)cc3nc(Nc4c(Cl)cncc4Cl)[nH]c23)O1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.060 g, 0.152 mmol), O-(benzotriazol-1-yl)-N,N,N',N'-tetramethyluronium tetrafluoroborate (0.098 g, 0.304 mmol), TEA (0.5 mL), DMF (1.0 mL), THF (5.0 mL) and morpholine (0.062 g, 0.304 mmol) to afford 0.010 g of the desired product. $^1$HNMR (DMSO-d$_6$): δ 1.41 (s, 6H), 2.96 (s, 2H), 3.37 (s, 4H), 3.56 (s, 4H), 6.64 (s, 1H), 8.40 (s, 2H), 10.82 (s, 1H), 11.26 (s, 1H); MS [M+H]$^+$: 462.23.

Example-21

N-(Cyclopropylmethyl)-2-[(3,5-dichloropyridin-4-yl)amino]-7,7-dimethyl-7,8-dihydro-1H-furo[3,2-e]benzimidazole-5-carboxamide

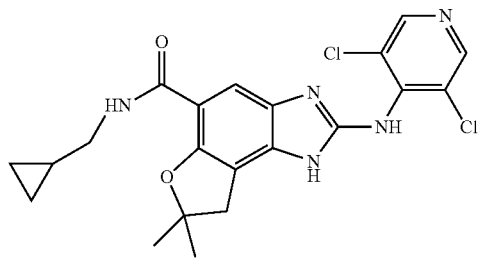 [SMILES: CC1(C)Cc2c(c(C(=O)NCC3CC3)cc3nc(Nc4c(Cl)cncc4Cl)[nH]c23)O1]

The title compound was prepared following the procedure as described for Example-1 using 2-[(3,5-dichloropyridin-4-yl)amino]-7,7-dimethyl-7,8-dihydro-1H-furo[3,2-e]benzimidazole-5-carboxylic acid (Intermediate-3, 0.080 g, 0.152 mmol), O-(benzotriazol-1-yl)-N,N,N',N'-tetramethyluronium tetrafluoroborate (0.130 g, 0.406 mmol), TEA (0.5 mL), DMF (1.0 mL), THF (5.0 mL) and 1-cyclopropylmethanamine (0.044 g, 0.406 mmol) to afford 0.015 g of the desired product. $^1$HNMR (DMSO-d$_6$): δ 0.220 (q, J=4.5 Hz, 2H), 0.44 (q, J=6.6 Hz, 2H), 1.01 (m, 1H), 1.51 (s, 6H), 3.02 (s, 2H), 3.19 (t, J=6.0 Hz, 2H), 7.22 (s, 1H), 7.77 (s, 1H), 8.43 (s, 2H), 10.99 (s, 1H), 11.40 (s, 1H); MS [M+H]$^+$: 446.27.

Example-22

2-[(3,5-Dichloropyridin-4-yl)amino]-N-(4-fluorobenzyl)-7-methyl-1H-furo[3,2-e]benzimidazole-5-carboxamide

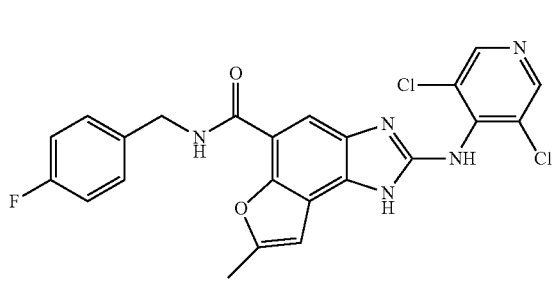 [SMILES: Cc1cc2c(o1)c(C(=O)NCc1ccc(F)cc1)cc1nc(Nc3c(Cl)cncc3Cl)[nH]c12]

The title compound was prepared following the procedure as described for Example-1 using 2-[(3,5-dichloropyridin-4-yl)amino]-7-methyl-1H-furo[3,2-e]benzimidazole-5-carboxylic acid (Intermediate-8, 0.060 g, 0.159 mmol), O-(benzotriazol-1-yl)-N,N,N',N'-tetramethyluronium tetrafluoroborate (0.102 g, 0.318 mmol), TEA (0.032 g, 0.318 mmol), THF (5.0 mL), DMF (1.0 mL), 4-fluoro benzyl amine (0.035 g, 0.318 mmol) to afford 0.015 g of the desired product. $^1$HNMR (DMSO-d$_6$): δ 2.49 (s, 3H), 4.55 (d, J=5.4 Hz, 2H), 6.22 (s, 1H), 7.13-7.16 (m, 2H), 7.41 (m, 3H), 8.44 (s, 2H), 8.61 (s, 1H), 11.22 (s, 1H), 11.76 (s, 1H); MS [M+H]$^+$: 484.24.

Example-23

2-[(3,5-Dichloropyridin-4-yl)amino]-N-(3,3-dimethylbutan-2-yl)-7-methyl-1H-furo[3,2-e]benzimidazole-5-carboxamide

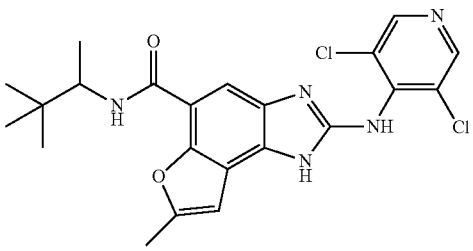 [SMILES: Cc1cc2c(o1)c(C(=O)NC(C)C(C)(C)C)cc1nc(Nc3c(Cl)cncc3Cl)[nH]c12]

The title compound was prepared following the procedure described for Example-1 using 2-[(3,5-dichloropyridin-4-yl)amino]-7-methyl-1H-furo[3,2-e]benzimidazole-5-carboxylic acid (Intermediate-8, 0.050 g, 0.132 mmol), propyl phosphonic anhydride (0.084 g, 0.265 mmol), TEA (0.027 g, 0.265 mmol), DMF (3.0 mL) and 3,3-dimethyl-2-butyl amine (0.027 g, 0.318 mmol) to afford 0.015 g of the desired product. $^1$HNMR (DMSO-d$_6$): δ 0.85 (t, J=6.9 Hz, 3H), 0.96 (s, 6H), 1.11 (d, J=6.9 Hz, 3H), 2.50 (m, 3H), 3.95-3.97 (m, 1H), 6.65 (s, 1H), 7.35 (s, 1H), 7.63 (d, J=9.0 Hz, 1H), 8.45 (s, 2H), 11.20 (s, 1H), 11.80 (s, 1H); MS [M+H]$^+$: 460.34.

Example-24

2-[(3,5-Dichloropyridin-4-yl)amino]-N-(4-fluorophenyl)-7,7-dimethyl-7,8-dihydro-1H-furo[3,2-e]benzimidazole-5-carboxamide

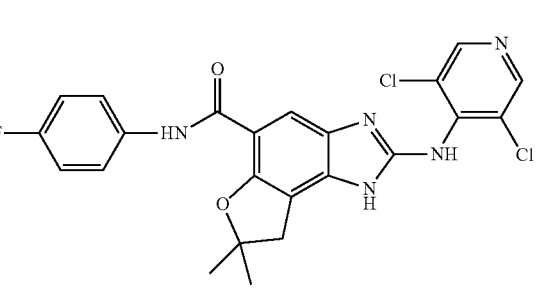

The title compound was prepared following the procedure described for Example-1 using Intermediate-3 (0.100 g, 0.253 mmol) in mixture of DMF (1.0 mL), THF (5.0 mL), O-(benzotriazol-1-yl)-N,N,N',N'-tetramethyluronium tetrafluoroborate (0.243 g, 0.760 mmol), TEA (1.0 mL), 4-fluoro aniline (0.085 g, 0.765 mmol) and THF (5.0 mL). The product obtained was further purified by column chromatography on neutral alumina eluting with 1.5-2.0% MeOH:DCM to afford 0.025 g of the desired product. $^1$HNMR (DMSO-d$_6$): δ 1.57 (s, 6H), 3.07 (s, 2H), 7.19 (t, J=8.70 Hz, 2H), 7.26 (s, 1H), 7.70 (m, 2H), 8.45 (s, 2H), 9.66 (s, 1H), 10.98 (s, 1H), 11.51 (s, 1H); MS [M+H]⁺: 486.18.

Example-25

2-[(3,5-Dichloropyridin-4-yl)amino]-7,7-dimethyl-N-(2,4,4-trimethylpentan-2-yl)-7,8-dihydro-1H-furo[3,2-e]benzimidazole-5-carboxamide

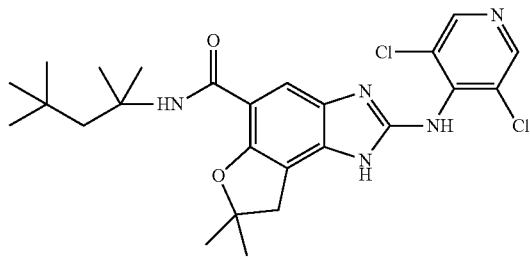 [SMILES: CC(C)(C)CC(C)(C)NC(=O)c1cc2nc(Nc3c(Cl)cncc3Cl)[nH]c2c2c1OC(C)(C)C2]

The title compound was prepared following the procedure described for example-1 using Intermediate-3 (0.080 g, 0.203 mmol), O-(benzotriazol-1-yl)-N,N,N',N'-tetramethyluronium tetrafluoroborate (0.195 g, 0.609 mmol), TEA (0.5 mL), DMF (1.0 mL), THF (5.0 mL) and tert octyl amine (0.079 g, 0.609 mmol). The product obtained was further purified by column chromatography on neutral alumina eluting with 1.5-2.0% MeOH:DCM to afford 0.010 g of the desired product. ¹HNMR (DMSO-d₆): δ 0.954 (s, 9H), 1.33 (s, 6H), 1.41 (s, 3H), 1.49 (s, 3H), 1.75 (s, 2H), 3.02 (s, 2H), 7.21 (s, 1H), 7.59 (s, 1H), 8.42 (s, 2H), 10.90 (s, 1H), 11.39 (s, 1H); MS [M−H]⁻: 502.27.

Example-26

2-[(3,5-Dichloropyridin-4-yl)amino]-N-(4-fluorobenzyl)-7,7-dimethyl-7,8-dihydro-1H-furo[3,2-e]benzimidazole-5-carboxamide

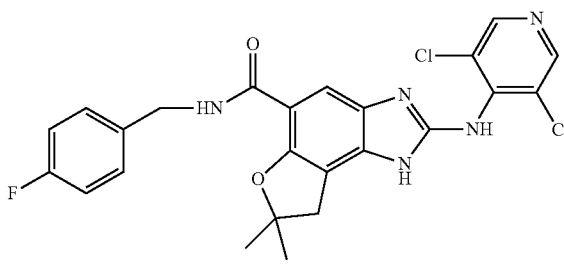 [SMILES: CC1(C)Cc2c(c(C(=O)NCc3ccc(F)cc3)cc3nc(Nc4c(Cl)cncc4Cl)[nH]c23)O1]

The title compound was prepared following the procedure described for example-1 using intermediate-3 (0.100 g, 0.253 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and 4-fluoro benzyl amine (0.095 g, 0.761 mmol). The product obtained was further purified by column chromatography on neutral alumina eluting with 1.5-2.0% MeOH:DCM to afford 0.012 g of the desired product. ¹HNMR (DMSO-d₆): δ 1.50 (s, 6H), 3.02 (s, 2H), 4.51 (m, 2H), 7.15 (t, J=8.4 Hz, 2H), 7.23 (s, 1H), 7.33 (t, J=7.5 Hz, 2H), 8.19 (m, 1H), 8.43 (s, 2H), 10.92 (s, 1H), 11.42 (s, 1H); MS [M−H]⁻: 498.14.

Example-27

N-(Cyclohexylmethyl)-2-[(3,5-dichloropyridin-4-yl)amino]-7,7-dimethyl-7,8-dihydro-1H-furo[3,2-e]benzimidazole-5-carboxamide

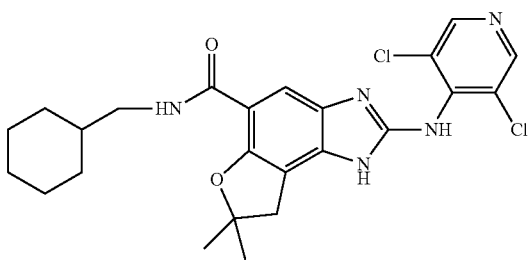 [SMILES: CC1(C)Cc2c(c(C(=O)NCC3CCCCC3)cc3nc(Nc4c(Cl)cncc4Cl)[nH]c23)O1]

The title compound was prepared following the procedure described for example-1 using Intermediate-3 (0.100 g, 0.253 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and cyclohexyl methanamine (0.086 g, 0.761 mmol). The product obtained was further purified by column chromatography on neutral alumina eluting with 1.5-2.0% MeOH:DCM to afford 0.010 g of the desired product. ¹HNMR (DMSO-d₆): δ 0.94-1.01 (m, 2H), 1.01-1.19 (m, 4H), 1.55 (s, 6H), 1.66-1.40 (m, 5H), 3.02 (s, 2H), 3.16 (t, J=5.7 Hz, 2H), 7.21 (s, 1H), 7.72 (s, 1H), 8.43 (s, 2H), 10.91 (s, 1H), 11.40 (s, 1H); MS [M−H]⁻: 486.21.

Example-28

N-Cyclohexyl-2-[(3,5-dichloropyridin-4-yl)amino]-7,7-dimethyl-7,8-dihydrofuro[2,3-g][1,3]benzothiazole-5-carboxamide

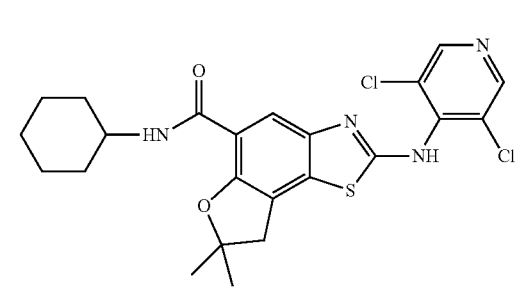 [SMILES: CC1(C)Cc2c(c(C(=O)NC3CCCCC3)cc3nc(Nc4c(Cl)cncc4Cl)sc23)O1]

The title compound was prepared following the procedure described for Example-1 using Intermediate-13 (0.080 g, 0.121 mmol), O-(benzotriazol-1-yl)-N,N,N',N'-tetramethyluronium tetrafluoroborate (0.115 g, 0.358 mmol), TEA (0.5 mL), DMF (0.5 mL), THF (3.0 mL) and cyclohexanamine (0.036 g, 0.358 mmol). The product obtained was further purified by column chromatography on neutral alumina eluting with 1.5-2.0% MeOH:DCM to afford 0.010 g of the desired product. ¹HNMR (DMSO-d₆): δ 1.22 (s, 4H), 1.48

(m, 6H), 1.83 (m, 2H), 3.03 (m, 2H), 3.24-3.30 (m, 4H), 3.80 (m, 1H), 7.40 (s, 1H), 7.67 (m, 1H), 8.59 (s, 2H), 12.15 (s, 1H); MS [M+H]⁺: 491.22.

Example-29

2-[(2,6-Dichlorophenyl)amino]-N-(4-fluorophenyl)-7,7-dimethyl-7,8-dihydro-1H-furo[3,2-e]benzimidazole-5-carboxamide

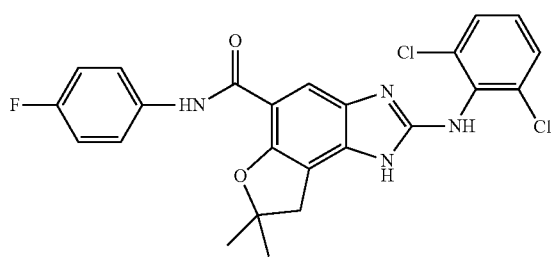 [SMILES: CC1(C)Cc2c(c(C(=O)Nc3ccc(F)cc3)cc3nc(Nc4c(Cl)cccc4Cl)[nH]c23)O1]

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and 4-fluoro aniline (0.085 g, 0.761 mmol). The product obtained was further purified by column chromatography on neutral alumina eluting with 1.5-2.0% MeOH:DCM to afford 0.010 g of the desired product. ¹HNMR (DMSO-d₆): δ 1.56 (s, 6H), 3.08 (s, 2H), 7.16-7.22 (m, 3H), 7.39 (m, 1H), 7.52-7.54 (m, 2H), 7.70 (m, 2H), 9.73 (s, 1H); MS [M+H]⁺: 485.24.

Example-30

2-[(2,6-Dichlorophenyl)amino]-N-(2-fluorophenyl)-7,7-dimethyl-7,8-dihydro-1H-furo[3,2-e]benzimidazole-5-carboxamide

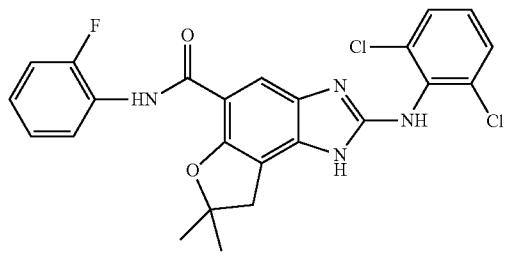 [SMILES: CC1(C)Cc2c(c(C(=O)Nc3ccccc3F)cc3nc(Nc4c(Cl)cccc4Cl)[nH]c23)O1]

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and 2-fluoro aniline (0.085 g, 0.761 mmol). The product obtained was further purified by column chromatography on neutral alumina eluting with 1.5-2.0% MeOH:DCM to afford 0.030 g of the desired product. ¹HNMR (DMSO-d₆): δ 1.55 (s, 6H), 3.11 (s, 2H), 7.11-7.35 (m, 4H), 7.44 (s, 1H), 7.54 (d, J=8.4 Hz, 2H), 8.45-8.48 (s, 1H), 10.10 (s, 1H); MS [M+H]⁺: 487.24.

Example-31

N-(Cyclopropylmethyl)-2-[(2,6-dichlorophenyl)amino]-7,7-dimethyl-7,8-dihydro-1H-furo[3,2-e]benzimidazole-5-carboxamide

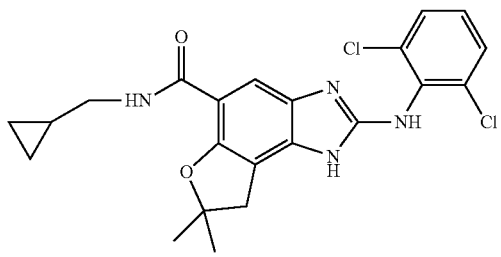 [SMILES: CC1(C)Cc2c(c(C(=O)NCC3CC3)cc3nc(Nc4c(Cl)cccc4Cl)[nH]c23)O1]

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and 1-cyclopropylmethanamine hydrochloride (0.082 g, 0.760 mmol). The product obtained was further purified by column chromatography on neutral alumina eluting with 1.5-2.0% MeOH:DCM to afford 0.010 g of the desired product. ¹HNMR (DMSO-d₆): δ 0.22 (m, 2H), 0.42-0.45 (m, 2H), 1.02 (s, 1H), 1.49 (s, 6H), 3.03 (s, 2H), 3.19 (m, 2H), 7.10 (s, 1H), 7.32 (s, 1H), 7.50-7.52 (m, 2H), 7.80 (m, 1H), 10-11 (s, 2H); MS [M+H]⁺: 445.22.

Example-32

2-[(3,5-Dichloropyridin-4-yl)amino]-7-methyl-N-[4-(trifluoromethyl)phenyl]-1H-furo[3,2-e]benzimidazole-5-carboxamide

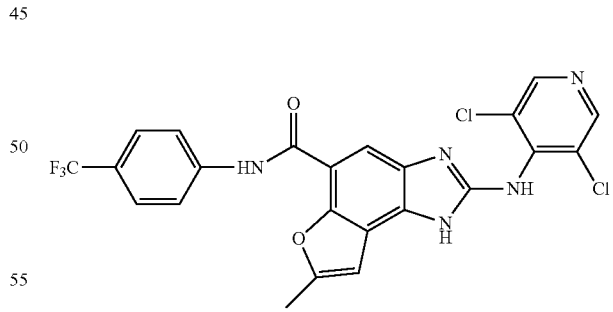

The title compound was prepared following the procedure described for Example-1 using Intermediate-8 (0.100 g, 0.265 mmol), O-(benzotriazol-1-yl)-N,N,N',N'-tetramethyluronium tetrafluoroborate (0.255 g, 0.795 mmol), TEA (0.080 g, 0.795 mmol), THF (10.0 mL), DMF (2.0 mL) and 4-trifluoromethyl phenyl amine (0.085 g, 0.530 mmol). The product obtained was further purified by column chromatography on neutral alumina eluting with 1.5-2.0% MeOH:DCM to afford 0.010 g of the desired product. ¹HNMR (DMSO-d₆):

δ 2.49 (s, 3H), 6.65 (S, 1H), 7.34 (m, 1H), 7.74 (m, 2H), 7.98 (m, 2H), 8.46 (s, 2H), 10.39 (s, 1H), 11.20 (s, 1H), 11.80 (s, 1H); MS [M−H]⁻: 518.16.

Example-33

N-(Cyclohexylmethyl)-2-[(3,5-dichloropyridin-4-yl)amino]-7-methyl-1H-furo[3,2-e]benzimidazole-5-carboxamide

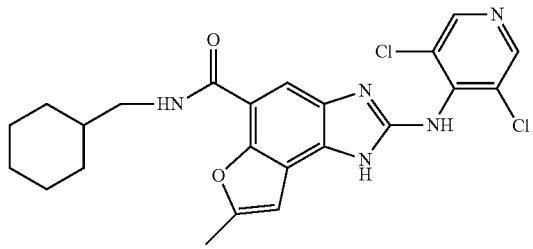 [SMILES: Cc1cc2c(o1)c(C(=O)NCC1CCCCC1)cc1nc(Nc3c(Cl)cncc3Cl)[nH]c12]

The title compound was prepared by following the procedure as described for Example-1 using Intermediate-8 (0.050 g, 0.132 mmol), O-(benzotriazol-1-yl)-N,N,N',N'-tetramethyluronium tetrafluoroborate (0.127 g, 0.397 mmol), TEA (0.040 g, 0.396 mmol), THF (5.0 mL), DMF (1.0 mL) and 1-cyclohexylmethanamine (0.030 g, 0.265 mmol). The product obtained was further purified by column chromatography on neutral alumina eluting with 1.5-2.0% MeOH:DCM to afford 0.008 g of the desired product. ¹HNMR (DMSO-d₆): δ 0.84-1.02 (m, 2H), 1.17-1.32 (m, 2H), 1.66-1.76 (m, 6H), 2.49 (s, 3H), 2.88 (s, 1H), 3.18-3.22 (m, 2H), 6.61 (s, 1H), 7.31 (s, 1H), 7.96 (m, 1H), 8.44 (s, 2H), 11.21 (s, 1H), 11.71 (s, 1H); MS [M]⁺: 472.29.

Example-34

2-[(3,5-Dichloropyridin-4-yl)amino]-7-methyl-N-(2,4,4-trimethylpentan-2-yl)-1H-furo[3,2-e]benzimidazole-5-carboxamide

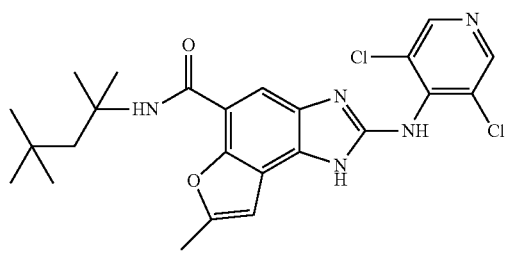 [SMILES: Cc1cc2c(o1)c(C(=O)NC(C)(C)CC(C)(C)C)cc1nc(Nc3c(Cl)cncc3Cl)[nH]c12]

The title compound was prepared following the procedure described for Example-1 using Intermediate-8 (0.060 g, 0.159 mmol), O-(benzotriazol-1-yl)-N,N,N',N'-tetramethyluronium tetrafluoroborate (0.153 g, 0.477 mmol), TEA (0.048 g, 0.477 mmol), THF (5.0 mL), DMF (1.0 mL) and 2,4,4-trimethylpentan-2-amine (0.042 g, 0.325 mmol). The product obtained was further purified by column chromatography on neutral alumina eluting with 1.5-2.0% MeOH:DCM to afford 0.008 g of the desired product. ¹HNMR (DMSO-d₆): δ 1.00 (s, 6H), 1.23 (s, 9H), 1.48 (s, 2H), 2.50 (s, 3H), 6.63 (s, 1H), 7.35 (s, 1H), 7.51 (s, 1H), 8.45 (s, 2H), 11.20 (s, 1H), 11.80 (s, 1H); MS [M]⁻: 488.31.

Example-35

2-[(2,6-Dichlorophenyl)amino]-N-(4-fluorobenzyl)-7-methyl-1H-furo[3,2-e]benzimidazole-5-carboxamide

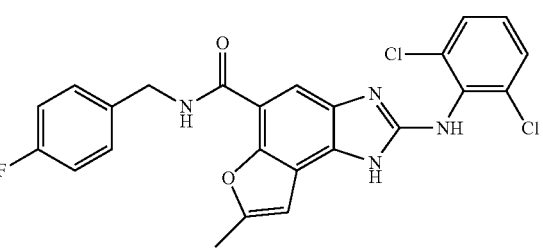 [SMILES: Cc1cc2c(o1)c(C(=O)NCc1ccc(F)cc1)cc1nc(Nc3c(Cl)cccc3Cl)[nH]c12]

The title compound was prepared following the procedure described for Example-1 using Intermediate-9 (0.100 g, 0.265 mmol), O-(benzotriazol-1-yl)-N,N,N',N'-tetramethyluronium tetrafluoroborate (0.255 g, 0795 mmol), TEA (0.053 g, 0.525 mmol), THF (5.0 mL), DMF (1.0 mL) and 1-(4-fluorophenyl)methanamine (0.066 g, 0.528 mmol). The product obtained was further purified by column chromatography on neutral alumina eluting with 1.5-2.0% MeOH:DCM to afford 0.025 g of the desired product. ¹HNMR (DMSO-d₆): δ 2.50 (s, 3H), 4.55-4.57 (m, 2H), 6.69 (s, 1H), 7.16 (t, J=8.7 Hz, 2H), 7.30 (s, 1H), 7.41 (t, J=7.8 Hz, 2H), 7.56-7.59 (m, 3H), 8.54 (s, 1H), 11-12 (s, 2H); MS [M]⁺²: 485.33.

Example-36

2-[(3,5-Dichloropyridin-4-yl)amino]-N-(4-fluorophenyl)-7-methyl-1H-furo[3,2-e]benzimidazole-5-carboxamide

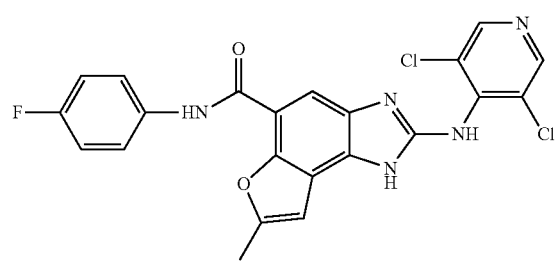 [SMILES: Cc1cc2c(o1)c(C(=O)Nc1ccc(F)cc1)cc1nc(Nc3c(Cl)cncc3Cl)[nH]c12]

The title compound was prepared following the procedure described for Example-1 using Intermediate-8, 0.100 g, 0.265 mmol), O-(benzotriazol-1-yl)-N,N,N',N'-tetramethyluronium tetrafluoroborate (0.255 g, 0.795 mmol), TEA (0.053 g, 0.530 mmol), THF (5.0 mL), DMF (1.0 mL) and 4-fluoro aniline (0.059 g, 0.530 mmol). The product obtained was further purified by column chromatography on neutral alumina eluting with 1.5-2.0% MeOH:DCM to afford 0.020 g of the desired product. ¹HNMR (DMSO-d₆): δ 3.04 (s, 3H), 6.68

(s, 1H), 7.18-7.23 (m, 3H), 7.78-7.82 (m, 2H), 8.28 (s, 2H), 9.81 (s, 1H), 11.20 (s, 1H), 11.80 (s, 1H); MS [M]⁻: 468.13

Example-37

2-[(2-Chloro-6-fluorophenyl)amino]-N-(4-fluorophenyl)-7,7-dimethyl-7,8-dihydro-1H-furo[3,2-e]benzimidazole-5-carboxamide

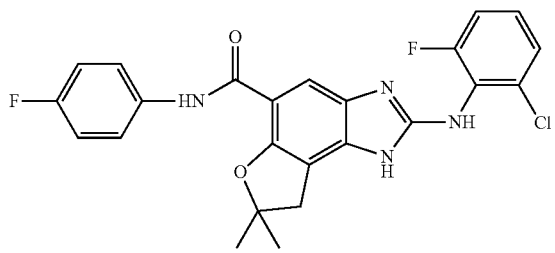 [SMILES: CC1(C)Cc2c(c(C(=O)Nc3ccc(F)cc3)cc3nc(Nc4c(F)cccc4Cl)[nH]c23)O1]

The title compound was prepared following the procedure described for Example-1 using Intermediate-15, 0.100 g, 0.267 mmol), O-(benzotriazol-1-yl)-N,N,N',N'-tetramethyluronium tetrafluoroborate (0.250 g, 0.800 mmol), TEA (1.mL), THF (5.0 mL), DMF (1.0 mL), 4-fluoro aniline (0.089 g, 0.802 mmol). The product obtained was further purified by column chromatography on neutral alumina eluting with 1.5-2.0% MeOH:DCM to afford 0.010 g of the desired product. ¹HNMR (DMSO-$d_6$): δ 1.56 (s, 6H), 3.09 (s, 2H), 7.19 (t, J=8.7 Hz, 2H), 7.32 (d, J=9.0 Hz, 2H), 7.41 (d, J=7.2 Hz, 1H), 7.47 (s, 1H), 7.69-7.73 (m, 2H), 9.75 (s, 1H), 11.07 (s, 2H); MS [M+H]⁺: 469.23.

Example-38

2-[(2,6-Dichlorophenyl)amino]-7,7-dimethyl-N-(5-methyl-1,3,4-thiadiazol-2-yl)-7,8-dihydro-1H-furo[3,2-e]benzimidazole-5-carboxamide

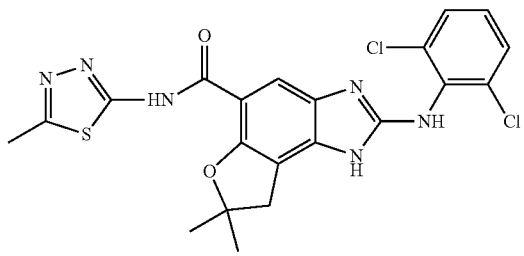 [SMILES: Cc1nnc(NC(=O)c2cc3nc(Nc4c(Cl)cccc4Cl)[nH]c3c3c2OC(C)(C)C3)s1]

The title compound was prepared following the procedure described for Example-1 using Intermediate-6, 0.100 g, 0.254 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL), 5-methyl-1,3,4-thiadiazol-2-amine (0.088 g, 0.765 mmol). The product obtained was further purified by column chromatography on neutral alumina eluting with 1.5-2.0% MeOH:DCM to afford 0.030 g of the desired product. ¹HNMR (DMSO-$d_6$): δ 1.58 (s, 6H), 2.63

(s, 3H), 3.11 (s, 2H), 7.27 (m, 1H), 7.41 (m, 1H), 7.55 (d, J=7.8 Hz, 2H), 11.00 (s, 1H); MS [M+H]⁺: 489.15.

Example-39

2-[(2-Chloro-6-fluorophenyl)amino]-N-(4-fluorobenzyl)-7,7-dimethyl-7,8-dihydro-1H-furo[3,2-e]benzimidazole-5-carboxamide

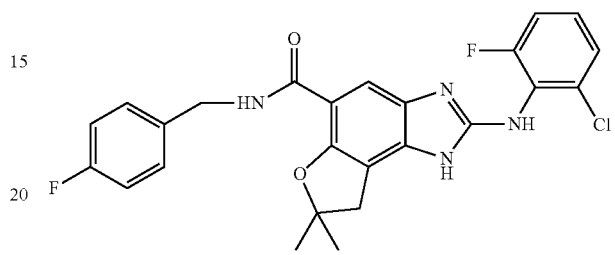

The title compound was prepared following the procedure described for Example-1 using Intermediate-15 (0.100 g, 0.267 mmol), O-(benzotriazol-1-yl)-N,N,N',N'-tetramethyluronium tetrafluoroborate (0.250 g, 0.800 mmol), TEA (1.mL), THF (5.0 mL), DMF (1.0 mL) and 1-(4-fluorophenyl)methanamine (0.100 g, 0.798 mmol). The product obtained was further purified by column chromatography on neutral alumina eluting with 1.5-2.0% MeOH:DCM to afford 0.040 g of the desired product. ¹HNMR (DMSO-$d_6$): δ 1.48 (s, 6H), 3.04 (s, 2H), 4.51 (d, J=5.4 Hz, 2H), 7.15 (t, J=9.0 Hz, 2H), 7.28-7.41 (m, 6H), 8.22 (m, 1H), 10-11 (s, 2H); MS [M+H]⁺: 483.36.

Example-40

2-[(2,6-Dichlorophenyl)amino]-7,7-dimethyl-N-(5-methyl-1,3-thiazol-2-yl)-7,8-dihydro-1H-furo[3,2-e]benzimidazole-5-carboxamide

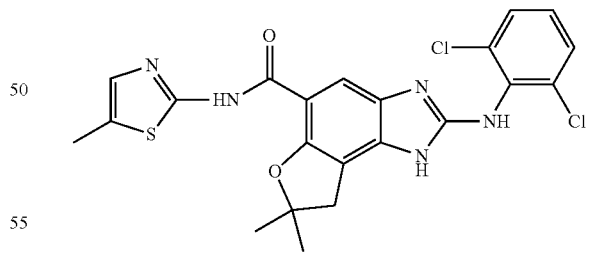

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and 5-methyl-1,3-thiazol-2-amine (0.088 g, 0.765 mmol). The product obtained was further purified by column chromatography on neutral alumina eluting with 1.5-2.0% MeOH:DCM to afford 0.010 g of the desired product. ¹HNMR (DMSO-$d_6$): δ 1.58 (s, 6H), 2.36 (s, 3H), 3.10 (s, 2H), 7.16 (s, 1H), 7.27 (s, 1H), 7.42 (s, 1H), 755 (d, J=7.8 Hz, 2H), 10.76 (s, 1H); MS [M+H]⁺: 488.17.

Example-41

2-[(2,6-Dichlorophenyl)amino]-7,7-dimethyl-N-(2-methylbutan-2-yl)-7,8-dihydro-1H-furo[3,2-e]benzimidazole-5-carboxamide

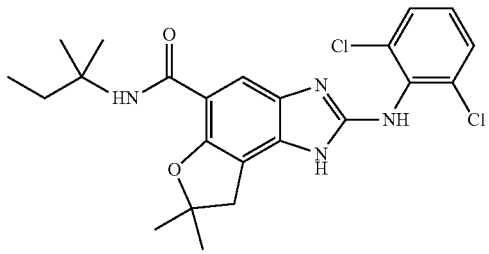 [SMILES: CCC(C)(C)NC(=O)c1cc2nc(Nc3c(Cl)cccc3Cl)[nH]c2c2c1OC(C)(C)C2]

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and 2-methylbutan-2-amine (0.067 g, 0.765 mmol). The product obtained was further purified by column chromatography on neutral alumina eluting with 1.5-2.0% MeOH:DCM to afford 0.025 g of the desired product. ¹HNMR (DMSO-d₆): δ 0.83 (t, J=6.9 Hz, 3H), 1.31 (s, 6H), 1.47 (s, 6H), 1.65-1.67 (m, 2H), 3.04 (s, 2H), 7.24 (m, 1H), 7.33 (s, 1H), 7.53 (d, J=7.8 Hz, 1H), 7.59 (s, 1H), 7.66 (s, 1H), 10-11 (s, 2H); MS [M+H]⁺: 461.30.

Example-42

2-[(2-Chloro-6-fluorophenyl)amino]-N-(cyclohexylmethyl)-7,7-dimethyl-7,8-dihydro-1H-furo[3,2-e]benzimidazole-5-carboxamide

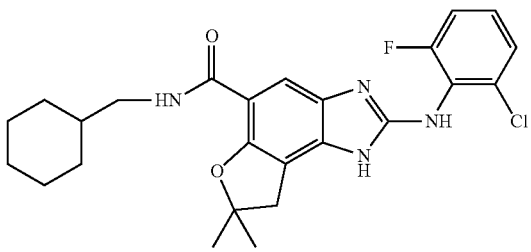 [SMILES: CC1(C)Cc2c(c(C(=O)NCC3CCCCC3)cc3nc(Nc4c(F)cccc4Cl)[nH]c23)O1]

The title compound was prepared following the procedure described for Example-1 using Intermediate-15 (0.100 g, 0.267 mmol), O-(benzotriazol-1-yl)-N,N,N',N'-tetramethyluronium tetrafluoroborate (0.250 g, 0.800 mmol), TEA (1.mL), THF (5.0 mL), DMF (1.0 mL) and 1-cyclohexylmethanamine (0.090 g, 0.798 mmol). The product obtained was further purified by column chromatography on neutral alumina eluting with 1.5-2.0% MeOH:DCM to afford 0.040 g of the desired product. ¹HNMR (DMSO-d₆): δ 0.94-0.98 (m, 2H), 1.16-1.33 (m, 4H), 1.48 (s, 6H), 1.67-1.70 (m, 5H), 3.04 (s, 2H), 3.17 (m, 2H), 7.27 (m, 2H), 7.40 (m, 2H), 7.78 (s, 1H), 11.00-11.20 (s, 2H); MS [M+H]⁺: 471.37.

Example-43

2-[(2,6-Dichlorophenyl)amino]-N-(2-hydroxypropyl)-7,7-dimethyl-7,8-dihydro-1H-furo[3,2-e]benzimidazole-5-carboxamide

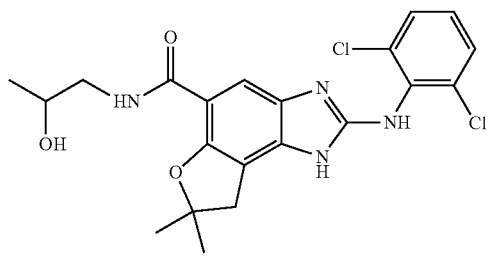 [SMILES: CC(O)CNC(=O)c1cc2nc(Nc3c(Cl)cccc3Cl)[nH]c2c2c1OC(C)(C)C2]

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.244 g, 0.761 mmol), TEA (1.0 mL), DMF (1.0 mL), THF (5.0 mL) and 1-aminopropan-2-ol (0.057 g, 0.765 mmol). The product obtained was further purified by column chromatography on neutral alumina eluting with 1.5-2.0% MeOH:DCM to afford 0.040 g of the desired product. ¹HNMR (DMSO-d₆): δ 1.07 (d, J=7.2 Hz, 3H), 1.48 (s, 6H), 3.03 (s, 2H), 3.14-3.16 (m, 2H), 3.73 (m, 1H), 4.83 (d, J=3.9 Hz, 1H), 7.19 (m, 1H), 7.33 (s, 1H), 7.51 (d, J=7.8 Hz, 2H), 7.95 (s, 1H), 10-11 (s, 2H); MS [M+H]⁺: 449.32.

Example-44

N-(Cyclopentylmethyl)-2-[(2,6-dichlorophenyl)amino]-7,7-dimethyl-7,8-dihydro-1H-furo[3,2-e]benzimidazole-5-carboxamide

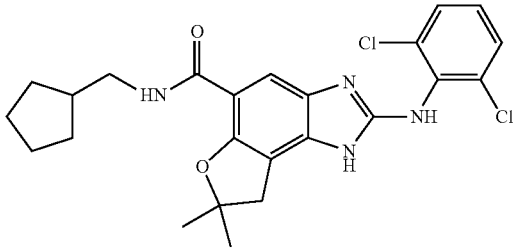 [SMILES: CC1(C)Cc2c(c(C(=O)NCC3CCCC3)cc3nc(Nc4c(Cl)cccc4Cl)[nH]c23)O1]

The title compound was prepared following the procedure described for Example-1 using Intermediate-6 (0.080 g, 0.204 mmol), O-(benzotriazol-1-yl)-N,N,N',N'-tetramethyluronium tetrafluoroborate (0.196 g, 0.610 mmol), TEA (1.0 mL), DMF (1.0 mL), THF (5.0 mL) and Intermediate-16 (0.060 g, 0.606 mmol). The product obtained was further purified by column chromatography on neutral alumina eluting with 1.5-2.0% MeOH:DCM to afford 0.020 g of the desired product. ¹HNMR (DMSO-d₆): δ 1.23 (s, 4H), 1.49 (s, 6H), 1.69 (m, 4H), 2.05-2.12 (m, 1H), 2.99 (s, 2H), 3.23 (t, J=6.0 Hz, 2H), 7.20 (s, 1H), 7.32 (s, 1H), 7.52 (d, J=7.8 Hz, 2H), 7.71 (m, 1H), 10-11 (s, 2H); MS [M+H]⁺: 473.29.

Example-45

2-[(2,6-Dichlorophenyl)amino]-N-(6-methoxypyridin-3-yl)-7,7-dimethyl-7,8-dihydro-1H-furo[3,2-e]benzimidazole-5-carboxamide

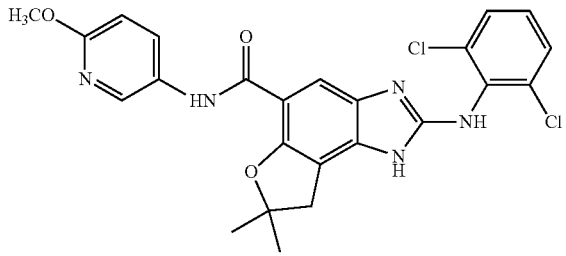 [SMILES: COc1ccc(NC(=O)c2cc3nc(Nc4c(Cl)cccc4Cl)[nH]c3c3c2OC(C)(C)C3)cn1]

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.245 g, 0.765 mmol), TEA (1.0 mL), DMF (1.0 mL), THF (5.0 mL) and 6-methoxypyridin-3-amine (0.094 g, 0.765 mmol). The product obtained was further purified by column chromatography on neutral alumina eluting with 1.5-2.0% MeOH:DCM to afford 0.040 g of the desired product. ¹HNMR (DMSO-$d_6$): δ 1.56 (s, 6H), 3.08 (s, 2H), 3.83 (s, 3H), 7.83 (d, J=8.7 Hz, 1H), 7.23 (s, 1H), 7.38 (s, 1H), 7.53 (d, J=8.1 Hz, 2H), 8.01-8.04 (m, 1H), 8.46 (s, 1H), 9.62 (s, 1H), 11.20 (s, 2H); MS [M+H]⁺: 498.25.

Example-46

2-[(2,6-Dichlorophenyl)amino]-7,7-dimethyl-N-(3-methylbutyl)-7,8-dihydro-1H-furo[3,2-e]benzimidazole-5-carboxamide

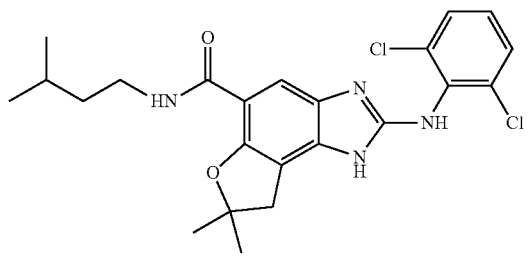 [SMILES: CC(C)CCNC(=O)c1cc2nc(Nc3c(Cl)cccc3Cl)[nH]c2c2c1OC(C)(C)C2]

The title compound was prepared following the procedure described for Example-1 using Intermediate-6 (0.100 g, 0.254 mmol), O-(benzotriazol-1-yl)-N,N,N',N'-tetramethyluronium tetrafluoroborate (0.245 g, 0.765 mmol), TEA (1.0 mL), DMF (1.0 mL), THF (5.0 mL) and 3-methylbutan-1-amine (0.066 g, 0.765 mmol). The product obtained was further purified by column chromatography on neutral alumina eluting with 1.5-2.0% MeOH:DCM to afford 0.050 g of the desired product. ¹HNMR (DMSO-$d_6$): δ 0.92 (s, 6H), 1.29 (s, 2H), 1.33-1.43 (m, 6H), 1.48-1.66 (m, 3H), 3.02 (s, 2H), 7.19 (s, 1H), 7.31 (s, 1H), 7.51 (d, J=7.8 Hz, 2H), 7.70 (m, 1H), 10-11 (s, 2H); MS [M+H]⁺: 461.31.

Example-47

2-[(2-Chloro-6-fluorophenyl)amino]-N-(4-fluorophenyl)-7-methyl-1H-furo[3,2-e]benzimidazole-5-carboxamide

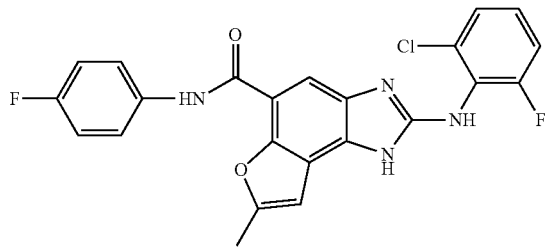 [SMILES: Cc1cc2c(o1)c(C(=O)Nc1ccc(F)cc1)cc1nc(Nc3c(F)cccc3Cl)[nH]c12]

The title compound was prepared following the procedure described for Example-1 using Intermediate-17 (0.100 g, 0.278 mmol), O-(benzotriazol-1-yl)-N,N,N',N'-tetramethyluronium tetrafluoroborate (0.268 g, 0.831 mmol), TEA (0.056 g, 0.557 mmol), THF (5.0 mL), DMF (1.0 mL) and 4-fluoroaniline (0.062 g, 0.557 mmol). The product obtained was further purified by column chromatography on neutral alumina eluting with 1.5-2.0% MeOH:DCM to afford 0.025 g of the desired product. ¹HNMR (DMSO-$d_6$): δ 2.50 (s, 3H), 6.73 (s, 1H), 7.20 (t, J=9.0 Hz, 2H), 7.35 (d, J=7.8 Hz, 2H), 7.43 (s, 1H), 7.55 (s, 1H), 7.79-7.83 (m, 2H), 9.20 (s, 1H), 10.02 (s, 1H), 11.44 (s, 1H); MS [M]⁺²: 453.32.

Example-48

2-[(2-Chloro-6-fluorophenyl)amino]-N-(4-fluorobenzyl)-7-methyl-1H-furo[3,2-e]benzimidazole-5-carboxamide

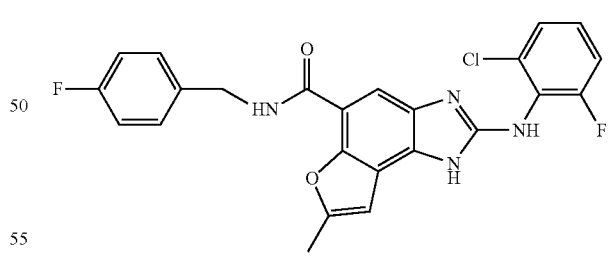

The title compound was prepared following the procedure described for Example-1 using Intermediate-17 (0.100 g, 0.278 mmol), O-(benzotriazol-1-yl)-N,N,N',N'-tetramethyluronium tetrafluoroborate (0.268 g, 0.831 mmol), TEA (0.056 g, 0.557 mmol), THF (5.0 mL), DMF (1.0 mL) and 1-(4-fluorophenyl)methanamine (0.070 g, 0.557 mmol). The product obtained was further purified by column chromatography on neutral alumina eluting with 1.5-2.0% MeOH:DCM to afford 0.012 g of the desired product. ¹HNMR (DMSO-$d_6$): δ 2.49 (s, 3H), 4.56 (d, J=5.1 Hz, 2H), 6.71 (s, 1H), 7.16 (t, J=8.7 Hz, 2H), 7.35-7.43 (m, 5H), 7.57 (s, 1H), 8.55 (s, 1H), 9.14 (s, 1H), 11.39 (s, 1H); MS [M+H]+: 467.34.

Example-49

2-[(2-Chloro-6-fluorophenyl)amino]-N-(cyclohexylmethyl)-7-methyl-1H-furo[3,2-e]benzimidazole-5-carboxamide

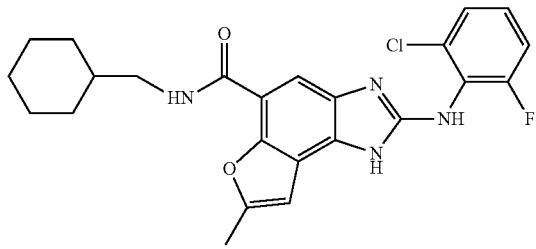 [SMILES: Cc1cc2c(o1)c(C(=O)NCC1CCCCC1)cc1nc(Nc3c(F)cccc3Cl)[nH]c12]

The title compound was prepared following the procedure described for Example-1 using Intermediate-17 (0.060 g, 0.167 mmol), O-(benzotriazol-1-yl)-N,N,N',N'-tetramethyluronium tetrafluoroborate (0.161 g, 0.501 mmol), TEA (0.034 g, 0.334 mmol), THF (5.0 mL), DMF (1.0 mL) and cyclohexyl methanamine (0.038 g, 0.334 mmol). The product obtained was further purified by column chromatography on neutral alumina eluting with 1.5-2.0% MeOH:DCM to afford 0.012 g of the desired product. $^1$HNMR (DMSO-$d_6$): δ 0.97-1.18 (m, 5H), 1.68-1.78 (m, 5H), 2.50 (m, 3H), 3.22 (m, 3H), 6.70 (s, 1H), 7.33 (m, 2H), 7.42 (m, 1H), 7.53 (s, 1H), 7.92 (s, 1H), 9.13 (s, 1H), 11.36 (s, 1H); MS [M+H]+: 455.37.

Example-50

2-[(3,5-Dichloropyridin-4-yl)amino]-7-methyl-N-(3-methylbutyl)-1H-furo[3,2-e]benzimidazole-5-carboxamide

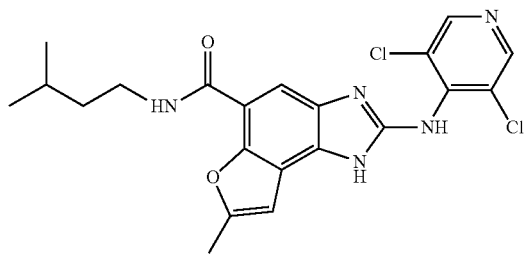 [SMILES: Cc1cc2c(o1)c(C(=O)NCCC(C)C)cc1nc(Nc3c(Cl)cncc3Cl)[nH]c12]

The title compound was prepared following the procedure described for Example-1 using Intermediate-8 (0.070 g, 0.185 mmol), O-(benzotriazol-1-yl)-N,N,N',N'-tetramethyluronium tetrafluoroborate (0.178 g, 0.556 mmol), TEA (0.037 g, 0.366 mmol), THF (5.0 mL), DMF (1.0 mL) and 3-methylbutan-1-amine (0.018 g, 0.204 mmol). The product obtained was further purified by column chromatography on neutral alumina eluting with 1.5-2.0% MeOH:DCM to afford 0.012 g of the desired product. $^1$HNMR (DMSO-$d_6$): δ 1.93 (s, 6H), 1.29-1.33 (m, 2H), 1.62-1.71 (m, 1H), 2.50 (s, 3H), 3.15 (m, 2H), 6.61 (s, 1H), 7.23 (s, 1H), 7.97 (m, 1H), 8.45 (s, 2H), 11-12 (s, 2H); MS [M+H]+: 446.33.

Example-51

2-[(2-Chloro-6-fluorophenyl)amino]-N-(2-fluorophenyl)-7,7-dimethyl-7,8-dihydro-1H-furo[3,2-e]benzimidazole-5-carboxamide

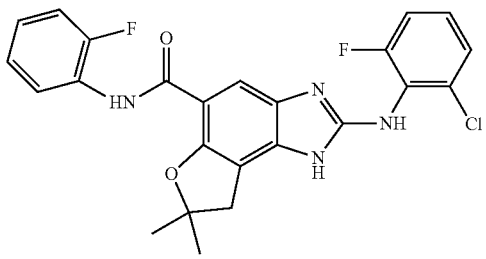 [SMILES: CC1(C)Cc2c(c(C(=O)Nc3ccccc3F)cc3nc(Nc4c(F)cccc4Cl)[nH]c23)O1]

The title compound was prepared following the procedure described for Example-1 using Intermediate-15, 0.100 g, 0.267 mmol), O-(benzotriazol-1-yl)-N,N,N',N'-tetramethyluronium tetrafluoroborate (0.256 g, 0.800 mmol), TEA (1.mL), THF (5.0 mL), DMF (1.0 mL), 2-fluoro aniline (0.090 g, 0.802 mmol) to afford 0.040 g product. The product obtained was further purified by column chromatography on neutral alumina eluting with 10% MeOH:DCM to afford 0.035 g of the desired product. $^1$HNMR (DMSO-$d_6$): δ 1.55 (s, 6H), 3.12 (s, 2H), 7.17-7.18 (m, 3H), 7.20-7.52 (m, 4H), 8.46-8.51 (m, 1H), 10.13 (s, 1H), 11.17 (s, 2H); MS [M+H]+: 469.28.

Example-52

2-[(2-Chloro-6-fluorophenyl)amino]-7,7-dimethyl-N-(2,4,4-trimethylpentan-2-yl)-7,8-dihydro-1H-furo[3,2-e]benzimidazole-5-carboxamide

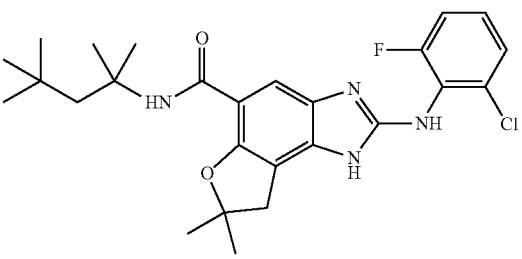 [SMILES: CC(C)(C)CC(C)(C)NC(=O)c1cc2nc(Nc3c(F)cccc3Cl)[nH]c2c2c1OC(C)(C)C2]

The title compound was prepared following the procedure described for Example-1 using Intermediate-15 (0.100 g, 0.267 mmol), O-(benzotriazol-1-yl)-N,N,N',N'-tetramethyluronium tetrafluoroborate (0.256 g, 0.800 mmol), TEA (1.mL), THF (5.0 mL), DMF (1.0 mL) and 2,4,4-trimethylpentan-2-amine (0.103 g, 0.798 mmol) to afford 0.030 g product. The product obtained was further purified by column chromatography on neutral alumina eluting with 1.5-2.0% MeOH:DCM to afford 0.030 g of the desired product. $^1$HNMR (DMSO-$d_6$): δ 1.02 (s, 9H), 1.41 (s, 6H), 1.488 (s, 6H), 1.76 (s, 2H), 3.04 (s, 2H), 7.30-7.38 (m, 4H), 7.67 (s, 1H), 11.00 (s, 2H); MS [M+H]⁺: 487.33.

Example-53

N-(4-tert-Butyl-1,3-thiazol-2-yl)-2-[(2-chloro-6-fluorophenyl)amino]-7,7-dimethyl-7,8-dihydro-1H-furo[3,2-e]benzimidazole-5-carboxamide

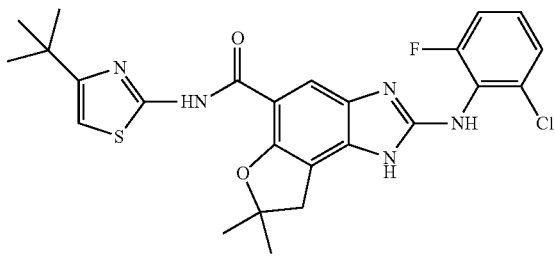 [SMILES: CC1(C)Cc2c(c(C(=O)Nc3nc(C(C)(C)C)cs3)cc3nc(Nc4c(F)cccc4Cl)[nH]c23)O1]

The title compound was prepared following the procedure described for Example-1 using Intermediate-15 (0.100 g, 0.267 mmol), O-(benzotriazol-1-yl)-N,N,N',N'-tetramethyluronium tetrafluoroborate (0.256 g, 0.800 mmol), TEA (1.mL), THF (5.0 mL), DMF (1.0 mL) and 4-tert-butyl-1,3-thiazol-2-amine (0.125 g, 0.802 mmol) to afford 0.015 g product. The product obtained was further purified by column chromatography on neutral alumina eluting with 1.5-2.0% MeOH:DCM to afford 0.005 g of the desired product. ¹HNMR (DMSO-d₆): δ 1.27 (s, 9H), 1.57 (s, 6H), 3.12 (s, 2H), 6.79 (s, 1H), 7.34-7.14 (m, 4H), 10.81 (s, 1H), 11.00-12.00 (s, 2H); MS [M+H]⁺: 514.21.

Example-54

2-[(2-Chloro-6-fluorophenyl)amino]-7,7-dimethyl-N-(4-methyl-1,3-thiazol-2-yl)-7,8-dihydro-1H-furo[3,2-e]benzimidazole-5-carboxamide

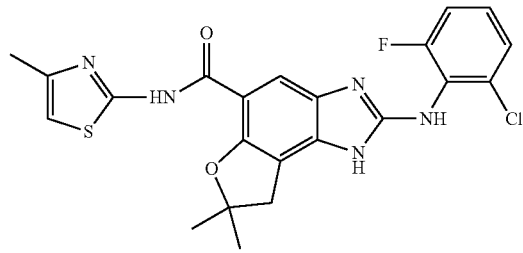 [SMILES: Cc1csc(NC(=O)c2cc3nc(Nc4c(F)cccc4Cl)[nH]c3c3c2OC(C)(C)C3)n1]

The title compound was prepared following the procedure described for Example-1 using Intermediate-15 (0.100 g, 0.267 mmol), O-(benzotriazol-1-yl)-N,N,N',N'-tetramethyluronium tetrafluoroborate (0.256 g, 0.800 mmol), TEA (1.mL), THF (5.0 mL), DMF (1.0 mL) and 4-methyl-1,3-thiazol-2-amine (0.092 g, 0.802 mmol) to afford 0.015 g product. The product obtained was further purified by column chromatography on neutral alumina eluting with 1.5-2.0% MeOH:DCM to afford 0.005 g of the desired product. ¹HNMR (DMSO-d₆): δ 1.57 (s, 6H), 2.27 (s, 3H), 3.12 (s, 2H), 6.80 (s, 1H), 7.36 (m, 4H), 10.83 (s, 1H), 11.00-12.00 (s, 2H); MS [M+H]⁺: 472.17.

Example-55

2-[(2-Chloro-6-fluorophenyl)amino]-N-(4,5-dimethyl-1,3-thiazol-2-yl)-7,7-dimethyl-7,8-dihydro-1H-furo[3,2-e]benzimidazole-5-carboxamide

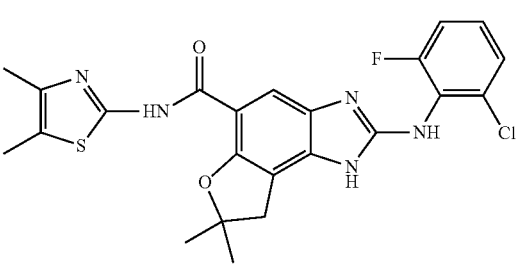 [SMILES: Cc1nc(NC(=O)c2cc3nc(Nc4c(F)cccc4Cl)[nH]c3c3c2OC(C)(C)C3)sc1C]

The title compound was prepared following the procedure described for Example-1 using Intermediate-15 (0.100 g, 0.267 mmol), O-(benzotriazol-1-yl)-N,N,N',N'-tetramethyluronium tetrafluoroborate (0.256 g, 0.800 mmol), TEA (1.mL), THF (5.0 mL), DMF (1.0 mL) and 4,5-dimethyl-1,3-thiazol-2-amine (0.132 g, 0.802 mmol) to afford 0.025 g product. The product obtained was further purified by column chromatography on neutral alumina eluting with 3.0-4.0% MeOH:DCM to afford 0.015 g of the desired product. ¹HNMR (DMSO-d₆): δ 1.56 (s, 6H), 2.17 (s, 3H), 2.59 (s, 3H), 3.11 (s, 2H), 7.33-7.42 (m, 4H), 10.66 (s, 1H), 11.00-12.00 (s, 2H); MS [M+H]⁺: 486.18.

Example-56

2-[(2-Chloro-6-fluorophenyl)amino]-N-(3-fluorophenyl)-7,7-dimethyl-7,8-dihydro-1H-furo[3,2-e]benzimidazole-5-carboxamide

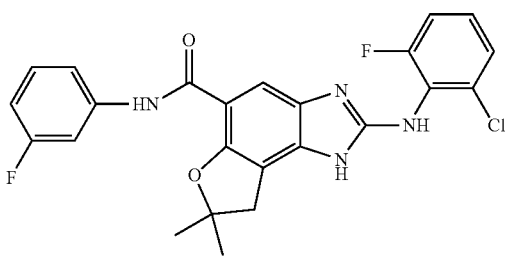 [SMILES: CC1(C)Cc2c(c(C(=O)Nc3cccc(F)c3)cc3nc(Nc4c(F)cccc4Cl)[nH]c23)O1]

The title compound was prepared following the procedure described for Example-1 using Intermediate-15 (0.100 g, 0.267 mmol), O-(benzotriazol-1-yl)-N,N,N',N'-tetramethyluronium tetrafluoroborate (0.256 g, 0.800 mmol), TEA (1.mL), THF (5.0 mL), DMF (1.0 mL) and 3-fluoro aniline (0.090 g, 0.802 mmol) to afford 0.025 g product. The product obtained was further purified by column chromatography on neutral alumina eluting with 3.0-4.0% MeOH:DCM to afford 0.015 g of product. ¹HNMR (DMSO-d₆): δ 1.57 (s, 6H), 3.10

(s, 2H), 6.91 (m, 1H), 7.36-7.46 (m, 6H), 7.76-7.80 (m, 1H), 9.87 (s, 1H), 11.20 (s, 2H); MS [M–H]⁻: 467.05.

Example-57

N-(Cyclopropylmethyl)-2-[(2,6-dichlorophenyl)amino]-7-methyl-1H-furo[3,2-e]benzimidazole-5-carboxamide

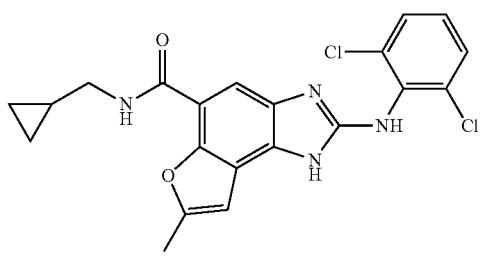 [SMILES: Cc1cc2c(o1)c(C(=O)NCC1CC1)cc1nc(Nc3c(Cl)cccc3Cl)[nH]c12]

The title compound was prepared following the procedure described for Example-1 using Intermediate-9 (0.070 g, 0.185 mmol), TBTU (0.179 g, 0.557 mmol), TEA (0.056 g, 0.557 mmol), THF (5.0 mL), DMF (1.0 mL) and 1-cyclopropylmethanamine (0.060 g, 0.557 mmol). The product obtained was further purified by column chromatography on neutral alumina eluting with 1.0-1.5% MeOH: DCM to afford 0.010 g of product. ¹HNMR (DMSO-d₆): δ 0.29 (d, J=4.2 Hz, 2H), 0.45 (d, J=4.8 Hz, 2H), 1.10-1.16 (m, 1H), 2.53 (s, 3H), 3.21 (m, 2H), 6.69 (s, 1H), 7.29 (m, 1H), 7.52-7.58 (m, 3H), 7.97-7.99 (s, 1H), 11.00-12.00 (s, 2H); MS [M+H]⁺: 429.35.

Example-58

2-[(2,6-Dichlorophenyl)amino]-7,7-dimethyl-N-(pyrrolidin-1-yl)-7,8-dihydro-1H-furo[3,2-e]benzimidazole-5-carboxamide

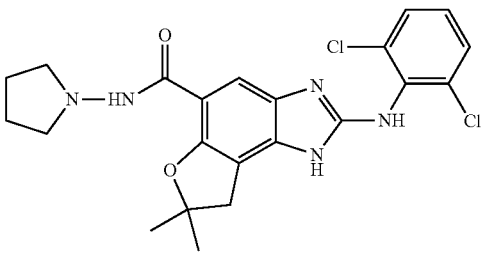 [SMILES: CC1(C)Cc2c(c(C(=O)NN3CCCC3)cc3nc(Nc4c(Cl)cccc4Cl)[nH]c23)O1]

The title compound was prepared following the procedure described for Example-1 using Intermediate-6 (0.100 g, 0.255 mmol), TBTU (0.245 g, 0.763 mmol), TEA (2.0 mL), THF (5.0 mL), DMF (1.0 mL) and pyrrolidin-1-amine hydrochloride (0.094 g, 0.766 mmol). The organic layer was washed with dilute acetic acid instead of dilute HCl. The product obtained was further purified by column chromatography on neutral alumina eluting with 3.0-4.0% MeOH:DCM to afford 0.020 g of the desired product. ¹HNMR (DMSO-d₆):
δ 1.49 (s, 6H), 1.77 (s, 4H), 2.91 (s, 4H), 3.02 (s, 2H), 7.29 (m, 2H), 7.50 (s, 2H), 8.51 (s, 1H), 10.89 (s, 2H); MS [M+H]⁺: 460.34.

Example-59

N-(4-Cyanophenyl)-2-[(2,6-dichlorophenyl)amino]-7,7-dimethyl-7,8-dihydro-1H-furo[3,2-e]benzimidazole-5-carboxamide

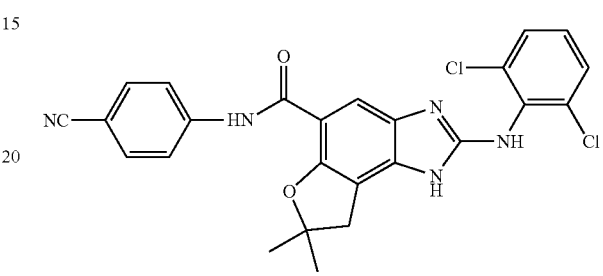

The title compound was prepared following the procedure described for Example-1 using Intermediate-6 (0.150 g, 0.382 mmol), TBTU (0.368 g, 1.14 mmol), TEA (1.0 mL), THF (5.0 mL), DMF (1.0 mL) and 4-aminobenzonitrile (0.134 g, 1.14 mmol). The product obtained was further purified by column chromatography on neutral alumina eluting with 3.0-4.0% MeOH:DCM to afford 0.010 g of the desired product. ¹HNMR (DMSO-d₆): δ 1.57 (s, 6H), 3.08 (s, 2H), 7.54 (m, 4H), 7.80 (d, J=8.7 Hz, 2H), 7.89 (d, J=8.1 Hz, 2H), 10.01 (s, 1H), 10.95 (s, 2H); MS [M–H]⁻: 490.25.

Example-60

2-[(2,6-Dichlorophenyl)amino]-N-(2,6-dimethylpyridin-3-yl)-7,7-dimethyl-7,8-dihydro-1H-furo[3,2-e]benzimidazole-5-carboxamide

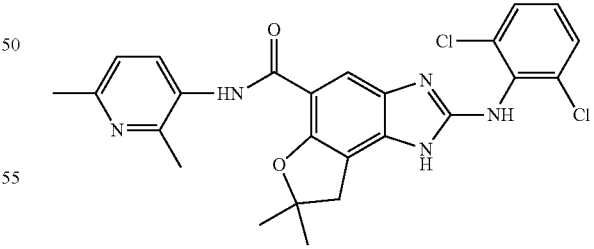

The title compound was prepared following the procedure described for Example-1 using Intermediate-6 (0.100 g, 0.255 mmol), TBTU (0.245 g, 0.765 mmol), TEA (1.0 mL), THF (5.0 mL), DMF (1.0 mL) and 2,6-dimethylpyridin-3-amine (0.094 g, 0.770 mmol). The product obtained was further purified by column chromatography on neutral alumina eluting with 3.0-4.0% MeOH:DCM to afford 0.010 g of the desired product. ¹HNMR (DMSO-d₆): δ 1.57 (s, 6H), 2.40

(s, 3H), 2.50 (s, 3H), 3.11-3.16 (m, 2H), 7.09 (s, 1H), 7.53 (m, 4H), 8.48 (m, 1H), 9.62 (s, 1H), 11.18 (s, 2H); MS [M+H]+: 496.29.

Example-61

2-[(2,6-Dichlorophenyl)amino]-N-[2-(dimethylamino)ethyl]-7,7-dimethyl-7,8-dihydro-1H-furo[3,2-e]benzimidazole-5-carboxamide

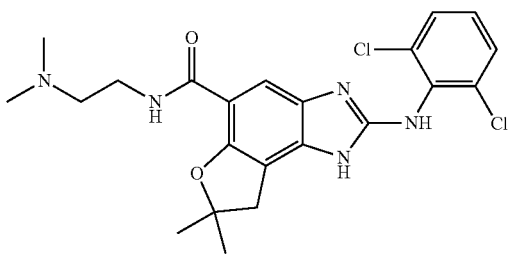 [SMILES: CN(C)CCNC(=O)c1cc2nc(Nc3c(Cl)cccc3Cl)[nH]c2c2c1OC(C)(C)C2]

The title compound was prepared following the procedure described for Example-1 using Intermediate-6, 0.080 g, 0.204 mmol), TBTU (0.196 g, 0.612 mmol), TEA (1.0 mL), THF (5.0 mL), DMF (1.0 mL) and N,N-dimethylethane-1,2-diamine (0.054 g, 0.612 mmol). The product obtained was further purified by column chromatography on neutral alumina eluting with 3.0-4.0% MeOH:DCM to afford 0.030 g of the desired product. $^1$HNMR (DMSO-d$_6$): δ 1.47 (s, 6H), 2.22 (s, 6H), 2.41 (s, 2H), 3.02 (s, 2H), 3.33 (s, 2H), 7.19 (s, 1H), 7.31 (s, 1H), 7.51 (d, J=8.1 Hz, 2H), 8.13 (s, 1H), 10.80 (s, 2H); MS [M+H]+: 462.21.

Example-62

2-[(2,6-Dichlorophenyl)amino]-7,7-dimethyl-N-(2,2,2-trifluoroethyl)-7,8-dihydro-1H-furo[3,2-e]benzimidazole-5-carboxamide

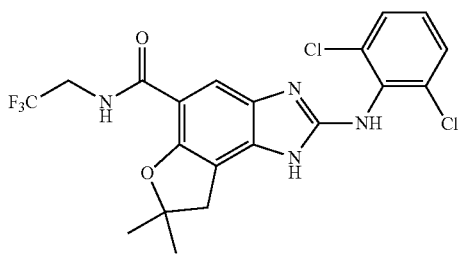 [SMILES: CC1(C)Cc2c(c(C(=O)NCC(F)(F)F)cc3nc(Nc4c(Cl)cccc4Cl)[nH]c23)O1]

The title compound was prepared following the procedure described for Example-1 using Intermediate-6 (0.080 g, 0.204 mmol), TBTU (0.196 g, 0.612 mmol), TEA (1.0 mL), THF (5.0 mL), DMF (1.0 mL) and 2,2,2-trifluoroethanamine (0.059 g, 0.612 mmol). The product obtained was further purified by column chromatography on neutral alumina eluting with 3.0-4.0% MeOH:DCM to afford 0.030 g of the desired product. $^1$HNMR (DMSO-d$_6$): δ 1.50 (s, 6H), 3.04 (s, 2H), 4.15-4.20 (m, 2H), 7.22 (s, 1H), 7.34 (s, 1H), 7.52 (d, J=8.4 Hz, 2H), 8.08 (s, 1H), 10.80 (s, 2H); MS [M+H]+: 473.26.

Example-63

2-[(2,6-Dichlorophenyl)amino]-N-(2-fluoroethyl)-7,7-dimethyl-7,8-dihydro-1H-furo[3,2-e]benzimidazole-5-carboxamide

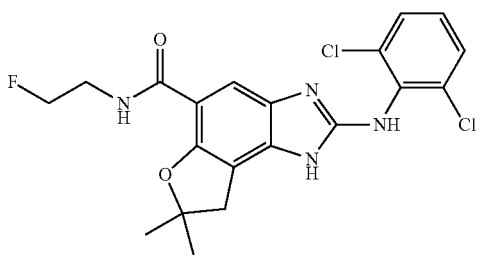 [SMILES: CC1(C)Cc2c(c(C(=O)NCCF)cc3nc(Nc4c(Cl)cccc4Cl)[nH]c23)O1]

The title compound was prepared by following the procedure described for Example-1 using Intermediate-6 (0.080 g, 0.204 mmol), TBTU (0.196 g, 0.612 mmol), TEA (1.0 mL), THF (5.0 mL), DMF (1.0 mL) and 2-fluoroethanamine (0.059 g, 0.612 mmol). The product obtained was further purified by column chromatography on neutral alumina eluting with 3.0-4.0% MeOH:DCM to afford 0.030 g of the desired product. $^1$HNMR (DMSO-d$_6$): δ 1.48 (s, 6H), 3.02 (s, 2H), 3.56 (q, J=5.4 Hz, 1H), 3.65 (q, J=5.4 Hz, 1H), 4.44 (t, J=5.7 Hz, 1H), 4.60 (t, J=5.7 Hz, 1H), 7.19 (s, 1H), 7.33 (s, 1H), 7.50 (d, J=7.2 Hz, 2H), 7.92 (m, 1H), 10.81 (s, 2H); MS [M+H]+: 437.27.

Example-64

2-[(2,6-Dichlorophenyl)amino]-7,7-dimethyl-N-(2,2,3,3,3-pentafluoropropyl)-7,8-dihydro-1H-furo[3,2-e]benzimidazole-5-carboxamide

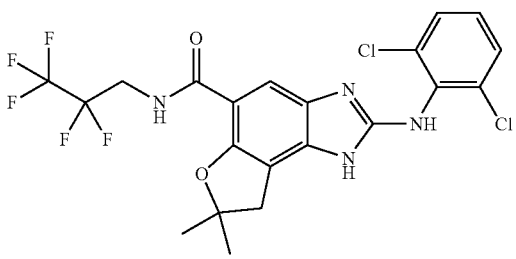 [SMILES: CC1(C)Cc2c(c(C(=O)NCC(F)(F)C(F)(F)F)cc3nc(Nc4c(Cl)cccc4Cl)[nH]c23)O1]

The title compound was prepared following the procedure described for Example-1 using Intermediate-6, 0.080 g, 0.204 mmol), TBTU (0.196 g, 0.612 mmol), TEA (1.0 mL), THF (5.0 mL), DMF (1.0 mL) and 2,2,3,3,3-pentafluoropropan-1-amine (0.092 g, 0.614 mmol). The product obtained was further purified by column chromatography on neutral alumina eluting with 3.0-4.0% MeOH:DCM to afford 0.010 g of the desired product. $^1$HNMR (DMSO-d$_6$): δ 1.94 (s, 6H), 3.05

(s, 2H), 4.12-4.31 (m, 2H), 7.26-7.36 (m, 2H), 7.52 (q, J=7.2 Hz, 2H), 8.08 (s, 1H), 11.00 (s, 2H); MS [M+H]⁺: 523.32.

Example-65

2-[(2,6-Dichlorophenyl)amino]-7-methyl-N-[4-(trifluoromethyl)phenyl]-1H-furo[3,2-e]benzimidazole-5-carboxamide

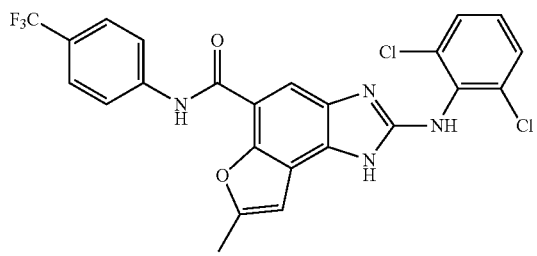 [SMILES: Cc1cc2c(o1)c(C(=O)Nc1ccc(C(F)(F)F)cc1)cc1nc(Nc3c(Cl)cccc3Cl)[nH]c12]

To a solution of Intermediate-9 (0.100 g, 0.265 mmol), thionyl chloride (5.0 mL) was added at 5-10° C. The reaction mixture was refluxed for 3 h. To a solution of 4-(trifluoromethyl)aniline (0.128 g, 0.795 mmol) in THF (5.0 mL), 60% NaH (0.057 g, 2.375 mmol) was added under N₂-atmosphere at 0-5° C. The solution was stirred for 1 h at RT and above prepared solution was added to reaction mixture and reaction mixture was stirred at RT for 1 hr. The thionyl chloride was removed under vacuum and co-evaporated with THF. The reaction mixture was quenched in ice water and extracted with ethyl acetate. The product obtained was further purified by column chromatography on neutral alumina eluting with 1.5-2.0% MeOH:DCM to afford 0.023 g of the desired product. ¹HNMR (DMSO-d₆): δ 2.50 (s, 3H), 6.73 (s, 1H), 7.23 (m, 1H), 7.52-7.60 (m, 3H), 7.72 (d, J=8.1 Hz, 2H), 8.02 (d, J=8.4 Hz, 2H), 9.32 (s, 1H), 10.30 (s, 1H), 11.37 (s, 1H); MS [M+H]⁺: 519.29.

Example-66

N-(4-Bromophenyl)-2-[(2,6-dichlorophenyl)amino]-7-methyl-1H-furo[3,2-e]benzimidazole-5-carboxamide

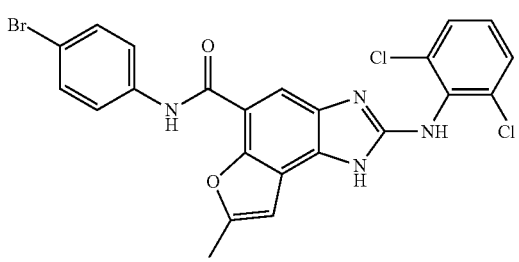 [SMILES: Cc1cc2c(o1)c(C(=O)Nc1ccc(Br)cc1)cc1nc(Nc3c(Cl)cccc3Cl)[nH]c12]

The title compound was prepared following the procedure described for example-65 using Intermediate-9 (0.100 g, 0.265 mmol), thionyl chloride (5.0 mL), 4-bromo aniline (0.137 g, 0.795 mmol), THF (5.0 mL) and 60% NaH (0.057 g, 2.38 mmol). The product obtained was further purified by column chromatography on neutral alumina eluting with 1.5-2.0% MeOH:DCM to afford 0.023 g of the desired product. ¹HNMR (DMSO-d₆): δ 2.50 (s, 3H), 6.72 (s, 1H), 7.55 (m, 5H), 7.97 (m, 3H), 9.28 (s, 1H), 10.07 (m, 1H), 11.38 (s, 1H); MS [M+H]⁺: 529.50.

Example-67

2-[(2,6-Dichlorophenyl)amino]-N-(2-fluorophenyl)-7-methyl-1H-furo[3,2-e]benzimidazole-5-carboxamide

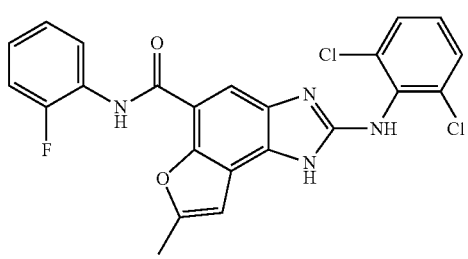 [SMILES: Cc1cc2c(o1)c(C(=O)Nc1ccccc1F)cc1nc(Nc3c(Cl)cccc3Cl)[nH]c12]

The title compound was prepared following the procedure described for Example-65 using Intermediate-9 (0.100 g, 0.265 mmol), thionyl chloride (5.0 mL), 2-fluoro aniline (0.088 g, 0.795 mmol), THF (5.0 mL) and 60% NaH (0.057 g, 2.38 mmol). The product obtained was further purified by column chromatography on neutral alumina eluting with 1.5-2.0% MeOH:DCM to afford 0.022 g of the desired product. ¹HNMR (DMSO-d₆): δ 2.50 (s, 3H), 6.77 (s, 1H), 7.15-7.25 (m, 3H), 7.30-7.37 (m, 1H), 7.58 (d, J=7.8 Hz, 2H), 7.67 (s, 1H), 8.29 (m, 1H), 9.37 (s, 1H), 981 (s, 1H), 11.39 (s, 1H); MS [M+H]⁺: 469.42.

Example-68

2-[(2,6-Dichlorophenyl)amino]-7-methyl-N-[3-(trifluoromethyl)phenyl]-1H-furo[3,2-e]benzimidazole-5-carboxamide

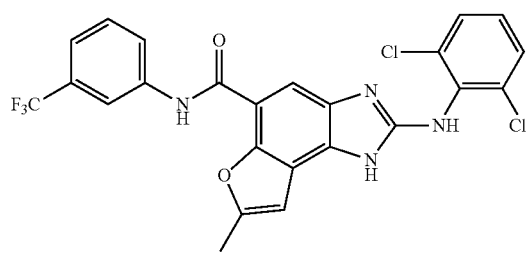 [SMILES: Cc1cc2c(o1)c(C(=O)Nc1cccc(C(F)(F)F)c1)cc1nc(Nc3c(Cl)cccc3Cl)[nH]c12]

The title compound was prepared following the procedure described for Example-65 using Intermediate-9 (0.100 g, 0.265 mmol), thionyl chloride (5.0 mL), 3-(trifluoromethyl) aniline (0.128 g, 0.795 mmol), THF (5.0 mL) and 60% NaH (0.057 g, 2.38 mmol). The product obtained was further purified by column chromatography on neutral alumina eluting with 1.5-2.0% MeOH:DCM to afford 0.018 g of the desired product. ¹HNMR (DMSO-d₆): δ 2.50 (s, 3H), 6.73 (s, 1H), 7.33 (s, 1H), 7.46-7.60 (m, 5H), 7.99 (d, J=7.5 Hz, 1H), 8.33 (s, 1H), 9.30 (s, 1H), 10.29 (s, 1H), 11.38 (s, 1H).

Example-69

2-[(2,6-Dichlorophenyl)amino]-N-(3-methoxypropyl)-7,7-dimethyl-7,8-dihydro-1H-furo[3,2-e]benzimidazole-5-carboxamide

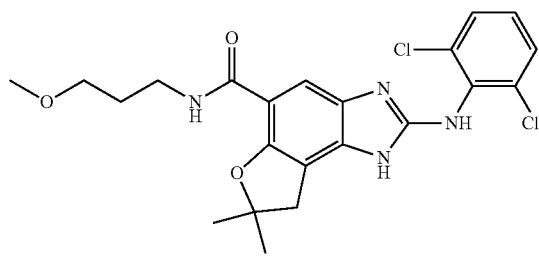 [SMILES: COCCCNC(=O)c1cc2nc(Nc3c(Cl)cccc3Cl)[nH]c2c2c1OC(C)(C)C2]

The title compound was prepared following the procedure described for Example-1 using Intermediate-6 (0.080 g, 0.204 mmol), TBTU (0.196 g, 0.612 mmol), TEA (1.0 mL), THF (5.0 mL), DMF (1.0 mL) and 3-methoxypropan-1-amine (0.054 g, 0.612 mmol). The product obtained was further purified by column chromatography on neutral alumina eluting with 3.0-4.0% MeOH:DCM to afford 0.020 g of the desired product. $^1$HNMR (DMSO-$d_6$): δ 1.47 (s, 6H), 1.71 (q, J=6.3 Hz, 2H), 3.00 (s, 2H), 3.24-3.37 (m, 7H), 7.16 (s, 1H), 7.30 (s, 1H), 7.49 (d, J=7.8 Hz, 2H), 7.77 (m, 1H), 10.72 (s, 2H); MS [M+H]$^+$: 463.34.

Example-70

2-[(2,6-Dichlorophenyl)amino]-7,7-dimethyl-N-[2-(morpholin-4-yl)ethyl]-7,8-dihydro-1H-furo[3,2-e]benzimidazole-5-carboxamide

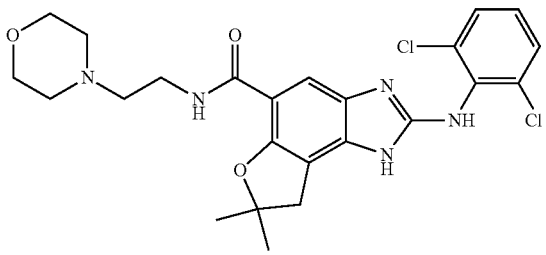 [SMILES: CC1(C)Cc2c(c(C(=O)NCCN3CCOCC3)cc3nc(Nc4c(Cl)cccc4Cl)[nH]c23)O1]

The title compound was prepared following the procedure described for Example-1 using Intermediate-6 (0.100 g, 0.255 mmol), TBTU (0.245 g, 0.765 mmol), TEA (1.0 mL), THF (5.0 mL), DMF (1.0 mL) and 2-(morpholin-4-yl)ethanamine (0.099 g, 0.765 mmol). The product obtained was further purified by column chromatography on neutral alumina eluting with 3.0-4.0% MeOH:DCM to afford 0.020 g of the desired product. $^1$HNMR (DMSO-$d_6$): δ 1.51 (s, 6H), 2.50 (m, 4H), 3.03 (s, 2H), 3.40 (m, 4H), 3.62 (s, 4H), 7.20 (m, 1H), 7.34 (m, 1H), 7.51 (d, J=6.9 Hz, 2H), 8.06 (s, 1H), 10.77 (s, 2H); MS [M+H]$^+$: 504.22.

Example-71

N-(5-Bromopyridin-2-yl)-2-[(2,6-dichlorophenyl)amino]-7-methyl-1H-furo[3,2-e]benzimidazole-5-carboxamide

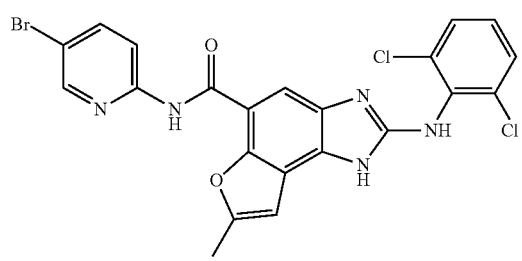 [SMILES: Cc1cc2c(o1)c(C(=O)Nc1ccc(Br)cn1)cc1nc(Nc3c(Cl)cccc3Cl)[nH]c12]

The title compound was prepared following the procedure described for Example-65 using Intermediate-9 (0.100 g, 0.265 mmol), thionyl chloride (5.0 mL), 5-bromopyridin-2-amine (0.137 g, 0.795 mmol), THF (5.0 mL) and 60% NaH (0.057 g, 2.38 mmol). The product obtained was further purified by column chromatography on neutral alumina eluting with 1.5-2.0% MeOH:DCM to afford 0.007 g of the desired product. $^1$HNMR (DMSO-$d_6$): δ 2.50 (s, 3H), 6.73 (s, 1H), 7.40 (t, J=8.4 Hz, 2H), 7.60 (d, J=8.4 Hz, 4H), 9.32 (s, 1H), 9.72 (s, 1H), 11.40 (s, 2H).

Example-72

N-(2-Bromophenyl)-2-[(2,6-dichlorophenyl)amino]-7,7-dimethyl-7,8-dihydro-1H-furo[3,2-e]benzimidazole-5-carboxamide

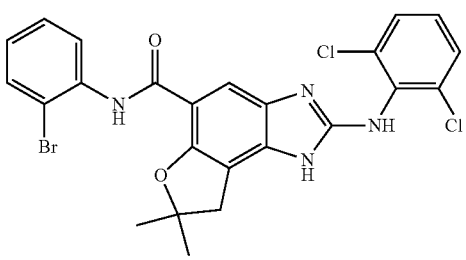

The title compound was prepared following the procedure described for Example-65 using Intermediate-6 (0.100 g, 0.255 mmol), thionyl chloride (1.0 mL), 2-bromoaniline (0.087 g, 0.510 mmol), THF (5.0 mL) and DIPEA (2 mL). The product obtained was further purified by column chromatography on neutral alumina eluting with 1.0-2.0% MeOH:DCM to afford 0.015 g of the desired product. $^1$HNMR (DMSO-$d_6$): δ 1.35 (s, 6H), 3.11 (s, 2H), 7.04 (t, J=8.1 Hz, 1H), 7.39 (t, J=7.8 Hz, 3H), 7.55 (s, 2H), 7.69 (d, J=7.2 Hz, 1H), 8.58 (d, J=7.8 Hz, 1H), 10.09 (s, 1H), 11.40 (s, 2H); MS [M+H]+: 547.18.

Example-73

2-[(2,6-Dichlorophenyl)amino]-7,7-dimethyl-N-[4-(trifluoromethyl)phenyl]-7,8-dihydro-1H-furo[3,2-e]benzimidazole-5-carboxamide

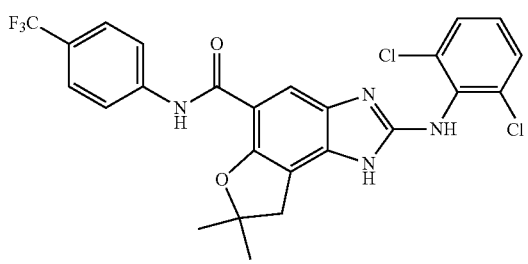 [SMILES: CC1(C)Cc2c(c(C(=O)Nc3ccc(C(F)(F)F)cc3)cc3nc(Nc4c(Cl)cccc4Cl)[nH]c23)O1]

The title compound was prepared following the procedure described for Example-65 using Intermediate-6 (0.100 g, 0.255 mmol), thionyl chloride (1.0 mL), 4-(trifluoromethyl)aniline (0.082 g, 0.510 mmol), THF (5.0 mL) and DIPEA (2 mL). The product obtained was further purified by column chromatography on neutral alumina eluting with 1.0-2.0% MeOH:DCM to afford 0.030 g of the desired product. $^1$HNMR (DMSO-$d_6$): δ 1.57 (s, 6H), 3.09 (s, 2H), 7.23 (s, 1H), 7.40 (s, 1H), 7.53 (d, J=7.8 Hz, 2H), 7.70 (d, J=8.4 Hz, 2H), 7.91 (d, J=9.0 Hz, 2H), 9.97 (s, 1H), 11.00 (s, 2H); MS [M+H]+: 535.31.

Example-74

N-(4-Bromophenyl)-2-[(2,6-dichlorophenyl)amino]-7,7-dimethyl-7,8-dihydro-1H-furo[3,2-e]benzimidazole-5-carbohydrazide

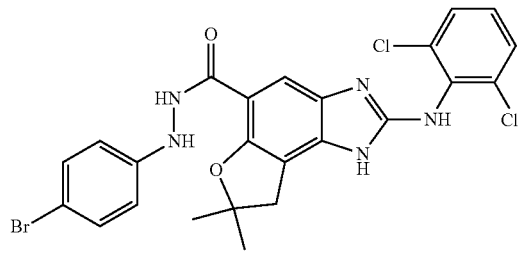 [SMILES: CC1(C)Cc2c(c(C(=O)NNc3ccc(Br)cc3)cc3nc(Nc4c(Cl)cccc4Cl)[nH]c23)O1]

The title compound was prepared following the procedure described for Example-65 using Intermediate-6 (0.100 g, 0.255 mmol), thionyl chloride (1.0 mL), (4-bromophenyl)hydrazine (0.114 g, 0.510 mmol), THF (5.0 mL) and DIPEA (2 mL). The product obtained was further purified by column chromatography on neutral alumina eluting with 1.0-2.0% MeOH:DCM to afford 0.040 g of the desired product. $^1$HNMR (DMSO-$d_6$): δ 1.53 (s, 6H), 3.07 (s, 2H), 6.68 (d, J=8.7 Hz, 2H), 7.30 (d, J=8.7 Hz, 4H), 7.51 (m, 2H), 8.14 (s, 1H), 9.25 (s, 1H), 11.00 (s, 2H); MS [M+H]+: 562.19.

Example-75

2-[(2,6-Dichlorophenyl)amino]-7,7-dimethyl-N-[2-(trifluoromethyl)phenyl]-7,8-dihydro-1H-furo[3,2-e]benzimidazole-5-carboxamide

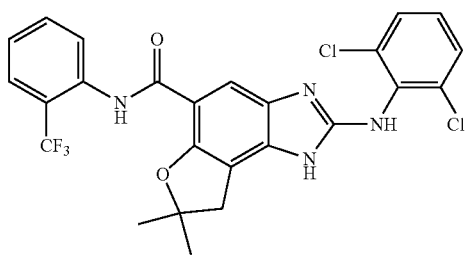 [SMILES: CC1(C)Cc2c(c(C(=O)Nc3ccccc3C(F)(F)F)cc3nc(Nc4c(Cl)cccc4Cl)[nH]c23)O1]

The title compound was prepared following the procedure described for Example-1 using Intermediate-6, 0.100 g, 0.255 mmol), thionyl chloride (1.0 mL), 2-(trifluoromethyl)aniline (0.082 g, 0.509 mmol), THF (5.0 mL) and DIPEA (2 mL). The product obtained was further purified by column chromatography on neutral alumina eluting with 1.0-2.0% MeOH:DCM to afford 0.030 g of the desired product. $^1$HNMR (DMSO-$d_6$): δ 1.53 (s, 6H), 3.31 (s, 2H), 7.31 (t, J=7.5 Hz, 2H), 7.53 (m, 3H), 7.66-7.75 (m, 2H), 8.44 (d, J=8.1 Hz, 1H), 10.05 (s, 1H), 10.97 (s, 2H); MS [M+H]+: 535.28.

Example-76

2-[(2,6-Dichlorophenyl)amino]-N-(2,6-difluorophenyl)-7,7-dimethyl-7,8-dihydro-1H-furo[3,2-e]benzimidazole-5-carboxamide

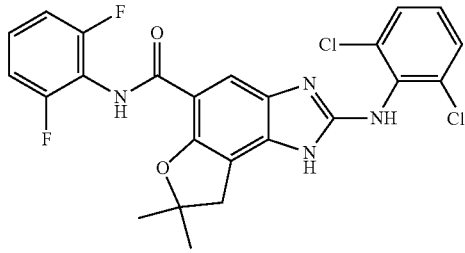 [SMILES: CC1(C)Cc2c(c(C(=O)Nc3c(F)cccc3F)cc3nc(Nc4c(Cl)cccc4Cl)[nH]c23)O1]

The title compound was prepared following the procedure described for Example-65 using Intermediate-6, 0.100 g, 0.255 mmol), thionyl chloride (1.0 mL), 2,6-difluoroaniline (0.066 g, 0.511 mmol), THF (5.0 mL) and DIPEA (2 mL). The product obtained was further purified by column chromatography on neutral alumina eluting with 1.0-2.0% MeOH:DCM to afford 0.020 g of the desired product. $^1$HNMR (DMSO-d$_6$): δ 1.53 (s, 6H), 3.08 (s, 2H), 7.18 (t, J=8.4 Hz, 3H), 7.37 (m, 2H), 7.53 (s, 2H), 9.19 (s, 1H), 10.94 (s, 2H); MS [M+H]$^+$: 503.26.

Example-77

2-[(2-Chloro-6-fluorophenyl)amino]-7,7-dimethyl-N-[2-(trifluoromethyl)phenyl]-7,8-dihydro-1H-furo[3,2-e]benzimidazole-5-carboxamide

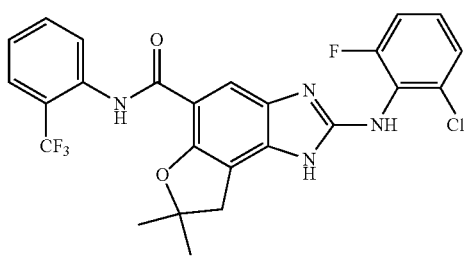 [SMILES: CC1(C)Cc2c(c(C(=O)Nc3ccccc3C(F)(F)F)cc3nc(Nc4c(F)cccc4Cl)[nH]c23)O1]

The title compound was prepared following the procedure described for Example-65 using Intermediate-15, 0.100 g, 0.266 mmol), thionyl chloride (1.0 mL), 2-(trifluoromethyl) aniline (0.086 g, 0.534 mmol), THF (5.0 mL) and DIPEA (2 mL). The product obtained was further purified by column chromatography on neutral alumina eluting with 1.0-2.0% MeOH:DCM to afford 0.015 g of the desired product. $^1$HNMR (DMSO-d$_6$): δ 1.53 (s, 6H), 3.34 (s, 2H), 7.31-7.40 (m, 5H), 7.66-7.75 (m, 2H), 8.45 (d, J=8.4 Hz, 1H), 10.08 (s, 1H), 11.20 (s, 2H); MS [M+H$^+$]: 519.29

Example-78

N-(4-Bromophenyl)-2-[(2-chlorophenyl)amino]-7,7-dimethyl-7,8-dihydro-1H-furo[3,2-e]benzimidazole-5-carboxamide

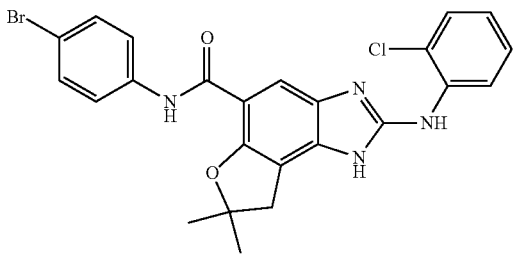

The title compound was prepared following the procedure described for example-65 using Intermediate-12 (0.100 g, 0.280 mmol), thionyl chloride (5.0 mL), 4-bromo aniline (0.144 g, 0.840 mmol), THF (5.0 mL) and 60% NaH (0.060 g, 2.52 mmol). The product obtained was further purified by column chromatography on neutral alumina eluting with 0.5-1.0% MeOH:DCM to afford 0.012 g of the desired product $^1$HNMR (DMSO-d$_6$): δ 1.59 (s, 6H), 3.16 (s, 2H), 7.05 (t, J=6.9 Hz, 1H), 7.38 (t, J=7.8 Hz, 1H), 7.48-7.55 (m, 3H), 7.69-7.74 (m, 3H), 8.59 (s, 1H), 9.10 (s, 1H), 9.86 (s, 1H), 11.03 (s, 1H); MS [M+H]$^+$: 511.27.

Example-79

2-[(2-Chlorophenyl)amino]-7,7-dimethyl-N-[2-(trifluoromethyl)phenyl]-7,8-dihydro-1H-furo[3,2-e]benzimidazole-5-carboxamide

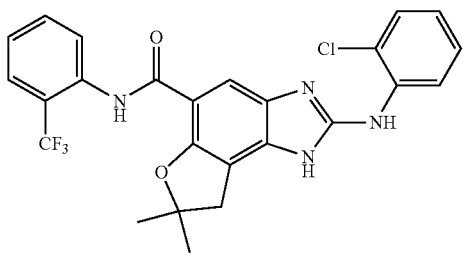 [SMILES: CC1(C)Cc2c(c(C(=O)Nc3ccccc3C(F)(F)F)cc3nc(Nc4ccccc4Cl)[nH]c23)O1]

The title compound was prepared following the procedure described for example-65 using Intermediate-12 (0.100 g, 0.280 mmol), thionyl chloride (5.0 mL), 2-(trifluoromethyl) aniline (0.135 g, 0.840 mmol), THF (5.0 mL) and 60% NaH (0.060 g, 2.52 mmol). The product obtained was further purified by column chromatography on neutral alumina eluting with 0.5-1.0% MeOH: DCM to afford 0.042 g of the desired product. $^1$HNMR (DMSO-d$_6$): δ 1.56 (s, 6H), 3.25 (s, 2H), 7.05 (t, J=6.9 Hz, 1H), 7.30-7.41 (m, 2H), 7.50 (d, J=7.8 Hz, 1H), 7.69-7.77 (m, 2H), 8.46 (s, 1H), 8.47 (d, J=7.8 Hz, 1H), 8.59 (d, J=7.5 Hz, 1H), 9.14 (s, 1H), 10.15 (s, 1H), 11.05 (s, 1H); MS [M+H]$^+$: 501.34.

Example-80

2-[(2-Chloro-6-fluorophenyl)amino]-7,7-dimethyl-N-[2-(trifluoromethyl)benzyl]-7,8-dihydro-1H-furo[3,2-e]benzimidazole-5-carboxamide

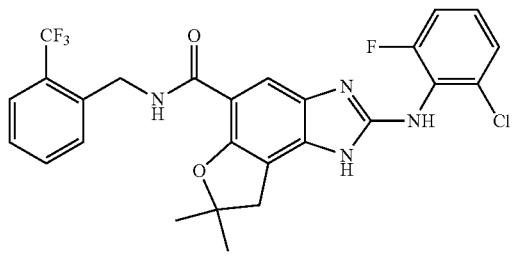 [SMILES: CC1(C)Cc2c(c(C(=O)NCc3ccccc3C(F)(F)F)cc3nc(Nc4c(F)cccc4Cl)[nH]c23)O1]

The title compound was prepared following the procedure described for Example-65 using Intermediate-15 (0.100 g, 0.266 mmol), thionyl chloride (1.0 mL), 1-[2-(trifluoromethyl)phenyl]methanamine (0.093 g, 0.531 mmol), THF (5.0 mL) and DIPEA (2 mL). The product obtained was further purified by column chromatography on neutral alumina eluting with 1.0-2.0% MeOH:DCM to afford 0.014 g of the desired product. $^1$HNMR (DMSO-d$_6$): δ 1.48 (s, 6H), 3.06 (s, 2H), 4.71 (d, J=5.4 Hz, 2H), 7.31 (d, J=7.8 Hz, 2H), 7.41-7.55

(m, 4H), 7.65 (t, J=7.5 Hz, 1H), 7.74 (d, J=7.8 Hz, 1H), 8.33 (t, J=5.7 Hz, 1H), 9.25 (s, 1H), 11.16 (s, 1H); MS [M+H]+: 533.38.

Example-81

2-[(2,6-Dichlorophenyl)amino]-7,7-dimethyl-N-phenyl-7,8-dihydro-1H-furo[3,2-e]benzimidazole-5-carboxamide

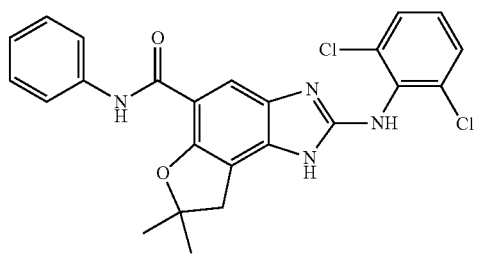 [SMILES: CC1(C)Cc2c(c(C(=O)Nc3ccccc3)cc3nc(Nc4c(Cl)cccc4Cl)[nH]c23)O1]

The title compound was prepared following the procedure described for Example-65 using Intermediate-6 (0.100 g, 0.255 mmol), thionyl chloride (1.0 mL), phenyl amine (0.047 g, 0.500 mmol), THF (5.0 mL) and DIPEA (2 mL). The product obtained was further purified by column chromatography on neutral alumina eluting with 1.0-2.0% MeOH:DCM to afford 0.020 g of the desired product. $^1$HNMR (DMSO-d$_6$): δ 1.57 (s, 6H), 3.09 (s, 2H), 7.08 (t, J=7.5 Hz, 1H), 7.23 (s, 1H), 7.23-7.38 (m, 3H), 7.54 (t, J=7.8 Hz, 2H), 7.68 (d, J=7.8 Hz, 2H), 9.74 (s, 1H), 10.88 (s, 2H); MS [M+H]+: 467.34.

Example-82

2-[(2,6-Dichlorophenyl)amino]-7,7-dimethyl-N-[2-(trifluoromethyl)benzyl]-7,8-dihydro-1H-furo[3,2-e]benzimidazole-5-carboxamide

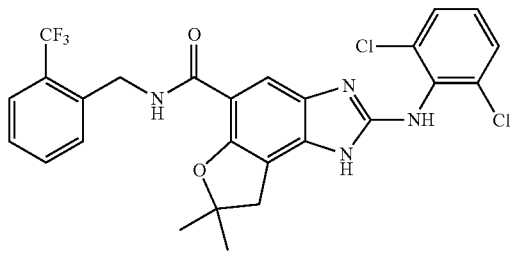 [SMILES: CC1(C)Cc2c(c(C(=O)NCc3ccccc3Br)cc3nc(Nc4c(Cl)cccc4Cl)[nH]c23)O1]

The title compound was prepared following the procedure described for Example-1 using Intermediate-6 (0.100 g, 0.255 mmol), TBTU (0.245 g, 0.765 mmol), TEA (1.0 mL), THF (5.0 mL), DMF (1.0 mL) and 1-[2-(trifluoromethyl)phenyl]methanamine (0.093 g, 0.531 mmol). The product obtained was further purified by column chromatography on neutral alumina eluting with 3.0-4.0% MeOH:DCM to afford 0.015 g of the desired product. $^1$HNMR (DMSO-d$_6$): δ 1.46 (s, 6H), 3.02 (s, 2H), 4.69 (d, J=5.4 Hz, 2H), 7.18 (s, 1H), 7.30 (s, 1H), 7.43-7.52 (m, 4H), 7.63 (t, J=7.2 Hz, 1H), 7.72 (d, J=7.2 Hz, 1H), 8.29 (s, 1H), 10.76 (s, 2H); MS [M+H]+: 549.37.

Example-83

N-[2-(4-Chlorophenyl)ethyl]-2-[(2,6-dichlorophenyl)amino]-7,7-dimethyl-7,8-dihydro-1H-furo[3,2-e]benzimidazole-5-carboxamide

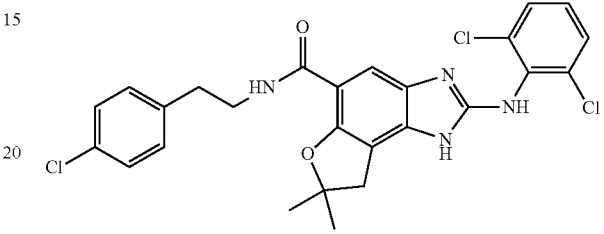

The title compound was prepared following the procedure described for Example-1 using Intermediate-6 (0.100 g, 0.255 mmol), TBTU (0.245 g, 0.765 mmol), TEA (1.0 mL), THF (5.0 mL), DMF (1.0 mL) and 2-(4-chlorophenyl)ethanamine (0.079 g, 0.500 mmol). The product obtained was further purified by column chromatography on neutral alumina eluting with 3.0-4.0% MeOH:DCM to afford 0.035 g of the desired product. $^1$HNMR (DMSO-d$_6$): δ 1.36 (s, 6H), 2.82 (t, J=6.3 Hz, 2H), 2.97 (s, 2H), 3.58 (q, J=6.0 Hz, 2H), 7.20 (s, 1H), 7.30 (d, J=8.4 Hz, 3H), 7.37 (d, J=8.1 Hz, 2H), 7.51 (t, J=7.8 Hz, 2H), 7.61 (s, 1H), 10.88 (s, 2H); MS [M+H]+: 529.38.

Example-84

N-(2-Bromobenzyl)-2-[(2,6-dichlorophenyl)amino]-7,7-dimethyl-7,8-dihydro-1H-furo[3,2-e]benzimidazole-5-carboxamide

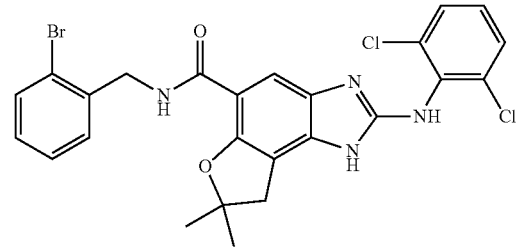

The title compound was prepared following the procedure described for Example-1 using Intermediate-6 (0.100 g, 0.255 mmol), TBTU (0.245 g, 0.765 mmol), TEA (1.0 mL), THF (5.0 mL), DMF (1.0 mL) and 1-(2-bromophenyl)methanamine (0.170 g, 0.765 mmol). The product obtained was further purified by column chromatography on neutral alumina eluting with 3.0-4.0% MeOH:DCM to afford 0.040 g of the desired product. $^1$HNMR (DMSO-d$_6$): δ 1.50 (s, 6H), 3.04

(s, 2H), 4.54 (d, J=5.7 Hz, 2H), 7.21 (s, 2H), 7.34 (s, 3H), 7.51 (d, J=7.2 Hz, 2H), 7.63 (d, J=7.8 Hz, 1H), 8.37 (s, 1H), 11.00 (s, 2H), [M+H]⁺: 559.28.

Example-85

2-[(2,6-Dichlorophenyl)amino]-7-methyl-N-[2-(trifluoromethyl)benzyl]-1H-furo[3,2-e]benzimidazole-5-carboxamide

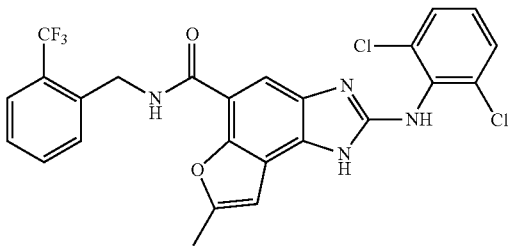 [SMILES: Cc1cc2c(o1)c(C(=O)NCc1ccccc1C(F)(F)F)cc1nc(Nc3c(Cl)cccc3Cl)[nH]c12]

The title compound was prepared following the procedure described for Example-1 using Intermediate-9 (0.100 g, 0.265 mmol), O-(benzotriazol-1-yl)-N,N,N',N'-tetramethyluronium tetrafluoroborate (0.255 g, 0.795 mmol), TEA (0.080 g, 0.795 mmol), THF (5.0 mL), DMF (1.0 mL) and 1-[2-(trifluoromethyl)phenyl]methanamine (0.139 g, 0.795 mmol) to afford 0.004 g of the desired product. ¹HNMR (DMSO-d₆): δ 2.50 (s, 3H), 4.79 (s, 2H), 6.72 (s, 1H), 7.31 (m, 1H), 7.48-7.66 (m, 6H), 7.75 (d, J=7.2 Hz, 1H), 8.61 (s, 1H), 11.27 (s, 2H); MS [M+H]⁺: 533.45.

Example-86

2-[(2-Chloro-4-fluorophenyl)amino]-7,7-dimethyl-N-[4-(trifluoromethyl)phenyl]-7,8-dihydro-1H-furo[3,2-e]benzimidazole-5-carboxamide

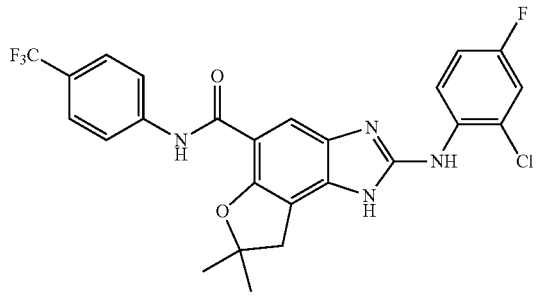 [SMILES: CC1(C)Cc2c(c(C(=O)Nc3ccc(C(F)(F)F)cc3)cc3nc(Nc4ccc(F)cc4Cl)[nH]c23)O1]

The title compound was prepared following the procedure described for Example-65 using Intermediate-19 (0.150 g, 0.400 mmol), thionyl chloride (2.0 mL), 4-(trifluoromethyl)aniline (0.128 g, 0.800 mmol), THF (5.0 mL) and DIPEA (2 mL). The product obtained was further purified by column chromatography on neutral alumina eluting with 0.7% MeOH:DCM to afford 0.030 g of the desired product. ¹HNMR (DMSO-d₆): δ 1.60 (s, 6H), 3.21 (s, 2H), 7.30 (t, J=5.8 Hz, 1H), 7.52 (dd, J=3.0 Hz, 2.4 Hz, 1H), 7.72 (d, J=8.4 Hz, 3H), 7.92 (d, J=8.4 Hz, 2H), 8.48 (s, 1H), 9.14 (s, 1H), 10.05 (s, 1H), 11.00 (s, 1H); MS [M]⁺: 519.31.

Example-87

2-[(2-Chloro-4-methylphenyl)amino]-7,7-dimethyl-N-[4-(trifluoromethyl)phenyl]-7,8-dihydro-1H-furo[3,2-e]benzimidazole-5-carboxamide

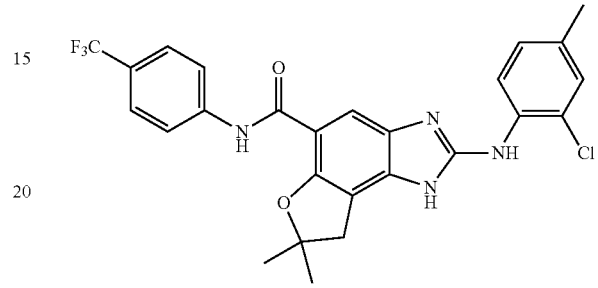

The title compound was prepared following the procedure described for Example-65 using Intermediate-21 (0.200 g, 0.539 mmol), thionyl chloride (2.0 mL), 4-(trifluoromethyl)aniline (0.173 g, 1.070 mmol), THF (5.0 mL) and DIPEA (2 mL). The product obtained was further purified by column chromatography on neutral alumina eluting with 0.7% MeOH:DCM to afford 0.030 g of the desired product. ¹HNMR (DMSO-d₆): δ 1.60 (s, 6H), 2.29 (s, 3H), 3.21 (s, 2H), 7.19 (d, J=8.4 Hz, 1H), 7.33 (s, 1H), 7.72 (d, J=7.8 Hz, 3H), 7.92 (d, J=8.1 Hz, 2H), 8.34 (d, J=8.1 Hz, 1H), 9.02 (s, 1H), 10.05 (s, 1H), 10.97 (s, 1H); MS [M]⁺: 515.37.

Example-88

2-[(2-Chlorophenyl)amino]-7,7-dimethyl-N-[2-(trifluoromethyl)benzyl]-7,8-dihydro-1H-furo[3,2-e]benzimidazole-5-carboxamide

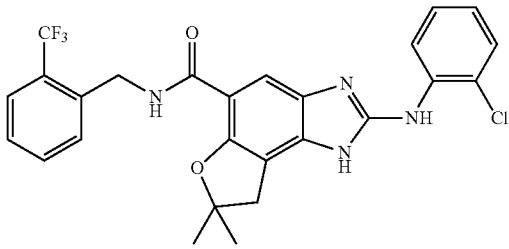 [SMILES: CC1(C)Cc2c(c(C(=O)NCc3ccccc3C(F)(F)F)cc3nc(Nc4ccccc4Cl)[nH]c23)O1]

The title compound was prepared following the procedure described for Example-65 by Intermediate-12 (0.100 g, 0.279 mmol), O-(benzotriazol-1-yl)-N,N,N',N'-tetramethyluronium tetrafluoroborate (0.268 g, 0.834 mmol), TEA (0.084 g, 0.831 mmol), THF (5.0 mL), DMF (1.0 mL) and 1-[2-(trifluoromethyl)phenyl]methanamine (0.146 g, 0.834 mmol) to afford 0.008 g of the desired product. ¹HNMR (DMSO-d₆): δ 1.51 (s, 6H), 3.19 (s, 2H), 4.74 (d, J=5.1 Hz, 2H), 7.03 (t, J=7.8 Hz, 1H), 7.37 (t, J=7.5 Hz, 1H), 7.57 (d, J=7.8 Hz, 2H), 7.64-7.69 (m, 2H), 7.75 (d, J=7.2 Hz, 2H), 8.38 (s, 1H), 8.58 (s, 1H), 9.00 (s, 1H), 10.98 (s, 1H); MS [M+H]⁺: 515.40.

Example-89

2-[(2-Chlorophenyl)amino]-7,7-dimethyl-N-[4-(trifluoromethyl)phenyl]-7,8-dihydro-1H-furo[3,2-e]benzimidazole-5-carboxamide

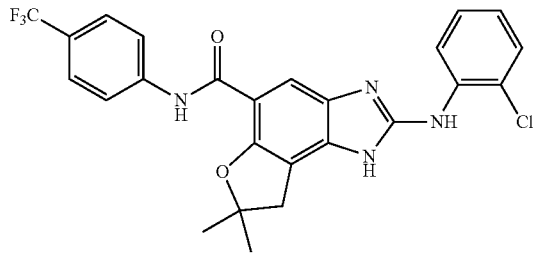 [SMILES: CC1(C)Cc2c(c(C(=O)Nc3ccc(C(F)(F)F)cc3)cc3nc(Nc4ccccc4Cl)[nH]c23)O1]

The title compound was prepared following the procedure described for Example-1 using by Intermediate-12 (0.100 g, 0.279 mmol), thionyl chloride (1.0 mL), 4-(trifluoromethyl) aniline (0.090 g, 0.559 mmol), THF (3.0 mL) and DIPEA (1 mL). The product obtained was further purified by column chromatography on neutral alumina eluting with 0.7% MeOH:DCM to afford 0.020 g of the desired product. ¹HNMR (DMSO-d₆): δ 1.61 (s, 6H), 3.15 (s, 2H), 7.07 (t, J=7.5 Hz, 1H), 7.39 (t, J=7.5 Hz, 1H), 7.49 (d, J=7.8 Hz, 1H), 7.74 (t, J=10.5 Hz, 3H), 7.93 (d, J=8.1 Hz, 2H), 8.58 (t, J=8.4 Hz, 1H), 9.11 (s, 1H), 10.06 (s, 1H), 11.04 (s, 1H); MS [M]⁺: 501.39.

Example-90

2-[(2,6-Dichlorophenyl)amino]-7,7-dimethyl-N-[4-(propan-2-yl)phenyl]-7,8-dihydro-1H-furo[3,2-e]benzimidazole-5-carboxamide

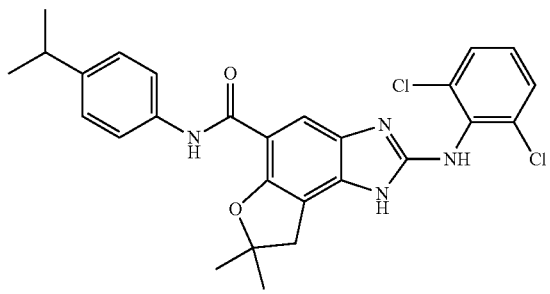 [SMILES: CC(C)c1ccc(NC(=O)c2cc3nc(Nc4c(Cl)cccc4Cl)[nH]c3c3c2OC(C)(C)C3)cc1]

The title compound was prepared following the procedure described for Example-65 using Intermediate-6 (0.100 g, 0.255 mmol), thionyl chloride (1.0 mL), 4-(propan-2-yl) aniline (0.103 g, 0.765 mmol), THF (5.0 mL) and DIPEA (2 mL). The product obtained was further purified by column chromatography on neutral alumina eluting with 0.9% MeOH:DCM to afford 0.08 g of the desired product. ¹HNMR (DMSO-d₆): δ 1.21 (d, J=8.1 Hz, 6H), 1.57 (s, 6H), 2.84-2.88 (m, 1H), 3.09 (s, 2H), 7.22 (d, J=8.4 Hz, 3H), 7.41 (m, 1H), 7.53-7.58 (m, 4H), 9.66 (s, 1H), 11.20 (s, 2H); MS [M+H]⁺: 509.40.

Example-91

2-[(2,4-Dichlorophenyl)amino]-7,7-dimethyl-N-[4-(trifluoromethyl)phenyl]-7,8-dihydro-1H-furo[3,2-e]benzimidazole-5-carboxamide

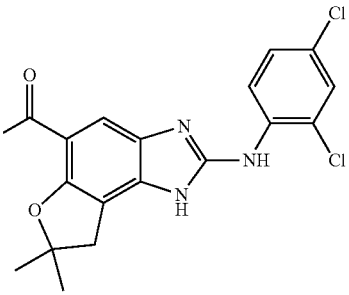

The title compound was prepared following the procedure described for Example-65 using Intermediate-24 (0.150 g, 0.382 mmol), thionyl chloride (2.0 mL), 4-(trifluoromethyl) aniline (0.123 g, 0.764 mmol), THF (5.0 mL) and DIPEA (2 mL). The product obtained was further purified by column chromatography on neutral alumina eluting with 0.7% MeOH:DCM to afford 0.030 g of the desired product. ¹HNMR (DMSO-d₆): δ 1.60 (s, 6H), 3.23 (s, 2H), 7.48 (d, J=9.3 Hz, 1H), 7.65 (s, 1H), 7.72 (d, J=8.4 Hz, 2H), 7.79 (s, 1H), 7.94 (d, J=8.4 Hz, 2H), 8.67 (s, 1H), 9.22 (s, 1H), 10.05 (s, 1H), 11.04 (s, 1H); MS [M]⁺: 535.44.

Example-92

2-[(2-Chloro-4-methylphenyl)amino]-7,7-dimethyl-N-[4-(trifluoromethyl)benzyl]-7,8-dihydro-1H-furo[3,2-e]benzimidazole-5-carboxamide

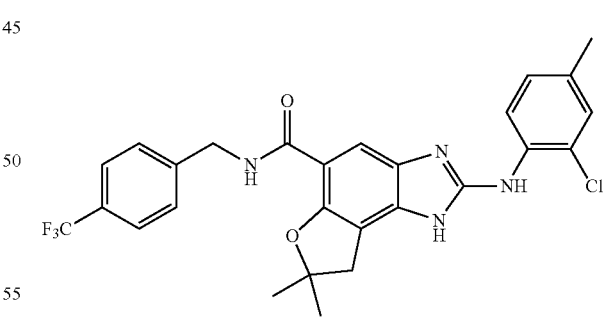

The title compound was prepared following the procedure described for Example-1 using Intermediate-21 (0.100 g, 0.269 mmol), O-(benzotriazol-1-yl)-N,N,N',N'-tetramethyluronium tetrafluoroborate (0.259 g, 0.807 mmol), TEA (0.084 g, 0.831 mmol), THF (5.0 mL), DMF (1.0 mL) and 1-[4-(trifluoromethyl)phenyl]methanamine (0.071 g, 0.404 mmol) to afford 0.039 g of the desired product. ¹HNMR (DMSO-d₆): δ 1.50 (s, 6H), 2.28 (s, 3H), 3.17 (s, 2H), 4.73 (d, J=5.4 Hz, 2H), 7.18 (d, J=8.4 Hz, 1H), 7.32 (s, 1H), 7.48 (t, J=7.2 Hz, 2H), 7.57 (d, J=7.5 Hz, 1H), 7.63-7.68 (m, 1H), 7.75 (d, J=7.5 Hz, 1H), 8.37 (s, 1H), 8.91 (s, 1H), 10.91 (s, 1H), 11.24 (s, 1H); MS [M+H]+: 529.43.

Example-93

2-[(2,6-Dichlorophenyl)amino]-N-(4,4-difluorocyclohexyl)-7,7-dimethyl-7,8-dihydro-1H-furo[3,2-e]benzimidazole-5-carboxamide

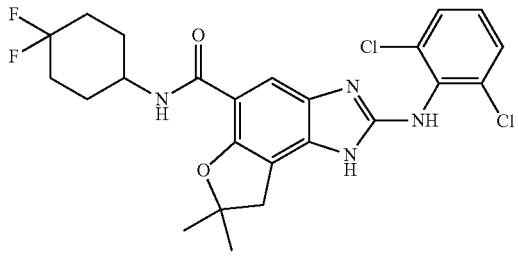 [SMILES: CC1(C)Cc2c(c(C(=O)NC3CCC(F)(F)CC3)cc3nc(Nc4c(Cl)cccc4Cl)[nH]c23)O1]

The title compound was prepared following the procedure described for Example-1 using Intermediate-6 (0.100 g, 0.255 mmol), O-(benzotriazol-1-yl)-N,N,N',N'-tetramethyluronium tetrafluoroborate (0.246 g, 0.765 mmol), TEA (0.103 g, 1.02 mmol), THF (5.0 mL), DMF (1.0 mL) and 4,4-difluorocyclohexanamine (0.066 g, 0.382 mmol) to afford 0.062 g of the desired product. ¹HNMR (DMSO-d₆): δ 1.48 (s, 6H), 1.57-1.60 (m, 2H), 1.90-1.96 (m, 6H), 3.03 (s, 2H), 3.97 (s, 2H), 7.21 (d, J=7.5 Hz, 1H), 7.31 (s, 1H), 7.51 (d, J=7.8 Hz, 1H), 7.72 (d, J=7.2 Hz, 1H), 10.67 (s, 2H); MS [M+H]+: 509.42.

Example-94

2-[(2-Chloro-4-fluorophenyl)amino]-7,7-dimethyl-N-(2,2,3,3,3-pentafluoropropyl)-7,8-dihydro-1H-furo[3,2-e]benzimidazole-5-carboxamide

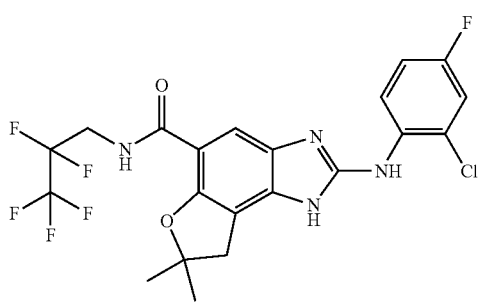 [SMILES: CC1(C)Cc2c(c(C(=O)NCC(F)(F)C(F)(F)F)cc3nc(Nc4ccc(F)cc4Cl)[nH]c23)O1]

The title compound was prepared following the procedure described for Example-1 using Intermediate-19 (0.150 g, 0.400 mmol), O-(benzotriazol-1-yl)-N,N,N',N'-tetramethyluronium tetrafluoroborate (0.256 g, 0.798 mmol), TEA (1 mL), THF (5.0 mL), DMF (1.0 mL) and 2,2,3,3,3-pentafluoropropan-1-amine (0.060 g, 0.399 mmol) to afford 0.030 g of the desired product. ¹HNMR (DMSO-d₆): δ 1.52 (s, 6H), 3.17 (s, 2H), 4.22-4.32 (m, 2H), 7.29 (t, J=6.0 Hz, 1H), 7.51 (d, J=6.3 Hz, 1H), 7.69 (s, 1H), 8.15 (m, 1H), 8.48 (s, 1H), 9.07 (s, 1H), 10.95 (s, 1H); MS [M+H]+: 507.39.

Example-95

2-[(2,6-Dichlorophenyl)amino]-N-(6-fluoro-1,3-benzothiazol-2-yl)-7,7-dimethyl-7,8-dihydro-1H-furo[3,2-e]benzimidazole-5-carboxamide

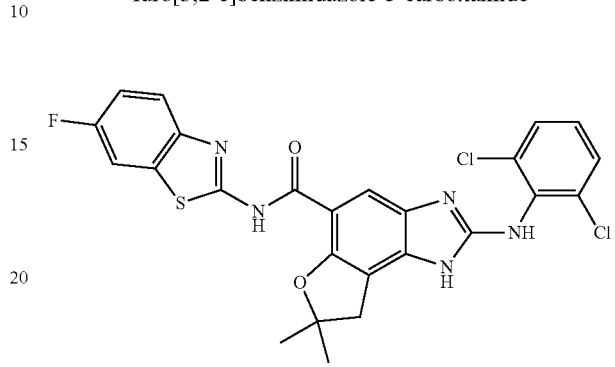

The title compound was prepared following the procedure described for Example-65 using Intermediate-6 (0.150 g, 0.382 mmol), thionyl chloride (1.0 mL), 6-fluoro-1,3-benzothiazol-2-amine (0.128 g, 0.761 mmol), THF (5.0 mL) and DIPEA (2 mL). The product obtained was further purified by column chromatography on neutral alumina eluting with 0.9% MeOH:DCM to afford 0.005 g of the desired product. ¹HNMR (DMSO-d₆): δ 1.58 (s, 6H), 3.11 (s, 2H), 7.25-7.32 (m, 2H), 7.44-7.56 (m, 4H), 7.77-7.89 (m, 1H), 7.91 (d, J=6.0 Hz, 1H), 11.03 (s, 2H); MS [M+H]+: 542.28.

Example-96

2-[(2,6-Dichlorophenyl)amino]-7,7-dimethyl-N-[6-(pyrrolidin-1-yl)pyridin-3-yl]-7,8-dihydro-1H-furo[3,2-e]benzimidazole-5-carboxamide

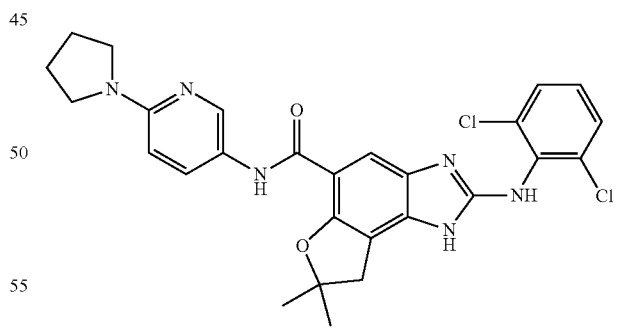

The title compound was prepared following the procedure described for Example-65 using Intermediate-6 (0.150 g, 0.382 mmol), thionyl chloride (1.0 mL), Intermediate-25 (0.125 g, 0.744 mmol), THF (5.0 mL) and DIPEA (2 mL). The product obtained was further purified by column chromatography on neutral alumina eluting with 0.9% MeOH: DCM to afford 0.008 g of the desired product. ¹HNMR (DMSO-d₆): δ 1.42 (s, 6H), 1.93 (s, 4H), 3.07 (s, 2H), 3.84 (s, 4H), 6.44 (d, J=9.0 Hz, 1H), 7.22 (s, 1H), 7.38 (s, 1H), 7.51-7.54 (m, 2H), 7.84 (d, J=6.9 Hz, 1H), 8.29 (s, 1H), 9.42 (s, 1H), 10.80-11.00 (s, 2H); MS [M+H]⁺: 537.41.

Example-97

2-[(2-Chloro-5-methylphenyl)amino]-7,7-dimethyl-N-[2-(trifluoromethyl)phenyl]-7,8-dihydro-1H-furo[3,2-e]benzimidazole-5-carboxamide

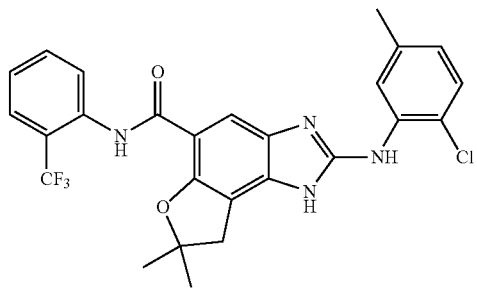 [SMILES: Cc1ccc(Cl)c(Nc2nc3cc(C(=O)Nc4ccccc4C(F)(F)F)c4c(c3[nH]2)CC(C)(C)O4)c1]

The title compound was prepared following the procedure described for Example-65 using Intermediate-27 (0.100 g, 0.269 mmol), thionyl chloride (2.0 mL), 2-trifluoromethyl phenylamine (0.065 g, 0.404 mmol), THF (10.0 mL) and DIPEA (2 mL). The product obtained was further purified by column chromatography on neutral alumina eluting with 0.9% MeOH:DCM to afford 0.010 g of the desired product. ¹HNMR (DMSO-d₆): δ 1.57 (s, 6H), 2.33 (s, 3H), 3.25 (s, 2H), 6.89 (d, J=7.8 Hz, 1H), 7.33-7.38 (m, 2H), 7.74 (q, J=8.4 Hz, 2H), 7.81 (s, 1H), 8.35 (s, 1H), 8.46 (d, J=8.4 Hz, 1H), 9.06 (s, 1H), 10.15 (s, 1H), 11.04 (s, 1H); MS [M+H]⁺: 515.51.

Example-98

2-[(2-tert-Butylphenyl)amino]-7,7-dimethyl-N-[2-(trifluoromethyl)phenyl]-7,8-dihydro-1H-furo[3,2-e]benzimidazole-5-carboxamide

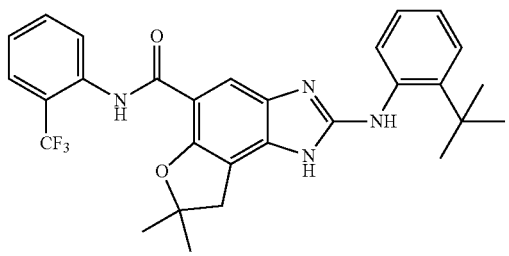 [SMILES: CC1(C)Cc2c(c(C(=O)Nc3ccccc3C(F)(F)F)cc3nc(Nc4ccccc4C(C)(C)C)[nH]c23)O1]

The title compound was prepared following the procedure described for Example-65 using Intermediate-29 (0.100 g, 0.263 mmol), thionyl chloride (2.0 mL), 2-trifluoromethyl phenyl amine (0.064 g, 0.395 mmol), THF (5.0 mL) and DIPEA (0.067 g, 0.526 mmol). The product obtained was further purified by column chromatography on neutral alumina eluting with 0.9% MeOH:DCM to afford 0.012 g of the desired product. ¹HNMR (DMSO-d₆): δ 1.37 (s, 9H), 1.54 (s, 6H), 3.14 (s, 2H), 7.30-7.33 (m, 3H), 7.48 (m, 1H), 7.56 (s, 1H), 7.65-7.75 (m, 3H), 8.46 (d, J=8.1 Hz, 1H), 8.74 (s, 1H), 10.09 (s, 1H), 10.77 (s, 1H); MS [M+H]⁺: 523.46.

Example-99

2-[(2,6-Dichlorophenyl)amino]-1-(2-methoxyethyl)-7,7-dimethyl-N-[4-(trifluoromethyl)phenyl]-7,8-dihydro-1H-furo[3,2-e]benzimidazole-5-carboxamide

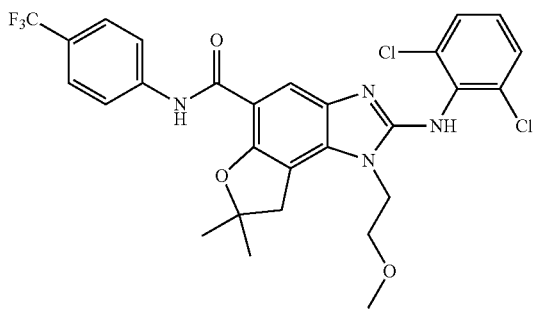 [SMILES: COCCn1c(Nc2c(Cl)cccc2Cl)nc2cc(C(=O)Nc3ccc(C(F)(F)F)cc3)c3c(c21)CC(C)(C)O3]

The title compound was prepared following the procedure described for Example-65 using Intermediate-31 (0.060 g, 0.133 mmol), thionyl chloride (1.0 mL), 4-trifluoromethyl phenylamine (0.64 g, 0.399 mmol), THF (5.0 mL) and DIPEA (2 mL). The product obtained was further purified by column chromatography on neutral alumina eluting with 20% EtOAc: petroleum ether to afford 0.015 g of the desired product. ¹HNMR (DMSO-d₆): δ 1.58 (s, 6H), 3.24 (s, 3H), 3.26 (s, 2H), 3.17 (s, 2H), 4.12 (s, 2H), 7.70 (t, J=7.8 Hz, 1H), 7.17 (s, 1H), 7.43 (d, J=7.8 Hz, 2H), 7.68 (d, J=8.1 Hz, 2H), 7.88 (d, J=8.4 Hz, 2H), 9.91 (s, 1H), 10.47 (s, 1H); MS [M+H]⁺: 594.51

Example-100

2-[(2,6-Dichlorophenyl)amino]-1-(2-methoxyethyl)-7,7-dimethyl-N-[2-(trifluoromethyl)phenyl]-7,8-dihydro-1H-furo[3,2-e]benzimidazole-5-carboxamide

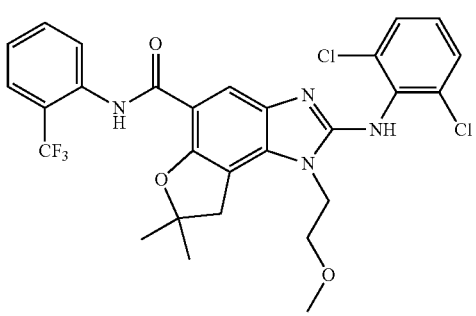 [SMILES: COCCn1c(Nc2c(Cl)cccc2Cl)nc2cc(C(=O)Nc3ccccc3C(F)(F)F)c3c(c21)CC(C)(C)O3]

The title compound was prepared following the procedure described for Example-65 using Intermediate-31 (0.100 g, 0.222 mmol), thionyl chloride (3.0 mL), 2-trifluoromethyl phenylamine (0.107 g, 0.666 mmol), THF (5.0 mL) and DIPEA (2 mL). The product obtained was further purified by column chromatography on neutral alumina eluting with 20% EtOAc:petroleum ether to afford 0.005 g of the desired product. ¹HNMR (DMSO-d₆): δ 1.56 (s, 6H), 3.25-3.33 (m, 5H), 3.73 (s, 2H), 4.14 (s, 2H), 7.02 (m, 1H), 7.32 (m, 1H), 7.45 (d, J=7.8 Hz, 2H), 7.60-7.76 (m, 3H), 8.40 (d, J=8.7 Hz, 1H), 10.00 (s, 1H), 10.49 (s, 1H); MS [M+H]⁺: 593.34.

Example-101

2-[(2,6-Dichlorophenyl)amino]-7,7-dimethyl-N-[5-(trifluoromethyl)pyridin-2-yl]-7,8-dihydro-1H-furo[3,2-e]benzimidazole-5-carboxamide

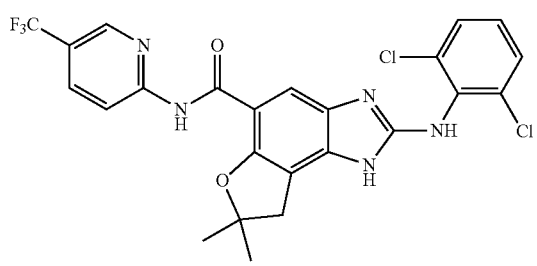 [SMILES: CC1(C)Cc2c(c(C(=O)Nc3ccc(C(F)(F)F)cn3)cc3nc(Nc4c(Cl)cccc4Cl)[nH]c23)O1]

The title compound was prepared following the procedure described for Example-65 using Intermediate-6 (0.100 g, 0.255 mmol), thionyl chloride (3.0 mL), 5-(trifluoromethyl)pyridin-2-amine (0.124 g, 0.765 mmol), THF (5.0 mL) and DIPEA (2 mL). The product obtained was further purified by column chromatography on neutral alumina eluting with 0.8% MeOH:DCM to afford 0.024 g of the desired product. ¹HNMR (DMSO-d₆): δ 1.57 (s, 6H), 3.11 (s, 2H), 7.25 (m, 1H), 7.47-7.56 (m, 3H), 8.23 (d, J=8.4 Hz, 1H), 8.47 (d, J=8.7 Hz, 1H), 8.75 (s, 1H), 10.45 (s, 1H), 11.00 (s, 2H); MS [M+H]⁺: 537.37.

Example-102

2-[(2-tert-Butylphenyl)amino]-7,7-dimethyl-N-[4-(trifluoromethyl)phenyl]-7,8-dihydro-1H-furo[3,2-e]benzimidazole-5-carboxamide

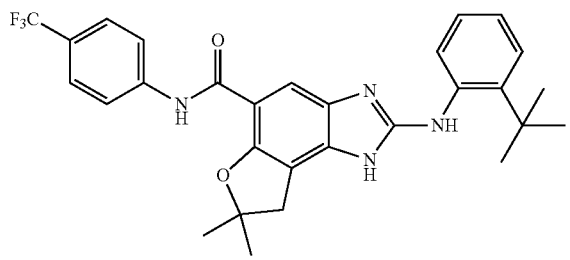 [SMILES: CC1(C)Cc2c(c(C(=O)Nc3ccc(C(F)(F)F)cc3)cc3nc(Nc4ccccc4C(C)(C)C)[nH]c23)O1]

The title compound was prepared following the procedure described for Example-65 using Intermediate-29 (0.100 g, 0.263 mmol), thionyl chloride (2.0 mL), 4-trifluoromethyl phenylamine (0.064 g, 0.395 mmol), THF (5.0 mL) and DIPEA (0.067 g, 0.526 mmol). The product obtained was further purified by column chromatography on neutral alumina eluting with 0.9% MeOH:DCM to afford 0.030 g of the desired product. ¹HNMR (DMSO-d₆): δ 1.37 (s, 9H), 1.59 (s, 6H), 3.13 (s, 2H), 7.29-7.33 (m, 3H), 7.46 (m, 1H), 7.51 (s, 1H), 7.70 (d, J=8.1 Hz, 2H), 7.90 (d, J=8.4 Hz, 2H), 8.72 (s, 1H), 10.01 (s, 1H), 10.76 (s, 1H); MS [M+H]⁺: 523.67.

Example-103

2-[(2,6-Dimethylpyridin-3-yl)amino]-7,7-dimethyl-N-[4-(trifluoromethyl)phenyl]-7,8-dihydro-1H-furo[3,2-e]benzimidazole-5-carboxamide

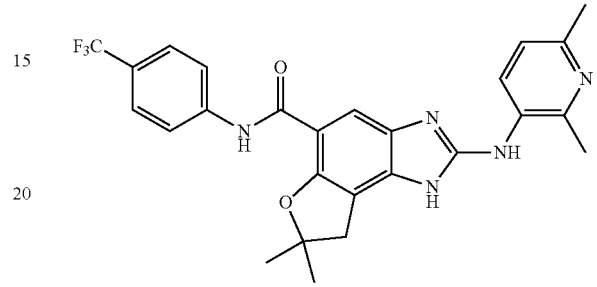

The title compound was prepared following the procedure described for Example-65 using Intermediate-33 (0.100 g, 0.283 mmol), thionyl chloride (2.0 mL), 4-trifluoromethyl phenylamine (0.063 g, 0.422 mmol), THF (5.0 mL) and DIPEA (0.073 g, 0.565 mmol). The product obtained was further purified by column chromatography on neutral alumina eluting with 0.9% MeOH:DCM to afford 0.020 g of the desired product. ¹HNMR (DMSO-d₆): δ 1.57 (s, 6H), 2.39 (s, 3H), 2.42 (s, 3H), 3.16 (s, 2H), 7.10 (d, J=8.4 Hz, 1H), 7.65 (s, 1H), 7.69 (d, J=8.4 Hz, 2H), 7.91 (d, J=9.0 Hz, 2H), 8.17 (d, J=8.40 Hz, 1H), 8.94 (s, 1H), 10.02 (s, 1H), 10.88 (s, 1H); MS [M+H]⁺: 496.33.

Example-104

2-[(2-Chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide

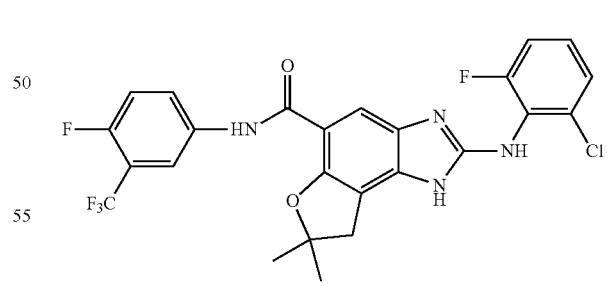

The title compound was prepared following the procedure described for Example-65 using Intermediate-15 (0.100 g, 0.266 mmol), thionyl chloride (2.0 mL), 4-fluoro-3-(trifluoromethyl)aniline (0.072 g, 0.400 mmol), THF (10.0 mL) and DIPEA (2 mL). The product obtained was further purified by column chromatography on neutral alumina eluting with 0.7-1.0% MeOH:DCM to afford 0.025 g of the desired product. ¹HNMR (DMSO-d₆): δ 1.56 (s, 6H), 3.09 (s, 2H), 7.31 (d, J=8.4 Hz, 2H), 7.40-7.54 (m, 3H), 7.83 (m, 1H), 8.33 (d, J=4.5 Hz, 1H), 9.19 (s, 1H), 11.00-12.00 (s, 2H); MS [M]⁻: 535.92.

Example-105

2-[(2-Chloro-6-fluorophenyl)amino]-N-(2-cyano-4-fluorophenyl)-7,7-dimethyl-7,8-dihydro-1H-furo[3,2-e]benzimidazole-5-carboxamide

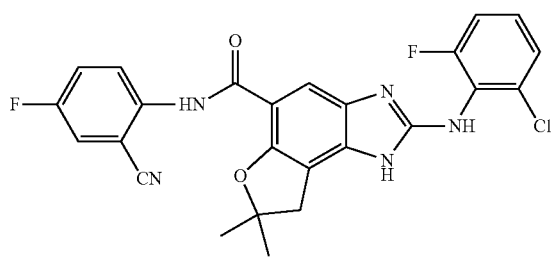 [SMILES: CC1(C)Cc2c(c(C(=O)Nc3ccc(F)cc3C#N)cc3nc(Nc4c(F)cccc4Cl)[nH]c23)O1]

The title compound was prepared following the procedure described for Example-65 using Intermediate-15 (0.100 g, 0.266 mmol), thionyl chloride (2.0 mL), 2-amino-5-fluorobenzonitrile (0.054 g, 0.400 mmol), THF (10.0 mL) and DIPEA (2 mL). The product obtained was further purified by column chromatography on neutral alumina eluting with 0.7-1.0% MeOH:DCM to afford 0.015 g of the desired product. ¹HNMR (DMSO-d₆): δ 1.59 (s, 6H), 3.12 (s, 2H), 7.32-7.41 (m, 3H), 7.54-7.62 (m, 2H), 7.86 (d, J=8.7 Hz, 1H), 8.63 (s, 1H), 10.30 (s, 1H), 11.00-12.00 (s, 2H); MS [M+H]⁺: 494.31

Example-106

2-[(2,6-Dimethylpyridin-3-yl)amino]-7,7-dimethyl-N-[2-(trifluoromethyl)phenyl]-7,8-dihydro-1H-furo[3,2-e]benzimidazole-5-carboxamide

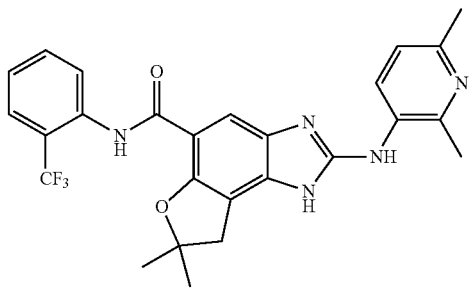 [SMILES: Cc1ccc(Nc2nc3cc(C(=O)Nc4ccccc4C(F)(F)F)c4c(c3[nH]2)CC(C)(C)O4)c(C)n1]

The title compound was prepared following the procedure described for Example-65 using Intermediate-33 (0.100 g, 0.283 mmol), thionyl chloride (2.0 mL), 2-trifluoromethyl phenylamine (0.063 g, 0.422 mmol), THF (5.0 mL) and DIPEA (0.073 g, 0.565 mmol). The product obtained was further purified by column chromatography on neutral alumina eluting with 0.9% MeOH:DCM to afford 0.015 g of the desired product. ¹HNMR (DMSO-d₆): δ 1.55 (s, 6H), 2.41 (s, 3H), 2.44 (s, 3H), 3.19 (s, 2H), 7.12 (d, J=8.4 Hz, 1H), 7.32 (d, J=7.8 Hz, 1H), 7.63-7.67 (m, 3H), 8.19 (d, J=8.4 Hz, 1H), 8.46 (d, J=8.10 Hz, 1H), 8.98 (s, 1H), 10.12 (s, 1H), 10.90 (s, 1H); MS [M+H]⁺: 496.36.

Example-107

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide

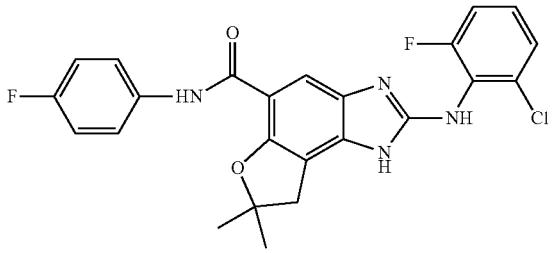 [SMILES: CC1(C)Cc2c(c(C(=O)Nc3ccc(F)cc3)cc3nc(Nc4c(F)cccc4Cl)[nH]c23)O1]

The title compound was prepared following the procedure described for Example-65 using Intermediate-15 (0.100 g, 0.266 mmol), thionyl chloride (2.0 mL), 4-trifluoromethyl phenylamine (0.064 g, 0.397 mmol), THF (10.0 mL) and DIPEA (0.069 g, 0.534 mmol). The product obtained was further purified by column chromatography on neutral alumina eluting with 0.7-1.0% MeOH:DCM to afford 0.012 g of the desired product. ¹HNMR (DMSO-d₆): δ 1.57 (s, 6H), 3.10 (s, 2H), 7.31-7.47 (m, 4H), 7.71 (s, 2H), 7.91 (s, 2H), 9.99 (s, 1H), 11.15 (s, 2H); MS [M+H]⁺: 519.23.

Example-108

2-[(2-Chloro-6-methylphenyl)amino]-7,7-dimethyl-N-[4-(trifluoromethyl)phenyl]-7,8-dihydro-1H-furo[3,2-e]benzimidazole-5-carboxamide

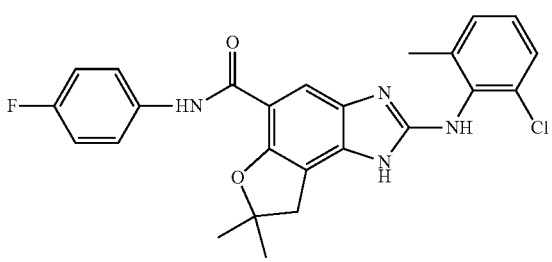 [SMILES: Cc1cccc(Cl)c1Nc1nc2cc(C(=O)Nc3ccc(F)cc3)c3c(c2[nH]1)CC(C)(C)O3]

To a solution of 2-[(2-chloro-6-methylphenyl)amino]-7,7-dimethyl-7,8-dihydro-1H-furo[3,2-e]benzimidazole-5-carboxylic acid (Intermediate-35, 0.100 g, 0.268 mmol) in benzene (2 mL), thionyl chloride (3.0 mL) was added at 5-10° C. and the reaction mass was refluxed for 3 h. To the reaction mixture, stirred solution of 4-trifluoromethyl phenyl amine (0.065 g, 0.403 mmol) and DIPEA (0.069 g, 0.534 mmol) in THF (10.0 mL) for 1 h at RT under N₂-atmosphere was added and stirring was continued for another 1 h at RT. Excess of thionyl chloride was co-evaporated with THF under vacuum. Water was added to the reaction mass and it was extracted with ethyl acetate. The organic layer was separated, dried over anhydrous sodium sulphate and concentrated. The obtained crude product was purified by column chromatography on neutral alumina eluting with 0.7-1.0% MeOH:DCM to afford 0.012 g of the desired product. ¹HNMR (DMSO-d₆): δ 1.58 (s, 6H), 2.24 (s, 3H), 3.44 (s, 2H), 7.25-7.31 (m, 2H), 7.42 (d, J=7.2 Hz, 1H), 7.50 (s, 1H), 7.70 (d, J=8.7 Hz, 2H), 7.91 (d, J=8.4 Hz, 2H), 9.09 (s, 1H), 10.01 (s, 1H), 10.94 (s, 1H); MS [M–H]⁻: 513.42.

Example-109

2-[(2-Chloro-6-methylphenyl)amino]-7,7-dimethyl-N-(2,4,6-trifluorophenyl)-7,8-dihydro-1H-furo[3,2-e]benzimidazole-5-carboxamide

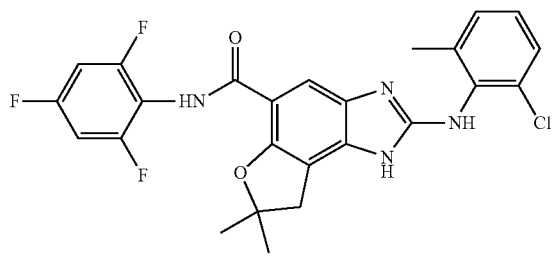 [SMILES: Cc1cccc(Cl)c1Nc1nc2cc(C(=O)Nc3c(F)cc(F)cc3F)c3c(c2[nH]1)CC(C)(C)O3]

The title compound was prepared by following the procedure described for Example-108 using 2-[(2-chloro-6-methylphenyl)amino]-7,7-dimethyl-7,8-dihydro-1H-furo[3,2-e]benzimidazole-5-carboxylic acid (Intermediate-35, 0.100 g, 0.268 mmol), thionyl chloride (3.0 mL), 2,4,6-trifluoroaniline (0.059 g, 0.403 mmol), THF (10.0 mL) and DIPEA (3 mL). The obtained crude product was purified by column chromatography on neutral alumina eluting with 0.7-1.0% MeOH:DCM to afford 0.015 g of the desired product. ¹HNMR (DMSO-d₆): δ 1.52 (s, 6H), 2.24 (s, 3H), 3.10 (s, 2H), 7.24-7.32 (m, 4H), 7.41 (d, J=7.2 Hz, 1H), 7.45 (s, 1H), 9.12 (s, 1H), 10.91 (s, 1H); MS [M+H]⁺: 501.37.

Example-110

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide

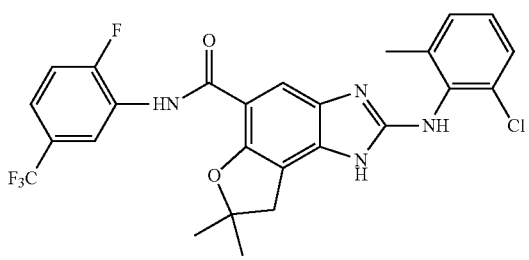 [SMILES: Cc1cccc(Cl)c1Nc1nc2cc(C(=O)Nc3cc(C(F)(F)F)ccc3F)c3c(c2[nH]1)CC(C)(C)O3]

The title compound was prepared by following the procedure described for Example-108 using 2-[(2-chloro-6-methylphenyl)amino]-7,7-dimethyl-7,8-dihydro-1H-furo[3,2-e]benzimidazole-5-carboxylic acid (Intermediate-35, 0.100 g, 0.268 mmol), thionyl chloride (3.0 mL), 2-fluoro-5-(trifluoromethyl) aniline (0.053 g, 0.296 mmol), THF (10.0 mL) and DIPEA (3 mL). The obtained crude product was purified by column chromatography on neutral alumina eluting with 0.7-1.0% MeOH:DCM to afford 0.014 g of the desired product. ¹HNMR (DMSO-d₆): δ 1.56 (s, 6H), 2.25 (s, 3H), 3.15 (s, 2H), 7.32 (m, 4H), 7.54 (m, 3H), 8.98 (s, 1H), 10.25 (s, 1H), 11.50 (s, 1H); MS [M+H]⁺: 533.37.

Example-111

2-[(2-Chloro-6-fluorophenyl)amino]-N-[2-fluoro-5-(trifluoromethyl)phenyl]-7,7-dimethyl-7,8-dihydro-1H-furo[3,2-e]benzimidazole-5-carboxamide

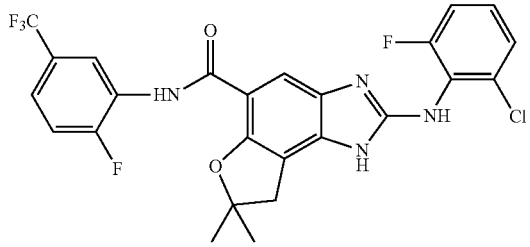 [SMILES: CC1(C)Cc2c(c(C(=O)Nc3cc(C(F)(F)F)ccc3F)cc3nc(Nc4c(F)cccc4Cl)[nH]c23)O1]

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 2-fluoro-5-(trifluoromethyl)aniline (0.071 g, 0.396 mmol), THF (10.0 mL) and DIPEA (2 mL). The obtained crude product was purified by column chromatography on neutral alumina eluting with 0.7-1.0% MeOH:DCM to afford 0.018 g of the desired product. ¹HNMR (DMSO-d₆): δ 1.56 (s, 6H), 3.14-3.17 (s, 2H), 7.33-7.41 (m, 3H), 7.53-7.62 (m, 3H), 8.92 (d, J=6.6 Hz, 1H), 9.40 (s, 1H), 10.32 (s, 1H), 11.25 (s, 1H); MS [M+H]⁺: 537.33.

Example-112

2-[(2-Chloro-6-fluorophenyl)amino]-N-[2-fluoro-4-(trifluoromethyl)phenyl]-7,7-dimethyl-7,8-dihydro-1H-furo[3,2-e]benzimidazole-5-carboxamide

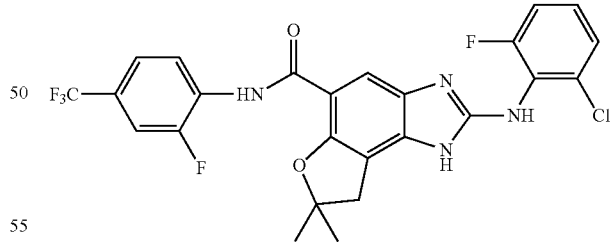

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 2-fluoro-4-(trifluoromethyl)aniline (0.071 g, 0.396 mmol), THF (10.0 mL) and DIPEA (2 mL). The obtained crude product was purified by column chromatography on neutral alumina eluting with 0.7-1.0% MeOH:DCM to afford 0.017 g of the desired product. ¹HNMR (DMSO-d₆): δ 1.56 (s, 6H), 3.14 (s, 2H), 7.33-7.54

(m, 3H), 7.62 (d, J=8.7 Hz, 2H), 7.81 (d, J=11.1 Hz, 1H), 8.73 (t, J=7.8 Hz, 1H), 10.34 (s, 1H), 11.25 (s, 2H); MS [M+H]⁺: 537.48.

Example-113

2-[(2-Chloro-6-fluorophenyl)amino]-7,7-dimethyl-N-[2-methyl-4-(trifluoromethyl)phenyl]-7,8-dihydro-1H-furo[3,2-e]benzimidazole-5-carboxamide

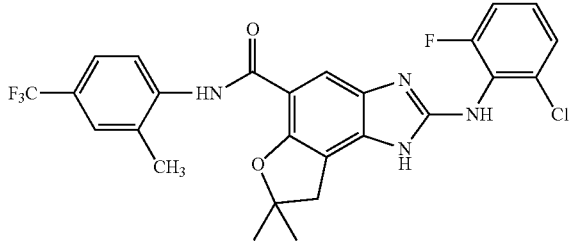 [SMILES: Cc1cc(C(F)(F)F)ccc1NC(=O)c1cc2nc(Nc3c(F)cccc3Cl)[nH]c2c2c1OC(C)(C)C2]

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 2-methyl-4-(trifluoromethyl)aniline (0.070 g, 0.400 mmol), THF (10.0 mL) and DIPEA (2 mL). The obtained crude product was purified by column chromatography on neutral alumina eluting with 0.7-1.0% MeOH:DCM to afford 0.015 g of the desired product. ¹HNMR (DMSO-d₆): δ 1.56 (s, 6H), 2.41 (s, 3H), 3.12 (s, 2H), 7.32-7.39 (m, 3H), 7.57 (d, J=7.2 Hz, 1H), 7.63 (s, 1H), 8.63 (d, J=8.4 Hz, 2H), 9.31 (s, 1H), 9.84 (s, 1H), 11.18 (s, 1H); MS [M−H]⁻: 531.41.

Example-114

N-(4-tert-Butylphenyl)-2-[(2-chloro-6-fluorophenyl)amino]-7,7-dimethyl-7,8-dihydro-1H-furo[3,2-e]benzimidazole-5-carboxamide

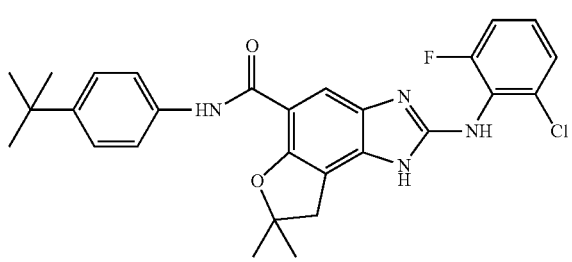 [SMILES: CC1(C)Cc2c(c(C(=O)Nc3ccc(C(C)(C)C)cc3)cc3nc(Nc4c(F)cccc4Cl)[nH]c23)O1]

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 4-tert-butylaniline (0.079 g, 0.400 mmol), THF (10.0 mL) and DIPEA (2 mL). The obtained crude product was purified by column chromatography on neutral alumina eluting with 0.7-1.0% MeOH:DCM to afford 0.055 g of the desired product. ¹HNMR (DMSO-d₆): δ 1.21 (s, 9H), 1.55 (s, 6H), 3.13 (s, 2H), 7.27-7.46 (m, 6H), 7.55 (d, J=8.7 Hz, 2H), 9.67 (s, 1H), 11.20 (s, 2H); MS [M+H]⁺: 507.50.

Example-115

2-[(2-Chloro-6-fluorophenyl)amino]-N-[6-(difluoromethoxy)pyridin-3-yl]-7,7-dimethyl-7,8-dihydro-1H-furo[3,2-e]benzimidazole-5-carboxamide

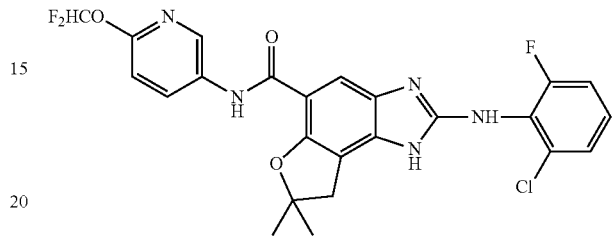

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 6-(difluoromethoxy)pyridin-3-amine (Intermediate-36, 0.065 g, 0.399 mmol), THF (5.0 mL) and DIPEA (2 mL). The obtained crude product was purified by column chromatography on basic alumina eluting with 0.7-1.0% MeOH:DCM to afford 0.020 g of the desired product. ¹HNMR (DMSO-d₆): δ 1.57 (s, 6H), 3.09 (s, 2H), 7.12 (d, J=8.7 Hz, 1H), 7.30-7.46 (m, 4H), 7.66 (s, 1H), 7.90 (s, 1H), 8.23 (d, J=9.0 Hz, 1H), 8.59 (s, 1H), 9.79 (s, 1H), 11.20 (s, 1H); MS [M+H]⁺: 518.24.

Example-116

2-[(2-Chloro-6-fluorophenyl)amino]-7,7-dimethyl-N-{1-[4-(trifluoromethyl)phenyl]cyclopropyl}-7,8-dihydro-1H-furo[3,2-e]benzimidazole-5-carboxamide

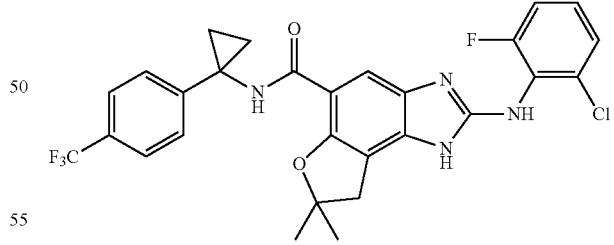

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 1-[4-(trifluoromethyl)phenyl]cyclopropanamine (Intermediate-37, 0.078 g, 0.388 mmol), THF (5.0 mL) and DIPEA (2 mL). The obtained crude product was purified by column chromatography on basic alumina eluting with 0.7-1.0% MeOH:DCM to afford 0.015 g of the desired product. ¹HNMR (DMSO-d₆):

δ 1.38 (d, J=9.0 Hz, 4H), 1.52 (s, 6H), 3.07 (s, 2H), 7.32-7.35 (m, 6H), 7.61-7.64 (m, 2H), 8.39 (s, 1H), 9.20 (s, 1H), 11.0 (s, 1H); MS [M+H]+: 559.25.

Example-117

2-[(2-Chloro-6-fluorophenyl)amino]-N-[4-fluoro-2-(trifluoromethyl)phenyl]-7,7-dimethyl-7,8-dihydro-1H-furo[3,2-e]benzimidazole-5-carboxamide

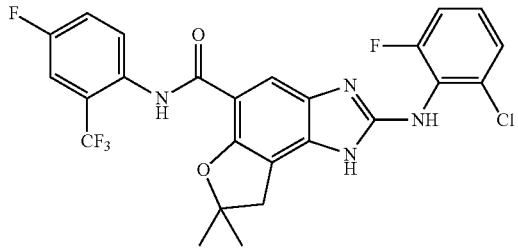 [SMILES: CC1(C)Cc2c(c(C(=O)Nc3ccc(F)cc3C(F)(F)F)cc3nc(Nc4c(F)cccc4Cl)[nH]c23)O1]

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 4-fluoro-2-(trifluoromethyl)aniline (0.095 g, 0.530 mmol), THF (10.0 mL) and DIPEA (2 mL). The obtained crude product was purified by column chromatography on neutral alumina eluting with 0.7-1.0% MeOH:DCM to afford 0.040 g of the desired product. $^1$HNMR (DMSO-d$_6$): δ 1.53 (s, 6H), 3.12 (s, 2H), 7.34-7.41 (m, 4H), 7.60-7.67 (m, 2H), 8.40 (m, 1H), 10.02 (s, 1H), 11.20 (s, 2H); MS [M+H]+: 537.17.

Example-118

2-[(2-Chloro-6-fluorophenyl)amino]-7,7-dimethyl-N-{1-[2-(trifluoromethyl)phenyl]cyclopropyl}-7,8-dihydro-1H-furo[3,2-e]benzimidazole-5-carboxamide

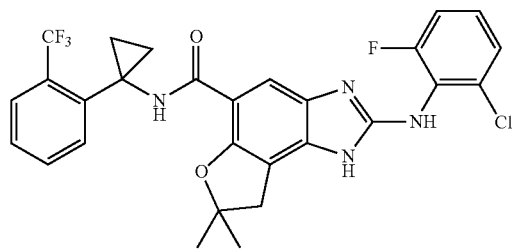 [SMILES: CC1(C)Cc2c(c(C(=O)NC3(c4ccccc4C(F)(F)F)CC3)cc3nc(Nc4c(F)cccc4Cl)[nH]c23)O1]

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 1-[2-(trifluoromethyl)phenyl]cyclopropanamine (Intermediate-38, 0.078 g, 0.388 mmol), THF (5.0 mL) and DIPEA (2 mL). The obtained crude product was purified by column chromatography on basic alumina eluting with 0.7-1.0% MeOH:DCM to afford 0.012 g of the desired product. $^1$HNMR (CDCl$_3$): δ 1.08-1.33 (m, 4H), 1.47 (s, 6H), 3.02 (s, 2H), 7.32-7.38 (m, 4H), 7.47 (t, J=6.6 Hz, 1H), 7.61-7.69 (m, 2H), 7.97 (d, J=7.8 Hz, 1H), 8.56 (s, 1H), 10.80-11.00 (s, 2H); MS [M+H]+: 559.26.

Example-119

2-[(2-Chloro-6-fluorophenyl)amino]-N-[3-(1,1-difluoroethyl)phenyl]-7,7-dimethyl-7,8-dihydro-1H-furo[3,2-e]benzimidazole-5-carboxamide

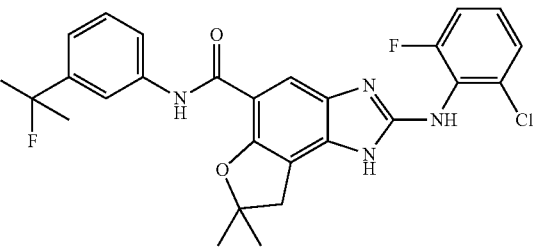

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.273 g, 0.736 mmol), thionyl chloride (2.0 mL), 3-(1,1-difluoroethyl)aniline (Intermediate-39, 0.120 g, 0.736 mmol), THF (5.0 mL) and DIPEA (3 mL). The obtained crude product was purified by column chromatography on basic alumina eluting with 0.7-1.0% MeOH:DCM to afford 0.025 g of the desired product. $^1$HNMR (DMSO d$_6$): δ 1.57 (s, 6H), 1.97 (t, J=19.2 Hz, 3H), 3.10 (s, 2H), 7.26-7.32 (m, 3H), 7.35-7.48 (m, 3H), 7.62 (d, J=8.4 Hz, 1H), 8.07 (s, 1H), 9.85 (s, 1H), 11.00 (s, 2H); MS [M−H]−: 513.14.

Example-120

2-[(2-Chloro-6-methylphenyl)amino]-N-[3-(1,1-difluoroethyl)phenyl]-7,7-dimethyl-7,8-dihydro-1H-furo[3,2-e]benzimidazole-5-carboxamide

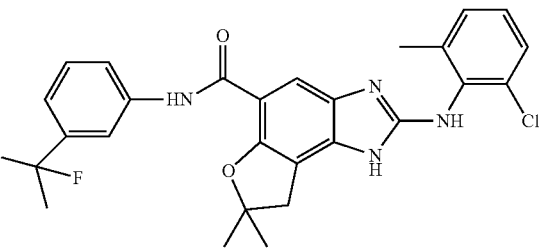

The title compound was prepared by following the procedure described for Example-108 using 2-[(2-chloro-6-methylphenyl)amino]-7,7-dimethyl-7,8-dihydro-1H-furo[3,2-e]benzimidazole-5-carboxylic acid (Intermediate-35, 0.200 g, 0.537 mmol), thionyl chloride (2.0 mL), 3-(1,1-difluoroethyl)aniline (Intermediate-39, 0.088 g, 0.537 mmol), THF (5.0 mL) and DIPEA (3.0 mL), benzene (2 mL). The obtained crude product was purified by column chromatography on neutral alumina eluting with 0.7-1.0% MeOH:DCM to afford 0.012 g of the desired product. $^1$HNMR (DMSO-d$_6$): δ 1.57 (s, 6H), 1.97 (s, 3H), 2.24 (s, 3H), 3.11 (s, 2H), 7.25-7.32 (m, 3H), 7.41-7.49 (m, 3H), 7.61 (d, J=7.8 Hz, 1H), 8.07 (s, 1H), 9.05 (m, 1H), 9.87 (s, 1H), 10.95 (s, 1H); MS [M–H]⁻: 513.42.

Example-121

2-[(2-Chloro-6-fluorophenyl)amino]-N-(5-chloropyridin-2-yl)-7,7-dimethyl-7,8-dihydro-1H-furo[3,2-e]benzimidazole-5-carboxamide

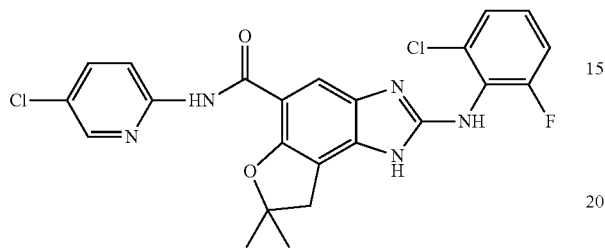

To a solution of 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol) in DMF (1.0 mL) was added BOP (0.293 g, 0.665 mmol) and DIPEA (0.085 g, 0.658 mmol). The reaction mass was stirred at RT for ½ h followed by the addition of solution of 2-amino-5-chloropyridine 1-oxide (Intermediate-40, 0.037 g, 0.289 mmol) in DMF and continued the stifling for 18 h at RT. The reaction mass was quenched in water and extracted with ethyl acetate. The organic layer was dried over anhydrous sodium sulphate and concentrated to afford the crude product.

To a solution of obtained crude product (0.100 g) in acetic acid (5.0 mL) was added iron powder (0.100 g). The reaction mass was stirred at 80° C. for 2-3 h. Excess of Iron powder was separated. The reaction mass was diluted with water, it was extracted with ethyl acetate. The reaction mass was filtered through celite bed and organic layer was separated, dried over anhydrous sodium sulphate and concentrated. The obtained crude was purified by column chromatography on basic alumina eluting with 1.5-2.0% MeOH:DCM to afford 0.025 g of the desired product. ¹HNMR (DMSO-d₆): δ 1.56 (s, 6H), 3.11 (s, 2H), 7.32 (m, 3H), 7.41 (m, 1H), 7.95 (d, J=9.30 Hz, 1H), 8.33 (d, J=8.70 Hz, 1H), 8.41 (s, 1H), 10.27 (s, 1H), 11.00-12.00 (s, 2H); MS [M+H]⁺: 486.18.

Example-122

2-[(2-Chloro-6-fluorophenyl)amino]-7,7-dimethyl-N-[5-(trifluoromethyl)pyridin-2-yl]-7,8-dihydro-1H-furo[3,2-e]benzimidazole-5-carboxamide

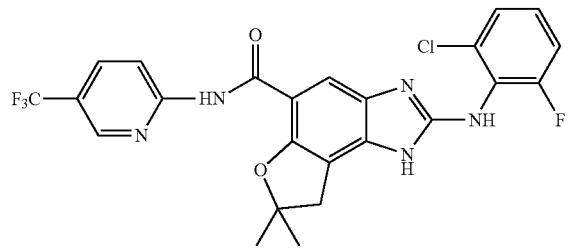 [SMILES: CC1(C)Cc2c(c(C(=O)Nc3ccc(C(F)(F)F)cn3)cc3nc(Nc4c(F)cccc4Cl)[nH]c23)O1]

The title compound was prepared by following the procedure described for Example-121 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), COMU (0.284 g, 0.663 mmol), DIPEA (0.085 g, 0.658 mmol), 2-amino-5-(trifluoromethyl)pyridine 1-oxide (Intermediate-41, 0.052 g, 0.292 mmol), DMF (5 mL), iron powder (0.100 g) and acetic acid (5.0 mL) to afford 0.012 g of the desired product. ¹HNMR (DMSO-d₆): δ 1.57 (s, 6H), 3.12 (s, 2H), 7.33 (m, 3H), 7.54 (s, 1H), 8.23 (d, J=8.7 Hz, 1H), 8.48 (d, J=8.70 Hz, 1H), 8.57 (s, 1H), 10.47 (s, 1H), 11.00-12.00 (s, 2H); MS [M]⁺: 520.18.

Example-123

2-[(2-Chloro-5-methylphenyl)amino]-7,7-dimethyl-N-[3-(trifluoromethyl)phenyl]-7,8-dihydro-1H-furo[3,2-e]benzimidazole-5-carboxamide

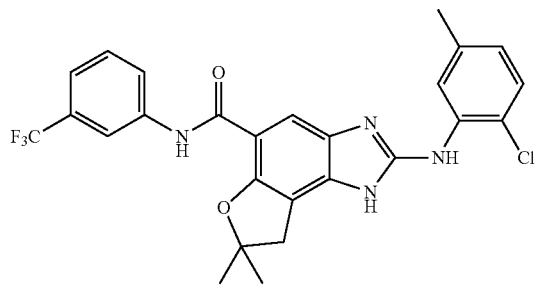 [SMILES: Cc1ccc(Cl)c(Nc2nc3cc(C(=O)Nc4cccc(C(F)(F)F)c4)c4c(c3[nH]2)CC(C)(C)O4)c1]

The title compound was prepared by following the procedure described for Example-108 using 2-[(2-chloro-5-methylphenyl)amino]-7,7-dimethyl-7,8-dihydro-1H-furo[3,2-e]benzimidazole-5-carboxylic acid (Intermediate-27, 0.175 g, 0.471 mmol), thionyl chloride (2.0 mL), 3-trifluoromethyl phenyl amine (0.114 g, 0.707 mmol), THF (5.0 mL) and DIPEA (2 mL). The obtained crude product was purified by column chromatography on neutral alumina eluting with 0.9% MeOH:DCM to afford 0.040 g of the desired product. ¹HNMR (DMSO-d₆): δ 1.61 (s, 6H), 2.33 (s, 3H), 3.16 (d, J=5.4 Hz, 2H), 6.87-6.88 (m, 1H), 7.35 (d, J=8.4 Hz, 1H), 7.44 (d, J=7.2 Hz, 1H), 7.60 (t, J=7.8 Hz, 1H), 7.73 (s, 1H), 7.78 (d, J=7.8 Hz, 1H), 8.34 (s, 2H), 9.00 (s, 1H), 10.01 (s, 1H), 10.05 (s, 1H); MS [M+H]⁺: 515.22.

Example-124

2-[(2-Chloro-6-methylphenyl)amino]-7,7-dimethyl-N-[5-(trifluoromethyl)pyridin-2-yl]-7,8-dihydro-1H-furo[3,2-e]benzimidazole-5-carboxamide

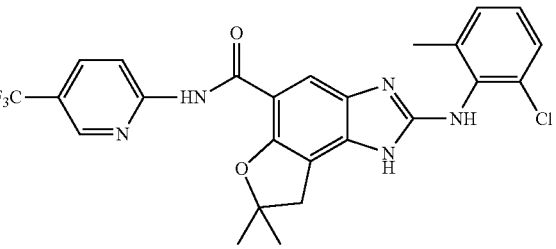

The title compound was prepared by following the procedure described for Example-121 using 2-[(2-chloro-6-methylphenyl)amino]-7,7-dimethyl-7,8-dihydro-1H-furo[3,2-e]benzimidazole-5-carboxylic acid (Intermediate-35, 0.200 g, 0.537 mmol), COMU (0.873 g, 1.34 mmol), DIPEA (0.173 g, 1.34 mmol) and 2-amino-5-(trifluoromethyl)pyridine 1-oxide (Intermediate-41, 0.105 g, 0.591 mmol), iron powder (0.050 g) and acetic acid (5.0 mL) to afford 0.080 g of the desired product. $^1$HNMR (DMSO-$d_6$): δ 1.57 (s, 6H), 2.24 (s, 3H), 3.13 (s, 2H), 7.25-7.33 (m, 2H), 7.42 (d, J=7.5 Hz, 1H), 7.56 (s, 1H), 8.22 (d, J=8.4 Hz, 1H), 8.49 (d, J=8.7 Hz, 1H), 8.75 (s, 1H), 9.16 (m, 1H), 10.49 (s, 1H), 10.99 (s, 1H); MS [M]$^+$: 516.06.

Example-125

2-[(2-Chloro-6-fluorophenyl)amino]-N-[6-(cyclopropylmethoxy)pyridin-3-yl]-7,7-dimethyl-7,8-dihydro-1H-furo[3,2-e]benzimidazole-5-carboxamide

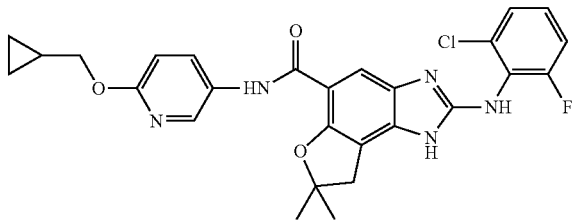 [SMILES: CC1(C)Cc2c(c(C(=O)Nc3ccc(OCC4CC4)nc3)cc3nc(Nc4c(F)cccc4Cl)[nH]c23)O1]

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.200 g, 0.533 mmol), thionyl chloride (2.0 mL), 6-(cyclopropylmethoxy)pyridin-3-amine (Intermediate-42, 0.132 g, 0.799 mmol), THF (5.0 mL), DIPEA (2 mL) and benzene (5 mL). The obtained crude product was purified by column chromatography on basic alumina eluting with 2.0% MeOH: DCM to afford 0.120 g of the desired product. $^1$HNMR (DMSO-$d_6$): δ 0.37-0.74 (m, 4H), 1.20 (m, 1H), 1.53 (s, 6H), 3.06 (s, 2H), 3.74 (d, J=6.9 Hz, 2H), 6.40 (d, J=6.6 Hz, 1H), 7.27-7.30 (m, 2H), 7.39-7.41 (m, 2H), 7.50 (d, J=9.6 Hz, 1H), 8.25 (s, 1H), 9.27 (s, 1H), 11.00 (s, 2H); MS [M+H]$^+$: 522.17.

Example-126

N-(5-Chloro-3-fluoropyridin-2-yl)-2-((2-chloro-6-fluorophenyl)amino)-7,7-dimethyl-7,8-dihydro-1H-benzofuro[4,5-d]imidazole-5-carboxamide

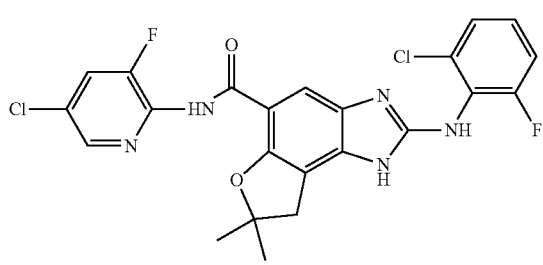 [SMILES: CC1(C)Cc2c(c(C(=O)Nc3ncc(Cl)cc3F)cc3nc(Nc4c(F)cccc4Cl)[nH]c23)O1]

The title compound was prepared by following the procedure described for Example-121 using 2-[(2-chloro-6-fluorophenyl)amino]-7,7-dimethyl-7,8-dihydro-1H-furo[3,2-e]benzimidazole-5-carboxylic acid (Intermediate-15, 0.200 g, 0.266 mmol), COMU (0.569 g, 0.663 mmol), DIPEA (0.732 g, 5.66 mmol), 2-amino-5-chloro-3-fluoropyridine 1-oxide (Intermediate-43, 0.095 g, 0.584 mmol), DMF (3.0 mL), iron powder (0.200 g, 3.57 mmol) and acetic acid (10.0 mL) to afford 0.018 g of the desired product. $^1$HNMR (DMSO-$d_6$): δ 1.54 (s, 6H), 3.10 (s, 2H), 7.30 (m, 3H), 7.40 (m, 1H), 8.17 (d, J=9.3 Hz, 1H), 8.36 (s, 1H), 9.85 (s, 1H), 11.00 (2H); MS [M]$^+$: 504.04.

Example-127

2-((2-Chloro-6-fluorophenyl)amino)-7,7-dimethyl-N-(1-(3-(trifluoromethyl)phenyl)cyclopropyl)-7,8-dihydro-1H-benzofuro[4,5-d]imidazole-5-carboxamide

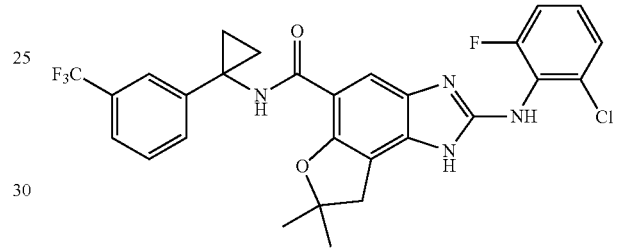

The title compound was prepared by following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.100 g, 0.266 mmol), thionyl chloride (2.0 mL), 1-[3-(trifluoromethyl)phenyl]cyclopropanamine (Intermediate-44, 0.078 g, 0.388 mmol), THF (5.0 mL) and DIPEA (2 mL). The obtained crude product was purified by column chromatography on basic alumina eluting with 0.7-1.0% MeOH:DCM to afford 0.010 g of the desired product. $^1$HNMR (DMSO-$d_6$): δ 1.17-1.37 (m, 4H), 1.51 (s, 6H), 3.06 (s, 2H), 7.34-7.51 (m, 8H), 8.39 (s, 1H), 11.00 (2H); MS [M+H]$^+$: 559.16.

Example-128

2-((2-Chloro-6-fluorophenyl)amino)-N-(2-fluoro-4-methylphenyl)-7,7-dimethyl-7,8-dihydro-1H-benzofuro[4,5-d]imidazole-5-carboxamide

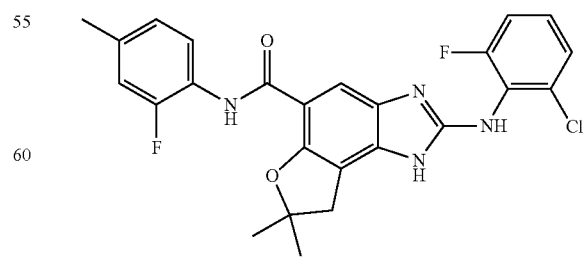

The title compound was prepared following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.150 g, 0.400 mmol), thionyl chloride (2.0 mL), 2-fluoro-4-methylaniline (0.075 g, 0.600 mmol), THF (5.0 mL) and DIPEA (3 mL). The obtained crude product was purified by column chromatography on basic alumina eluting with 0.7-1.0% MeOH:DCM to afford 0.100 g of the desired product. $^{1}$HNMR (DMSO-d$_6$): δ 1.54 (s, 6H), 2.29 (s, 3H), 3.17 (s, 2H), 7.00 (d, J=8.4 Hz, 1H), 7.16 (d, J=12.3 Hz, 1H), 7.30 (s, 2H), 7.40 (m, 1H), 7.51 (s, 1H), 8.33 (t, J=8.4 Hz, 1H), 10.02 (s, 1H), 11.12 (s, 2H); MS [M+H]$^+$: 483.17.

Example-129

2-((2-Chloro-6-fluorophenyl)amino)-N-(4-fluoro-2-(trifluoromethyl)benzyl)-7,7-dimethyl-7,8-dihydro-1H-benzofuro[4,5-d]imidazole-5-carboxamide

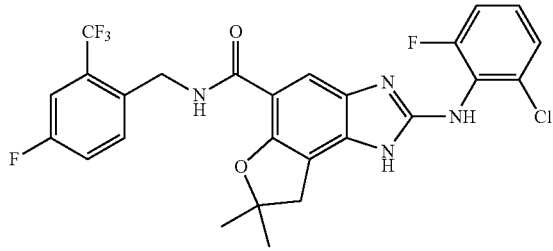 [SMILES: CC1(C)Cc2c(c(C(=O)NCc3ccc(F)cc3C(F)(F)F)cc3nc(Nc4c(F)cccc4Cl)[nH]c23)O1]

The title compound was prepared following the procedure described for Example-1 using 2-[(2-chloro-6-fluorophenyl)amino]-7,7-dimethyl-7,8-dihydro-1H-furo[3,2-e]benzimidazole-5-carboxylic acid (Intermediate-15, 0.150 g, 0.400 mmol), TBTU (0.388 g, 1.20 mmol), TEA (2.0 mL), THF (5.0 mL), DMF (5.0 mL) and 4-fluoro-2-(trifluoromethyl)phenyl)methanamine (Intermediate-45, 0.116 g, 0.604 mmol). The obtained crude product was purified by column chromatography on neutral alumina eluting with 3.0-4.0% MeOH:DCM to afford 0.100 g of the desired product. $^{1}$HNMR (DMSO-d$_6$): δ 1.48 (s, 6H), 3.05 (s, 2H), 4.67 (d, J=4.8 Hz, 2H), 7.30 (d, J=9.3 Hz, 2H), 7.40 (m, 2H), 7.56 (t, J=5.4 Hz, 2H), 7.64 (d, J=8.7 Hz, 1H), 8.33 (t, 1H), 11.00 (s, 2H); MS [M+H]$^+$: 551.30.

Example-130

2-((2-Chloro-6-methylphenyl)amino)-N-(4-fluoro-2-(trifluoromethyl)benzyl)-7,7-dimethyl-7,8-dihydro-1H-benzofuro[4,5-d]imidazole-5-carboxamide

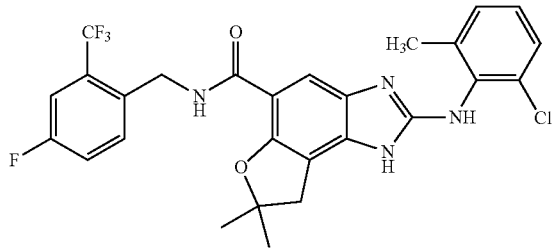 [SMILES: Cc1cccc(Cl)c1Nc1nc2cc(C(=O)NCc3ccc(F)cc3C(F)(F)F)c3c(c2[nH]1)CC(C)(C)O3]

The title compound was prepared following the procedure described for Example-1 using 2-[(2-chloro-6-methylphenyl)amino]-7,7-dimethyl-7,8-dihydro-1H-furo[3,2-e]benzimidazole-5-carboxylic acid (Intermediate-35, 0.100 g, 0.266 mmol), TBTU (0.256 g, 0.798 mmol), TEA (2.0 mL), THF (5.0 mL), DMF (5.0 mL) and 4-fluoro-2-(trifluoromethyl)phenyl)methanamine (Intermediate-45, 0.077 g, 0.399 mmol). The obtained crude product was purified by column chromatography on neutral alumina eluting with 3.0-4.0% MeOH:DCM to afford 0.040 g of the desired product. $^{1}$HNMR (DMSO-d$_6$): δ 1.48 (s, 6H), 2.23 (s, 3H), 3.06 (s, 2H), 4.67 (d, J=5.4 Hz, 2H), 7.22-7.31 (m, 2H), 7.39-7.42 (m, 2H), 7.53-7.64 (m, 3H), 8.33 (m, 1H), 8.97 (s, 1H), 10.86 (s, 1H); MS [M+H]$^+$: 547.72.

Example-131

2-((2-Chloro-6-fluorophenyl)amino)-N-(5-(difluoromethyl)-2-fluorophenyl)-7,7-dimethyl-7,8-dihydro-1H-benzofuro[4,5-d]imidazole-5-carboxamide

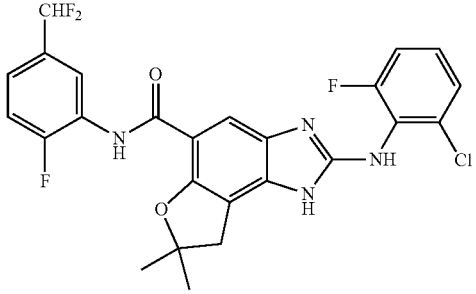 [SMILES: CC1(C)Cc2c(c(C(=O)Nc3cc(C(F)F)ccc3F)cc3nc(Nc4c(F)cccc4Cl)[nH]c23)O1]

The title compound was prepared by following the same procedure as described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.150 g, 0.400 mmol), thionyl chloride (2.0 mL), 5-(difluoromethyl)-2-fluoroaniline (Intermediate-46, 0.097 g, 0.600 mmol), THF (5.0 mL) and DIPEA (2 mL). The obtained crude product was purified by column chromatography on basic alumina eluting with 0.7-1.0% MeOH:DCM to afford 0.012 g of the desired product. $^{1}$HNMR (DMSO-d$_6$): δ 1.56 (s, 6H), 3.13 (s, 2H), 7.07 (t, J=55.5 Hz, 1H), 7.33-7.52 (m, 6H), 8.76 (d, J=6.9 Hz, 1H), 10.24 (s, 1H), 11.20 (s, 2H); MS [M+H]$^+$: 519.20.

Example-132

2-((2-Chloro-6-methylphenyl)amino)-7,7-dimethyl-N-(1-(3-(trifluoromethyl)phenyl)cyclopropyl)-7,8-dihydro-1H-benzofuro[4,5-d]imidazole-5-carboxamide

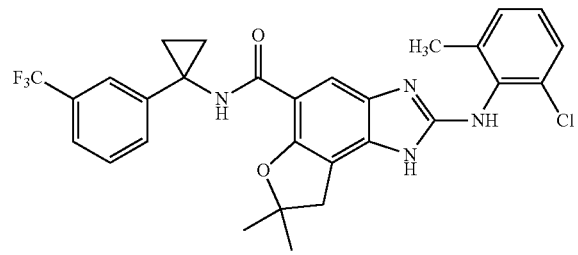 [SMILES: Cc1cccc(Cl)c1Nc1nc2cc(C(=O)NC3(c4cccc(C(F)(F)F)c4)CC3)c3c(c2[nH]1)CC(C)(C)O3]

The title compound was prepared following the procedure described for Example-108 using 2-[(2-chloro-6-methylphenyl)amino]-7,7-dimethyl-7,8-dihydro-1H-furo[3,2-e]benzimidazole-5-carboxylic acid (Intermediate-35, 0.150 g, 0.403 mmol), thionyl chloride (2.0 mL), 1-(3-(trifluoromethyl)phenyl)cyclopropanamine (Intermediate-44, 0.121 g, 0.604 mmol), benzene (4 mL), THF (6.0 mL) and DIPEA (4 mL).

Example-133

2-((2-Chloro-6-methylphenyl)amino)-N-(4-fluoro-3-(trifluoromethyl)phenyl)-7,7-dimethyl-7,8-dihydro-1H-benzofuro[4,5-d]imidazole-5-carboxamide

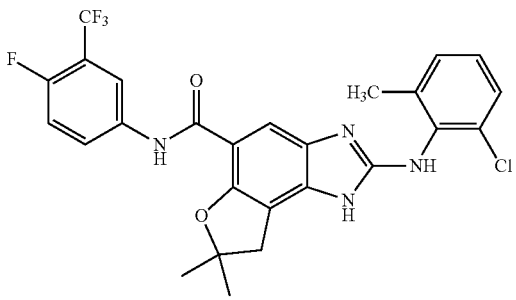 [SMILES: Cc1cccc(Cl)c1Nc1nc2cc(C(=O)Nc3ccc(F)c(C(F)(F)F)c3)c3c(c2[nH]1)CC(C)(C)O3]

The title compound was prepared by following the procedure as described for Example-108 using 2-[(2-chloro-6-methylphenyl)amino]-7,7-dimethyl-7,8-dihydro-1H-furo[3,2-e]benzimidazole-5-carboxylic acid (Intermediate-35, 0.150 g, 0.403 mmol), thionyl chloride (2.0 mL), 4-fluoro-3-(trifluoromethyl)aniline (0.108 g, 0.604 mmol), benzene (4 mL), THF (6.0 mL) and DIPEA (4 mL). The obtained crude product was purified by column chromatography on basic alumina eluting with 0.7-1.0% MeOH:DCM to afford 0.012 g of the desired product. $^1$HNMR (DMSO-$d_6$): δ 1.57 (s, 6H), 2.24 (s, 3H), 3.10 (s, 2H), 7.30-7.54 (m, 5H), 7.82 (m, 1H), 8.36 (m, 1H), 9.08 (s, 1H), 9.92 (s, 1H), 10.96 (s, 1H); MS [M+H]$^+$: 533.25.

Example-134

2-((2-Chloro-6-fluorophenyl)amino)-N-(5-cyclopropyl-2-fluorophenyl)-7,7-dimethyl-7,8-dihydro-1H-benzofuro[4,5-d]imidazole-5-carboxamide

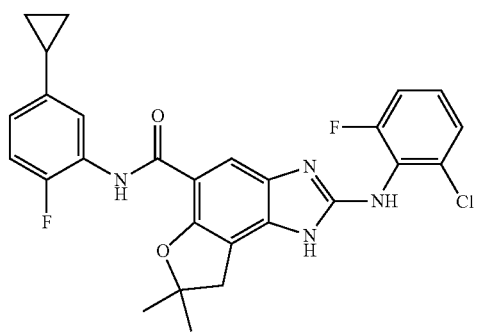 [SMILES: CC1(C)Cc2c(c(C(=O)Nc3cc(C4CC4)ccc3F)cc3nc(Nc4c(F)cccc4Cl)[nH]c23)O1]

The title compound was prepared by following the procedure as described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.150 g, 0.400 mmol), thionyl chloride (2.0 mL), 5-cyclopropyl-2-fluoroaniline (Intermediate-47, 0.090 g, 0.600 mmol), THF (5.0 mL) and DIPEA (2 mL). The obtained crude product was purified by column chromatography on basic alumina eluting with 0.7-1.0% MeOH:DCM to afford 0.045 g of the desired product. $^1$HNMR (DMSO-$d_6$): δ 0.62-0.63 (m, 2H), 0.93-0.96 (m, 2H), 1.54 (s, 6H), 1.93 (m, 1H), 3.13 (s, 2H), 6.80 (s, 1H), 7.14-7.50 (m, 5H), 8.24 (t, J=7.8 Hz, 1H), 10.07 (s, 1H), 11.20 (s, 2H); MS [M+H]$^+$: 509.23.

Example-135

2-((2-Chloro-6-methylphenyl)amino)-N-(5-(difluoromethyl)-2-fluorophenyl)-7,7-dimethyl-7,8-dihydro-1H-benzofuro[4,5-d]imidazole-5-carboxamide

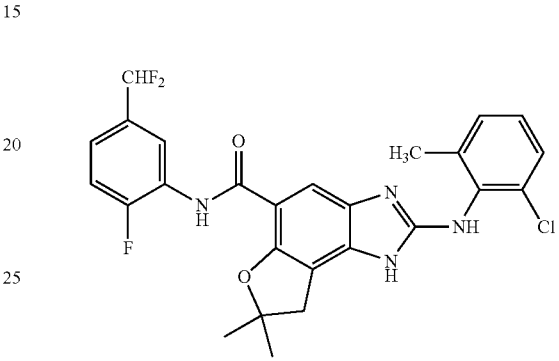

The title compound was prepared by following the procedure as described for Example-108 using 2-[(2-chloro-6-methylphenyl)amino]-7,7-dimethyl-7,8-dihydro-1H-furo[3,2-e]benzimidazole-5-carboxylic acid (Intermediate-35, 0.100 g, 0.269 mmol), thionyl chloride (2.0 mL), 5-(difluoromethyl)-2-fluoroaniline (Intermediate-46, 0.065 g, 0.403 mmol), benzene (4 mL), THF (6.0 mL) and DIPEA (4 mL). The obtained crude product was purified by column chromatography on basic alumina eluting with 0.7-1.0% MeOH:DCM to afford 0.010 g of the desired product. $^1$HNMR (DMSO-$d_6$): δ 1.56 (s, 6H), 2.24 (s, 3H), 3.14 (s, 2H), 6.88-7.23 (t, J=5.8 Hz, 1H), 7.51-7.13 (m, 5H), 7.54 (s, 1H), 8.78 (d, J=6.9 Hz, 1H), 9.01 (s, 1H), 10.26 (s, 1H), 10.98 (s, 1H); MS [M+H]$^+$: 515.17.

Example-136

2-((2-Chloro-6-methylphenyl)amino)-N-(5-cyclopropyl-2-fluorophenyl)-7,7-dimethyl-7,8-dihydro-1H-benzofuro[4,5-d]imidazole-5-carboxamide

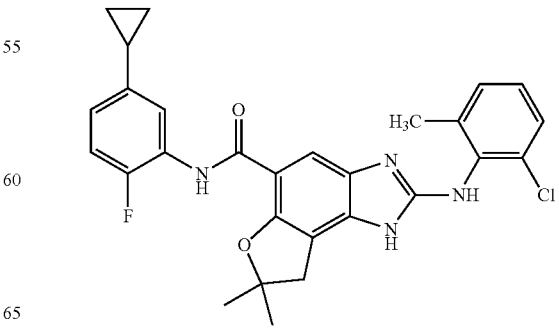

The title compound was prepared by following the procedure as described for Example-108 using 2-[(2-chloro-6-methylphenyl)amino]-7,7-dimethyl-7,8-dihydro-1H-furo[3,2-e]benzimidazole-5-carboxylic acid (Intermediate-35, 0.150 g, 0.400 mmol), thionyl chloride (2.0 mL), 5-cyclopropyl-2-fluoroaniline (Intermediate-47, 0.090 g, 0.600 mmol), THF (5.0 mL) and DIPEA (2 mL). The obtained crude product was purified by column chromatography on basic alumina eluting with 0.7-1.0% MeOH:DCM to afford 0.045 g of the desired product. $^1$HNMR (DMSO-$d_6$): δ 0.62-0.63 (m, 2H), 0.93-0.96 (m, 2H), 1.54 (s, 6H), 1.93 (m, 1H), 3.13 (s, 2H), 6.80 (s, 1H), 7.14-7.50 (m, 5H), 8.24 (d, J=7.8 Hz, 1H), 10.07 (s, 1H), 11.20 (s, 2H); MS [M+H]$^+$: 505.23.

Example-137

2-((2-Chloro-4-methylpyridin-3-yl)amino)-7,7-dimethyl-N-(3-(trifluoromethyl)phenyl)-7,8-dihydro-1H-benzofuro[4,5-d]imidazole-5-carboxamide

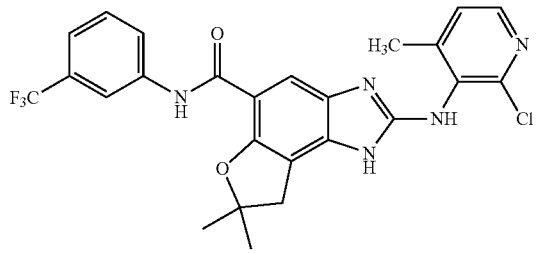 [SMILES: Cc1ccnc(Cl)c1Nc1nc2cc(C(=O)Nc3cccc(C(F)(F)F)c3)c3c(c2[nH]1)CC(C)(C)O3]

Under inert atmosphere to a solution of methyl 2-((2-chloro-4-methylpyridin-3-yl)amino)-7,7-dimethyl-7,8-dihydro-1H-benzofuro[4,5-d]imidazole-5-carboxylate (Intermediate-48, 0.200 g, 0.516 mmol) in dry toluene was added 3-trifluoromethyl aniline (0.124 g, 0.774 mmol) and trimethyl aluminium (2.0 M solution in toluene) (0.037 g, 0.516 mmol). The reaction mixture was refluxed for 1 h. The reaction mass was quenched in water and extracted with ethyl acetate. The organic layer was dried over anhydrous sodium sulphate and concentrated. The obtained crude product was purified by column chromatography on neutral alumina eluting with 40.0% Acetone: petroleum ether to afford 0.150 g of the desired product. $^1$HNMR (DMSO-$d_6$): δ 1.56 (s, 6H), 2.24 (s, 3H), 3.08 (s, 2H), 7.45-7.37 (m, 3H), 7.59 (t, J=7.8 Hz, 1H), 7.72 (d, J=8.4 Hz, 1H), 8.15 (d, J=4.2 Hz, 1H), 8.33 (s, 1H), 9.93 (s, 1H), 11 (bs, 1H); MS [M+H]$^+$: 516.35.

Example-138

2-((2-Chloro-6-fluorophenyl)amino)-1,7,7-trimethyl-N-(4-(trifluoromethyl)phenyl)-7,8-dihydro-1H-benzofuro[4,5-d]imidazole-5-carboxamide

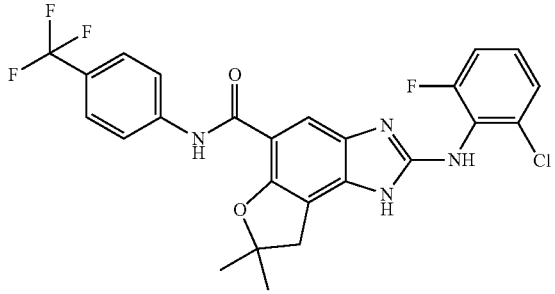 [SMILES: CC1(C)Cc2c(c(C(=O)Nc3ccc(C(F)(F)F)cc3)cc3nc(Nc4c(F)cccc4Cl)[nH]c23)O1]

The title compound was prepared by following the procedure as described for Example-108 using 2-((2-chloro-6-fluorophenyl)amino)-1,7,7-trimethyl-7,8-dihydro-1H-benzofuro[4,5-d]imidazole-5-carboxylic acid (Intermediate-49, 0.100 g, 0.2564 mmol), thionyl chloride (2.0 mL), 4-trifluoromethyl aniline (0.124 g, 0.769 mmol), THF (5.0 mL) and DIPEA (2 mL). The obtained crude product was purified by column chromatography on basic alumina eluting with 0.7-1.0% MeOH:DCM to afford 0.010 g of the desired product. $^1$HNMR (DMSO-$d_6$): δ 1.61 (s, 6H), 3.47 (s, 3H), 3.56 (s, 2H), 7.17-7.01 (m, 1H), 7.21 (bs, 2H), 7.29 (d, J=8.4 Hz, 1H), 7.70 (d, J=8.4 Hz, 2H), 7.90 (d, J=7.8 Hz, 2H), 9.92 (bs, 1H), 10.52 (bs, 1H): MS [M+H]$^+$: 533.25.

Example-139

2-((2-Chloro-6-fluorophenyl)amino)-1,7,7-trimethyl-N-(3-(trifluoromethyl)phenyl)-7,8-dihydro-1H-benzofuro[4,5-d]imidazole-5-carboxamide

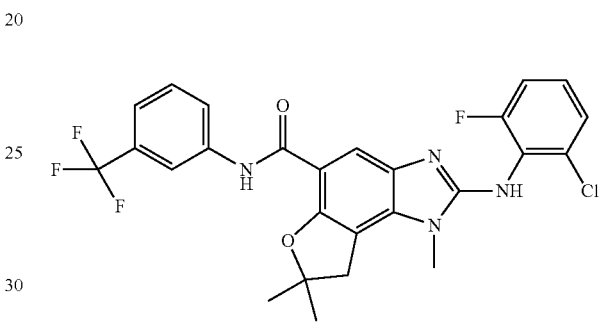

The title compound was prepared by following the procedure as described for Example-108 using 2-((2-chloro-6-fluorophenyl)amino)-1,7,7-trimethyl-7,8-dihydro-1H-benzofuro[4,5-d]imidazole-5-carboxylic acid (Intermediate-49, 0.100 g, 0.256 mmol), thionyl chloride (2.0 mL), 3-trifluoromethyl aniline (0.124 g, 0.769 mmol), THF (5.0 mL) and DIPEA (2 mL). The obtained crude product was purified by column chromatography on basic alumina eluting with 0.7-1.0% MeOH:DCM to afford 0.015 g of the desired product. $^1$HNMR (DMSO-$d_6$): δ 1.61 (s, 6H), 3.46 (s, 2H), 3.56 (s, 3H), 7.00 (m, 1H), 7.20 (m, 2H), 7.28 (d, 2H), 7.28 (d, 1H), 7.45 (d, 1H), 7.56 (t, 1H), 7.75 (d, J=7.2 Hz, 1H), 8.31 (s, 1H), 9.98 (s, 1H), 10.51 (s, 1H); MS [M+H]$^+$: 533.27.

Example-140

2-((2-Chloro-6-fluorophenyl)amino)-N-(4-cyclopropylphenyl)-7,7-dimethyl-7,8-dihydro-1H-benzofuro[4,5-d]imidazole-5-carboxamide

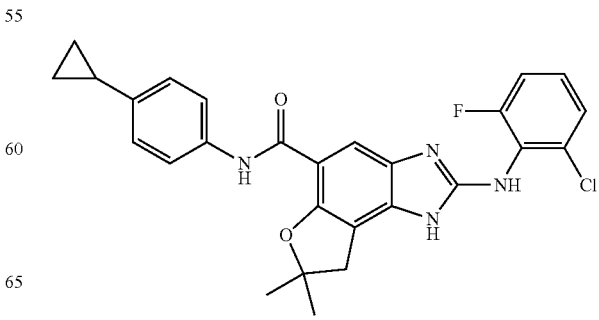

The title compound was prepared following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.150 g, 0.399 mmol), thionyl chloride (2.0 mL), 4-cyclopropylaniline (Intermediate-50, 0.079 g, 0.598 mmol), THF (5.0 mL) and DIPEA (2 mL). The obtained crude product was purified by column chromatography on basic alumina eluting with 0.7-1.0% MeOH:DCM to afford 0.045 g of the desired product. ¹HNMR (DMSO-d₆): δ 0.62-0.63 (m, 2H), 0.90-0.92 (m, 2H), 1.56 (s, 6H), 1.89 (m, 1H), 3.09 (s, 2H), 7.05 (d, J=8.4 Hz, 2H), 7.29-7.47 (m, 4H), 7.54 (d, J=8.4 Hz, 2H), 9.67 (s, 1H), 11.00 (s, 2H); MS [M+H]⁺: 491.28.

Example-141

2-((2,6-Dichlorophenyl)amino)-7,7-dimethyl-N-(2,4,5-trifluorophenyl)-7,8-dihydro-1H-benzofuro[4,5-d]imidazole-5-carboxamide

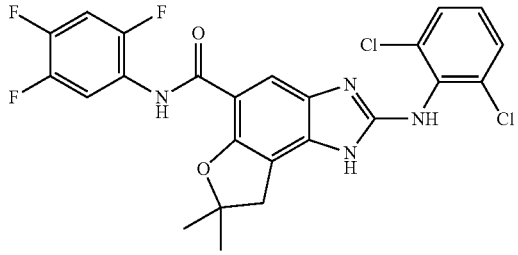 [SMILES: CC1(C)Cc2c(c(C(=O)Nc3cc(F)c(F)cc3F)cc3nc(Nc4c(Cl)cccc4Cl)[nH]c23)O1]

The title compound was prepared following the procedure described for Example-137 using methyl 2-[(2,6-dichlorophenyl)amino]-7,7-dimethyl-7,8-dihydro-1H-furo[3,2-e]benzimidazole-5-carboxylate (Step-1 of Intermediate-6, 0.200 g, 0.493 mmol) and 2,4,5-trifloro aniline (0.108 g, 0.740 mmol), trimethyl aluminium (2M solution in toluene) (0.071 g, 0.986 mmol) and dry toluene (5.0 mL) to afford 0.100 g of the desired product. ¹HNMR (DMSO-d₆): δ 1.55 (s, 6H), 3.11 (s, 2H), 7.21 (m, 2H), 7.53 (m, 2H), 7.73 (q, J=7.8 Hz, 1H), 8.48 (m, 1H), 10.11 (bs, 1H), 11.00 (s, 2H); MS [M+H]⁺: 521.14.

Example-142

2-((2,6-Dichlorophenyl)amino)-N-(2-fluoro-4-methylphenyl)-7,7-dimethyl-7,8-dihydro-1H-benzofuro[4,5-d]imidazole-5-carboxamide

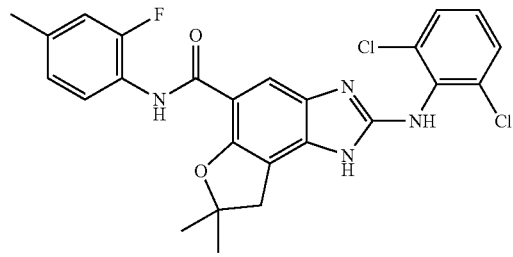 [SMILES: Cc1ccc(NC(=O)c2cc3nc(Nc4c(Cl)cccc4Cl)[nH]c3c3c2OC(C)(C)C3)c(F)c1]

The title compound was prepared following the procedure described for Example-108 using 2-[(2,6-dichlorophenyl)amino]-7,7-dimethyl-7,8-dihydro-1H-furo[3,2-e]benzimidazole-5-carboxylic acid (Intermediate-6, 0.200 g, 0.512 mmol), thionyl chloride (2.0 mL), 2-fluoro-4-methylaniline (0.128 g, 1.025 mmol), THF (5.0 mL) and DIPEA (2 mL). The obtained crude product was purified by column chromatography on basic alumina eluting with 0.7-1.0% MeOH:DCM to afford 0.075 g of the desired product. ¹HNMR (DMSO-d₆): δ 1.55 (s, 6H), 2.29 (s, 3H), 3.10 (s, 2H), 7.00 (d, J=8.1 Hz, 1H), 7.15 (d, J=12 Hz, 1H), 7.24 (m, 1H), 7.42 (m, 1H), 7.53 (d, J=8.1 Hz, 2H), 8.33 (t, J=8.4 Hz, 1H), 9.99 (s, 1H), 11.00 (s, 2H); MS [M+H]⁺: 500.39.

Example-143

2-(2-Chloro-6-fluorobenzamido)-7,7-dimethyl-N-(3-(trifluoromethyl)phenyl)-7,8-dihydro-1H-benzofuro[4,5-d]imidazole-5-carboxamide

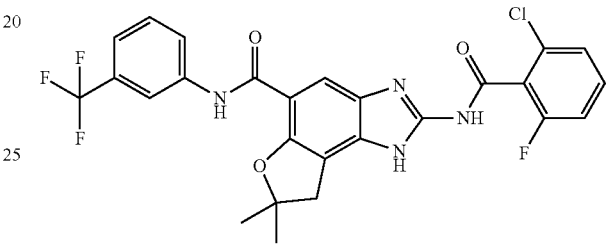

The title compound was prepared by following the procedure as described for Example-137 using methyl 2-(2-chloro-6-fluorobenzamido)-7,7-dimethyl-7,8-dihydro-1H-benzofuro[4,5-d]imidazole-5-carboxylate (Intermediate-51, 0.200 g, 0.477 mmol), 3-trifloromethyl aniline (0.230 g, 1.43 mmol), trimethyl aluminium (2M solution in toluene) (0.5 mL) and dry toluene (5.0 mL). The reaction mass was stirred at RT for 4-5 h. The obtained crude was purified on preparative TLC using 4% DCM:MeOH as solvent system to afford 0.011 g of the desired product. ¹HNMR (DMSO-d₆): δ 1.57 (s, 6H), 3.14 (s, 2H), 6.30 (s, 1H), 7.43 (d, J=7.8 Hz, 2H), 7.56-7.70 (m, 4H), 7.86 (q, J=6.3 Hz, 1H), 8.15 (bs, 2H), 9.71 (s, 1H); MS [M+H]⁺: 547.06.

Example-144

2-((2-Chlorobenzyl)amino)-7,7-dimethyl-N-(3-(trifluoromethyl)phenyl)-7,8-dihydro-1H-benzofuro[4,5-d]imidazole-5-carboxamide

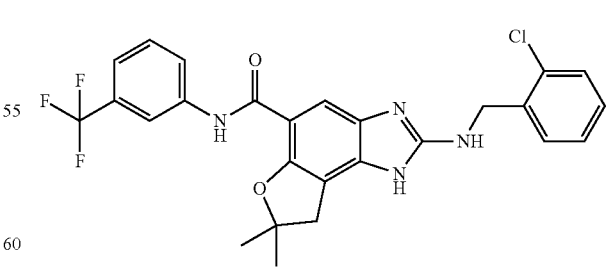

The title compound was prepared following the procedure described for Example-137 using methyl 2-((2-chlorobenzyl)amino)-7,7-dimethyl-7,8-dihydro-1H-benzofuro[4,5-d]imidazole-5-carboxylate (Intermediate-52, 0.200 g, 0.519 mmol), 3-trifluoromethyl aniline (0.167 g, 1.038 mmol), trimethyl aluminium (2M solution in toluene) (0.5 mL) and dry toluene (5.0 mL). The obtained crude was purified by column chromatography eluting with 0.5% DCM:MeOH to afford 0.0650 g of the desired product. $^1$HNMR (DMSO-d$_6$): δ 1.57 (s, 6H), 3.16 (s, 2H), 7.00 (d, J=6 Hz, 2H), 7.30-7.42 (m, 2H), 7.44-7.64 (m, 6H), 7.72 (d, J=7.8 Hz, 1H), 8.35 (s, 1H), 9.96 (s, 1H), 10.90 (s, 1H); [M+H]$^+$: 515.19.

Example-145

2-((2-Chlorobenzyl)amino)-N-(2-fluoro-5-(trifluoromethyl)phenyl)-7,7-dimethyl-7,8-dihydro-1H-benzofuro[4,5-d]imidazole-5-carboxamide

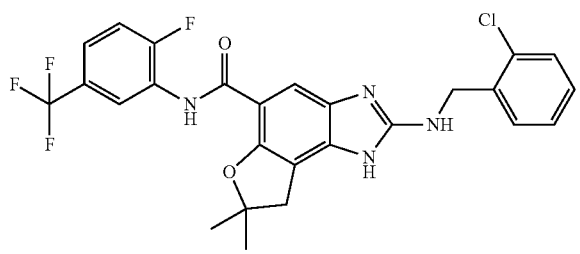 [SMILES: CC1(C)Cc2c(c(C(=O)Nc3cc(C(F)(F)F)ccc3F)cc3nc(NCc4ccccc4Cl)[nH]c23)O1]

The title compound was prepared following the procedure described for Example-137 using methyl 2-((2-chlorobenzyl)amino)-7,7-dimethyl-7,8-dihydro-1H-benzofuro[4,5-d]imidazole-5-carboxylate (Intermediate-52, 0.200 g, 0.519 mmol), 2-fluoro-5-trifluoromethyl aniline (0.237 g, 1.0389 mmol), trimethyl aluminium (2M solution in toluene) (0.5 mL) and dry toluene (5.0 mL). The obtained crude was purified by column chromatography eluting with 0.5% DCM: MeOH to afford 0.013 g of the desired product. $^1$HNMR (DMSO-d$_6$): δ 1.55 (s, 6H), 3.14 (s, 2H), 4.61 (m, 2H), 7.32 (m, 2H), 7.40 (m, 1H), 7.49-7.62 (m, 5H), 7.69 (m, 1H), 8.93 (d, J=6.3 Hz, 1H), 10.34 (bs, 1H), 11.00 (bs, 1H). [M+H]$^+$: 533.08.

Example-146

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide hydrochloride To a solution of 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g) in THF was added HCl saturated DEE. The reaction mass was refluxed for 3 h. The reaction mass was filtered. The obtained residue was washed with pentane and DEE to afford 0.100 g of the desired product.

Example-147

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide Oxalate To a solution of 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g) in acetone was added oxalic acid. The reaction mass was refluxed for 3 h. The reaction mass was filtered. The obtained residue was washed with pentane and DEE to afford 0.100 g of the desired product.

Example-148

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide 2-hydroxypropane-1,2,3-tricarboxylate To a solution of 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g) in acetone was added citric acid. The reaction mass was refluxed for 3 h. The reaction mass was filtered and the obtained residue was washed with DEE to afford 0.100 g of the desired product.

Example-149

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide Hydrochloride The title compound was prepared following the procedure described for Example-146 using 2-[(2-chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide (Example-110, 0.100 g), THF (10 mL) and solution of HCl in DEE to afford 0.100 g of the desired product.

Example-150

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide 2,2,2-trifluoroacetate To a solution of 2-[(2-chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide (Example-110, 0.100 g) in THF was added trifluoro acetic acid (3 eq.) The reaction mass was refluxed for 3 h. The reaction mass was filtered and obtained residue was washed with DEE to afford 0.100 g desired product.

Example-151

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide Oxalate To a solution of 2-[(2-chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide (Example-110, 0.100 g) in acetone was added oxalic acid. The reaction mass was refluxed for 3 h. The reaction mass was filtered and obtained residue was washed with DEE to afford 0.100 g desired product.

Example-152

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide 2-hydroxypropane-1,2,3-tricarboxylate To a solution of 2-[(2-chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide (Example-110, 0.100 g) in acetone was added of citric acid. The reaction mass was refluxed for 3 h. The reaction mass was filtered and obtained residue was washed with DEE to afford 0.100 g of the desired product.

Example-153

2-((2-Chloro-6-fluorophenyl)amino)-1,7,7-trimethyl-N-(6-(trifluoromethyl)pyridin-3-yl)-7,8-dihydro-1H-benzofuro[4,5-d]imidazole-5-carboxamide

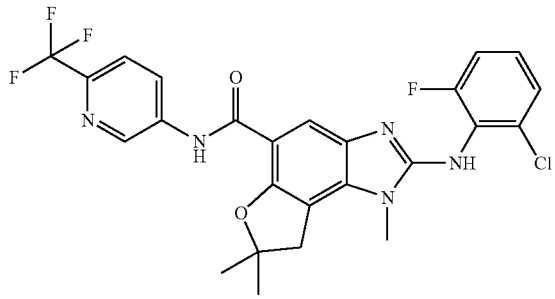 [SMILES: Cn1c(Nc2c(F)cccc2Cl)nc2cc(C(=O)Nc3ccc(C(F)(F)F)nc3)c3c(c21)CC(C)(C)O3]

The title compound was prepared by following the same procedure as described for Example-137 using methyl 2-((2-chloro-6-fluorophenyl)amino)-1,7,7-trimethyl-7,8-dihydro-1H-benzofuro[4,5-d]imidazole-5-carboxylate (step-7 of Intermediate-49, 0.100 g, 0.247 mmol), 5-amino-2-triflorom-ethylpyridine (0.162 g, 0.371 mmol), trimethyl aluminium (2M solution in toluene) (1 mL) to afford 0.025 g of the desired product. $^1$HNMR (DMSO-d$_6$): δ 1.61 (s, 6H), 3.46 (s, 2H), 3.57 (s, 3H), 7.01 (m, 1H), 7.28 (s, 2H), 7.30 (d, 1H), 7.90 (d, J=8.7 Hz, 1H), 8.45 (d, J=7.8 Hz, 1H), 9.00 (s, 1H), 10.02 (s, 1H), 10.53 (s, 1H). MS [M−H]$^-$: 532.19.

Example-154

2-((2-Chloro-6-fluorophenyl)amino)-N-(2-fluoro-4-methylphenyl)-1,7,7-trimethyl-7,8-dihydro-1H-benzofuro[4,5-d]imidazole-5-carboxamide

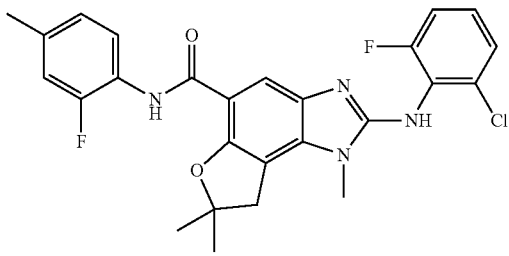 [SMILES: Cc1ccc(NC(=O)c2cc3nc(Nc4c(F)cccc4Cl)n(C)c3c3c2OC(C)(C)C3)c(F)c1]

The title compound was prepared following the procedure described for Example-137 using methyl 2-((2-chloro-6-fluorophenyl)amino)-1,7,7-trimethyl-7,8-dihydro-1H-benzofuro[4,5-d]imidazole-5-carboxylate (Step-7 of Intermediate-49, 0.100 g, 0.247 mmol), 2-fluoro-4-methyl aniline (0.046 g, 0.371 mmol), trimethyl aluminium (2M solution in toluene) (1 mL) and dry toluene (5.0 mL) to afford 0.025 g of the desired product. $^1$HNMR (DMSO-d$_6$): δ 1.58 (s, 6H), 2.29 (s, 3H), 3.48 (s, 2H), 3.56 (s, 3H), 7.00 (d, J=8.4 Hz, 2H), 7.13-7.30 (m, 4H), 8.29 (t, J=9 Hz, 1H), 9.94 (s, 1H), 10.51 (s, 1H). MS [M+H]$^+$: 497.23.

Example-155

2-(2-((2-Chloro-6-fluorophenyl)amino)-1,7,7-trimethyl-7,8-dihydro-1H-benzofuro[4,5-d]imidazole-5-carboxamido)-5-(trifluoromethyl)pyridine 1-oxide

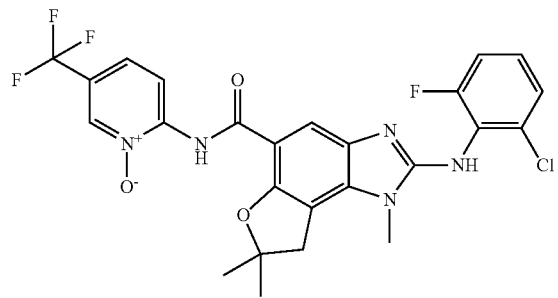 [SMILES: Cn1c(Nc2c(F)cccc2Cl)nc2cc(C(=O)Nc3ccc(C(F)(F)F)c[n+]3[O-])c3c(c21)CC(C)(C)O3]

The title compound was prepared following the procedure described for Example-108 using 2-((2-chloro-6-fluorophenyl)amino)-1,7,7-trimethyl-7,8-dihydro-1H-benzofuro[4,5-d]imidazole-5-carboxylic acid (Intermediate-49, 0.100 g, 0.2564 mmol), thionyl chloride (2.0 mL), 2-amino-5-(trifluoromethyl)pyridine 1-oxide (Intermediate-41, 0.0835 g, 0.5128 mmol), THF (5.0 mL) and DIPEA (2 mL). The obtained crude product was purified by column chromatography on basic alumina eluting with 0.7-1.0% MeOH:DCM to afford 0.015 g of the desired product. $^1$HNMR (DMSO-d$_6$): δ 1.60 (s, 6H), 3.49 (s, 2H), 3.53 (s, 3H), 7.02 (m, 1H), 7.18-7.36 (m, 3H), 7.80 (d, J=9.9 Hz, 1H), 8.64 (d, J=8.7 Hz, 1H), 8.95 (s, 1H), 10.56 (s, 1H), 12.21 (s, 1H); MS [M+H]$^+$: 550.08.

Example-156

N-(2-Chloro-6-fluorophenyl)-5-(3-isopropyl-1,2,4-oxadiazol-5-yl)-7,7-dimethyl-7,8-dihydro-1H-benzofuro[4,5-d]imidazol-2-amine

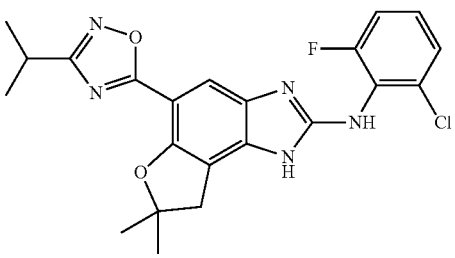 [SMILES: CC(C)c1noc(-c2cc3nc(Nc4c(F)cccc4Cl)[nH]c3c3c2OC(C)(C)C3)n1]

Under nitrogen atmosphere, to a solution of N'-hydroxy-isobutyrimidamide (0.028 g, 0.268 mmol) in THF was added sodium hydride (0.021 g, 0.51 mmol). The reaction mass was refluxed for 15-20 minutes. Then added methyl 2-((2-chloro-6-fluorophenyl)amino)-7,7-dimethyl-7,8-dihydro-1H-benzofuro[4,5-d]imidazole-5-carboxylate (Step-1 of Intermediate-15, 0.100 g, 0.255 mmol) and continued reflux for 4-5 h. The reaction mass was diluted with water and extracted with ethyl acetate. The organic layer was dried over anhydrous sodium sulphate and concentrated. The obtained crude was purified column chromatography to afford 0.020 g of the desired product. $^1$HNMR (DMSO-d$_6$): δ 1.28 (d, 6H), 1.48 (s, 6H), 3.09 (m, 3H), 7.24 (m, 1H), 7.39 (m, 1H), 7.54 (d, J=7.2 Hz, 1H), 9-10 (s, 1H), 10.5 (s, 1H); MS [M]$^+$: 458.14.

Example-157

2-((2-Chloro-6-fluorophenyl)amino)-1,7,7-trimethyl-N-(5-(trifluoromethyl)pyridin-2-yl)-7,8-dihydro-1H-benzofuro[4,5-d]imidazole-5-carboxamide

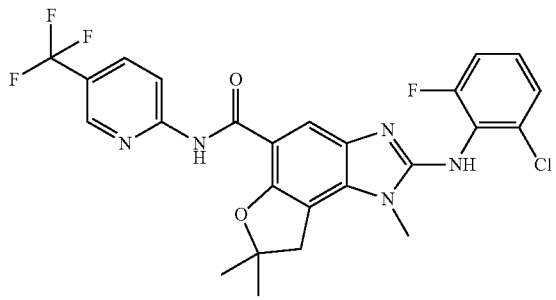 [SMILES: Cn1c(Nc2c(F)cccc2Cl)nc2cc(C(=O)Nc3ccc(C(F)(F)F)cn3)c3c(c21)CC(C)(C)O3]

The title compound was prepared by following the procedure as described for Example-137 using methyl 2-((2-chloro-6-fluorophenyl)amino)-1,7,7-trimethyl-7,8-dihydro-1H-benzofuro[4,5-d]imidazole-5-carboxylate (step-7 of Intermediate-49, 0.100 g, 0.247 mmol) and 5-(trifluoromethyl)pyridin-2-amine (0.053 g, 0.371 mmol), trimethyl aluminium (2M solution in toluene) (1 mL) and dry toluene (5.0 mL) to afford 0.025 g of the desired product. $^1$HNMR (DMSO-d$_6$): δ 1.61 (s, 6H), 3.49 (s, 2H), 3.57 (s, 3H), 7.17-7.31 (m, 4H), 8.22 (d, J=9 Hz, 1H), 8.44 (d, J=9 Hz, 1H), 8.75 (s, 1H), 8.79 (s, 1H), 10.39 (s, 1H), 10.55 (s, 1H); MS [M+H]$^+$: 534.21.

Example-158

2-(2-((2-Chloro-6-fluorophenyl)amino)-7,7-dimethyl-7,8-dihydro-1H-benzofuro[4,5-d]imidazole-5-carboxamido)-5-(trifluoromethyl)pyridine 1-oxide

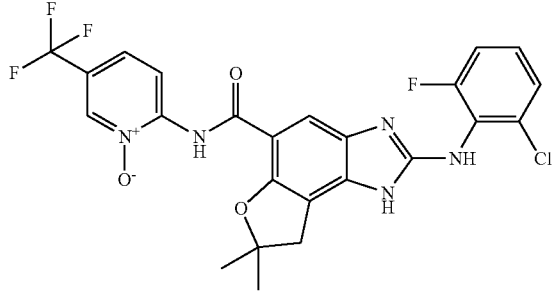

The title compound was prepared following the procedure described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.150 g, 0.400 mmol), thionyl chloride (2.0 mL), 2-amino-5-(trifluoromethyl)pyridine 1-oxide (Intermediate-41, 0.096 g, 0.600 mmol), THF (5.0 mL) and DIPEA (3 mL). The obtained crude product was purified by column chromatography on basic alumina eluting with 0.7-1.0% MeOH:DCM to afford 0.075 g of the desired product. $^1$HNMR (DMSO-d$_6$): δ 1.56 (s, 6H), 3.12 (s, 2H), 7.32 (m, 2H), 7.41 (m, 1H), 7.52 (s, 1H), 7.80 (d, J=9.3 Hz, 1H), 8.67 (d, J=8.7 Hz, 1H), 8.94 (s, 1H), 9.50 (s, 1H), 11.21 (s, 1H), 12.30 (s, 1H); MS [M+H]$^+$: 536.12.

Example-159

N-(5-Cyclopropyl-2-fluorophenyl)-2-((2,6-dichlorophenyl)amino)-7,7-dimethyl-7,8-dihydro-1H-benzofuro[4,5-d]imidazole-5-carboxamide

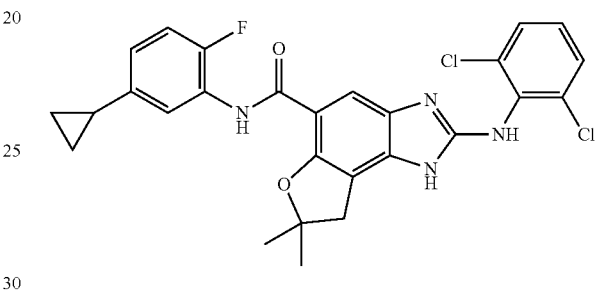

The title compound was prepared following the procedure described for Example-108 using 2-[(2,6-dichlorophenyl)amino]-7,7-dimethyl-7,8-dihydro-1H-furo[3,2-e]benzimidazole-5-carboxylic acid (Intermediate-6, 0.100 g, 0.255 mmol), thionyl chloride (1.0 mL), 5-cyclopropyl-2-fluoro aniline (Intermediate-47, 0.077 g, 0.511 mmol), THF (5.0 mL) and DIPEA (2 mL). The obtained crude product was purified by column chromatography on neutral alumina eluting with 1.0-2.0% MeOH:DCM to afford 0.020 g of the desired product $^1$HNMR (DMSO-d$_6$): δ 0.62 (m 2H), 0.94 (d, J=6.3 Hz, 2H), 1.54 (s, 6H), 1.93 (m, 1H), 3.11 (s, 2H), 6.80 (m, 1H), 7.17 (m, 2H), 7.54 (m, 3H), 8.22 (s, 1H), 10.04 (s, 1H), 11-11.5 (s, 2H); MS [M]$^+$: 525.15.

Example-160

2-((2-Chloro-6-methylphenyl)amino)-7,7-dimethyl-N-(6-(trifluoromethyl)pyridin-3-yl)-7,8-dihydro-1H-benzofuro[4,5-d]imidazole-5-carboxamide

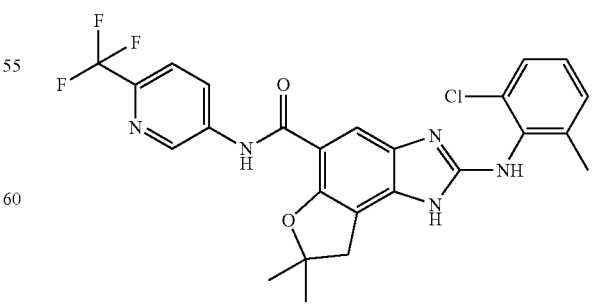

The title compound was prepared by following the procedure as described for Example-137 using methyl 2-[(2- chloro-6-methylphenyl)amino]-7,7-dimethyl-7,8-dihydro-1H-furo[3,2-e]benzimidazole-5-carboxylate (Step-1 of Intermediate-35, 0.150 g, 0.301 mmol), 6-(trifluoromethyl)pyridine-3-amine (0.067 g, 0.451 mmol), trimethyl aluminium (2M solution in toluene) (1 mL) and dry toluene (5.0 mL) to afford 0.075 g of the desired product. $^1$HNMR (DMSO-d$_6$): δ 1.56 (s, 6H), 2.23 (s, 3H), 3.09 (s, 2H), 7.23-7.31 (m, 2H), 7.40 (d, J=7.8 Hz, 1H), 7.47 (s, 1H), 7.87 (d, J=8.7 Hz, 1H), 8.45 (d, J=8.4 Hz, 1H), 8.98 (s, 1H), 9.10 (bs, 1H), 10.08 (s, 1H), 10.90 (bs, 1H); MS [M]$^+$: 516.16.

Example-161

5-(3-(3-Chloro-4-fluorophenyl)-1,2,4-oxadiazol-5-yl)-N-(2,6-dichlorophenyl)-7,7-dimethyl-7,8-dihydro-1H-benzofuro[4,5-d]imidazol-2-amine

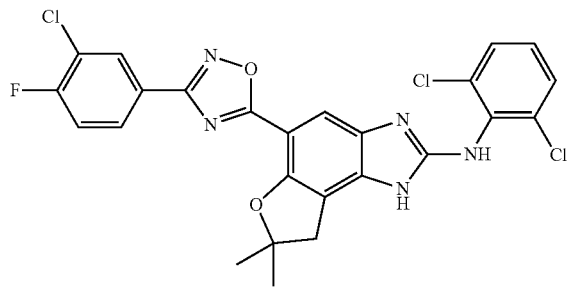 [SMILES: CC1(C)Cc2c(c(-c3nc(-c4ccc(F)c(Cl)c4)no3)cc3nc(Nc4c(Cl)cccc4Cl)[nH]c23)O1]

The title compound was prepared by following the procedure as described for Example-156 using 3-chloro-4-fluoro-N'-hydroxybenzimidamide (Intermediate-53, 0.072 g, 0.30 mmol), sodium hydride (0.021 g, 0.51 mmol), methyl 2-((2-chloro-6-chlorophenyl)amino)-7,7-dimethyl-7,8-dihydro-1H-benzofuro[4,5-d]imidazole-5-carboxylate (Step-1 of Intermediate-6, 0.100 g, 0.255 mmol) and THF (5.0 mL) to afford 0.029 g of the desired product. $^1$HNMR (DMSO-d$_6$): δ 1.33 (s, 6H), 3.08 (s, 2H), 7.26 (bs, 1H), 7.55 (m, 3H), 7.65 (t, J=8.7 Hz, 1H), 8.06 (s, 1H), 8.06 (s, 1H), 8.16 (d, J=5.7 Hz, 1H), 11 (bs, 2H); MS [M+H]$^+$: 544.17.

Example-162

N-(2,6-Dichlorophenyl)-5-(3-(3,5-dimethoxyphenyl)-1,2,4-oxadiazol-5-yl)-7,7-dimethyl-7,8-dihydro-1H-benzofuro[4,5-d]imidazol-2-amine

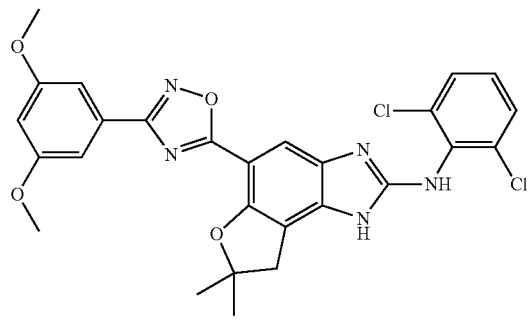 [SMILES: COc1cc(OC)cc(-c2noc(-c3cc4nc(Nc5c(Cl)cccc5Cl)[nH]c4c4c3OC(C)(C)C4)n2)c1]

The title compound was prepared by following the procedure as described for Example-156 using N'-hydroxy-3,5-dimethoxybenzimidamide (Intermediate-54, 0.075 g, 0.30 mmol), sodium hydride (0.021 g, 0.51 mmol), methyl 2-((2-chloro-6-chlorophenyl)amino)-7,7-dimethyl-7,8-dihydro-1H-benzofuro[4,5-d]imidazole-5-carboxylate (Step-1 of Intermediate-6, 0.100 g, 0.255 mmol) and THF to afford 0.029 g of the desired product. $^1$HNMR (DMSO-d$_6$): δ 1.29 (d, J=7.8 Hz, 6H), 3.09 (s, 2H), 3.85 (s, 6H), 6.58 (s, 1H), 7.30 (m, 3H), 7.44 (d, 1H), 7.78 (s, 1H). MS [M+H]$^+$: 552.09.

Example-163

2-(2-((2-Chloro-6-methylphenyl)amino)-7,7-dimethyl-7,8-dihydro-1H-benzofuro[4,5-d]imidazole-5-carboxamido)-5-(trifluoromethyl)pyridine 1-oxide

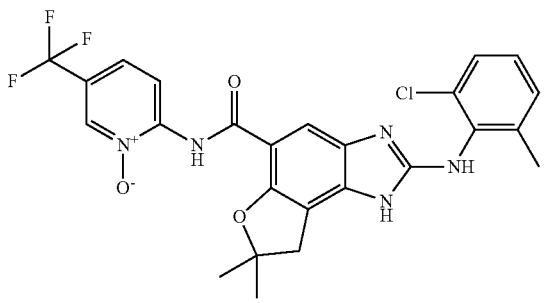 [SMILES: Cc1cccc(Cl)c1Nc1nc2cc(C(=O)Nc3ccc(C(F)(F)F)c[n+]3[O-])c3c(c2[nH]1)CC(C)(C)O3]

The title compound was prepared following the procedure described for Example-137 using methyl 2-[(2-chloro-6-methylphenyl)amino]-7,7-dimethyl-7,8-dihydro-1H-furo[3,2-e]benzimidazole-5-carboxylate (Step-1 of Intermediate-35, 0.100 g, 0.207 mmol) and 2-amino-5-trifluoromethylpyridine-N-oxide (Intermediate-41, 0.053 g, 0.301 mmol), trimethyl aluminium (2M solution in toluene) (1 mL) and dry toluene (5.0 mL) to afford 0.030 g of the desired product. $^1$HNMR (DMSO-d$_6$): δ 1.56 (s, 6H), 2.25 (s, 3H), 3.13 (s, 2H), 7.26-7.33 (m, 2H), 7.43 (d, J=6.9 Hz, 1H), 7.53 (s, 1H), 7.79 (d, J=6.9 Hz, 1H), 8.68 (d, J=9.3 Hz, 1H), 8.94 (s, 1H), 9.20 (s, 1H), 11.02 (s, 1H), 12.26 (s, 1H); MS [M+H]$^+$: 532.11.

Example-164

2-((2-Chloro-6-methylphenyl)amino)-N-(2-fluoro-3-(trifluoromethyl)phenyl)-7,7-dimethyl-7,8-dihydro-1H-benzofuro[4,5-d]imidazole-5-carboxamide

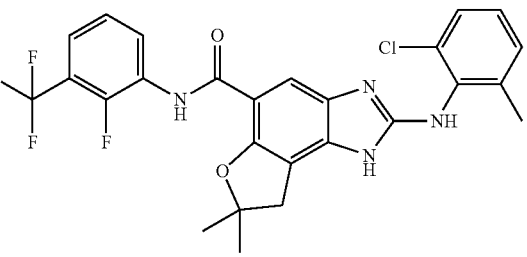

The title compound was prepared by following the procedure as described for Example-137 using methyl 2-[(2-chloro-6-methylphenyl)amino]-7,7-dimethyl-7,8-dihydro-1H-furo[3,2-e]benzimidazole-5-carboxylate (Step-1 of Intermediate-35, 0.100 g, 0.207 mmol) and 2-fluoro-3-trifluoromethyl aniline (0.044 g, 0.301 mmol), trimethyl aluminium (2M solution in toluene) (1 mL) and dry toluene (5.0 mL) to afford 0.025 g of the desired product. ¹HNMR (DMSO-d₆): δ 1.56 (s, 6H), 2.25 (s, 3H), 3.14 (s, 2H), 7.23-7.33 (m, 2H), 7.39-7.49 (m, 3H), 7.54 (s, 1H), 8.77 (m, 1H), 9.11 (s, 1H), 10.22 (s, 1H), 11.01 (s, 1H): MS [M−H]⁻: 531.08.

Example-165

2-((2-Chloro-6-fluorophenyl)amino)-N-(3-cyclopropylphenyl)-7,7-dimethyl-7,8-dihydro-1H-benzofuro[4,5-d]imidazole-5-carboxamide

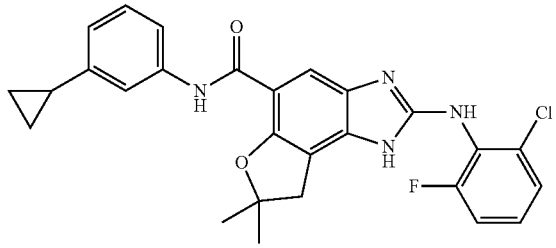 [SMILES: CC1(C)Cc2c(c(C(=O)Nc3cccc(C4CC4)c3)cc3nc(Nc4c(F)cccc4Cl)[nH]c23)O1]

The title compound was prepared by following the same procedure as described for Example-108 using 2-[(2-chloro-6-fluorophenyl)amino]-7,7-dimethyl-7,8-dihydro-1H-furo[3,2-e]benzimidazole-5-carboxylic acid (Intermediate-15, 0.150 g, 0.400 mmol), thionyl chloride (2.0 mL), 3-cyclopropyl aniline (0.079 g, 0.598 mmol), THF (5.0 mL) and DIPEA (2 mL). The obtained crude product was purified by column chromatography on basic alumina eluting with 0.7-1.0% MeOH:DCM to afford 0.070 g of the desired product. ¹HNMR (DMSO-d₆): δ 0.66 (d, J=4.8 Hz, 2H), 0.93 (d, J=2.1 Hz, 2H), 1.57 (s, 6H), 1.92 (m, 1H), 3.10 (s, 2H), 6.77 (d, J=7.8 Hz, 1H), 7.18-7.48 (m, 7H), 9.69 (s, 1H), 11.13 (s, 2H); MS [M]⁺: 491.30.

Example-166

2-((2,6-Dichlorophenyl)amino)-7,7-dimethyl-N-(6-(trifluoromethyl)pyridin-3-yl)-7,8-dihydro-1H-benzofuro[4,5-d]imidazole-5-carboxamide

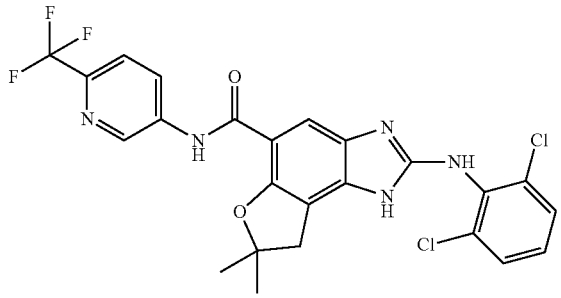 [SMILES: CC1(C)Cc2c(c(C(=O)Nc3ccc(C(F)(F)F)nc3)cc3nc(Nc4c(Cl)cccc4Cl)[nH]c23)O1]

The title compound was prepared by following the procedure as described for Example-137 using methyl 2-[(2,6-dichlorophenyl)amino]-7,7-dimethyl-7,8-dihydro-1H-furo[3,2-e]benzimidazole-5-carboxylate (Step-1 of Intermediate-6, 0.200 g, 0.493 mmol) and 6-(trifluoromethyl)pyridin-3-amine (0.119 g, 0.740 mmol), trimethyl aluminium (2M solution in toluene) (0.071 g, 0.986 mmol) and dry toluene (5.0 mL) to afford 0.100 g of the desired product. ¹HNMR (DMSO-d₆): δ 1.58 (s, 6H), 3.09 (s, 2H), 7.39 (m, 3H), 7.53 (m, 1H), 7.89 (d, J=8.4 Hz, 1H), 8.46 (d, J=9.0 Hz, 1H), 8.99 (s, 1H), 10.07 (s, 1H), 10.94 (s, 2H); MS [M]⁺: 536.17.

Example-167

2-((2-Chloro-6-fluorophenyl)amino)-N-(4-cyclopropylphenyl)-1,7,7-trimethyl-7,8-dihydro-1H-benzofuro[4,5-d]imidazole-5-carboxamide

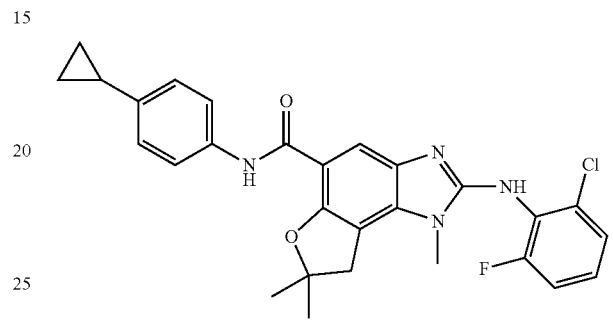

The title compound was prepared following the procedure described for Example-108 using 2-((2-chloro-6-fluorophenyl)amino)-1,7,7-trimethyl-7,8-dihydro-1H-benzofuro[4,5-d]imidazole-5-carboxylic acid (Intermediate-49, 0.100 g, 0.256 mmol), thionyl chloride (2.0 mL), 4-cyclopropyl aniline (0.102 g, 0.769 mmol), THF (5.0 mL) and DIPEA (2 mL). The obtained crude product was purified by column chromatography on basic alumina eluting with 0.7-1.0% MeOH:DCM to afford 0.017 g of the desired product. ¹HNMR (DMSO-d₆): δ 0.62 (d, J=3.9 Hz, 2H), 0.91 (d, J=6.3 Hz, 2H), 1.60 (s, 6H), 1.88 (m, 1H), 3.45 (s, 2H), 3.55 (s, 3H), 6.98-7.16 (m, 3H), 7.19-7.36 (m, 3H), 7.53 (d, J=8.1 Hz, 2H), 9.60 (s, 1H), 10.48 (s, 1H); MS [M+H]⁺: 505.26.

Example-168

2-((2-Chloro-6-fluorophenyl)amino)-N-(2-fluoro-3-(trifluoromethyl)phenyl)-7,7-dimethyl-7,8-dihydro-1H-benzofuro[4,5-d]imidazole-5-carboxamide

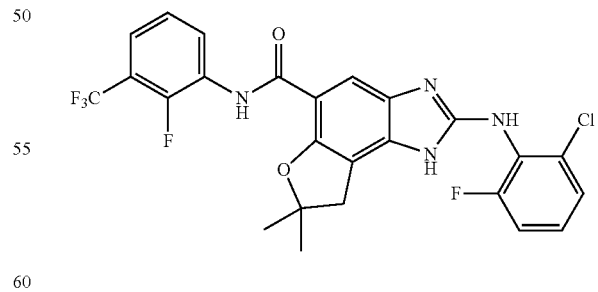

The title compound was prepared following the procedure described for Example-137 using methyl 2-[(2-chloro-6-fluorophenyl)amino]-7,7-dimethyl-7,8-dihydro-1H-furo[3,2-e]benzimidazole-5-carboxylate (Step-1 of Intermediate-15, 0.100 g, 0.256 mmol), 2-fluoro-3-(trifluoromethyl)aniline (0.068 g, 0.379 mmol), trimethyl aluminium (2M solution in toluene) (0.5 mL) and dry toluene (5.0 mL) to afford 0.050 g of the desired product. ¹HNMR (DMSO-d₆): δ 1.56 (s, 6H), 3.13 (s, 2H), 7.32 (m, 2H), 7.42-7.45 (m, 4H), 8.76 (m, 1H), 10.20 (s, 1H), 11.20 (s, 2H); MS [M+H]⁺: 537.19.

Example-169

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide methanesulfonate To a solution of 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g) in acetone was added methane sulphonic acid. The reaction mass was refluxed for 3 h followed by stirring at RT for 18 h. The reaction mass was filtered and the obtained residue was washed with DEE to afford 0.080 g of the desired product. ¹HNMR (DMSO-d₆): δ 1.59 (s, 6H), 2.30 (s, 3H), 3.19 (s, 2H), 7.57 (m, 3H), 7.64 (s, 1H), 7.73 (d, J=8.4 Hz, 2H), 7.93 (d, J=8.7 Hz, 2H), 10.03 (s, 1H), 12.0 (br, 3H).

Example-170

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide Maleate The title compound was prepared following the procedure described for Example-169 using 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g), acetone and maleic acid to afford 0.075 g of the desired product. ¹HNMR (DMSO-d₆): δ 1.58 (s, 6H), 3.12 (s, 2H), 6.18 (s, 2H), 7.36 (d, J=6.6 Hz, 2H), 7.44 (s, 1H), 7.51 (s, 1H), 7.71 (d, J=7.8 Hz, 2H), 10.0 (s, 1H), 11.0-12.0 (br, 4H).

Example-171

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide fumarate The title compound was prepared following the procedure described for Example-169 using 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g), acetone and fumaric acid to afford 0.065 g of the desired product. ¹HNMR (DMSO-d₆): δ 1.58 (s, 6H), 3.10 (s, 2H), 6.62 (s, 2H), 7.30 (m, 2H), 7.41 (d, J=6.9 Hz, 1H), 7.48 (s, 1H), 7.70 (d, J=8.7 Hz, 2H), 7.91 (d, J=8.4 Hz, 2H), 9.99 (s, 1H), 11.0-12.0 (br, 4H).

Example-172

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide Succinate The title compound was prepared following the procedure described for Example-169 using 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g), acetone and succinic acid to afford 0.065 g of the desired product. ¹HNMR (DMSO-d₆): δ 1.57 (s, 6H), 2.08 (s, 2H), 2.41 (s, 2H), 3.10 (s, 2H), 7.30-7.33 (m, 2H), 7.41 (d, J=6.9 Hz, 1H), 7.48 (s, 1H), 7.70 (d, J=8.7 Hz, 2H), 7.92 (d, J=8.4 Hz, 2H), 9.59 (s, 1H), 11.0-12.0 (br, 4H).

Example-173

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide Phosphate The title compound was prepared following the procedure described for Example-169 using 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g), acetone and phosphoric acid to afford 0.040 g of the desired product. ¹HNMR (DMSO-d₆): δ 1.57 (s, 6H), 3.10 (s, 2H), 7.30-7.33 (m, 2H), 7.41 (d, J=7.5 Hz, 1H), 7.47 (s, 1H), 7.70 (d, J=8.1 Hz, 2H), 7.91 (d, J=8.7 Hz, 2H), 7.99 (s, 1H), 13.0 (br, 5H).

Example-174

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide Sulfate The title compound was prepared following the procedure described for Example-169 using 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.100 g), acetone and sulphuric acid to afford 0.040 g of the desired product. ¹HNMR (DMSO-d₆): δ 1.57 (s, 6H), 2.08 (s, 2H), 3.20 (s, 2H), 7.51-7.55 (m, 3H), 7.58 (s, 1H), 7.73 (d, J=8.7 Hz, 2H), 7.93 (d, J=8.7 Hz, 2H), 10.03 (s, 1H), 13.0-14.0 (br, 2H).

Example-175

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide, Sodium Salt To a solution of 2-[(2-chloro-6-fluorophenyl)amino]-7,7-dimethyl-N-[4-(trifluoromethyl)phenyl]-7,8-dihydro-1H-furo[3,2-e]benzimidazole-5-carboxamide (Example-107, 0.050 g, 0.096 mmol) in THF was added 60% NaH (0.004 g, 0.096) and sodium tert-butoxide (0.009 g, 0.095 mmol). The reaction mass was stirred at RT for 18 h. The reaction mass was filtered and the obtained residue was washed with DEE to afford 0.050 g of the desired product. ¹HNMR (DMSO-d₆): δ 1.54 (s, 6H), 2.96 (s, 2H), 6.84 (s, 1H), 7.02 (s, 1H), 7.15 (s, 2H), 7.66 (s, 2H), 7.85 (s, 2H), 10.02 (s, 1H).

Example-176

N-(4-Bromophenyl)-2-[(2,6-dichlorophenyl)amino]-7,7-dimethyl-7,8-dihydro-1H-furo[3,2-e]benzimidazole-5-carboxamidehydrochloride The title compound was prepared following the procedure described for Example-146 using N-(4-bromophenyl)-2-[(2,6-dichlorophenyl)amino]-7,7-dimethyl-7,8-dihydro-1H-furo[3,2-e]benzimidazole-5-carboxamide (Example-11, 0.100 g), THF and conc. HCl to afford 0.060 g of the desired product. ¹HNMR (DMSO-d₆): δ 1.56 (s, 6H), 2.20 (s, 2H), 7.51-7.57 (m, 3H), 7.64-7.74 (m, 5H), 9.81 (s, 1H), 12.0-13.0 (br, 3H).

Example-177

7-[(2,6-Dichlorophenyl)amino]-N-(4-fluorophenyl)-2-methyl-8H-imidazo[4,5-e][1,3]benzoxazole-4-carboxamide

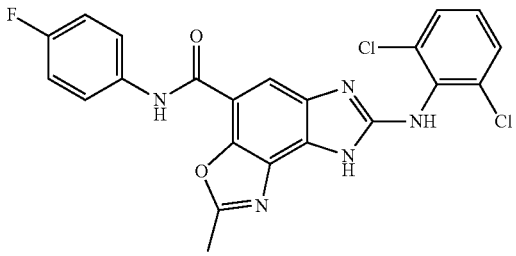 [SMILES: Cc1nc2c(o1)c(C(=O)Nc1ccc(F)cc1)cc1nc(Nc3c(Cl)cccc3Cl)[nH]c12]

To a solution of 7-[(2,6-dichlorophenyl)amino]-2-methyl-8H-imidazo[4,5-e][1,3]benzoxazole-4-carboxylic acid (Intermediate-55, 0.100 g, 0.276 mmol) in benzene (4 mL), thionyl chloride (5.0 mL) was added at 5-10° C. The reaction mass was refluxed for 3 h. Thionyl chloride was removed under vacuum and stripped out with benzene. The solution of 4-fluoroaniline (0.091 g, 0.828 mmol) in THF (5.0 mL) was added 60% NaH (0.033 g, 0.825 mmol) under N₂-atmosphere at 0-5° C. The solution was stirred for 30 minutes at same temperature and above prepared solution was added to reaction mixture. The reaction mass was stirred at RT for 1 h. The reaction mass was quenched in ice water and extracted with ethyl acetate. The obtained product was further purified by column chromatography on neutral alumina eluting with 1.5-2.0% MeOH:DCM to afford 0.020 g of the desired product. ¹HNMR (DMSO-d₆): δ 2.65 (s, 3H), 7.17-7.20 (m, 4H), 7.38-7.50 (m, 1H), 7.61 (s, 2H), 7.79 (s, 1H), 8.96-9.04 (m, 1H), 9.40-9.60 (s, 1H), 11-12 (s, 1H); MS [M+H]⁺: 470.23.

Example-178

7-[(2,6-Dichlorophenyl)amino]-2-methyl-N-[4-(trifluoromethyl)phenyl]-8H-imidazo[4,5-e][1,3]benzoxazole-4-carboxamide

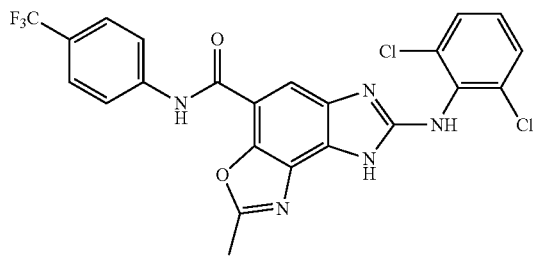 [SMILES: Cc1nc2c(o1)c(C(=O)Nc1ccc(C(F)(F)F)cc1)cc1nc(Nc3c(Cl)cccc3Cl)[nH]c12]

The title compound was prepared following the procedure as described for Example-177 using 7-[(2,6-dichlorophenyl)amino]-2-methyl-8H-imidazo[4,5-e][1,3]benzoxazole-4-carboxylic acid (Intermediate-55, 0.100 g, 0.276 mmol), benzene (4 mL), thionyl chloride (5.0 mL), 4-(trifluoro methyl)aniline (0.133 g, 0.828 mmol), THF (5.0 mL) and 60% NaH (0.033 g, 0.825 mmol). The obtained product was further purified by column chromatography on neutral alumina eluting with 1.5-2.0% MeOH:DCM to afford 0.018 g of the desired product. ¹HNMR (DMSO-d₆): δ 2.72 (s, 3H), 7.41 (s, 2H), 7.63 (s, 2H), 7.73 (d, J=8.4 Hz, 2H), 8.00 (d, J=8.4 Hz, 2H), 9.47 (s, 1H), 11.39 (s, 1H), 11.60 (s, 1H); MS [M+H]⁺: 520.39.

Example-179

N-(4-Bromophenyl)-7-[(2,6-dichlorophenyl)amino]-2-methyl-8H-imidazo[4,5-e][1,3]benzoxazole-4-carboxamide

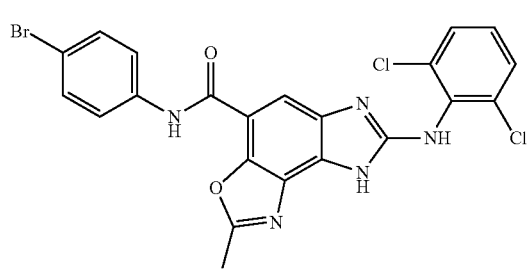 [SMILES: Cc1nc2c(o1)c(C(=O)Nc1ccc(Br)cc1)cc1nc(Nc3c(Cl)cccc3Cl)[nH]c12]

The title compound was prepared following the procedure as described for Example-177 using 7-[(2,6-dichlorophenyl)amino]-2-methyl-8H-imidazo[4,5-e][1,3]benzoxazole-4-carboxylic acid (Intermediate-55, 0.100 g, 0.276 mmol), benzene (4 mL), thionyl chloride (5.0 mL), 4-bromo aniline (0.142 g, 0.828 mmol), THF (5.0 mL) and 60% NaH (0.033 g, 0.825 mmol). The obtained product was further purified by column chromatography on neutral alumina eluting with 1.5-2.0% MeOH:DCM to afford 0.022 g of the desired product. ¹HNMR (DMSO-d₆): δ 2.70 (s, 3H), 6.54 (s, 1H), 6.67 (d, J=8.4 Hz, 1H), 6.83 (s, 1H), 6.98 (d, J=8.1 Hz, 1H), 7.12-7.26 (m, 2H), 7.33-7.38 (m, 2H), 8.61 (s, 1H), 9.04 (s, 1H); MS [M+H]⁺: 532.47.

Example-180

N-(4-tert-Butylphenyl)-7-[(2,6-dichlorophenyl)amino]-2-methyl-8H-imidazo[4,5-e][1,3]benzoxazole-4-carboxamide

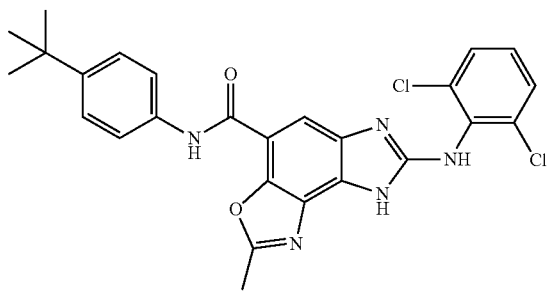 [SMILES: Cc1nc2c(o1)c(C(=O)Nc1ccc(C(C)(C)C)cc1)cc1nc(Nc3c(Cl)cccc3Cl)[nH]c12]

The title compound was prepared following the procedure as described for Example-177 using 7-[(2,6-dichlorophenyl)amino]-2-methyl-8H-imidazo[4,5-e][1,3]benzoxazole-4-carboxylic acid (Intermediate-55, 0.100 g, 0.276 mmol), benzene (4 mL), thionyl chloride (5.0 mL), 4-tert-butylaniline (0.123 g, 0.828 mmol), THF (5.0 mL) and 60% NaH (0.033 g, 0.825 mmol). The obtained product was further purified by column chromatography on neutral alumina eluting with 1.5-2.0% MeOH:DCM to afford 0.015 g of the desired product. ¹HNMR (DMSO-d₆): δ 1.28 (s, 9H), 2.65 (s, 3H), 6.54 (s, 1H), 7.37 (d, J=7.8 Hz, 3H), 7.60-7.68 (m, 4H), 9.43 (s, 1H), 9.93 (s, 1H), 11.56 (s, 1H); MS [M+H]⁺: 508.57.

Example-181

7-[(2,6-Dichlorophenyl)amino]-N-hexyl-2-methyl-8H-imidazo[4,5-e][1,3]benzoxazole-4-carboxamide

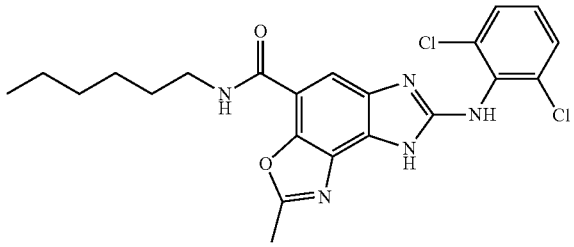 [SMILES: CCCCCCNC(=O)c1cc2nc(Nc3c(Cl)cccc3Cl)[nH]c2c2nc(C)oc12]

To a solution of 7-[(2,6-dichlorophenyl)amino]-2-methyl-8H-imidazo[4,5-e][1,3]benzoxazole-4-carboxylic acid (Intermediate-55, 0.050 g, 0.132 mmol) in benzene (2 mL) was added thionyl chloride (1.5 mL) at 5-10° C. The reaction mass was refluxed for 3 h. To a solution of hexan-1-amine (0.020 g, 0.198 mmol) in THF (5.0 mL), DIPEA (0.086 g, 0.663 mmol) was added under N₂-atmosphere at RT. The solution was stirred for 1 h at RT and above prepared solution was added to reaction mixture. The whole reaction mass was stirred at RT for 1 h. Thionyl chloride was removed under vacuum and stripped out with THF. The reaction mass was quenched in ice water and extracted with ethyl acetate. The organic layer was concentrated. The obtained product was further purified by column chromatography on neutral alumina eluting with 1.5-2.0% MeOH:DCM to afford 0.020 g of the desired product. ¹HNMR (DMSO-d₆): δ 0.83-0.85 (s, 3H), 1.26 (s, 6H), 1.51-1.54 (m, 2H), 2.61 (s, 3H), 3.30 (m, 2H), 7.30 (s, 1H), 7.57 (s, 3H), 7.90 (s, 1H), 9.30 (s, 1H), 11.40-11.50 (s, 1H); MS [M+H]⁺: 460.41

Example-182

7-[(2-Chloro-6-fluorophenyl)amino]-N-(4-fluorophenyl)-2-methyl-8H-imidazo[4,5-e][1,3]benzoxazole-4-carboxamide

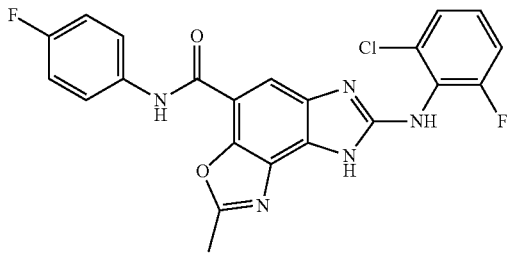 [SMILES: Cc1nc2c(o1)c(C(=O)Nc1ccc(F)cc1)cc1nc(Nc3c(F)cccc3Cl)[nH]c12]

The title compound was prepared following the procedure as described for Example-177 using 7-[(2-chloro-6-fluorophenyl)amino]-2-methyl-8H-imidazo[4,5-e][1,3]benzoxazole-4-carboxylic acid (Intermediate-56, 0.050 g, 0.138 mmol), thionyl chloride (2.0 mL), 4-fluoro aniline (0.052 g, 0.138 mmol), THF (5.0 mL) and 60% NaH (0.017 g, 0.692 mmol). The obtained product was further purified by column chromatography on neutral alumina eluting with 1.5-2.0% MeOH: DCM to afford 0.020 g of the desired product. ¹HNMR (DMSO-d₆): δ 2.65 (s, 3H), 7.20 (t, J=7.8 Hz, 2H), 7.40-7.46 (m, 3H), 7.63 (s, 1H), 7.80-7.82 (m, 2H), 9.34 (s, 1H), 10.08 (s, 1H), 11.63 (s, 1H); MS [M−H]⁻: 452.23.

Example-183

N-(Cyclohexylmethyl)-7-[(2,6-dichlorophenyl)amino]-2-methyl-8H-imidazo[4,5-e][1,3]benzoxazole-4-carboxamide

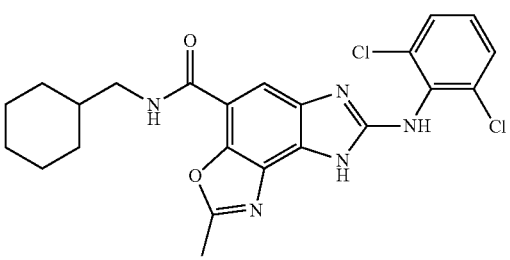 [SMILES: Cc1nc2c(o1)c(C(=O)NCC1CCCCC1)cc1nc(Nc3c(Cl)cccc3Cl)[nH]c12]

The title compound was prepared following the procedure described for Example-181 using 7-[(2,6-dichlorophenyl)amino]-2-methyl-8H-imidazo[4,5-e][1,3]benzoxazole-4-carboxylic acid (Intermediate-55, 0.050 g, 0.132 mmol), thionyl chloride (2.0 mL), 1-cyclohexylmethanamine (0.023 g, 0.138 mmol), THF (5.0 mL) and DIPEA (0.086 g, 0.663 mmol). The obtained product was further purified by column chromatography on neutral alumina eluting with 1.5-2.0% MeOH: DCM to afford 0.020 g of the desired product. ¹HNMR (DMSO-d₆): δ 1.04-1.31 (m, 6H), 1.62-1.75 (m, 5H), 2.54 (s, 3H), 3.00 (t, J=18.6 Hz, 2H), 7.34 (s, 1H), 7.53-7.59 (m, 3H), 7.94 (s, 1H), 9.39 (s, 1H), 11.51 (s, 1H); MS [M+H]⁺: 472.43.

Example-184

N-(4-tert-Butylphenyl)-2-cyclopropyl-7-[(2,6-dichlorophenyl)amino]-8H-imidazo[4,5-e][1,3]benzoxazole-4-carboxamide

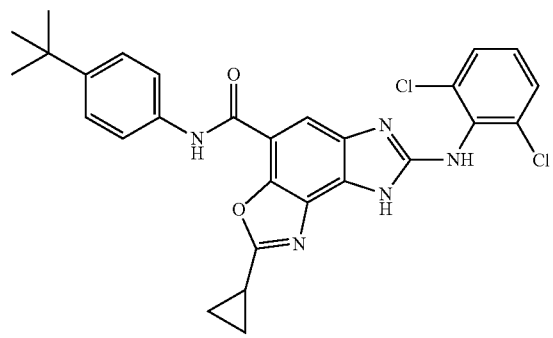 [SMILES: CC(C)(C)c1ccc(NC(=O)c2cc3nc(Nc4c(Cl)cccc4Cl)[nH]c3c3nc(C4CC4)oc23)cc1]

The title compound was prepared following the procedure as described for Example-177 using 2-cyclopropyl-7-[(2,6-dichlorophenyl)amino]-8H-imidazo[4,5-e][1,3]benzoxazole-4-carboxylic acid (Intermediate-58, 0.100 g, 0.248 mmol), benzene (4 mL), thionyl chloride (5.0 mL), 4-tert-butylaniline (0.055 g, 0.369 mmol), THF (5.0 mL) and 60% NaH (0.095 g, 0.744 mmol). The obtained product was further purified by column chromatography on neutral alumina eluting with 1.5-2.0% MeOH:DCM to afford 0.015 g of the desired product. ¹HNMR (DMSO-d₆): δ 1.20 (s, 4H), 1.29 (s, 9H), 2.32 (m, 1H), 7.28 (d, J=7.8 Hz, 3H), 7.59 (s, 3H), 7.68 (d, J=8.4 Hz, 2H), 9.36 (s, 1H), 9.90 (s, 1H), 11.55 (s, 1H); MS [M+H]⁺: 534.32.

Example-185

7-((2-Chloro-6-fluorophenyl)amino)-2-cyclopropyl-N-(2-fluoro-5-(trifluoromethyl)phenyl)-8H-imidazo[4',5':5,6]benzo[1,2-d]oxazole-4-carboxamide

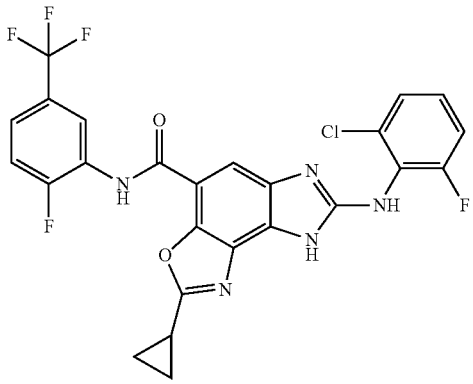 [SMILES: O=C(Nc1cc(C(F)(F)F)ccc1F)c1cc2nc(Nc3c(F)cccc3Cl)[nH]c2c2nc(C3CC3)oc12]

To a solution of methyl 7-((2-chloro-6-fluorophenyl)amino)-2-cyclopropyl-8H-imidazo[4',5':5,6]-benzo[1,2-d]oxazole-4-carboxylate (Intermediate-59, 0.050 g, 0.125 mmol) in dry toluene (5.0 mL) was added 2-fluoro-5-trifluoromethylaniline (0.022 g, 0.125 mmol) and trimethyl aluminium (2M solution in toluene) (0.009 g, 0.125 mmol). The reaction mass was refluxed for 1 h. The reaction mass was quenched with water and extracted with 10% DCM: MeOH. The organic layer was dried over anhydrous sodium sulphate and concentrated. The obtained crude was purified by column chromatography to afford 0.012 g of the desired product. ¹HNMR (DMSO-d₆): δ 1.23 (m, 4H), 2.33 (m, 1H), 7.40-7.47 (m, 3H), 7.62 (m, 2H), 7.75 (s, 1H), 8.68 (s, 1H), 9.42 (s, 1H), 9.89 (s, 1H), 11.69 (s, 1H); MS [M+H]⁺: 547.81.

Example-186

7-((2-Chloro-6-fluorophenyl)amino)-N-(2-fluoro-5-(trifluoromethyl)phenyl)-2-methyl-8H-imidazol[4',5':5,6]-benzo[1,2-d]oxazole-4-carboxamide

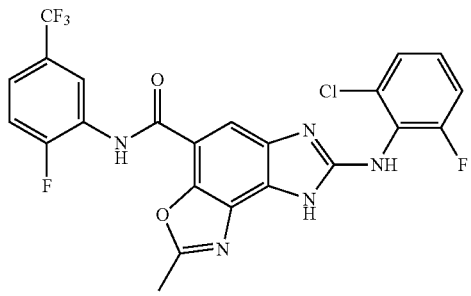 [SMILES: Cc1nc2c(o1)c(C(=O)Nc1cc(C(F)(F)F)ccc1F)cc1nc(Nc3c(F)cccc3Cl)[nH]c12]

The title compound was prepared following the procedure as described for Example-185 using methyl 7-[(2-chloro-6-fluorophenyl)amino]-2-methyl-8H-imidazo[4,5-e][1,3]benzoxazole-4-carboxylate (Step-3 of Intermediate-56, 0.100 g, 0.266 mmol), 2-fluoro-5-trifluoromethylaniline (0.071 g, 0.125 mmol), trimethyl aluminium (2M solution in toluene) (0.5 mL) and dry toluene (5.0 mL) to afford 0.015 g of the desired product. ¹HNMR (DMSO-d₆): δ 2.72 (s, 3H), 7.41-7.47 (m, 3H), 7.63 (s, 2H), 7.76 (s, 1H), 8.54 (d, J=6.9 Hz, 1H), 9.45 (s, 1H), 9.92 (s, 1H), 11.71 (s, 1H); MS [M+H]⁺: 522.12.

Example-187

7-((2-Chloro-6-fluorophenyl)amino)-N-(4-fluoro-3-(trifluoromethyl)phenyl)-2-methyl-8H-imidazo[4',5':5,6]benzo[1,2-d]oxazole-4-carboxamide

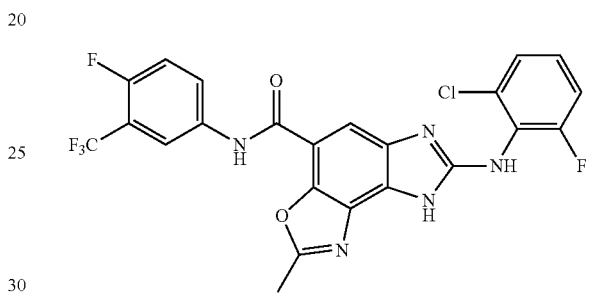

Under inert atmosphere to a solution of methyl 7-[(2-chloro-6-fluorophenyl)amino]-2-methyl-8H-imidazo[4,5-e][1,3]benzoxazole-4-carboxylate (Step-3 of Intermediate-56, 0.100 g, 0.297 mmol) in dry toluene was added 4-fluoro-3-trifluoromethyl aniline (0.080 g, 0.446 mmol) and trimethyl aluminium (2.0 M solution in toluene) (0.037 g, 0.516 mmol). The reaction mixture was refluxed for 1 h. The reaction mass was quenched in water and extracted with ethyl acetate. The organic layer was dried over anhydrous sodium sulphate and concentrated. The obtained crude was purified by column chromatography on basic alumina eluting with 0.75-1% DCM: MeOH to afford 0.030 g of the desired product. ¹HNMR (DMSO-d₆): δ 2.65 (s, 3H), 7.40-7.57 (m, 4H), 7.65 (s, 1H), 8.06 (m, 1H), 8.30 (s, 1H), 9.37 (s, 1H), 10.40 (s, 1H), 11.68 (s, 1H); MS [M+H]⁺: 522.14.

Example-188

7-[(2,6-Dichlorophenyl)amino]-2-methyl-N-[2-(trifluoromethyl)benzyl]-8H-imidazo[4,5-e][1,3]benzoxazole-4-carboxamide

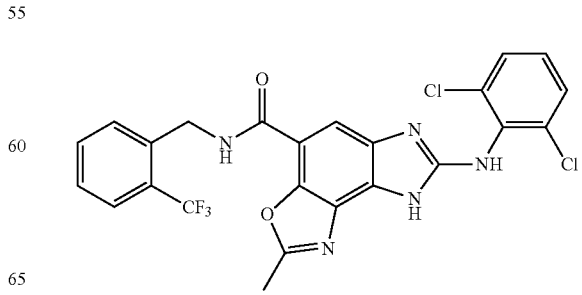

The title compound was prepared following the procedure described for Example-177 using 7-[(2,6-dichlorophenyl)amino]-2-methyl-8H-imidazo[4,5-e][1,3]benzoxazole-4-carboxylic acid (Intermediate-55, 0.050 g, 0.132 mmol), oxalyl chloride (0.1 mL), 1-[2-(trifluoromethyl)phenyl]methanamine (0.046 g, 0.262 mmol), THF (5.0 mL) and 60% NaH (0.021 g, 0.525 mmol). The obtained crude product was purified by column chromatography on neutral alumina eluting with 1.5-2.0% MeOH:DCM to afford 0.027 g of the desired product. $^1$HNMR (DMSO-$d_6$): δ 2.64 (s, 3H), 4.76 (s, 2H), 7.37-7.47 (m, 2H), 7.61-7.63 (m, 5H), 7.75 (d, J=6.9 Hz, 1H), 8.65 (s, 1H), 9.43 (s, 1H), 11.53 (s, 1H); MS [M+H]$^+$: 534.43.

Example-189

7-[(2,6-Dichlorophenyl)amino]-N-(4,4-difluorocyclohexyl)-2-methyl-8H-imidazo[4,5-e][1,3]benzoxazole-4-carboxamide

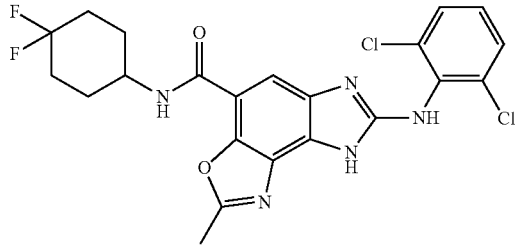 [SMILES: Cc1nc2c(o1)c(C(=O)NC1CCC(F)(F)CC1)cc1nc(Nc3c(Cl)cccc3Cl)[nH]c12]

The title compound was prepared following the procedure described for Example-177 using 7-[(2,6-dichlorophenyl)amino]-2-methyl-8H-imidazo[4,5-e][1,3]benzoxazole-4-carboxylic acid (Intermediate-55, 0.100 g, 0.265 mmol), oxalyl chloride (0.2 mL), 4,4-difluorocyclohexanamine (0.069 g, 0.397 mmol), THF (5.0 mL), DIPEA (0.103 g, 0.795 mmol) and TEA (0.2 mL). The obtained crude product was further purified by column chromatography on neutral alumina eluting with 1.5-2.0% MeOH:DCM to afford 0.015 g of the desired product. $^1$HNMR (DMSO-$d_6$): δ 1.66-1.68 (m, 2H), 1.90-2.15 (m, 6H), 2.60 (s, 3H), 4.01 (s, 1H), 7.36 (m, 1H), 7.50 (s, 1H), 7.58 (d, J=7.2 Hz, 2H), 7.89 (s, 1H), 9.38 (s, 1H), 11.46 (s, 1H); MS [M+H]$^+$: 494.41.

Example-190

N-[4-(2-Cyanopropan-2-yl)phenyl]-7-[(2,6-dichlorophenyl)amino]-2-methyl-8H-imidazo[4,5-e][1,3]benzoxazole-4-carboxamide

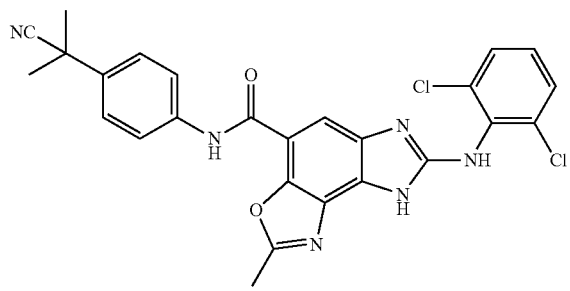 [SMILES: Cc1nc2c(o1)c(C(=O)Nc1ccc(C(C)(C)C#N)cc1)cc1nc(Nc3c(Cl)cccc3Cl)[nH]c12]

The title compound was prepared following the procedure described for Example-177 using 7-[(2,6-dichlorophenyl)amino]-2-methyl-8H-imidazo[4,5-e][1,3]benzoxazole-4-carboxylic acid (Intermediate-55, 0.100 g, 0.265 mmol), oxalyl chloride (0.2 mL), 2-(4-aminophenyl)-2-methylpropanenitrile (Intermediate-22, 0.063 g, 0.397 mmol), THF (5.0 mL), DIPEA (0.103 g, 0.795 mmol) and TEA (0.2 mL). The obtained crude product was further purified by column chromatography on neutral alumina eluting with 1.5-2.0% MeOH:DCM to afford 0.012 g of the desired product. $^1$HNMR (DMSO-$d_6$): δ 1.69 (s, 6H), 2.66 (s, 3H), 7.42 (t, J=7.8 Hz, 1H), 7.51 (d, J=8.7 Hz, 2H), 7.61 (s, 3H), 7.82 (d, J=9.0 Hz, 2H), 9.45 (s, 1H), 10.11 (s, 1H), 11.58 (s, 1H); MS [M+H]$^+$: 519.32.

Example-191

2-((2-Chloro-6-fluorophenyl)amino)-7,7-dimethyl-N-(6-(trifluoromethyl)pyridin-3-yl)-7,8-dihydro-1H-benzofuro[4,5-d]imidazole-5-carboxamide

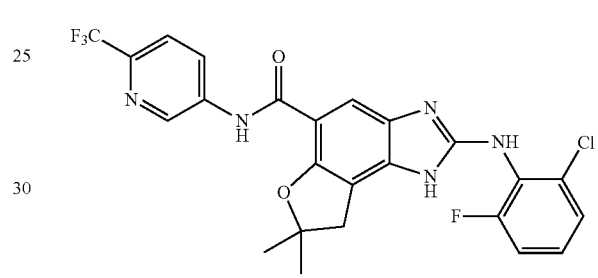

The title compound was prepared by following the procedure described for Example-137 by using methyl 2-[(2-chloro-6-fluorophenyl)amino]-7,7-dimethyl-7,8-dihydro-1H-furo[3,2-e]benzimidazole-5-carboxylate (Step-1 of Intermediate-15, 0.100 g, 0.256 mmol), 6-(trifluoromethyl)pyridin-3-amine (0.062 g, 0.387 mmol), trimethyl aluminium (2M solution in toluene) (0.5 mL), dry toluene (5.0 mL) to afford 0.013 g of the desired product. $^1$HNMR (DMSO-$d_6$): δ 1.58 (s, 6H), 3.33 (s, 2H), 7.33-7.41 (m, 4H), 7.89 (d, J=9.0 Hz, 1H), 8.47 (d, J=6.6 Hz, 1H), 9.00 (s, 1H), 10.09 (s, 1H), 11.20 (br s, 2H); MS [M+H]$^+$: 520.11

Example-192

2-((2-Chloro-6-methylphenyl)amino)-7,7-dimethyl-N-(2,4,5-trifluorophenyl)-7,8-dihydro-1H-benzofuro[4,5-d]imidazole-5-carboxamide

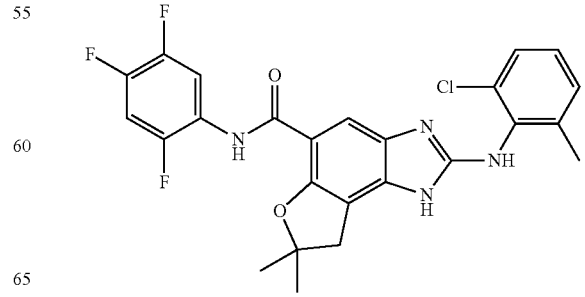

The title compound was prepared by following the procedure described for Example-137 by using methyl 2-[(2-chloro-6-methylphenyl)amino]-7,7-dimethyl-7,8-dihydro-1H-furo[3,2-e]benzimidazole-5-carboxylate (Step-1 of Intermediate-35, 0.200 g, 0.414 mmol) and 2,4,5-trifluoroaniline (0.090 g, 0.602 mmol), trimethyl aluminium (2M solution in toluene) (1 mL) and dry toluene (5.0 mL) to afford 0.070 g of the desired product. $^1$HNMR (DMSO-d$_6$): δ 1.54 (s, 6H), 2.24 (s, 3H), 3.17 (s, 2H), 7.25-7.33 (m, 2H), 7.42 (d, J=8.80 Hz, 1H), 7.52 (s, 1H), 7.72 (q, J=8.4 Hz, 10.8 Hz, 1H), 8.48-8.58 (m, 1H), 9.13 (br s, 1H), 10.16 (s, 1H), 10.98 (br s, 1H): MS [M+H]$^+$: 501.0

Example-193

2-((2-Chloro-6-fluorophenyl)amino)-7,7-dimethyl-N-(2,4,5-trifluorophenyl)-7,8-dihydro-1H-benzofuro[4,5-d]imidazole-5-carboxamide

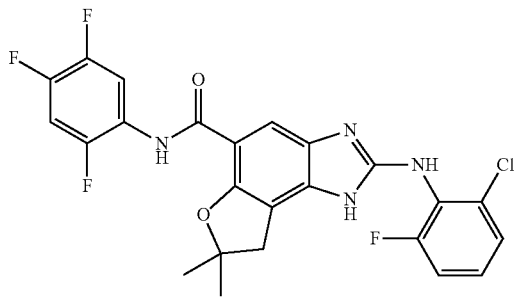 [SMILES: CC1(C)Cc2c(c(C(=O)Nc3cc(F)c(F)cc3F)cc3nc(Nc4c(F)cccc4Cl)[nH]c23)O1]

The title compound was prepared following the procedure described for Example-137 by using methyl 2-[(2-chloro-6-fluorophenyl)amino]-7,7-dimethyl-7,8-dihydro-1H-furo[3,2-e]benzimidazole-5-carboxylate (Step-1 of Intermediate-15, 0.100 g, 0.256 mmol), 2,4,5-trifluoroaniline (0.056 g, 0.383 mmol), trimethyl aluminium (2M solution in toluene) (0.5 mL), dry toluene (5.0 mL) to afford 0.050 g of the desired product. $^1$HNMR (DMSO-d$_6$): δ 1.55 (s, 6H), 3.15 (s, 2H), 7.34 (m, 2H), 7.41 (m, 1H), 7.51 (br s, 1H), 7.73 (q, J=10.8 Hz, 10.8 Hz, 1H), 8.54 (m, 1H), 10.13 (s, 1H), 11.27 (br s, 2H); MS [M+H]$^+$: 505.08.

Example-194

2-((3,5-Dichloropyridin-4-yl)amino)-N-(2-fluoro-4-(trifluoromethyl)phenyl)-7,7-dimethyl-7,8-dihydro-1H-benzofuro[4,5-d]imidazole-5-carboxamide

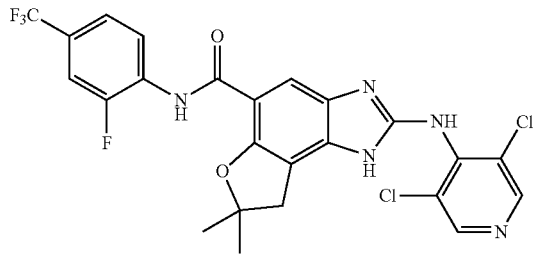 [SMILES: CC1(C)Cc2c(c(C(=O)Nc3ccc(C(F)(F)F)cc3F)cc3nc(Nc4c(Cl)cncc4Cl)[nH]c23)O1]

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.100 g, 0.245 mmol), 2-fluoro-4-(trifluoromethyl)aniline (0.064 g, 0.357 mmol), trimethyl aluminium (2M solution in toluene) (0.5 mL), dry toluene (5.0 mL) at room temperature to afford 0.050 g of the desired product. $^1$HNMR (DMSO-d$_6$): δ 1.57 (s, 6H), 3.11 (s, 2H), 7.31 (s, 1H), 7.62 (d, J=8.1 Hz, 1H), 7.81 (d, J=11.4 Hz, 1H), 8.46 (s, 2H), 8.70 (t, J=8.4 Hz, 1H), 10.23 (s, 1H), 11.03 (br s, 1H), 11.60 (br s, 1H); MS [M+H]$^+$: 552.33.

Example-195

2-((3,5-Dichloropyridin-4-yl)amino)-N-(2-fluoro-5-(trifluoromethyl)phenyl)-7,7-dimethyl-7,8-dihydro-1H-benzofuro[4,5-d]imidazole-5-carboxamide

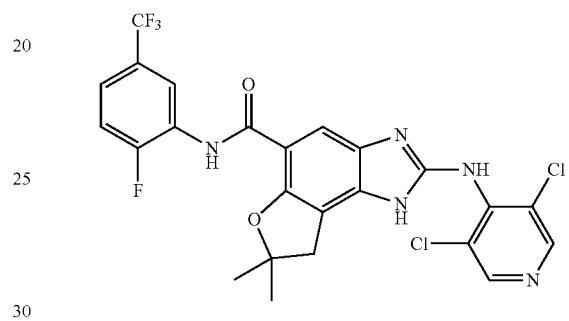

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.100 g, 0.245 mmol), 2-fluoro-5-(trifluoromethyl)aniline (0.064 g, 0.357 mmol), trimethyl aluminium (2M solution in toluene) (0.5 mL), dry toluene (5.0 mL) at room temperature to afford 0.045 g of the desired product. $^1$HNMR (DMSO-d$_6$): δ 1.57 (s, 6H), 3.10 (s, 2H), 7.30 (s, 1H), 7.53-7.63 (m, 2H), 8.45 (s, 2H), 8.87 (d, J=6.6 Hz, 1H), 10.20 (s, 1H), 11.02 (br s, 1H), 11.59 (br s, 1H); MS [M+H]$^+$: 551.97.

Example-196

2-((3,5-Dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide

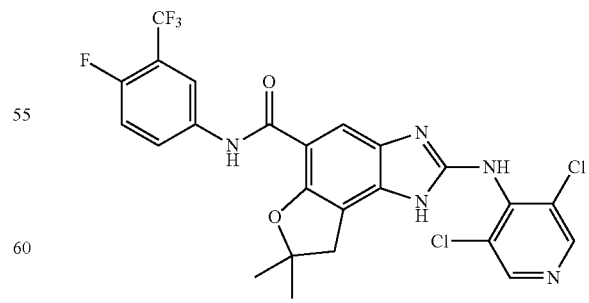

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.100 g, 0.245 mmol), 4-fluoro-3-(trifluoromethyl)aniline (0.064 g, 0.357 mmol), trimethyl aluminium (2M solution in toluene) (0.5 mL), dry toluene (5.0 mL) at room temperature to afford 0.048 g of the desired product. ¹HNMR (DMSO-d₆): δ 1.57 (s, 6H), 3.06 (s, 2H), 7.24 (s, 1H), 7.51 (t, J=9.6 Hz, 1H), 7.84 (m, 1H), 8.30 (d, J=4.2 Hz, 1H), 8.45 (s, 2H), 9.84 (s, 1H), 11.99 (br s, 1H), 11.53 (br s, 1H); MS [M+H]⁺: 554.54.

Example-197

2-((3,5-Dichloropyridin-4-yl)amino)-N-(2,4-difluorophenyl)-7,7-dimethyl-7,8-dihydro-1H-benzofuro[4,5-d]imidazole-5-carboxamide

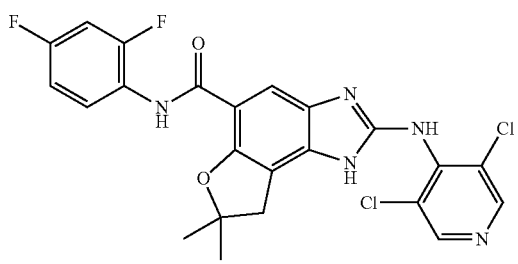 [SMILES: CC1(C)Cc2c(c(C(=O)Nc3ccc(F)cc3F)cc3nc(Nc4c(Cl)cncc4Cl)[nH]c23)O1]

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.100 g, 0.245 mmol), 2,4-difluoro aniline (0.047 g, 0.364 mmol), trimethyl aluminium (2M solution in toluene) (0.5 mL), dry toluene (5.0 mL) at room temperature to afford 0.035 g of the desired product. ¹HNMR (DMSO-d₆): δ 1.56 (s, 6H), 3.09 (s, 2H), 7.11 (t, J=8.4 Hz, 1H), 7.30 (s, 1H), 7.41 (t, J=8.7 Hz, 1H), 8.39-8.45 (m, 3H), 9.91 (s, 1H), 11.01 (br s, 1H), 11.55 (br s, 1H); MS [M]⁺: 504.22.

Example-198

N-(2-Chloro-4-methylphenyl)-2-((3,5-dichloropyridin-4-yl)amino)-7,7-dimethyl-7,8-dihydro-1H-benzofuro[4,5-d]imidazole-5-carboxamide

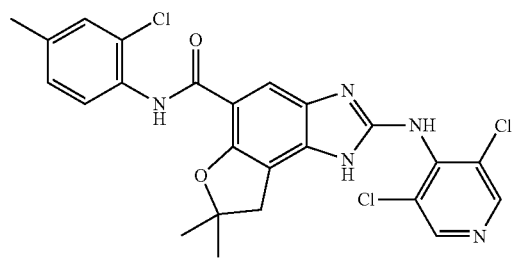 [SMILES: Cc1ccc(NC(=O)c2cc3nc(Nc4c(Cl)cncc4Cl)[nH]c3c3c2OC(C)(C)C3)c(Cl)c1]

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.100 g, 0.245 mmol), 2-chloro-4-methylaniline (0.052 g, 0.361 mmol), trimethyl aluminium (2M solution in toluene) (0.5 mL), dry toluene (5.0 mL) at room temperature to afford 0.030 g of the desired product. ¹HNMR (DMSO-d₆): δ 1.55 (s, 6H), 2.26 (s, 3H), 3.08 (s, 2H), 7.16 (t, J=7.8 Hz, 1H), 7.30 (s, 1H), 7.36 (s, 1H), 8.43 (s, 2H), 8.46 (s, 1H), 10.09 (s, 1H), 10.99 (br s, 1H), 11.52 (br s, 1H); MS [M+H]⁺: 517.97.

Example-199

2-((3,5-Dichloropyridin-4-yl)amino)-7,7-dimethyl-N-(2,4,5-trifluorophenyl)-7,8-dihydro-1H-benzofuro[4,5-d]imidazole-5-carboxamide

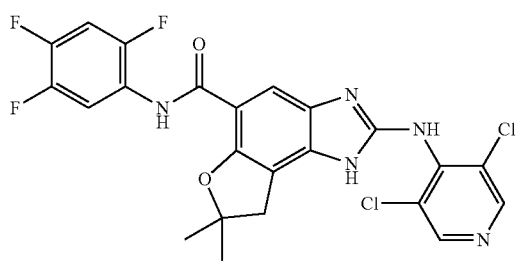 [SMILES: CC1(C)Cc2c(c(C(=O)Nc3cc(F)c(F)cc3F)cc3nc(Nc4c(Cl)cncc4Cl)[nH]c23)O1]

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.250 g, 0.612 mmol), 2,4,5-trifluoroaniline (0.132 g, 0.9025 mmol), trimethyl aluminium (2M solution in toluene) (0.5 mL), dry toluene (10.0 mL) at room temperature to afford 0.210 g of the desired product. ¹HNMR (DMSO-d₆): δ 1.55 (s, 6H), 3.09 (s, 2H), 7.28 (s, 1H), 7.73 (q, J=10.2 Hz, 10.2 Hz, 1H), 8.43 (m, 3H), 10.02 (s, 1H), 11.00 (br s, 1H), 11.48 (br s, 1H); MS [M]⁺: 522.00.

Example-200

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide methanesulfonate To a solution of 2-[(2-chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide (Example-110, 0.100 g) in acetone was added of methanesulphonic acid. The reaction mass was refluxed for 3 h. The reaction mass was filtered and obtained residue was washed with DEE to afford 0.087 g desired product. ¹HNMR (DMSO-d₆): δ 1.60 (s, 6H), 2.31 (d, J=8.4 Hz, 6H), 3.24 (s, 2H), 7.46 (m, 2H), 7.56-7.66 (m, 3H), 7.72 (s, 1H), 8.84 (d, J=6.9 Hz, 1H), 10.24 (s, 1H), 11.0 (br, 2H).

Example-201

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide Sulfate To a solution of 2-[(2-chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide (Example-110, 0.100 g) in acetone was added of sulphuric acid. The reaction mass was refluxed for 3 h. The reaction mass was filtered and obtained residue was washed with DEE to afford 0.081 g desired product. ¹HNMR (DMSO-d₆): δ ¹HNMR (DMSO-d₆): δ 1.60 (s, 6H), 2.33 (s, 3H), 3.24 (s, 2H), 7.47

(m, 2H), 7.58 (m, 3H), 7.72 (s, 1H), 8.85 (d, J=5.4 Hz, 1H), 10.24 (s, 1H), 11.0 (br, 2H); 13 (br s, 1H).

Example-202

2-((2-Chloro-6-methylphenyl)amino)-7,7-dimethyl-N-(2,3,4-trifluorophenyl)-7,8-dihydro-1H-benzofuro[4,5-d]imidazole-5-carboxamide

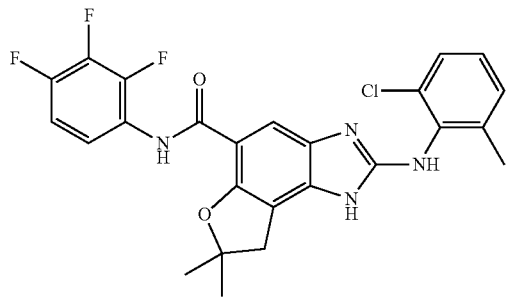 [SMILES: Cc1cccc(Cl)c1Nc1nc2cc(C(=O)Nc3ccc(F)c(F)c3F)c3c(c2[nH]1)CC(C)(C)O3]

The title compound was prepared by following the procedure as described for Example-137 by using methyl 2-[(2-chloro-6-methylphenyl)amino]-7,7-dimethyl-7,8-dihydro-1H-furo[3,2-e]benzimidazole-5-carboxylate (Step-1 of Intermediate-35, 0.200 g, 0.414 mmol) and 2,3,4-trifluoroaniline (0.090 g, 0.602 mmol), trimethyl aluminium (2M solution in toluene) (1 mL) and dry toluene (5.0 mL) to afford 0.100 g of the desired product. $^1$HNMR (DMSO-$d_6$): δ 1.55 (s, 6H), 2.24 (s, 3H), 3.13 (s, 2H), 7.25-7.43 (m, 4H), 7.52 (s, 1H), 8.24 (m, 1H), 9.10 (m, 1H), 10.06 (s, 1H), 10.96 (m, 1H): MS [M+H]$^+$: 501.04.

Example-203

N-(5-Cyclopropyl-2-fluorophenyl)-2-((3,5-dichloropyridin-4-yl)amino)-7,7-dimethyl-7,8-dihydro-1H-benzofuro[4,5-d]imidazole-5-carboxamide

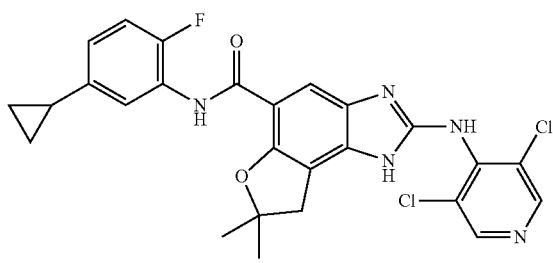 [SMILES: CC1(C)Cc2c(c(C(=O)Nc3cc(C4CC4)ccc3F)cc3nc(Nc4c(Cl)cncc4Cl)[nH]c23)O1]

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.100 g, 0.245 mmol), 5-cyclopropyl-2-fluoroaniline (0.053 g, 0.357 mmol), trimethyl aluminium (2M solution in toluene) (0.5 mL), dry toluene (5.0 mL) at room temperature to afford 0.075 g of the desired product. $^1$HNMR (DMSO-$d_6$): δ 0.62 (d, J=6.3 Hz, 2H), 0.95 (d, J=8.4 Hz, 2H), 1.55 (s, 6H), 1.91 (m, 1H), 3.09 (s, 2H), 6.82 (m, 1H), 7.17 (t, J=10.5 Hz, 1H), 7.30 (s, 1H), 8.19 (d, J=5.7 Hz, 1H), 8.45 (s, 2H), 9.95 (s, 1H), 10.99 (s, 1H), 11.56 (br s, 1H); MS [M+H]$^+$: 526.12.

Example-204

N-(5-Chloro-3-fluoropyridin-2-yl)-2-((2-chloro-6-methylphenyl)amino)-7,7-dimethyl-7,8-dihydro-1H-benzofuro[4,5-d]imidazole-5-carboxamide

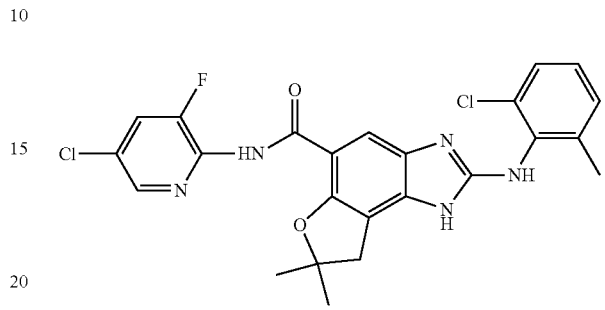

The title compound was prepared by following the same procedure described for Example-108 by using 2-[(2-Chloro-6-methylphenyl)amino]-7,7-dimethyl-7,8 dihydro-1H-furo[3,2-e]benzimidazole-5-carboxylic acid (Intermediate-35, 0.200 g, 0.536 mmol), 2-amino-5-chloro-3-fluoropyridine 1-oxide (Intermediate-43, 0.104 g, 0.643 mmol), thionyl chloride (2 mL), DIPEA (2 mL), benzene (5.0 mL). To a solution of obtained crude product (0.200 g) in acetic acid (10.0 mL) was added iron powder (0.200 g). The reaction mass was stirred at 80° C. for 2-3 h. Excess of Iron powder was separated. The reaction mass was diluted with water, it was extracted with ethyl acetate. The reaction mass was filtered through celite bed and organic layer was separated, dried over anhydrous sodium sulphate and concentrated. The obtained crude was purified by column chromatography on basic alumina eluting with 1.5-2.0% MeOH:DCM to afford 0.021 g of the desired product. $^1$HNMR (DMSO-$d_6$): $^1$HNMR (DMSO-$d_6$): δ 1.52 (s, 6H), 2.23 (s, 3H), 3.10 (s, 2H), 7.23-7.31 (m, 2H), 7.40 (d, J=7.8 Hz, 1H), 7.47 (s, 1H), 8.14 (d, J=9.6 Hz, 1H), 8.33 (s, 1H), 9.07 (br s, 1H), 9.84 (s, 1H), 10.92 (brs, 1H); MS [M+H]$^+$: 500.12.

Example-205

N-(5-Chloro-3-fluoropyridin-2-yl)-2-((2,6-dichlorophenyl)amino)-7,7-dimethyl-7,8-dihydro-1H-benzofuro[4,5-d]imidazole-5-carboxamide

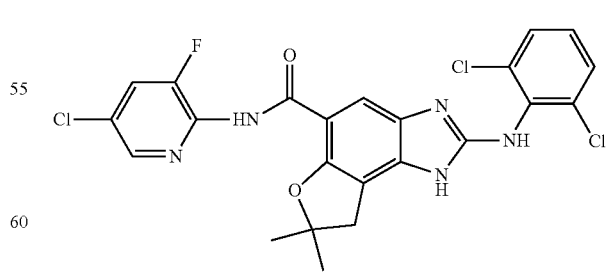

The title compound was prepared by following the same procedure described for Example-65 by using 2-[(2,6-Dichlorophenyl)amino]-7,7-dimethyl-7,8-dihydro-1H-furo[3,2-e]benzimidazole-5-carboxylic acid (Intermediate-6, 0.200 g, 0.51 mmol), thionyl chloride (1.0 mL), 2-amino-5-chloro-3-fluoropyridine 1-oxide (Intermediate-43, 0.099 g, 0.612 mmol), DIPEA (2 mL), THF (5.0 mL). To a solution of obtained crude product (0.200 g) in acetic acid (10.0 mL) was added iron powder (0.200 g). The reaction mass was stirred at 80° C. for 2-3 h. Excess of Iron powder was separated. The reaction mass was diluted with water, it was extracted with ethyl acetate. The reaction mass was filtered through celite bed and organic layer was separated, dried over anhydrous sodium sulphate and concentrated. The obtained crude was purified by column chromatography on basic alumina eluting with 1.5-2.0% MeOH:DCM to afford 0.025 g of the desired product. $^1$HNMR (DMSO-d$_6$): δ 1.54 (s, 6H), 3.09 (s, 2H), 7.25 (m, 1H), 7.38 (m, 1H), 7.53 (d, J=7.8 Hz, 2H), 8.16 (d, J=9.6 Hz, 1H), 8.36 (s, 1H), 9.82 (s, 1H), 11.00 (br s, 2H); MS [M]$^+$: 522.02.

Example-206

2-[(2-Chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide Hydrochloride The title compound was prepared following the procedure described for Example-146 by using 2-[(2-chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide (Example-104, 0.100 g), THF, conc.HCl to afford 0.065 g of the desired product. $^1$HNMR (DMSO-d$_6$): δ 1.58 (s, 6H), 3.19 (s, 2H), 7.50-7.63 (m, 4H), 7.88 (m, 2H), 8.30 (d, J=4.2 Hz, 1H), 9.98 (s, 1H), 11.50 (br s, 1H), 12.70 (br s, 2H).

Example-207

2-[(2-Chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide Methanesulfonate The title compound was prepared following the procedure described for Example-169 by using 2-[(2-chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide (Example-104, 0.100 g), acetone, methanesulphonic acid to afford 0.071 g of the desired product. $^1$HNMR (DMSO-d$_6$): δ 1.58 (s, 6H), 2.34 (s, 3H), 3.21 (s, 2H), 7.51-7.66 (m, 5H), 7.89 (m, 1H), 8.30 (m, 1H), 9.99 (s, 1H), 11.20 (br s, 1H), 13.20 (br s, 2H).

Example-208

2-((3,5-Dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide Hydrochloride The title compound was prepared following the procedure described for Example-146 by using 2-((3,5-dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide (Example-196, 0.100 g), THF, conc.HCl to afford 0.057 g of the desired product. $^1$HNMR (DMSO-d$_6$): δ 1.58 (s, 6H), 3.11 (s, 2H), 7.38 (s, 1H), 7.52 (t, J=5.4 Hz, 1H), 7.68 (m, 1H), 8.30 (d, J=10.2 Hz, 1H), 8.59 (s, 2H), 9.90 (s, 1H), 12.00 (br s, 4H).

Example-209

2-((3,5-Dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide methanesulfonate The title compound was prepared following the procedure described for Example-169 by using 2-((3,5-dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide (Example-196, 0.100 g), acetone, methanesulphonic acid to afford 0.051 g of the desired product. $^1$HNMR (DMSO-d$_6$): δ 1.58 (s, 6H), 2.31 (s, 6H), 3.10 (s, 2H), 7.35 (s, m1H), 7.52 (t, J=9.9 Hz, 1H), 7.86 (m, 1H), 8.29 (m, 1H), 8.56 (s, 2H), 9.88 (s, 1H), 11-12.00 (br s, 4H).

Example-210

2-[(2,6-Dichlorophenyl)amino]-7,7-dimethyl-N-[5-(trifluoromethyl)pyridin-2-yl]-7,8-dihydro-1H-furo[3,2-e]benzimidazole-5-carboxamide hydrochloride The title compound was prepared following the procedure described for Example-146 by using 2-[(2,6-Dichlorophenyl)amino]-7,7-dimethyl-N-[5-(trifluoromethyl)pyridin-2-yl]-7,8-dihydro-1H-furo[3,2-e]benzimidazole-5-carboxamide (Example-101, 0.100 g), THF, conc.HCl to afford 0.045 g of the desired product. $^1$HNMR (DMSO-d$_6$): δ 1.60 (s, 6H), 3.25 (s, 2H), 7.58 (m, 1H), 7.75 (m, 3H), 8.28 (d, 1H), 8.46 (d, J=8.7 Hz, 1H), 8.78 (s, 1H), 10.42 (s, 1H), 12.00 (s, 1H), 13.20 (s, 2H).

Example-211

2-[(2,6-Dichlorophenyl)amino]-7,7-dimethyl-N-[5-(trifluoromethyl)pyridin-2-yl]-7,8-dihydro-1H-furo[3,2-e]benzimidazole-5-carboxamide Methanesulfonate The title compound was prepared following the procedure described for Example-169 by using 2-[(2,6-dichlorophenyl)amino]-7,7-dimethyl-N-[5-(trifluoromethyl)pyridin-2-yl]-7,8-dihydro-1H-furo[3,2-e]benzimidazole-5-carboxamide (Example-101, 0.100 g), acetone, methanesulphonic acid to afford 0.059 g of the desired product. $^1$HNMR (DMSO-d$_6$): δ 1.60 (s, 6H), 2.38 (s, 3H), 3.25 (s, 2H), 7.61 (m, 1H), 7.77 (m, 3H), 8.27 (d, J=7.3 Hz, 1H), 8.46 (d, J=8.7 Hz, 1H), 8.79 (s, 1H), 10.42 (s, 1H), 11.50 (br s, 1H), 13.00 (br s, 2H).

Example-212

2-((3,5-Dichloropyridin-4-yl)amino)-7,7-dimethyl-N-(2,3,4-trifluorophenyl)-7,8-dihydro-1H-benzofuro[4,5-d]imidazole-5-carboxamide

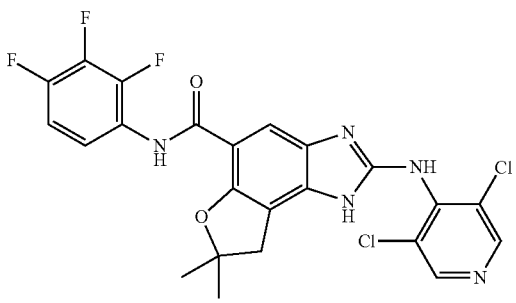 [SMILES: CC1(C)Cc2c(c(C(=O)Nc3ccc(F)c(F)c3F)cc3nc(Nc4c(Cl)cncc4Cl)[nH]c23)O1]

The title compound was prepared following the procedure described for Example-137 by using methyl 2-[(3,5-dichloropyridin-4-yl)amino]-7,7-dimethyl-7,8-dihydro-1H-furo[3,2-e]benzimidazole-5-carboxylate (Step-1 of Intermediate-3, 0.100 g, 0.245 mmol), 2,3,4-trifluoroaniline (0.078 g, 0.530 mmol), trimethyl aluminium (2M solution in toluene) (0.5 mL), dry toluene (5.0 mL) at room temperature to afford 0.075 g of the desired product. $^1$HNMR (DMSO-$d_6$): δ 1.57 (s, 6H), 3.09 (s, 2H), 7.28-7.39 (m, 2H), 8.15 (m, 1H), 8.45 (s, 2H), 9.92 (s, 1H), 11.02 (br s, 1H), 11.58 (br s, 1H); MS [M+H]$^+$: 521.93.

Example-213

2-((3,5-Dichloropyridin-4-yl)amino)-N-(4-fluoro-3-(trifluoromethyl)phenyl)-1,7,7-trimethyl-7,8-dihydro-1H-benzofuro[4,5-d]imidazole-5-carboxamide

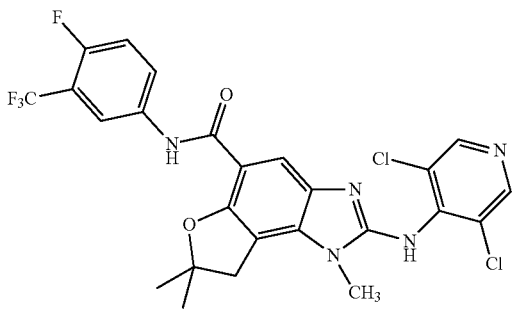 [SMILES: Cn1c(Nc2c(Cl)cncc2Cl)nc2cc(C(=O)Nc3ccc(F)c(C(F)(F)F)c3)c3c(c21)CC(C)(C)O3]

The title compound was prepared following the procedure described for Example-143 by using methyl 2-((3,5-dichloropyridin-4-yl)amino)-1,7,7-trimethyl-7,8-dihydro-1H-benzofuro[4,5-d]imidazole-5-carboxylate (Intermediate-60, 0.100 g, 0.237 mmol), 4-fluoro-3-(trifluoromethyl) aniline (0.063 g, 0.356 mmol), trimethyl aluminium (2M solution in toluene) (0.5 mL), dry toluene (5.0 mL) to afford 0.070 g of the desired product. $^1$HNMR (DMSO-$d_6$): δ 1.60 (s, 6H), 3.48 (s, 2H), 3.59 (s, 3H), 7.22 (s, 1H), 7.51 (t, J=9.9 Hz, 1H), 7.85-7.88 (m, 1H), 8.30 (m, 1H), 8.47 (s, 2H), 9.87 (s, 1H), 10.90 (s, 1H); MS [M]$^+$: 568.03.

Example-214

2-((3,5-Dichloropyridin-4-yl)amino)-1,7,7-trimethyl-N-(3-(trifluoromethyl)phenyl)-7,8-dihydro-1H-benzofuro[4,5-d]imidazole-5-carboxamide

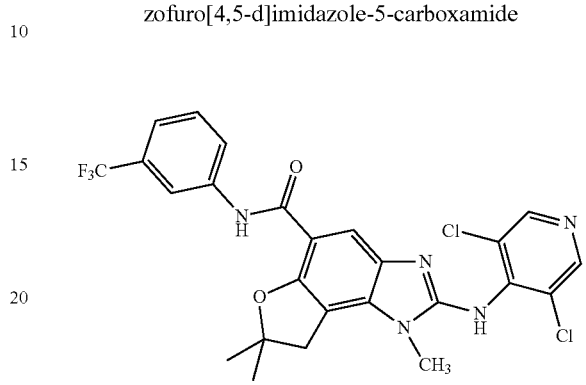

The title compound was prepared following the procedure described for Example-143 by using methyl 2-((3,5-dichloropyridin-4-yl)amino)-1,7,7-trimethyl-7,8-dihydro-1H-benzofuro[4,5-d]imidazole-5-carboxylate (Intermediate-60, 0.100 g, 0.237 mmol), 3-(trifluoromethyl) aniline (0.057 g, 0.356 mmol), trimethyl aluminium (2M solution in toluene) (0.5 mL), dry toluene (5.0 mL) to afford 0.050 g of the desired product. $^1$HNMR (DMSO-$d_6$): δ 1.61 (s, 6H), 3.49 (s, 2H), 3.59 (s, 3H), 7.24 (s, 1H), 7.45 (d, J=7.8 Hz, 1H), 7.59 (t, J=7.8 Hz, 1H), 7.78 (d, J=8.4 Hz, 1H), 8.31 (s, 1H), 8.47 (s, 2H), 9.90 (s, 1H), 10.91 (s, 1H); MS [M]$^+$: 550.11.

Example-215

2-((3,5-dichloropyridin-4-yl)amino)-1,7,7-trimethyl-N-(4-(trifluoromethyl)phenyl)-7,8-dihydro-1H-benzofuro[4,5-d]imidazole-5-carboxamide

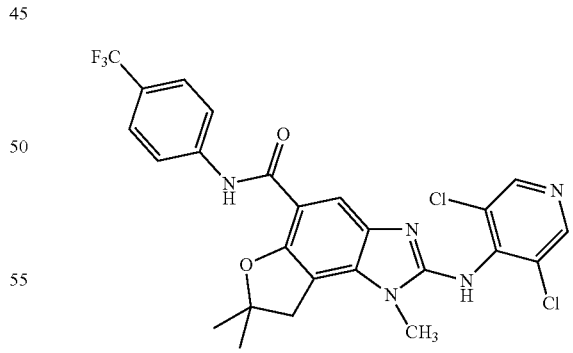

The title compound was prepared following the procedure described for Example-143 by using methyl 2-((3,5-dichloropyridin-4-yl)amino)-1,7,7-trimethyl-7,8-dihydro-1H-benzofuro[4,5-d]imidazole-5-carboxylate (Intermediate-60, 0.100 g, 0.237 mmol), 4-(trifluoromethyl) aniline (0.057 g, 0.356 mmol), trimethyl aluminium (2M solution in toluene) (0.5 mL), dry toluene (5.0 mL) to afford 0.075 g of the desired product. $^1$HNMR (DMSO-$d_6$): δ 1.61 (s, 6H), 3.49 (s, 2H), 3.60 (s, 3H), 7.25 (s, 1H), 7.71 (d, J=8.1 Hz, 2H), 7.91 (t, J=8.1 Hz, 2H), 8.47 (s, 2H), 9.94 (s, 1H), 10.91 (s, 1H); MS [M+]+: 550.29.

Example-216

N-(4-Cyclopropylphenyl)-2-((3,5-dichloropyridin-4-yl)amino)-1,7,7-trimethyl-7,8-dihydro-1H-benzofuro[4,5-d]imidazole-5-carboxamide

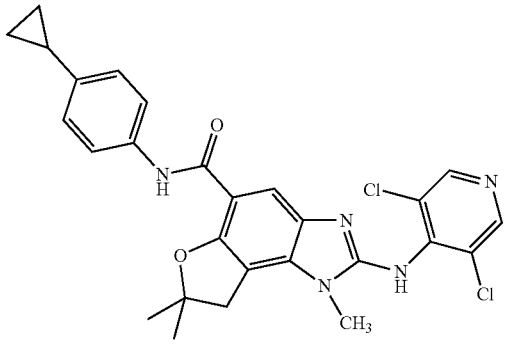 [SMILES: Cn1c(Nc2c(Cl)cncc2Cl)nc2cc(C(=O)Nc3ccc(C4CC4)cc3)c3c(c21)CC(C)(C)O3]

The title compound was prepared following the procedure described for Example-143 by using methyl 2-((3,5-dichloropyridin-4-yl)amino)-1,7,7-trimethyl-7,8-dihydro-1H-benzofuro[4,5-d]imidazole-5-carboxylate (Intermediate-60, 0.100 g, 0.245 mmol), 4-cyclopropylaniline (Intermediate-50, 0.047 g, 0.356 mmol), trimethyl aluminium (2M solution in toluene) (0.5 mL), dry toluene (5.0 mL) to afford 0.045 g of the desired product. $^1$HNMR (DMSO-$d_6$): δ 0.63 (m, 2H), 0.91 (d, J=6.6 Hz, 2H), 1.60 (s, 6H), 1.89 (m, 1H), 3.48 (s, 2H), 3.59 (s, 3H), 7.05 (d, J=7.8 Hz, 2H), 7.26 (s, 1H), 7.54 (d, J=8.1 Hz, 2H), 8.46 (s, 2H), 9.61 (br s, 1H), 10.88 (br s, 1H); MS [M−H]−: 520.06.

Example-217

N-(5-Cyclopropyl-2-fluorophenyl)-2-((3,5-dichloropyridin-4-yl)amino)-1,7,7-trimethyl-7,8-dihydro-1H-benzofuro[4,5-d]imidazole-5-carboxamide

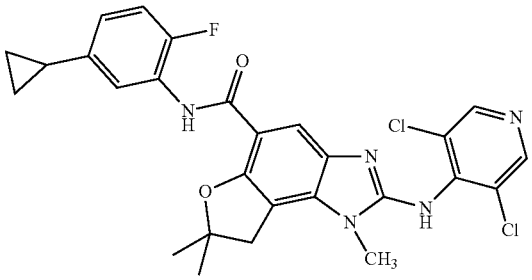 [SMILES: Cn1c(Nc2c(Cl)cncc2Cl)nc2cc(C(=O)Nc3cc(C4CC4)ccc3F)c3c(c21)CC(C)(C)O3]

The title compound was prepared following the procedure described for Example-143 by using methyl 2-((3,5-dichloropyridin-4-yl)amino)-1,7,7-trimethyl-7,8-dihydro-1H-benzofuro[4,5-d]imidazole-5-carboxylate (Intermediate-60, 0.100 g, 0.245 mmol), 5-cyclopropyl-2-fluoroaniline (Intermediate-47, 0.080 g, 0.529 mmol), trimethyl aluminium (2M solution in toluene) (0.5 mL), dry toluene (5.0 mL) to afford 0.042 g of the desired product. $^1$HNMR (DMSO-$d_6$): δ 0.62 (d, J=5.4 Hz, 2H), 0.94 (d, J=8.4 Hz, 2H), 1.59 (s, 6H), 1.93 (m, 1H), 3.51 (s, 2H), 3.59 (s, 3H), 6.82 (m, 1H), 7.18 (t, J=8.7 Hz, 1H), 7.29 (s, 1H), 8.18 (d, J=7.2 Hz, 1H), 8.47 (s, 2H), 9.99 (br s, 1H), 10.92 (br s, 1H); MS [M]+: 540.20.

Example-218

2-((3,5-Dichloropyridin-4-yl)amino)-N-(2-fluoro-5-(trifluoromethyl)phenyl)-1,7,7-trimethyl-7,8-dihydro-1H-benzofuro[4,5-d]imidazole-5-carboxamide

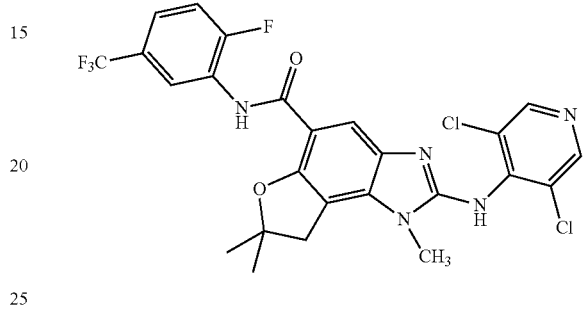

The title compound was prepared following the procedure described for Example-143 by using methyl 2-((3,5-dichloropyridin-4-yl)amino)-1,7,7-trimethyl-7,8-dihydro-1H-benzofuro[4,5-d]imidazole-5-carboxylate (Intermediate-60, 0.100 g, 0.245 mmol), 2-fluoro-5-(trifluoromethyl)aniline (0.065 g, 0.363 mmol), trimethyl aluminium (2M solution in toluene) (0.5 mL), dry toluene (5.0 mL) to afford 0.048 g of the desired product. $^1$HNMR (DMSO-$d_6$): δ 1.60 (s, 6H), 3.52 (s, 2H), 3.60 (s, 3H), 7.29 (s, 1H), 7.53-7.63 (m, 2H), 8.48 (s, 2H), 8.86 (d, J=5.4 Hz, 1H), 10.22 (m, 1H), 10.94 (s, 1H); MS [M]+: 568.08.

Example-219

2-((3,5-Dichloropyridin-4-yl)amino)-1,7,7-trimethyl-N-(5-(trifluoromethyl)pyridin-2-yl)-7,8-dihydro-1H-benzofuro[4,5-d]imidazole-5-carboxamide

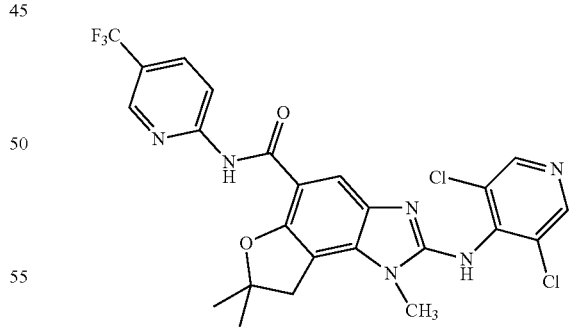

The title compound was prepared by following the same procedure described for Example-205 by using 2-((3,5-dichloropyridin-4-yl)amino)-1,7,7-trimethyl-7,8-dihydro-1H-benzofuro[4,5-d]imidazole-5-carboxylic acid (Intermediate-61, 0.200 g, 0.491 mmol), 2-Amino-5-(trifluoromethyl) pyridine 1-oxide (Intermediate-41, 0.131 g, 0.737 mmol), thionyl chloride (2 mL), DIPEA (10 mL), THF (5.0 mL), acetic acid (10.0 mL), iron powder (0.200 g) to afford 0.025 g of the desired product. $^1$HNMR (DMSO-$d_6$): δ 1.61 (s, 6H), 3.52 (s, 2H), 3.60 (s, 3H), 7.31 (s, 1H), 8.23 (d, J=10.5 Hz, 1H), 8.44 (s, 1H), 8.48 (s, 2H), 8.76 (s, 1H), 10.40 (s, 1H), 10.93 (s, 1H); MS [M]$^+$: 551.07.

Example-220

N-(Cyclopropylmethyl)-2-((3,5-dichloropyridin-4-yl)amino)-1,7,7-trimethyl-7,8-dihydro-1H-benzofuro[4,5-d]imidazole-5-carboxamide

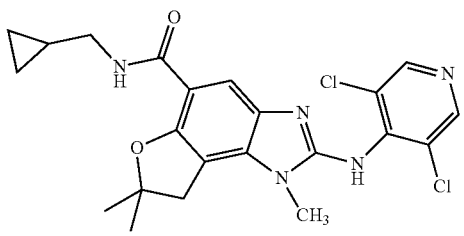 [SMILES: Cn1c(Nc2c(Cl)cncc2Cl)nc2cc(C(=O)NCC3CC3)c3c(c21)CC(C)(C)O3]

The title compound was prepared following the procedure described for Example-1 by using 2-((3,5-dichloropyridin-4-yl)amino)-1,7,7-trimethyl-7,8-dihydro-1H-benzofuro[4,5-d] imidazole-5-carboxylic acid (Intermediate-61, 0.100 g, 0.245 mmol), cyclopropylmethanamine (0.025 g, 0.363 mmol), TBTU (0.157 g, 0.49 mmol), DMF (5 mL), THF (3 mL) to afford 0.021 g of the desired product. $^1$HNMR (DMSO-d$_6$): δ 0.22 (d, J=4.2 Hz, 2H), 0.44 (d, J=6.6 Hz, 2H), 1.02 (m, 1H), 1.54 (s, 6H), 3.19 (m, 2H), 3.44 (s, 2H), 3.56 (s, 3H), 7.22 (s, 1H), 7.80 (m, 1H), 8.45 (s, 2H), 10.79 (s, 1H); MS [M+]$^+$: 459.03.

Pharmacological Activity

In-Vitro Protocol for Screening of mPGES-1 Inhibitors:

mPGES-1 (microsomal prostaglandin E synthase-1) is a microsomal enzyme that converts endoperoxide substrate PGH$_2$ (prostaglandin H$_2$) to product PGE$_2$ (prostaglandin E$_2$) by isomerization in the presence of reduced glutathione (GSH). mPGES-1 inhibitors were screened by assessing their ability to inhibit formation of PGE$_2$ from PGH$_2$ in presence of mPGES-1 using anti-PGE$_2$ antibody based detection method. Recombinant human mPGES-1 was generated in-house by expressing in CHO cells (Ouellet M et al. (2002), Protein Expression and Purification 26: 489-495). Assay was set up using crude microsomal fractions at protein concentration of 40-60 µg/mL. Test compounds were prepared in 100% dimethyl sulfoxide (DMSO) to obtain 20 mM stock solution and then diluted using assay buffer comprising 0.1 M Potassium phosphate buffer with 2 mM EDTA. Final concentration of DMSO in reaction was 0.5% (v/v). Negative controls comprised of all assay reagents except the enzyme. Positive controls comprised of enzyme reaction in the absence of any inhibitor. Test compounds were incubated for 10 minutes in assay buffer containing 2.5 mM GSH and mPGES-1 enzyme followed by addition of PGH$_2$ at a concentration of 15 µM for 1 minute. Reaction was stopped by addition of Stannous chloride (11 mg/ml) and PGE$_2$ levels were measured (Masse F et al. (2005), Journal of Biomolecular Screening 10(6) 599-605, Goedken R E et al. (2008), Journal of Biomolecular Screening 13(7): 619-625) by HTRF kit (CisBio).

Inhibition of mPGES-1 enzyme activity was measured using percent of reaction occurring in the positive control. Concentration response curves were plotted using percent inhibition of maximum enzyme reaction. IC$_{50}$ value was calculated from concentration response curve by nonlinear regression analysis using GraphPad PRISM software.

The compounds prepared were tested using the above assay procedure and the results obtained are given in Table 1. Percentage inhibition at concentrations of 1.0 µM and 10.0 µM are given in the table along with IC$_{50}$ (nM) details for selected examples. The compounds prepared were tested using the above assay procedure and were found to have IC$_{50}$ less than 200 nM, preferably less than 100 nM, more preferably less than 50 nM or most preferably less than 20 nM.

The IC$_{50}$ (nM) values of the compounds are set forth in Table 1 wherein "A" refers to an IC$_{50}$ value of less than 50 nM, "B" refers to IC$_{50}$ value in range of 50.01 to 100.0 nM and "C" refers to IC$_{50}$ values more than 100 nM.

TABLE 1

| Sr. No. | Example No. | Percentage inhibition at 1 µM | Percentage inhibition at 10 µM | IC$_{50}$ (nM) |
|---|---|---|---|---|
| 1 | Example-1 | 97.97 | 97.83 | A |
| 2 | Example-2 | 97.01 | 99.60 | A |
| 3 | Example-3 | 99.13 | 99.51 | A |
| 4 | Example-4 | 94.40 | 94.98 | A |
| 5 | Example-5 | 97.70 | 97.81 | A |
| 6 | Example-6 | 93.41 | 95.46 | A |
| 7 | Example-7 | 100.00 | 96.20 | A |
| 8 | Example-8 | 92.62 | 90.14 | A |
| 9 | Example-9 | 82.97 | 83.06 | A |
| 10 | Example-10 | 83.38 | 91.77 | A |
| 11 | Example-11 | 100.00 | 100.00 | A |
| 12 | Example-11 | 97.45 | 100.00 | A |
| 13 | Example-13 | 94.23 | 97.53 | A |
| 14 | Example-14 | 100.00 | 100.00 | A |
| 15 | Example-15 | 97.45 | 95.49 | A |
| 16 | Example-16 | 73.48 | 94.90 | |
| 17 | Example-17 | 98.05 | 96.08 | A |
| 18 | Example-18 | 98.37 | 99.78 | A |
| 19 | Example-19 | 97.80 | 98.27 | A |
| 20 | Example-20 | 10.48 | 44.93 | — |
| 21 | Example-21 | 96.78 | 99.82 | A |
| 22 | Example-22 | 85.77 | 98.82 | C |
| 23 | Example-23 | 94 | 97.11 | A |
| 24 | Example-24 | 95.26 | 95.03 | A |
| 25 | Example-25 | 91.98 | 98.21 | A |
| 26 | Example-26 | 90.15 | 97.78 | A |
| 27 | Example-27 | 93.73 | 93.00 | A |
| 28 | Example-28 | 87.32 | 98.90 | C |
| 29 | Example-29 | 92.97 | 91.28 | A |
| 30 | Example-30 | 93.76 | 92.49 | A |
| 31 | Example-31 | 87.44 | 99.17 | A |
| 32 | Example-32 | 99.03 | 100.00 | A |
| 33 | Example-33 | 95.49 | 99.07 | A |
| 34 | Example-34 | 95.55 | 98.73 | A |
| 35 | Example-35 | 89.28 | 99.08 | B |
| 36 | Example-36 | 92.39 | 99.33 | C |
| 37 | Example-37 | 99.42 | 100.00 | A |
| 38 | Example-38 | 74.51 | 81.54 | — |
| 39 | Example-39 | 92.47 | 70.72 | A |
| 40 | Example-40 | 88.71 | 94.56 | A |
| 41 | Example-41 | 99.23 | 95.70 | A |
| 42 | Example-42 | 83.17 | 89.90 | A |
| 43 | Example-43 | 43.82 | 72.33 | A |
| 44 | Example-44 | 97.27 | 99.01 | A |
| 45 | Example-45 | 95.21 | 99.35 | A |
| 46 | Example-46 | 100.00 | 100.00 | A |
| 47 | Example-47 | 95.28 | 95.58 | A |
| 48 | Example-48 | 70.78 | 96.69 | — |
| 49 | Example-49 | 91.61 | 96.09 | A |
| 50 | Example-50 | 89.23 | 99.33 | B |
| 51 | Example-51 | 96.86 | 99.39 | A |
| 52 | Example-52 | 94.26 | 96.03 | A |
| 53 | Example-53 | 47.17 | 85.38 | — |
| 54 | Example-54 | 79.24 | 92.75 | — |
| 55 | Example-55 | 91.83 | 94.21 | C |
| 56 | Example-56 | 96.05 | 98.15 | A |
| 57 | Example-57 | 61.66 | 88.24 | — |

TABLE 1-continued

| Sr. No. | Example No. | Percentage inhibition at 1 µM | 10 µM | IC$_{50}$ (nM) |
|---|---|---|---|---|
| 58 | Example-58 | 63.29 | 95.44 | — |
| 59 | Example-59 | 96.76 | 98.11 | A |
| 60 | Example-60 | 93.14 | 98.08 | A |
| 61 | Example-61 | 6.50 | 69.85 | — |
| 62 | Example-62 | 96.77 | 94.33 | A |
| 63 | Example-63 | 88.04 | 96.56 | B |
| 64 | Example-64 | 99.18 | 97.40 | A |
| 65 | Example-65 | 98.78 | 93.10 | A |
| 66 | Example-66 | 96.43 | 95.16 | A |
| 67 | Example-67 | 92.82 | 96.17 | A |
| 68 | Example-68 | 97.56 | 98.46 | A |
| 69 | Example-69 | 86.15 | 97.97 | A |
| 70 | Example-70 | 69.10 | 88.24 | — |
| 71 | Example-71 | 93.86 | 98.38 | A |
| 72 | Example-72 | 93.15 | 93.72 | A |
| 73 | Example-73 | 95.00 | 88.87 | A |
| 74 | Example-74 | 93.40 | 94.71 | B |
| 75 | Example-75 | 94.77 | 94.97 | A |
| 76 | Example-76 | 95.77 | 99.60 | A |
| 77 | Example-77 | 93.11 | 89.94 | A |
| 78 | Example-78 | 88.45 | 96.36 | A |
| 79 | Example-79 | 97.44 | 91.87 | B |
| 80 | Example-80 | 93.18 | 91.96 | A |
| 81 | Example-81 | 92.10 | 99.41 | A |
| 82 | Example-82 | 94.08 | 97.58 | A |
| 83 | Example-83 | 87.69 | 89.35 | A |
| 84 | Example-84 | 93.68 | 94.42 | A |
| 85 | Example-85 | 93.30 | 95.39 | B |
| 86 | Example-86 | 94.97 | 98.66 | A |
| 87 | Example-87 | 87.39 | 92.15 | A |
| 88 | Example-88 | 85.51 | 99.40 | C |
| 89 | Example-89 | 97.14 | 97.10 | A |
| 90 | Example-90 | 97.66 | 98.36 | A |
| 91 | Example-91 | 43.94 | 60.16 | — |
| 92 | Example-92 | 75.39 | 75.96 | — |
| 93 | Example-93 | 83.12 | 80.91 | A |
| 94 | Example-94 | 66.05 | 76.39 | — |
| 95 | Example-95 | 90.62 | 91.85 | A |
| 96 | Example-96 | 90.39 | 95.09 | A |
| 97 | Example-97 | 96.65 | 95.33 | A |
| 98 | Example-98 | 12.01 | 13.86 | — |
| 99 | Example-99 | 95.29 | 99.67 | A |
| 100 | Example-100 | 96.63 | 95.60 | A |
| 101 | Example-101 | 97.58 | 98.00 | A |
| 102 | Example-102 | 19.34 | 22.83 | — |
| 103 | Example-103 | 7.88 | 25.84 | — |
| 104 | Example-104 | 100.00 | 91.95 | A |
| 105 | Example-105 | 91.22 | 95.52 | C |
| 106 | Example-106 | 9.35 | 46.23 | — |
| 107 | Example-107 | 96.80 | 94.42 | A |
| 108 | Example-108 | 93.91 | 96.32 | A |
| 109 | Example-109 | 93.79 | 98.82 | B |
| 110 | Example-110 | 96.64 | 97.20 | A |
| 111 | Example-111 | 96.37 | 99.82 | A |
| 112 | Example-112 | 96.85 | 96.16 | A |
| 113 | Example-113 | 99.44 | 98.67 | A |
| 114 | Example-114 | 99.37 | 99.10 | A |
| 115 | Example-115 | 100.00 | 100.00 | A |
| 116 | Example-116 | 96.90 | 99.81 | A |
| 117 | Example-117 | 100.00 | 98.68 | A |
| 118 | Example-118 | 97.01 | 98.71 | C |
| 119 | Example-119 | 98.10 | 100.00 | A |
| 120 | Example-120 | 90.48 | 99.04 | A |
| 121 | Example-121 | 100.00 | 100.00 | A |
| 122 | Example-122 | 96.05 | 98.14 | A |
| 123 | Example-123 | 91.11 | 98.94 | A |
| 124 | Example-124 | 97.06 | 100.00 | A |
| 125 | Example-125 | 10.55 | 76.73 | — |
| 126 | Example-126 | 96.57 | 97.65 | A |
| 127 | Example-127 | 94.71 | 99.03 | A |
| 128 | Example-128 | 90.52 | 93.97 | A |
| 129 | Example-129 | 88.28 | 97.09 | A |
| 130 | Example-130 | 74.61 | 96.81 | — |
| 131 | Example-131 | 96.89 | 98.10 | A |
| 132 | Example-132 | 92.41 | 98.04 | A |
| 133 | Example-133 | 91.36 | 96.50 | A |
| 134 | Example-134 | 99.94 | 99.37 | A |
| 135 | Example-135 | 97.49 | 98.64 | A |
| 136 | Example-136 | 89.41 | 96.94 | A |
| 137 | Example-137 | 95.34 | 100.00 | A |
| 138 | Example-138 | 95.05 | 96.79 | A |
| 139 | Example-139 | 95.91 | 99.18 | A |
| 140 | Example-140 | 97.06 | 98.90 | A |
| 141 | Example-141 | 96.39 | 98.56 | A |
| 142 | Example-142 | 97.91 | 97.50 | A |
| 143 | Example-143 | 19.63 | 39.18 | — |
| 144 | Example-144 | 37.28 | 46.01 | — |
| 145 | Example-145 | 59.47 | 60.37 | — |
| 146 | Example-153 | 100.00 | 99.86 | A |
| 147 | Example-154 | 99.83 | 100.00 | A |
| 148 | Example-155 | 87.89 | 99.83 | C |
| 149 | Example-156 | 33.06 | 92.16 | — |
| 150 | Example-157 | 98.93 | 99.65 | A |
| 151 | Example-158 | 76.98 | 97.43 | — |
| 152 | Example-159 | 98.93 | 99.96 | A |
| 153 | Example-160 | 99.23 | 99.98 | B |
| 154 | Example-161 | 79.17 | 87.96 | C |
| 155 | Example-162 | 62.27 | 80.82 | — |
| 156 | Example-163 | 62.76 | 96.87 | — |
| 157 | Example-164 | 93.46 | 94.53 | A |
| 158 | Example-165 | 99.37 | 98.14 | A |
| 159 | Example-166 | 97.65 | 99.56 | A |
| 160 | Example-167 | 96.91 | 98.27 | A |
| 161 | Example-168 | 92.45 | 97.66 | A |
| 162 | Example-177 | 80.78 | 89.38 | A |
| 163 | Example-178 | 91.38 | 98.23 | A |
| 164 | Example-179 | 93.66 | 97.37 | A |
| 165 | Example-180 | 98.74 | 97.32 | A |
| 166 | Example-181 | 89.46 | 93.92 | A |
| 167 | Example-182 | 84.62 | 95.25 | C |
| 168 | Example-183 | 97.52 | 93.1 | A |
| 169 | Example-184 | 96.89 | 95.93 | A |
| 170 | Example-185 | 94.39 | 98.48 | A |
| 171 | Example-186 | 98.61 | 98.54 | A |
| 172 | Example-187 | 95.79 | 83.02 | A |
| 173 | Example-188 | 98.12 | 99.39 | B |
| 174 | Example-189 | 53.85 | 91.13 | — |
| 175 | Example-190 | 81.16 | 89.48 | C |
| 176 | Example-191 | 96.10 | 96.35 | A |
| 177 | Example-192 | 97.09 | 96.51 | A |
| 178 | Example-193 | 96.37 | 94.74 | A |
| 179 | Example-194 | 99.16 | 100 | A |
| 180 | Example-195 | 98.83 | 98.99 | A |
| 181 | Example-196 | 100 | 98.83 | A |
| 182 | Example-197 | 99.57 | 99.45 | A |
| 183 | Example-198 | 98.72 | 99.74 | A |
| 184 | Example-199 | 99.36 | 100.00 | A |
| 185 | Example-202 | 95.14 | 100 | A |
| 186 | Example-203 | 100 | 94.77 | A |
| 187 | Example-204 | 97.98 | 100 | A |
| 188 | Example-205 | 99.92 | 100 | A |
| 189 | Example-212 | 95.06 | 98.78 | A |
| 190 | Example-213 | 96.34 | 97.29 | — |
| 191 | Example-214 | 98.41 | 96.49 | — |
| 192 | Example-215 | 96.29 | 94.1 | — |
| 193 | Example-216 | 96.53 | 96.42 | — |
| 194 | Example-217 | 96.19 | 99.91 | — |
| 195 | Example-218 | 99.38 | 100.00 | — |
| 196 | Example-219 | 97.81 | 98.55 | — |
| 197 | Example-220 | 81.53 | 99.75 | — |

Screening for mPGES-1 Inhibitors Using the A549 Cell Based Assay

The inhibition of mPGES-1 enzyme in A549 cell line was monitored as inhibition of IL-1β induced PGE$_2$ release. A549 cells were maintained in DMEM medium with 10% FBS and 1% Penicillin-Streptomycin Solution in 5% CO$_2$ at 37° C. Cells were seeded 24 h prior to the assay in 96 well plates in DMEM containing 1% Penicillin-Streptomycin and 2% FBS so as to get ~40,000 cells per well on the day of experiment.

Assay was carried out in a total volume of 200 μL. Test compounds were dissolved in dimethyl sulfoxide (DMSO) to prepare 2 mM stock solution and then diluted using plain DMEM. Final concentration of DMSO in the reaction was 0.55% (v/v). Cells were treated with test compounds for 30 minutes followed by addition of IL-1β at a final concentration of 10 ng/mL for 16-20 h. Plates were then centrifuged at 1000 rpm for 10 min at 4° C. Supernatants were collected & analyzed by the addition of $PGE_2$-D2 & anti-$PGE_2$ cryptate conjugate supplied by the CisBio HTRF kit in a 96 well half area blackwell EIA/RIA plate. The assay plate was incubated overnight at 4-5° C. before being read in Artemis (K-101) (Japan) HTRF plate reader and levels of $PGE_2$ calculated by extrapolation from the standard curve.

Concentration response curves were plotted as % of maximal response obtained in the absence of test antagonist. $IC_{50}$ value was calculated from concentration response curve by nonlinear regression analysis using GraphPad PRISM software.

The compounds prepared were tested using the above assay procedure and were found to have $IC_{50}$ less than 200 nM, preferably less than 100 nM, more preferably less than 50 nM and most preferably less than 20 nM.

The invention claimed is:
1. A compound of formula (II):

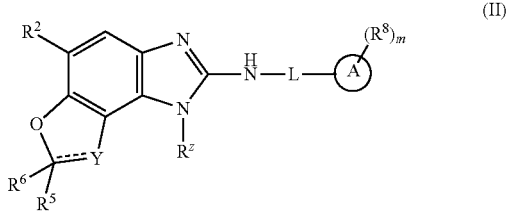

or a pharmaceutically acceptable salt thereof,
wherein,
A is phenyl or pyridinyl;
Y is selected from $—CR^3R^4—$, and $—NR^4—$;
L is a bond or is selected from $—(CH_2)—$ and $—C(O)—$;
$R^2$ is selected from $—C(O)OR^a$, $—C(O)NR^aR^b$ and substituted or unsubstituted heterocyclyl ring selected from morpholinyl, oxazolinyl, oxazolidinyl, oxadiazolyl, thiazolinyl and thiazolidinyl;
$R^3$ and $R^4$, which may be same or different, are independently selected from hydrogen and $C_{1-4}$ alkyl;
$R^5$ and $R^6$, which may be same or different, are independently selected from hydrogen, $C_{1-4}$ alkyl and $C_{3-6}$ cycloalkyl;
at each occurrence $R^8$, which may be same or different, is independently selected from halogen, nitro, cyano, hydroxyl, substituted or unsubstituted alkyl and substituted or unsubstituted haloalkyl;
at each occurrence, $R^a$ and $R^b$ which may be the same or different, are independently selected from hydrogen, substituted or unsubstituted alkyl, substituted or unsubstituted haloalkyl, substituted or unsubstituted haloalkoxy, substituted or unsubstituted alkoxyalkyl, substituted or unsubstituted hydroxyalkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, substituted or unsubstituted heteroarylalkyl, $—(CH_2)_p$ $NR^xR^y$, and $—(CH_2)_p CHR^xR^y$; or $R^a$ and $R^b$ together with the atom to which they are attached, may form cyclic ring; substituted or unsubstituted; the cyclic ring may optionally contain one or more hetero atoms selected from O, N or S;
at each occurrence, $R^x$ and $R^y$, which may be the same or different, are independently selected from hydrogen, $C_{1-4}$ alkyl, substituted or unsubstituted aryl and substituted or unsubstituted arylalkyl;
$R^z$ is selected from hydrogen, $C_{1-4}$ alkyl, and substituted or unsubstituted alkoxyalkyl;
dotted line [—] inside the ring represents an optional bond; with a proviso that when dotted line [—] inside the ring represents a bond, then both $R^4$ and $R^5$ are absent;
'm' is an integer ranging from 0 to 5, both inclusive; and
'p' is an integer ranging from 0 to 6, both inclusive.

2. The compound according to claim 1, wherein Y is $—CH_2—$.

3. The compound according to claim 1, wherein Y is $—N—$ or $—CH—$ and the line [—] inside the ring represents a bond.

4. The compound according to claim 1, wherein $R^5$ and $R^6$ are hydrogen, methyl or cyclopropyl.

5. The compound according to claim 1, wherein $R^z$ is hydrogen, methyl or methoxyethyl.

6. The compound according to claim 1, wherein L is a bond.

7. The compound according to claim 1, wherein A is phenyl, pyridin-4-yl or pyridin-3-yl.

8. The compound according to claim 1, wherein $R^8$ is independently Cl, F, methyl, tert-butyl or $—CF_3$.

9. The compound according to claim 1, wherein $R^2$ is oxadiazolyl which is optionally substituted by one or more substituents selected from isopropyl, and phenyl optionally substituted with one or more substituents selected from F, Cl, methyl and methoxy.

10. The compound according to claim 1, wherein $R^2$ is $—C(O)OR^a$.

11. The compound according to claim 10, wherein $R^a$ is methyl, ethyl or benzyl.

12. The compound according to claim 1, wherein $R^2$ is $—C(O)NR^aR^b$.

13. The compound according to claim 12, wherein $R^a$ is hydrogen and $R^b$ is alkyl, alkoxyalkyl, haloalkyl, hydroxyalkyl, cycloalkyl, cycloalkylalkyl, heteroaryl, heterocyclyl, heterocyclylalkyl, aryl, arylalkyl, or $—(CH_2)_p NR^xR^y$ or $R^a$ and $R^b$ together forms morpholinyl ring.

14. The compound according to claim 12, wherein $R^a$ is hydrogen and $R^b$ is n-pentyl, n-hexyl, 3,3-dimethyl-butan-2-yl, 2,4,4-trimethylpentan-2-yl, 2-methylbutan-2-yl, 3-methylbutyl, 3-methoxypropyl, fluoroethyl, 2,2,2-trifluoroethyl, 2,2,3,3,3-pentafluoropropyl, 2-hydroxypropyl, hydroxypropanyl, cyclohexyl, cyclopropyl, cyclopropylmethyl optionally substituted with phenyl optionally substituted with one or more selected from fluoro, trifluoromethyl and methyl, 3,3-dimethylcyclohexyl, 4,4-difluorocyclohexyl, 3,6,6-trimethylbicyclo[3.1.1]hept-2-yl, adamantyl, 1-cyclohexylethyl, cyclopropylmethyl, cyclopentylmethyl, cyclohexylmethyl, $—(CH_2)_2 N(CH_3)_2$, or $—NHPh$-p-Br.

15. The compound according to claim 12, wherein $R^a$ is hydrogen and $R^b$ is pyrrolidinyl, morpholinylethyl, thiadiazolyl, thiazolyl, benzthiazolyl or pyridinyl which are optionally substituted with Cl, F, Br, methyl, ethyl, tert-butyl, methoxy, cyclopropylmethoxy, trifluoromethyl, difluoromethoxy or pyrrolidinyl.

16. A compound according to claim 1 of the formula (IV),

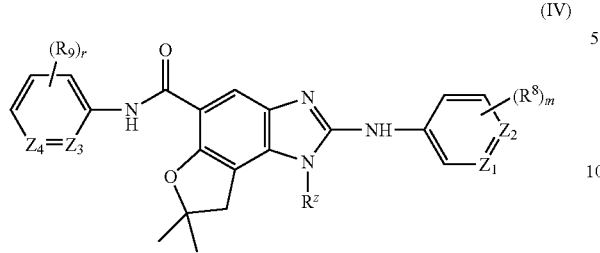

(IV)

or a pharmaceutically acceptable salt thereof, wherein,
- $Z_1$ and $Z_2$ are independently selected from —N— or —CH—; with the proviso that $Z_1$ and $Z_2$ simultaneously are not N;
- $Z_3$ and $Z_4$ are independently selected from —N— or —CH—; with the proviso that $Z_3$ and $Z_4$ simultaneously are not N;
- at each occurrence $R^8$, which may be same or different, is independently selected from halogen, nitro, cyano, hydroxyl, substituted or unsubstituted alkyl and substituted or unsubstituted haloalkyl;
- at each occurrence $R^9$ which may be same or different, are independently selected from halogen, nitro, cyano, hydroxyl, $C_{1-6}$ alkyl, $C_{3-6}$ cycloalkyl, substituted or unsubstituted alkoxy, substituted or unsubstituted alkoxyalkyl, substituted or unsubstituted haloalkyl, substituted or unsubstituted haloalkoxy, substituted or unsubstituted aryl, substituted or unsubstituted 5 to 7 membered heterocyclyl, substituted or unsubstituted 5 to 7 membered heterocyclylalkyl and substituted or unsubstituted heteroaryl;
- $R^z$ is selected from hydrogen, $C_{1-4}$ alkyl, and substituted or unsubstituted alkoxyalkyl;
- 'm' is an integer ranging from 0 to 5, both inclusive; and
- 'r' is an integer ranging from 0 to 5, both inclusive.

17. The compound according to claim 16, wherein $Z_1$, $Z_2$, $Z_3$ and $Z_4$ are —CH—.

18. The compound according to claim 16, wherein $Z_1$ is —N— and $Z_2$ is —CH—.

19. The compound according to claim 16, wherein $Z_1$ is —CH— and $Z_2$ is —N—.

20. The compound according to claim 16, wherein $Z_3$ is —N— and $Z_4$ is —CH—.

21. The compound according to claim 16, wherein $Z_3$ is —CH— and $Z_4$ is —N—.

22. The compound according to claim 16, wherein $R^z$ is hydrogen, methyl or methoxyethyl.

23. The compound according to claim 16, wherein $R^8$ is independently selected from Cl, F, methyl, tert-butyl and —$CF_3$ and m is 1 or 2.

24. The compound according to claim 16, wherein $R^9$ is independently selected from halogen, cyano, $C_{1-6}$ alkyl, $C_{3-6}$ cycloalkyl, alkoxy, haloalkyl, haloalkoxy and 5 membered heterocyclyl and r is 1, 2 or 3.

25. The compound according to claim 16, wherein $R^9$ is independently selected from F, Cl, Br, $CF_3$, $OCH_3$, CN, $CH_3$, $OCHF_2$, propan-2-yl, tert-butyl, pyrrolidinyl, 1,1-difluoroethyl, cyclopropyl and cyclopropylmethoxy.

26. The compound according to claim 1 selected from

N-Cyclohexyl-2-[(3,5-dichloropyridin-4-yl)amino]-7,7-dimethyl-7,8-dihydro-1H-furo[3,2-e]benzimidazole-5-carboxamide;

2-[(3,5-Dichloropyridin-4-yl)amino]-N-hexyl-7,7-dimethyl-7,8-dihydro-1H-furo[3,2-e]benzimidazole-5-carboxamide;

2-[(3,5-Dichloropyridin-4-yl)amino]-7,7-dimethyl-N-pentyl-7,8-dihydro-1H-furo[3,2-e]benzimidazole-5-carboxamide;

N-(1-Cyclohexylethyl)-2-[(3,5-dichloropyridin-4-yl)amino]-7,7-dimethyl-7,8-dihydro-1H-furo[3,2-e]benzimidazole-5-carboxamide;

2-[(3,5-Dichloropyridin-4-yl)amino]-N—[R(−)3,3-dimethylbutan-2-yl)]-7,7-dimethyl-7,8-dihydro-1H-furo[3,2-e]benzimidazole-5-carboxamide;

N-Cyclohexyl-2-[(2,6-dichlorophenyl)amino]-7,7-dimethyl-7,8-dihydro-1H-furo[3,2-e]benzimidazole-5-carboxamide;

2-[(2,6-Dichlorophenyl)amino]-7,7-dimethyl-N-pentyl-7,8-dihydro-1H-furo[3,2-e]benzimidazole-5-carboxamide;

2-[(3,5-Dichloropyridin-4-yl)amino]-N-(3,3-dimethylcyclohexyl)-7,7-dimethyl-7,8-dihydro-1H-furo[3,2-e]benzimidazole-5-carboxamide;

2-[(3,5-Dichloropyridin-4-yl)amino]-7,7-dimethyl-N-(3,6,6-trimethylbicyclo[3.1.1]hept-2-yl)-7,8-dihydro-1H-furo[3,2-e]benzimidazole-5-carboxamide;

N-Adamantan-1-yl-2-[(3,5-dichloropyridin-4-yl)amino]-7,7-dimethyl-7,8-dihydro-1H-furo[3,2-e]benzimidazole-5-carboxamide;

{2-[(3,5-Dichloropyridin-4-yl)amino]-7,7-dimethyl-7,8-dihydro-1H-furo[3,2-e]benzimidazol-5-yl}(morpholin-4-yl)methanone;

N-(Cyclopropylmethyl)-2-[(3,5-dichloropyridin-4-yl)amino]-7,7-dimethyl-7,8-dihydro-1H-furo[3,2-e]benzimidazole-5-carboxamide;

2-[(3,5-Dichloropyridin-4-yl)amino]-7,7-dimethyl-N-(2,4,4-trimethylpentan-2-yl)-7,8-dihydro-1H-furo[3,2-e]benzimidazole-5-carboxamide;

N-(Cyclohexylmethyl)-2-[(3,5-dichloropyridin-4-yl)amino]-7,7-dimethyl-7,8-dihydro-1H-furo[3,2-e]benzimidazole-5-carboxamide;

N-(Cyclopropylmethyl)-2-[(2,6-dichlorophenyl)amino]-7,7-dimethyl-7,8-dihydro-1H-furo[3,2-e]benzimidazole-5-carboxamide;

2-[(2,6-Dichlorophenyl)amino]-7,7-dimethyl-N-(5-methyl-1,3,4-thiadiazol-2-yl)-7,8-dihydro-1H-furo[3,2-e]benzimidazole-5-carboxamide;

2-[(2,6-Dichlorophenyl)amino]-7,7-dimethyl-N-(5-methyl-1,3-thiazol-2-yl)-7,8-dihydro-1H-furo[3,2-e]benzimidazole-5-carboxamide;

2-[(2,6-Dichlorophenyl)amino]-7,7-dimethyl-N-(2-methylbutan-2-yl)-7,8-dihydro-1H-furo[3,2-e]benzimidazole-5-carboxamide;

2-[(2-Chloro-6-fluorophenyl)amino]-N-(cyclohexylmethyl)-7,7-dimethyl-7,8-dihydro-1H-furo[3,2-e]benzimidazole-5-carboxamide;

2-[(2,6-Dichlorophenyl)amino]-N-(2-hydroxypropyl)-7,7-dimethyl-7,8-dihydro-1H-furo[3,2-e]benzimidazole-5-carboxamide;

N-(Cyclopentylmethyl)-2-[(2,6-dichlorophenyl)amino]-7,7-dimethyl-7,8-dihydro-1H-furo[3,2-e]benzimidazole-5-carboxamide;

2-[(2,6-Dichlorophenyl)amino]-7,7-dimethyl-N-(3-methylbutyl)-7,8-dihydro-1H-furo[3,2-e]benzimidazole-5-carboxamide;

2-[(2-Chloro-6-fluorophenyl)amino]-7,7-dimethyl-N-(2,4,4-trimethylpentan-2-yl)-7,8-dihydro-1H-furo[3,2-e]benzimidazole-5-carboxamide;

N-(4-tert-Butyl-1,3-thiazol-2-yl)-2-[(2-chloro-6-fluorophenyl)amino]-7,7-dimethyl-7,8-dihydro-1H-furo[3,2-e]benzimidazole-5-carboxamide;

2-[(2-Chloro-6-fluorophenyl)amino]-7,7-dimethyl-N-(4-methyl-1,3-thiazol-2-yl)-7,8-dihydro-1H-furo[3,2-e]benzimidazole-5-carboxamide;

2-[(2-Chloro-6-fluorophenyl)amino]-N-(4,5-dimethyl-1,3-thiazol-2-yl)-7,7-dimethyl-7,8-dihydro-1H-furo[3,2-e]benzimidazole-5-carboxamide;

2-[(2,6-Dichlorophenyl)amino]-7,7-dimethyl-N-(pyrrolidin-1-yl)-7,8-dihydro-1H-furo[3,2-e]benzimidazole-5-carboxamide;

2-[(2,6-Dichlorophenyl)amino]-N-[2-(dimethylamino)ethyl]-7,7-dimethyl-7,8-dihydro-1H-furo[3,2-e]benzimidazole-5-carboxamide;

2-[(2,6-Dichlorophenyl)amino]-7,7-dimethyl-N-(2,2,2-trifluoroethyl)-7,8-dihydro-1H-furo[3,2-e]benzimidazole-5-carboxamide;

2-[(2,6-Dichlorophenyl)amino]-N-(2-fluoroethyl)-7,7-dimethyl-7,8-dihydro-1H-furo[3,2-e]benzimidazole-5-carboxamide;

2-[(2,6-Dichlorophenyl)amino]-7,7-dimethyl-N-(2,2,3,3,3-pentafluoropropyl)-7,8-dihydro-1H-furo[3,2-e]benzimidazole-5-carboxamide;

2-[(2,6-Dichlorophenyl)amino]-N-(3-methoxypropyl)-7,7-dimethyl-7,8-dihydro-1H-furo[3,2-e]benzimidazole-5-carboxamide;

2-[(2,6-Dichlorophenyl)amino]-7,7-dimethyl-N-[2-(morpholin-4-yl)ethyl]-7,8-dihydro-1H-furo[3,2-e]benzimidazole-5-carboxamide;

N'-(4-Bromophenyl)-2-[(2,6-dichlorophenyl)amino]-7,7-dimethyl-7,8-dihydro-1H-furo[3,2-e]benzimidazole-5-carbohydrazide;

2-[(2,6-Dichlorophenyl)amino]-N-(4,4-difluorocyclohexyl)-7,7-dimethyl-7,8-dihydro-1H-furo[3,2-e]benzimidazole-5-carboxamide;

2-[(2-Chloro-4-fluorophenyl)amino]-7,7-dimethyl-N-(2,2,3,3,3-pentafluoropropyl)-7,8-dihydro-1H-furo[3,2-e]benzimidazole-5-carboxamide;

2-[(2,6-Dichlorophenyl)amino]-N-(6-fluoro-1,3-benzothiazol-2-yl)-7,7-dimethyl-7,8-dihydro-1H-furo[3,2-e]benzimidazole-5-carboxamide;

2-[(3,5-Dichloropyridin-4-yl)amino]-7,7-dimethyl-N-[2-(trifluoromethyl)benzyl]-7,8-dihydro-1H-furo[3,2-e]benzimidazole-5-carboxamide;

2-[(3,5-Dichloropyridin-4-yl)amino]-N-(4-fluorobenzyl)-7,7-dimethyl-7,8-dihydro-1H-furo[3,2-e]benzimidazole-5-carboxamide;

2-[(2-Chloro-6-fluorophenyl)amino]-N-(4-fluorobenzyl)-7,7-dimethyl-7,8-dihydro-1H-furo[3,2-e]benzimidazole-5-carboxamide;

2-[(2-Chloro-6-fluorophenyl)amino]-7,7-dimethyl-N-[2-(trifluoromethyl)benzyl]-7,8-dihydro-1H-furo[3,2-e]benzimidazole-5-carboxamide;

2-[(2,6-Dichlorophenyl)amino]-7,7-dimethyl-N-[2-(trifluoromethyl)benzyl]-7,8-dihydro-1H-furo[3,2-e]benzimidazole-5-carboxamide;

N-[2-(4-Chlorophenyl)ethyl]-2-[(2,6-dichlorophenyl)amino]-7,7-dimethyl-7,8-dihydro-1H-furo[3,2-e]benzimidazole-5-carboxamide;

N-(2-Bromobenzyl)-2-[(2,6-dichlorophenyl)amino]-7,7-dimethyl-7,8-dihydro-1H-furo[3,2-e]benzimidazole-5-carboxamide;

2-[(2-Chlorophenyl)amino]-7,7-dimethyl-N-[2-(trifluoromethyl)benzyl]-7,8-dihydro-1H-furo[3,2-e]benzimidazole-5-carboxamide;

2-[(2-Chloro-4-methylphenyl)amino]-7,7-dimethyl-N-[4-(trifluoromethyl)benzyl]-7,8-dihydro-1H-furo[3,2-e]benzimidazole-5-carboxamide;

2-[(2-Chloro-6-fluorophenyl)amino]-7,7-dimethyl-N-{1-[4-(trifluoromethyl)phenyl]cyclopropyl}-7,8-dihydro-1H-furo[3,2-e]benzimidazole-5-carboxamide;

2-[(2-Chloro-6-fluorophenyl)amino]-7,7-dimethyl-N-{1-[2-(trifluoromethyl)phenyl]cyclopropyl}-7,8-dihydro-1H-furo[3,2-e]benzimidazole-5-carboxamide;

2-((2-Chloro-6-fluorophenyl)amino)-7,7-dimethyl-N-(1-(3-(trifluoromethyl)phenyl)cyclopropyl)-7,8-dihydro-1H-benzofuro[4,5-d]imidazole-5-carboxamide;

2-((2-Chloro-6-fluorophenyl)amino)-N-(4-fluoro-2-(trifluoromethyl)benzyl)-7,7-dimethyl-7,8-dihydro-1H-benzofuro[4,5-d]imidazole-5-carboxamide;

2-((2-Chloro-6-methylphenyl)amino)-N-(4-fluoro-2-(trifluoromethyl)benzyl)-7,7-dimethyl-7,8-dihydro-1H-benzofuro[4,5-d]imidazole-5-carboxamide;

2-((2-Chloro-6-methylphenyl)amino)-7,7-dimethyl-N-(1-(3-(trifluoromethyl)phenyl)cyclopropyl)-7,8-dihydro-1H-benzofuro[4,5-d]imidazole-5-carboxamide;

2-(2-Chloro-6-fluorobenzamido)-7,7-dimethyl-N-(3-(trifluoromethyl)phenyl)-7,8-dihydro-1H-benzofuro[4,5-d]imidazole-5-carboxamide;

2-((2-Chlorobenzyl)amino)-7,7-dimethyl-N-(3-(trifluoromethyl)phenyl)-7,8-dihydro-1H-benzofuro[4,5-d]imidazole-5-carboxamide;

2-((2-Chlorobenzyl)amino)-N-(2-fluoro-5-(trifluoromethyl)phenyl)-7,7-dimethyl-7,8-dihydro-1H-benzofuro[4,5-d]imidazole-5-carboxamide;

N-(2-Chloro-6-fluorophenyl)-5-(3-isopropyl-1,2,4-oxadiazol-5-yl)-7,7-dimethyl-7,8-dihydro-1H-benzofuro[4,5-d]imidazol-2-amine;

5-(3-(3-Chloro-4-fluorophenyl)-1,2,4-oxadiazol-5-yl)-N-(2,6-dichlorophenyl)-7,7-dimethyl-7,8-dihydro-1H-benzofuro[4,5-d]imidazol-2-amine;

N-(2,6-Dichlorophenyl)-5-(3-(3,5-dimethoxyphenyl)-1,2,4-oxadiazol-5-yl)-7,7-dimethyl-7,8-dihydro-1H-benzofuro[4,5-d]imidazol-2-amine; and N-(Cyclopropylmethyl)-2-((3,5-dichloropyridin-4-yl)amino)-1,7,7-trimethyl-7,8-dihydro-1H-benzofuro[4,5-d]imidazole-5-carboxamide or a pharmaceutically acceptable salt thereof.

27. The compound according to claim 1 selected from

N-Cyclohexyl-2-[(3,5-dichloropyridin-4-yl)amino]-7-methyl-1H-furo[3,2-e]benzimidazole-5-carboxamide;

N-Cyclohexyl-2-[(2,6-dichlorophenyl)amino]-7-methyl-1H-furo[3,2-e]benzimidazole-5-carboxamide;

2-[(2-Chlorophenyl)amino]-N-cyclohexyl-7-methyl-1H-furo[3,2-e]benzimidazole-5-carboxamide;

2-[(3,5-Dichloropyridin-4-yl)amino]-N-(4-fluorobenzyl)-7-methyl-1H-furo[3,2-e]benzimidazole-5-carboxamide;

2-[(3,5-Dichloropyridin-4-yl)amino]-N-(3,3-dimethylbutan-2-yl)-7-methyl-1H-furo[3,2-e]benzimidazole-5-carboxamide;

2-[(3,5-Dichloropyridin-4-yl)amino]-7-methyl-N-[4-(trifluoromethyl)phenyl]-1H-furo[3,2-e]benzimidazole-5-carboxamide;

N-(Cyclohexylmethyl)-2-[(3,5-dichloropyridin-4-yl)amino]-7-methyl-1H-furo[3,2-e]benzimidazole-5-carboxamide;

2-[(3,5-Dichloropyridin-4-yl)amino]-7-methyl-N-(2,4,4-trimethylpentan-2-yl)-1H-furo[3,2-e]benzimidazole-5-carboxamide;

2-[(2,6-Dichlorophenyl)amino]-N-(4-fluorobenzyl)-7-methyl-1H-furo[3,2-e]benzimidazole-5-carboxamide;

2-[(3,5-Dichloropyridin-4-yl)amino]-N-(4-fluorophenyl)-7-methyl-1H-furo[3,2-e]benzimidazole-5-carboxamide;
2-[(2-Chloro-6-fluorophenyl)amino]-N-(4-fluorophenyl)-7-methyl-1H-furo[3,2-e]benzimidazole-5-carboxamide;
2-[(2-Chloro-6-fluorophenyl)amino]-N-(4-fluorobenzyl)-7-methyl-1H-furo[3,2-e]benzimidazole-5-carboxamide;
2-[(2-Chloro-6-fluorophenyl)amino]-N-(cyclohexylmethyl)-7-methyl-1H-furo[3,2-e]benzimidazole-5-carboxamide;
2-[(3,5-Dichloropyridin-4-yl)amino]-7-methyl-N-(3-methylbutyl)-1H-furo[3,2-e]benzimidazole-5-carboxamide;
N-(Cyclopropylmethyl)-2-[(2,6-dichlorophenyl)amino]-7-methyl-1H-furo[3,2-e]benzimidazole-5-carboxamide;
2-[(2,6-Dichlorophenyl)amino]-7-methyl-N-[4-(trifluoromethyl)phenyl]-1H-furo[3,2-e]benzimidazole-5-carboxamide;
N-(4-Bromophenyl)-2-[(2,6-dichlorophenyl)amino]-7-methyl-1H-furo[3,2-e]benzimidazole-5-carboxamide;
2-[(2,6-Dichlorophenyl)amino]-N-(2-fluorophenyl)-7-methyl-1H-furo[3,2-e]benzimidazole-5-carboxamide;
2-[(2,6-Dichlorophenyl)amino]-7-methyl-N-[3-(trifluoromethyl)phenyl]-1H-furo[3,2-e]benzimidazole-5-carboxamide;
N-(5-Bromopyridin-2-yl)-2-[(2,6-dichlorophenyl)amino]-7-methyl-1H-furo[3,2-e]benzimidazole-5-carboxamide;
2-[(2,6-Dichlorophenyl)amino]-7-methyl-N-[2-(trifluoromethyl)benzyl]-1H-furo[3,2-e]benzimidazole-5-carboxamide;
7-[(2,6-Dichlorophenyl)amino]-N-(4-fluorophenyl)-2-methyl-8H-imidazo[4,5-e][1,3]benzoxazole-4-carboxamide;
7-[(2,6-Dichlorophenyl)amino]-2-methyl-N-[4-(trifluoromethyl)phenyl]-8H-imidazo[4,5-e][1,3]benzoxazole-4-carboxamide;
N-(4-Bromophenyl)-7-[(2,6-dichlorophenyl)amino]-2-methyl-8H-imidazo[4,5-e][1,3]benzoxazole-4-carboxamide;
N-(4-tert-Butylphenyl)-7-[(2,6-dichlorophenyl)amino]-2-methyl-8H-imidazo[4,5-e][1,3]benzoxazole-4-carboxamide;
7-[(2,6-Dichlorophenyl)amino]-N-hexyl-2-methyl-8H-imidazo[4,5-e][1,3]benzoxazole-4-carboxamide;
7-[(2-Chloro-6-fluorophenyl)amino]-N-(4-fluorophenyl)-2-methyl-8H-imidazo[4,5-e][1,3]benzoxazole-4-carboxamide;
N-(Cyclohexylmethyl)-7-[(2,6-dichlorophenyl)amino]-2-methyl-8H-imidazo[4,5-e][1,3]benzoxazole-4-carboxamide;
N-(4-tert-Butylphenyl)-2-cyclopropyl-7-[(2,6-dichlorophenyl)amino]-8H-imidazo[4,5-e][1,3]benzoxazole-4-carboxamide;
7-((2-Chloro-6-fluorophenyl)amino)-2-cyclopropyl-N-(2-fluoro-5-(trifluoromethyl)phenyl)-8H-imidazo[4',5':5,6]benzo[1,2-d]oxazole-4-carboxamide;
7-((2-Chloro-6-fluorophenyl)amino)-N-(2-fluoro-5-(trifluoromethyl)phenyl)-2-methyl-8H-imidazo[4',5':5,6]benzo[1,2-d]oxazole-4-carboxamide;
7-((2-Chloro-6-fluorophenyl)amino)-N-(4-fluoro-3-(trifluoromethyl)phenyl)-2-methyl-8H-imidazo[4',5':5,6]benzo[1,2-d]oxazole-4-carboxamide;
7-[(2,6-Dichlorophenyl)amino]-2-methyl-N-[2-(trifluoromethyl)benzyl]-8H-imidazo[4,5-e][1,3]benzoxazole-4-carboxamide;
7-[(2,6-Dichlorophenyl)amino]-N-(4,4-difluorocyclohexyl)-2-methyl-8H-imidazo[4,5-e][1,3]benzoxazole-4-carboxamide; and
N-[4-(2-Cyanopropan-2-yl)phenyl]-7-[(2,6-dichlorophenyl)amino]-2-methyl-8H-imidazo[4,5-e][1,3]benzoxazole-4-carboxamide or a pharmaceutically acceptable salt thereof.

28. The compound according to claim 1 selected from
N-(4-Bromophenyl)-2-[(3,5-dichloropyridin-4-yl)amino]-7,7-dimethyl-7,8-dihydro-1H-furo[3,2-e]benzimidazole-5-carboxamide;
2-[(3,5-Dichloropyridin-4-yl)amino]-7,7-dimethyl-N-[4-(trifluoromethyl)phenyl]-7,8-dihydro-1H-furo[3,2-e]benzimidazole-5-carboxamide;
N-(4-Bromophenyl)-2-[(2,6-dichlorophenyl)amino]-7,7-dimethyl-7,8-dihydro-1H-furo[3,2-e]benzimidazole-5-carboxamide;
N-(4-Chlorophenyl)-2-[(3,5-dichloropyridin-4-yl)amino]-7,7-dimethyl-7,8-dihydro-1H-furo[3,2-e]benzimidazole-5-carboxamide;
N-(4-Chlorophenyl)-2-[(2-chlorophenyl)amino]-7,7-dimethyl-7,8-dihydro-1H-furo[3,2-e]benzimidazole-5-carboxamide;
2-[(3,5-Dichloropyridin-4-yl)amino]-N-(4-fluorophenyl)-7,7-dimethyl-7,8-dihydro-1H-furo[3,2-e]benzimidazole-5-carboxamide;
2-[(2,6-Dichlorophenyl)amino]-N-(4-fluorophenyl)-7,7-dimethyl-7,8-dihydro-1H-furo[3,2-e]benzimidazole-5-carboxamide;
2-[(2,6-Dichlorophenyl)amino]-N-(2-fluorophenyl)-7,7-dimethyl-7,8-dihydro-1H-furo[3,2-e]benzimidazole-5-carboxamide;
2-[(2-Chloro-6-fluorophenyl)amino]-N-(4-fluorophenyl)-7,7-dimethyl-7,8-dihydro-1H-furo[3,2-e]benzimidazole-5-carboxamide;
2-[(2,6-Dichlorophenyl)amino]-N-(6-methoxypyridin-3-yl)-7,7-dimethyl-7,8-dihydro-1H-furo[3,2-e]benzimidazole-5-carboxamide;
2-[(2-Chloro-6-fluorophenyl)amino]-N-(2-fluorophenyl)-7,7-dimethyl-7,8-dihydro-1H-furo[3,2-e]benzimidazole-5-carboxamide;
2-[(2-Chloro-6-fluorophenyl)amino]-N-(3-fluorophenyl)-7,7-dimethyl-7,8-dihydro-1H-furo[3,2-e]benzimidazole-5-carboxamide;
N-(4-Cyanophenyl)-2-[(2,6-dichlorophenyl)amino]-7,7-dimethyl-7,8-dihydro-1H-furo[3,2-e]benzimidazole-5-carboxamide;
2-[(2,6-Dichlorophenyl)amino]-N-(2,6-dimethylpyridin-3-yl)-7,7-dimethyl-7,8-dihydro-1H-furo[3,2-e]benzimidazole-5-carboxamide;
N-(2-Bromophenyl)-2-[(2,6-dichlorophenyl)amino]-7,7-dimethyl-7,8-dihydro-1H-furo[3,2-e]benzimidazole-5-carboxamide;
2-[(2,6-Dichlorophenyl)amino]-7,7-dimethyl-N-[4-(trifluoromethyl)phenyl]-7,8-dihydro-1H-furo[3,2-e]benzimidazole-5-carboxamide;
2-[(2,6-Dichlorophenyl)amino]-7,7-dimethyl-N-[2-(trifluoromethyl)phenyl]-7,8-dihydro-1H-furo[3,2-e]benzimidazole-5-carboxamide;
2-[(2,6-Dichlorophenyl)amino]-N-(2,6-difluorophenyl)-7,7-dimethyl-7,8-dihydro-1H-furo[3,2-e]benzimidazole-5-carboxamide;

2-[(2-Chloro-6-fluorophenyl)amino]-7,7-dimethyl-N-[2-(trifluoromethyl)phenyl]-7,8-dihydro-1H-furo[3,2-e]benzimidazole-5-carboxamide;

N-(4-Bromophenyl)-2-[(2-chlorophenyl)amino]-7,7-dimethyl-7,8-dihydro-1H-furo[3,2-e]benzimidazole-5-carboxamide;

2-[(2-Chlorophenyl)amino]-7,7-dimethyl-N-[2-(trifluoromethyl)phenyl]-7,8-dihydro-1H-furo[3,2-e]benzimidazole-5-carboxamide;

2-[(2,6-Dichlorophenyl)amino]-7,7-dimethyl-N-phenyl-7,8-dihydro-1H-furo[3,2-e]benzimidazole-5-carboxamide;

2-[(2-Chloro-4-fluorophenyl)amino]-7,7-dimethyl-N-[4-(trifluoromethyl)phenyl]-7,8-dihydro-1H-furo[3,2-e]benzimidazole-5-carboxamide;

2-[(2-Chloro-4-methylphenyl)amino]-7,7-dimethyl-N-[4-(trifluoromethyl)phenyl]-7,8-dihydro-1H-furo[3,2-e]benzimidazole-5-carboxamide;

2-[(2-Chlorophenyl)amino]-7,7-dimethyl-N-[4-(trifluoromethyl)phenyl]-7,8-dihydro-1H-furo[3,2-e]benzimidazole-5-carboxamide;

2-[(2,6-Dichlorophenyl)amino]-7,7-dimethyl-N-[4-(propan-2-yl)phenyl]-7,8-dihydro-1H-furo[3,2-e]benzimidazole-5-carboxamide;

2-[(2,4-Dichlorophenyl)amino]-7,7-dimethyl-N-[4-(trifluoromethyl)phenyl]-7,8-dihydro-1H-furo[3,2-e]benzimidazole-5-carboxamide;

2-[(2,6-Dichlorophenyl)amino]-7,7-dimethyl-N-[6-(pyrrolidin-1-yl)pyridin-3-yl]-7,8-dihydro-1H-furo[3,2-e]benzimidazole-5-carboxamide;

2-[(2-Chloro-5-methylphenyl)amino]-7,7-dimethyl-N-[2-(trifluoromethyl)phenyl]-7,8-dihydro-1H-furo[3,2-e]benzimidazole-5-carboxamide;

2-[(2-tert-Butylphenyl)amino]-7,7-dimethyl-N-[2-(trifluoromethyl)phenyl]-7,8-dihydro-1H-furo[3,2-e]benzimidazole-5-carboxamide;

2-[(2,6-Dichlorophenyl)amino]-1-(2-methoxyethyl)-7,7-dimethyl-N-[4-(trifluoromethyl)phenyl]-7,8-dihydro-1H-furo[3,2-e]benzimidazole-5-carboxamide;

2-[(2,6-Dichlorophenyl)amino]-1-(2-methoxyethyl)-7,7-dimethyl-N-[2-(trifluoromethyl)phenyl]-7,8-dihydro-1H-furo[3,2-e]benzimidazole-5-carboxamide;

2-[(2,6-Dichlorophenyl)amino]-7,7-dimethyl-N-[5-(trifluoromethyl)pyridin-2-yl]-7,8-dihydro-1H-furo[3,2-e]benzimidazole-5-carboxamide;

2-[(2-tert-Butylphenyl)amino]-7,7-dimethyl-N-[4-(trifluoromethyl)phenyl]-7,8-dihydro-1H-furo[3,2-e]benzimidazole-5-carboxamide;

2-[(2,6-Dimethylpyridin-3-yl)amino]-7,7-dimethyl-N-[4-(trifluoromethyl)phenyl]-7,8-dihydro-1H-furo[3,2-e]benzimidazole-5-carboxamide;

2-[(2-Chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide;

2-[(2-Chloro-6-fluorophenyl)amino]-N-(2-cyano-4-fluorophenyl)-7,7-dimethyl-7,8-dihydro-1H-furo[3,2-e]benzimidazole-5-carboxamide;

2-[(2,6-Dimethylpyridin-3-yl)amino]-7,7-dimethyl-N-[2-(trifluoromethyl)phenyl]-7,8-dihydro-1H-furo[3,2-e]benzimidazole-5-carboxamide;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide;

2-[(2-Chloro-6-methylphenyl)amino]-7,7-dimethyl-N-[4-(trifluoromethyl)phenyl]-7,8-dihydro-1H-furo[3,2-e]benzimidazole-5-carboxamide;

2-[(2-Chloro-6-methylphenyl)amino]-7,7-dimethyl-N-(2,4,6-trifluorophenyl)-7,8-dihydro-1H-furo[3,2-e]benzimidazole-5-carboxamide;

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide;

2-[(2-Chloro-6-fluorophenyl)amino]-N-[2-fluoro-5-(trifluoromethyl)phenyl]-7,7-dimethyl-7,8-dihydro-1H-furo[3,2-e]benzimidazole-5-carboxamide;

2-[(2-Chloro-6-fluorophenyl)amino]-N-[2-fluoro-4-(trifluoromethyl)phenyl]-7,7-dimethyl-7,8-dihydro-1H-furo[3,2-e]benzimidazole-5-carboxamide;

2-[(2-Chloro-6-fluorophenyl)amino]-7,7-dimethyl-N-[2-methyl-4-(trifluoromethyl)phenyl]-7,8-dihydro-1H-furo[3,2-e]benzimidazole-5-carboxamide;

N-(4-tert-Butylphenyl)-2-[(2-chloro-6-fluorophenyl)amino]-7,7-dimethyl-7,8-dihydro-1H-furo[3,2-e]benzimidazole-5-carboxamide;

2-[(2-Chloro-6-fluorophenyl)amino]-N-[6-(difluoromethoxy)pyridin-3-yl]-7,7-dimethyl-7,8-dihydro-1H-furo[3,2-e]benzimidazole-5-carboxamide;

2-[(2-Chloro-6-fluorophenyl)amino]-N-[4-fluoro-2-(trifluoromethyl)phenyl]-7,7-dimethyl-7,8-dihydro-1H-furo[3,2-e]benzimidazole-5-carboxamide;

2-[(2-Chloro-6-fluorophenyl)amino]-N-[3-(1,1-difluoroethyl)phenyl]-7,7-dimethyl-7,8-dihydro-1H-furo[3,2-e]benzimidazole-5-carboxamide;

2-[(2-Chloro-6-methylphenyl)amino]-N-[3-(1,1-difluoroethyl)phenyl]-7,7-dimethyl-7,8-dihydro-1H-furo[3,2-e]benzimidazole-5-carboxamide;

2-[(2-Chloro-6-fluorophenyl)amino]-N-(5-chloropyridin-2-yl)-7,7-dimethyl-7,8-dihydro-1H-furo[3,2-e]benzimidazole-5-carboxamide;

2-[(2-Chloro-6-fluorophenyl)amino]-7,7-dimethyl-N-[5-(trifluoromethyl)pyridin-2-yl]-7,8-dihydro-1H-furo[3,2-e]benzimidazole-5-carboxamide;

2-[(2-Chloro-5-methylphenyl)amino]-7,7-dimethyl-N-[3-(trifluoromethyl)phenyl]-7,8-dihydro-1H-furo[3,2-e]benzimidazole-5-carboxamide;

2-[(2-Chloro-6-methylphenyl)amino]-7,7-dimethyl-N-[5-(trifluoromethyl)pyridin-2-yl]-7,8-dihydro-1H-furo[3,2-e]benzimidazole-5-carboxamide;

2-[(2-Chloro-6-fluorophenyl)amino]-N-[6-(cyclopropylmethoxy)pyridin-3-yl]-7,7-dimethyl-7,8-dihydro-1H-furo[3,2-e]benzimidazole-5-carboxamide;

N-(5-Chloro-3-fluoropyridin-2-yl)-2-((2-chloro-6-fluorophenyl)amino)-7,7-dimethyl-7,8-dihydro-1H-benzofuro[4,5-d]imidazole-5-carboxamide;

2-((2-Chloro-6-fluorophenyl)amino)-N-(2-fluoro-4-methylphenyl)-7,7-dimethyl-7,8-dihydro-1H-benzofuro[4,5-d]imidazole-5-carboxamide;

2-((2-Chloro-6-fluorophenyl)amino)-N-(5-(difluoromethyl)-2-fluorophenyl)-7,7-dimethyl-7,8-dihydro-1H-benzofuro[4,5-d]imidazole-5-carboxamide;

2-((2-Chloro-6-methylphenyl)amino)-N-(4-fluoro-3-(trifluoromethyl)phenyl)-7,7-dimethyl-7,8-dihydro-1H-benzofuro[4,5-d]imidazole-5-carboxamide;

2-((2-Chloro-6-fluorophenyl)amino)-N-(5-cyclopropyl-2-fluorophenyl)-7,7-dimethyl-7,8-dihydro-1H-benzofuro[4,5-d]imidazole-5-carboxamide;

2-((2-Chloro-6-methylphenyl)amino)-N-(5-(difluoromethyl)-2-fluorophenyl)-7,7-dimethyl-7,8-dihydro-1H-benzofuro[4,5-d]imidazole-5-carboxamide;

2-((2-Chloro-6-methylphenyl)amino)-N-(5-cyclopropyl-2-fluorophenyl)-7,7-dimethyl-7,8-dihydro-1H-benzofuro[4,5-d]imidazole-5-carboxamide;

2-((2-Chloro-4-methylpyridin-3-yl)amino)-7,7-dimethyl-N-(3-(trifluoromethyl)phenyl)-7,8-dihydro-1H-benzofuro[4,5-d]imidazole-5-carboxamide;

2-((2-Chloro-6-fluorophenyl)amino)-1,7,7-trimethyl-N-(4-(trifluoromethyl)phenyl)-7,8-dihydro-1H-benzofuro[4,5-d]imidazole-5-carboxamide;

2-((2-Chloro-6-fluorophenyl)amino)-1,7,7-trimethyl-N-(3-(trifluoromethyl)phenyl)-7,8-dihydro-1H-benzofuro[4,5-d]imidazole-5-carboxamide;

2-((2-Chloro-6-fluorophenyl)amino)-N-(4-cyclopropylphenyl)-7,7-dimethyl-7,8-dihydro-1H-benzofuro[4,5-d]imidazole-5-carboxamide;

2-((2,6-Dichlorophenyl)amino)-7,7-dimethyl-N-(2,4,5-trifluorophenyl)-7,8-dihydro-1H-benzofuro[4,5-d]imidazole-5-carboxamide;

2-((2,6-Dichlorophenyl)amino)-N-(2-fluoro-4-methylphenyl)-7,7-dimethyl-7,8-dihydro-1H-benzofuro[4,5-d]imidazole-5-carboxamide;

2-((2-Chloro-6-fluorophenyl)amino)-1,7,7-trimethyl-N-(6-(trifluoromethyl)pyridin-3-yl)-7,8-dihydro-1H-benzofuro[4,5-d]imidazole-5-carboxamide;

2-((2-Chloro-6-fluorophenyl)amino)-N-(2-fluoro-4-methylphenyl)-1,7,7-trimethyl-7,8-dihydro-1H-benzofuro[4,5-d]imidazole-5-carboxamide;

2-(2-((2-Chloro-6-fluorophenyl)amino)-1,7,7-trimethyl-7,8-dihydro-1H-benzofuro[4,5-d]imidazole-5-carboxamido)-5-(trifluoromethyl)pyridine 1-oxide;

2-((2-Chloro-6-fluorophenyl)amino)-1,7,7-trimethyl-N-(5-(trifluoromethyl)pyridin-2-yl)-7,8-dihydro-1H-benzofuro[4,5-d]imidazole-5-carboxamide;

2-(2-((2-Chloro-6-fluorophenyl)amino)-7,7-dimethyl-7,8-dihydro-1H-benzofuro[4,5-d]imidazole-5-carboxamido)-5-(trifluoromethyl)pyridine 1-oxide;

N-(5-Cyclopropyl-2-fluorophenyl)-2-((2,6-dichlorophenyl)amino)-7,7-dimethyl-7,8-dihydro-1H-benzofuro[4,5-d]imidazole-5-carboxamide;

2-((2-Chloro-6-methylphenyl)amino)-7,7-dimethyl-N-(6-(trifluoromethyl)pyridin-3-yl)-7,8-dihydro-1H-benzofuro[4,5-d]imidazole-5-carboxamide;

2-(2-((2-Chloro-6-methylphenyl)amino)-7,7-dimethyl-7,8-dihydro-1H-benzofuro[4,5-d]imidazole-5-carboxamido)-5-(trifluoromethyl)pyridine 1-oxide;

2-((2-Chloro-6-methylphenyl)amino)-N-(2-fluoro-3-(trifluoromethyl)phenyl)-7,7-dimethyl-7,8-dihydro-1H-benzofuro[4,5-c]imidazole-5-carboxamide;

2-((2-Chloro-6-fluorophenyl)amino)-N-(3-cyclopropylphenyl)-7,7-dimethyl-7,8-dihydro-1H-benzofuro[4,5-d]imidazole-5-carboxamide;

2-((2,6-Dichlorophenyl)amino)-7,7-dimethyl-N-(6-(trifluoromethyl)pyridin-3-yl)-7,8-dihydro-1H-benzofuro[4,5-d]imidazole-5-carboxamide;

2-((2-Chloro-6-fluorophenyl)amino)-N-(4-cyclopropylphenyl)-1,7,7-trimethyl-7,8-dihydro-1H-benzofuro[4,5-d]imidazole-5-carboxamide;

2-((2-Chloro-6-fluorophenyl)amino)-N-(2-fluoro-3-(trifluoromethyl)phenyl)-7,7-dimethyl-7,8-dihydro-1H-benzofuro[4,5-d]imidazole-5-carboxamide;

2-((2-Chloro-6-fluorophenyl)amino)-7,7-dimethyl-N-(6-(trifluoromethyl)pyridin-3-yl)-7,8-dihydro-1H-benzofuro[4,5-d]imidazole-5-carboxamide;

2-((2-Chloro-6-methylphenyl)amino)-7,7-dimethyl-N-(2,4,5-trifluorophenyl)-7,8-dihydro-1H-benzofuro[4,5-d]imidazole-5-carboxamide;

2-((2-Chloro-6-fluorophenyl)amino)-7,7-dimethyl-N-(2,4,5-trifluorophenyl)-7,8-dihydro-1H-benzofuro[4,5-d]imidazole-5-carboxamide;

2-((3,5-Dichloropyridin-4-yl)amino)-N-(2-fluoro-4-(trifluoromethyl)phenyl)-7,7-dimethyl-7,8-dihydro-1H-benzofuro[4,5-d]imidazole-5-carboxamide;

2-((3,5-Dichloropyridin-4-yl)amino)-N-(2-fluoro-5-(trifluoromethyl)phenyl)-7,7-dimethyl-7,8-dihydro-1H-benzofuro[4,5-d]imidazole-5-carboxamide;

2-((3,5-Dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide;

2-((3,5-Dichloropyridin-4-yl)amino)-N-(2,4-difluorophenyl)-7,7-dimethyl-7,8-dihydro-1H-benzofuro[4,5-d]imidazole-5-carboxamide;

N-(2-Chloro-4-methylphenyl)-2-((3,5-dichloropyridin-4-yl)amino)-7,7-dimethyl-7,8-dihydro-1H-benzofuro[4,5-d]imidazole-5-carboxamide;

2-((3,5-Dichloropyridin-4-yl)amino)-7,7-dimethyl-N-(2,4,5-trifluorophenyl)-7,8-dihydro-1H-benzofuro[4,5-d]imidazole-5-carboxamide;

2-((2-Chloro-6-methylphenyl)amino)-7,7-dimethyl-N-(2,3,4-trifluorophenyl)-7,8-dihydro-1H-benzofuro[4,5-d]imidazole-5-carboxamide;

N-(5-Cyclopropyl-2-fluorophenyl)-2-((3,5-dichloropyridin-4-yl)amino)-7,7-dimethyl-7,8-dihydro-1H-benzofuro[4,5-d]imidazole-5-carboxamide;

N-(5-Chloro-3-fluoropyridin-2-yl)-2-((2-chloro-6-methylphenyl)amino)-7,7-dimethyl-7,8-dihydro-1H-benzofuro[4,5-d]imidazole-5-carboxamide;

N-(5-Chloro-3-fluoropyridin-2-yl)-2-((2,6-dichlorophenyl)amino)-7,7-dimethyl-7,8-dihydro-1H-benzofuro[4,5-d]imidazole-5-carboxamide;

2-((3,5-Dichloropyridin-4-yl)amino)-7,7-dimethyl-N-(2,3,4-trifluorophenyl)-7,8-dihydro-1H-benzofuro[4,5-d]imidazole-5-carboxamide;

2-((3,5-Dichloropyridin-4-yl)amino)-N-(4-fluoro-3-(trifluoromethyl)phenyl)-1,7,7-trimethyl-7,8-dihydro-1H-benzofuro[4,5-d]imidazole-5-carboxamide;

2-((3,5-Dichloropyridin-4-yl)amino)-1,7,7-trimethyl-N-(3-(trifluoromethyl)phenyl)-7,8-dihydro-1H-benzofuro[4,5-d]imidazole-5-carboxamide;

2-((3,5-dichloropyridin-4-yl)amino)-1,7,7-trimethyl-N-(4-(trifluoromethyl)phenyl)-7,8-dihydro-1H-benzofuro[4,5-d]imidazole-5-carboxamide;

N-(4-Cyclopropylphenyl)-2-((3,5-dichloropyridin-4-yl)amino)-1,7,7-trimethyl-7,8-dihydro-1H-benzofuro[4,5-d]imidazole-5-carboxamide;

N-(5-Cyclopropyl-2-fluorophenyl)-2-((3,5-dichloropyridin-4-yl)amino)-1,7,7-trimethyl-7,8-dihydro-1H-benzofuro[4,5-d]imidazole-5-carboxamide;

2-((3,5-Dichloropyridin-4-yl)amino)-N-(2-fluoro-5-(trifluoromethyl)phenyl)-1,7,7-trimethyl-7,8-dihydro-1H-benzofuro[4,5-d]imidazole-5-carboxamide; and 2-((3,5-Dichloropyridin-4-yl)amino)-1,7,7-trimethyl-N-(5-(trifluoromethyl)pyridin-2-yl)-7,8-dihydro-1H-benzofuro[4,5-d]imidazole-5-carboxamide;

or a pharmaceutically acceptable salt thereof.

29. The compound according to claim 1 selected from

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide hydrochloride;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide oxalate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide 2-hydroxypropane-1,2,3-tricarboxylate;

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide hydrochloride;

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide 2,2,2-trifluoroacetate;

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide oxalate;

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide 2-hydroxypropane-1,2,3-tricarboxylate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide methanesulfonate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide maleate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide fumarate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide succinate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide phosphate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide sulphate;

2-[(2-Chloro-6-fluorophenyl)amino]-7,7-dimethyl-N-[4-(trifluoromethyl)phenyl]-7,8-dihydro-1H-furo[3,2-e]benzimidazole-5-carboxamide, sodium salt;

N-(4-Bromophenyl)-2-[(2,6-dichlorophenyl)amino]-7,7-dimethyl-7,8-dihydro-1H-furo[3,2-e]benzimidazole-5-carboxamidehydrochloride 2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide methanesulfonate;

2-[(2-Chloro-6-methylphenyl)amino]-N-[2-fluoro-5-(trifluoromethyl)phenyl]-7,7-dimethyl-7,8-dihydro-1H-furo[3,2-e]benzimidazole-5-carboxamide sulphate;

2-[(2-Chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide hydrochloride;

2-[(2-Chloro-6-fluorophenyl)amino]-N-[4-fluoro-3-(trifluoromethyl)phenyl]-7,7-dimethyl-7,8-dihydro-1H-furo[3,2-e]benzimidazole-5-carboxamide methanesulfonate;

2-((3,5-Dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide hydrochloride;

2-((3,5-Dichloropyridin-4-yl)amino)-N-(4-fluoro-3-(trifluoromethyl)phenyl)-7,7-dimethyl-7,8-dihydro-1H-benzofuro[4,5-d]imidazole-5-carboxamide methanesulfonate;

2-[(2,6-Dichlorophenyl)amino]-7,7-dimethyl-N-[5-(trifluoromethyl)pyridin-2-yl]-7,8-dihydro-1H-furo[3,2-e]benzimidazole-5-carboxamide hydrochloride; and 2-[(2,6-Dichlorophenyl)amino]-7,7-dimethyl-N-[5-(trifluoromethyl)pyridin-2-yl]-7,8-dihydro-1H-furo[3,2-e]benzimidazole-5-carboxamide methanesulfonate.

30. The compound according to claim 1 selected from

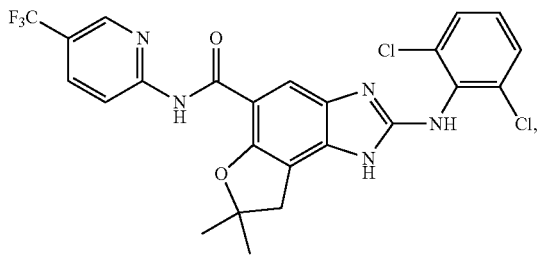

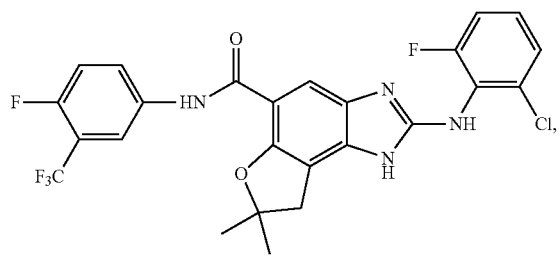

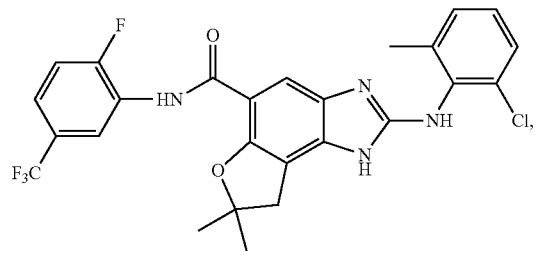

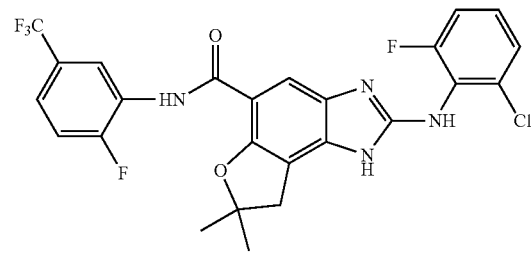

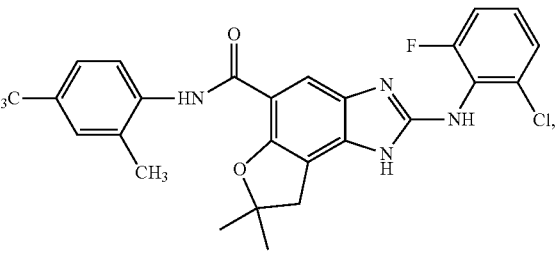

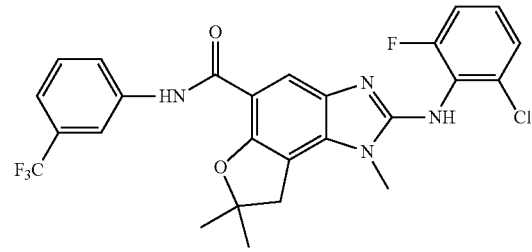

-continued

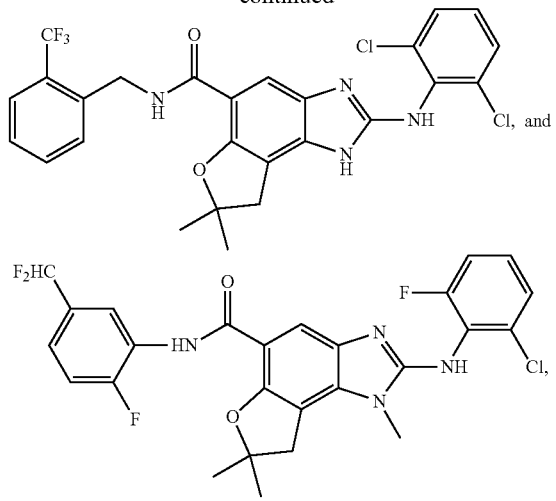

or a pharmaceutically acceptable salt thereof.

31. A compound selected from
2-[(2,6-Dichlorophenyl)amino]-7,7-dimethyl-7,8-dihydro-1H-furo[3,2-e]benzimidazole-5-carboxylic acid;
Methyl 2-[(2,6-dichlorophenyl)amino]-7,7-dimethyl-7,8-dihydro-1H-furo[3,2-e]benzimidazole-5-carboxylate;
2-[(2-Chloro-6-fluorophenyl)amino]-7,7-dimethyl-7,8-dihydro-1H-furo[3,2-e]benzimidazole-5-carboxylic acid;
Methyl 2-[(2-chloro-6-fluorophenyl)amino]-7,7-dimethyl-7,8-dihydro-1H-furo[3,2-e]benzimidazole-5-carboxylate;
2-[(2-Chloro-6-methylphenyl)amino]-7,7-dimethyl-7,8-dihydro-1H-furo[3,2-e]benzimidazole-5-carboxylic acid;
Methyl 2-[(2-chloro-6-methylphenyl)amino]-7,7-dimethyl-7,8-dihydro-1H-furo[3,2-e]benzimidazole-5-carboxylate;
2-((2-Chloro-6-fluorophenyl)amino)-1,7,7-trimethyl-7,8-dihydro-1H-benzofuro[4,5-d]imidazole-5-carboxylic acid;
Methyl 2-((2-chloro-6-fluorophenyl)amino)-1,7,7-trimethyl-7,8-dihydro-1H-benzofuro[4,5-d]imidazole-5-carboxylate;
Methyl 4-amino-2-[(2-methylprop-2-en-1-yl)oxy]-5-nitrobenzoate;
4-amino-2-hydroxy-3-(2-methylprop-2-en-1-yl)-5-nitrobenzoate;
Methyl 4-amino-2,2-dimethyl-5-nitro-2,3-dihydro-1-benzofuran-7-carboxylate;
Methyl 4,5-diamino-2,2-dimethyl-2,3-dihydro-1-benzofuran-7-carboxylate;
Methyl 2-((2-methylallyl)oxy)-4-(methylamino)-5-nitrobenzoate;
Methyl 2,2-dimethyl-4-(methylamino)-5-nitro-2,3-dihydrobenzofuran-7-carboxylate; and
Methyl 5-amino-2,2-dimethyl-4-(methylamino)-2,3-dihydrobenzofuran-7-carboxylate.

32. A pharmaceutical composition comprising a compound according to claim 1, either as a free base or pharmaceutically acceptable salt form and a pharmaceutically acceptable excipient.

33. The pharmaceutical composition according to claim 32, wherein the pharmaceutically acceptable excipient is a carrier or diluent.

* * * * *